United States Patent
Park et al.

(10) Patent No.: US 11,807,628 B2
(45) Date of Patent: *Nov. 7, 2023

(54) BENZODIAZEPINE DERIVATIVES AND USES THEREOF

(71) Applicant: IntoCell, Inc., Daejeon (KR)

(72) Inventors: Taekyo Park, Daejeon (KR); Sung Ho Woo, Sejong-Si (KR); Sunyoung Kim, Daejeon (KR); Suho Park, Daejeon (KR); Jongun Cho, Daejeon (KR); Doohwan Jung, Daejeon (KR); Donghoon Seo, Daejeon (KR); Jaeho Lee, Sejong-Si (KR); Sangkwang Lee, Daejeon (KR); Sanghyeon Yun, Daejeon (KR); Hyang Sook Lee, Daejeon (KR); Okku Park, Daejeon (KR); Beomseok Seo, Daejeon (KR); Sena Kim, Daejeon (KR); Minah Seol, Daejeon (KR)

(73) Assignee: IntoCell, Inc., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/363,814

(22) Filed: Jun. 30, 2021

(65) Prior Publication Data
US 2022/0162190 A1    May 26, 2022

Related U.S. Application Data

(63) Continuation of application No. 16/425,237, filed on May 29, 2019, now Pat. No. 11,084,801.

(60) Provisional application No. 62/677,498, filed on May 29, 2018.

(51) Int. Cl.
C07D 403/12    (2006.01)
C07H 17/02    (2006.01)
C07D 519/00    (2006.01)

(52) U.S. Cl.
CPC ......... *C07D 403/12* (2013.01); *C07D 519/00* (2013.01); *C07H 17/02* (2013.01)

(58) Field of Classification Search
None
See application file for complete search history.

(56) References Cited

U.S. PATENT DOCUMENTS

| | | |
|---|---|---|
| 9,399,073 B2 | 7/2016 | Howard et al. |
| 9,617,270 B2 | 4/2017 | Li et al. |
| 9,676,794 B2 | 6/2017 | Zhang et al. |
| 11,084,801 B2 | 8/2021 | Park et al. |
| 2011/0196148 A1 | 8/2011 | Howard et al. |
| 2017/0029490 A1 | 2/2017 | Winters et al. |
| 2022/0009946 A1 | 1/2022 | Park et al. |

FOREIGN PATENT DOCUMENTS

| | | |
|---|---|---|
| KR | 10-2019-0064619 A | 6/2019 |
| KR | 10-2020-0107837 A | 9/2020 |
| KR | 10-2021-0068591 A | 6/2021 |
| WO | WO-97/44000 A2 | 11/1997 |
| WO | WO-2010/043880 A1 | 4/2010 |
| WO | WO-2010/091150 A1 | 8/2010 |
| WO | WO-2013/055993 A1 | 4/2013 |
| WO | WO-2014/031566 A1 | 2/2014 |
| WO | WO-2014/080251 A1 | 5/2014 |
| WO | WO-2016/001485 A1 | 1/2016 |
| WO | WO-2016/115191 A1 | 7/2016 |
| WO | WO-2016/115201 A1 | 7/2016 |
| WO | WO-2016/149535 A1 | 9/2016 |
| WO | WO-2016/149546 A1 | 9/2016 |
| WO | WO-2017/201442 A1 | 11/2017 |
| WO | WO-2018/053552 A2 | 3/2018 |
| WO | WO-2018/175994 A1 | 9/2018 |
| WO | WO-2018/195243 A1 | 10/2018 |
| WO | WO-2019/008441 A1 | 1/2019 |
| WO | WO-2019/043417 A1 | 3/2019 |
| WO | WO-2019/229536 A2 | 12/2019 |
| WO | WO-2020/089687 A2 | 5/2020 |
| WO | WO-2021/260438 A1 | 12/2021 |

OTHER PUBLICATIONS

Arima et al., "Studies on Tomaymycin, A New Antibiotic. I Isolation and Properties of Tomaymycin," The Journal of Antibiotics, 25(8): 437-444 (1972).

Bai et al., "Site-Specific Conjugation of the Indolinobenzodiazepine DGN549 to Antibodies Affords Antibody-Drug Conjugates with an Improved Therapeutic Index as Compared with Lysine Conjugation," Bioconjugate Chem., 31: 93-103 (2020).

Bose et al., "New Approaches To Pyrrolo[2,1-c][1,4]Benzodiazepines: Synthesis, DNA-Binding and Cytotoxicity of DC-81," Tetrahedron, 48(4): 751-758 (1992).

Donnell et al., "Macrocyclic pyrrolobenzodiazepine dimers as antibody-drug conjugate payloads," Bioorganic & Medicinal Chemistry Letters, 27: 5267-5271 (2017).

Extended European Search Report for EP Application No. 19811692.3 dated Nov. 25, 2021.

Gerratana, "Biosynthesis, Synthesis, and Biological Activities of Pyrrolobenzodiazepines," Medicinal Research Reviews, 32(2): 254-293 (2012).

Gregson et al., "Synthesis and evaluation of pyrrolobenzodiazepine dimer antibody-drug conjugates with dual b-glucuronide and dipeptide triggers," European Journal of Medicinal Chemistry, 179: 591-607 (2019).

Hara et al., "102, A New Glycosidic Pyrrolo( 1,4)Benzodiazepine Antibiotic Produced by Streptomyces," The Journal of Antibiotics, 41(5): 702-704 (1988).

Hartley, "The development of pyrrolobenzodiazepines as antitumour agents," Expert Opin. Investig. Drugs, 20(6): 733-744 (2011).

Hochlowski et al., "Abbeymycin, A New Anthramycin-Type Antibiotic Produced By A Streptomycete," The Journal of Antiobiotics, 40(2):145-148 (1987).

(Continued)

*Primary Examiner* — Dale R Miller

(74) *Attorney, Agent, or Firm* — Foley Hoag LLP; David P. Halstead; Lucas P. Watkins

(57) ABSTRACT

The present disclosure provides compounds and compositions capable of extending lifespan, and methods of use thereof.

20 Claims, 7 Drawing Sheets

(56) References Cited

OTHER PUBLICATIONS

Hurley et al., "Covalent Binding of Antitumor Antibiotics in the Minor Groove of DNA. Mechanism of Action of CC-1065 and the Pyrrolo( 1,4) benzodiazepines," Acc. Chem. Res., 19: 230-237 (1986).
International Search Report and Written Opinion for International Application No. PCT/IB2019/000691 dated Jan. 10, 2020.
International Search Report and Written Opinion for International Application No. PCT/IB2019/001175 dated Apr. 17, 2020.
Intocell, "OHPAS Linker: New Self-Immolative Group for Phenolic & Non-phenolic Payloads," Sep. 15-18 World ADC Digital (2020).
Itoh et al., "Sibanomicin, A New Pyrrolo[1,4]-Benzodiazepine Antitumor Antibiotic Produced by A *Micromonospora* sp.," The Journal of Antibiotics, 41(9): 1281-1284 (1988).
Konishi et al., "Chicamycin, A New Antitumor Antibiotic II. Structure Determination of Chicamycins A and B," The Journal of Antibiotics, 37(3): 200-206 (1984).
Kovtun et al., "IMGN632: A Novel Antibody-Drug Conjugate (ADC) of a CD123-Targeting Antibody With a Potent DNA-Alkylator is Highly Active in Preclinical Models of AML With Poor Prognosis," EHA 21st congress. Jun. 9-12, 2016.
Kuminoto et al., "Mazethramycin, A New Member of Anthramycin Group Antibiotics," The Journal of Antibiotics, 33(6): 665-667 (1980).
Langley et al., "A Versatile and Efficient Synthesis of Carbinolamine-Containing Pyrrolo[1,4]benzodiazepines via the Cyclization of N-(2-Aminobenzoyl)pyrrolidine-2-carboxaldehyde Diethyl Thioacetals: Total Synthesis of Prothracarcin," J. Org. Chem., 52:91-97(1987).
Leber et al.. "A Revised Structure for Sibiromycin," J. Am. Chem. Soc., 110: 2992-2993 (1988).
Leimgruber et al., "Isolation and Characterization of Anthramycin, a New Antitumor Antibiotic," Journal of the American Chemical Society, 87(24): 5791-5793 (1965).
Leimgruber et al., "The Structure of Anthramycin," Journal of the American Chemical Society, 87(24): 5793-5795 (1965).
Miller et al., "A new class of antibody-drug conjugates with potent DNA alkylating activity," Mol Cancer Ther, 15(8):1870-1878 (2016).
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker," Bioconjugate Chemistry, 30: 1957-1968 (2019).
Park et al., "Introduction of Para-Hydroxy Benzyl Spacer Greatly Expands the Utility of Ortho-Hydroxy-Protected Aryl Sulfate System: Application to Nonphenolic Payloads," Bioconjugate Chemistry, 30:1969-1978 (2019).
Park et al., "Sulfonate Version of OHPAS Linker has Two Distinct Pathways of Breakdown: Elimination Route Allows Para-Hydroxy-Protected Benzylsulfonate (PHP-BS) to Serve as an Alternative Self-Immolative Group," Bioconjugate Chem., Manuscript (2020).
Prabhakar et al., "Synthesis of C8-C8/C2-C8-linked triazolo pyrrolobenzodiazepine dinners by employing 'click'chemistry and their DNA-binding affinity," Tetrahedron Letters, 49(22): 3620-3624 (2008).
Reid et al., "Design synthesis and evaluation of novel, potent DNA alkylating agents and their antibody-drug conjugates (ADCs)," Bioorganic & Medicinal Chemistry Letters, 29:2455-2458 (2019).
Shimizu et al., "Prothracarcin, A Novel Antitumor Antibiotic," The Journal of Antibiotics, 35(8): 972-978(1982).
Sonzini et al., "Improved Physical Stability of an Antibody-Drug Conjugate Using Host-Guest Chemistry," Bioconjugate Chem., 31(1): 123-129 (2020).
Takeuchi et al., "Neothramycins A and B, New Antitumor Antibiotics," The Journal of Antibiotics, 29(1): 93-96 (1976).
Thurston et al., "Synthesis of DNA-Interactive Pyrrole[ 2, 1-c][ 1,4]benzodiazepines," Chem. Rev., 94: 433-465 (1994).
Tsunakawa et al., "Porothramycin, A New Antibiotic of the Anthramycin Group: Production, Isolation, Structure and Biological Activity," The Journal of Antibiotics, 41(10): 1366-1373 (1988).
Watkins et al., "IMGN779, a CD33-Targeted Antibody-Drug Conjugate (ADC) with a Novel DNA-Alkylating Effector Molecule, Induces DNA Damage, Cell Cycle Arrest, and Apoptosis in AML Cells," Abstract 1366. 57th Annual Meeting of the American Society of Hematology. Dec. 5-7, 2015.
White et al., "Design and characterization of homogenous antibody-drug conjugates with a drug-to-antibody ratio of one prepared using an engineered antibody and a dual-maleimide pyrrolobenzodiazepine dimer," MABS, 11(3): 500-515 (2019).
Whiteman et al., "IMGN779: A CD33-Targeted Antibody-Drug Conjugate (ADC) Utilizing a Novel DNA Alkylator, DGN462, is Highly Active in Vitro Against Primary Patient AML Cells and in Vivo Against AML Xenografts in Mice," 19th Congress—European Hematology Association Jun. 12-15, 2014. Abstract Code: P802.
Zhang et al., "Immolation of p-Aminobenxyl ether linker and payload potency and stability determine the cell-killing activity of antibody-drug conjugates with phenol-containing payloads," Bioconjugate Chem, 29(2):267-274 (2018).
Zhang et al., "Intratumoral Payload Concentration Correlates with the Activity of Antibody-Drug Conjugates," Mol Cancer Ther; 17(3):677-685 (2018).
Extended European Search Report for EP Application No. 19880141.7 dated Jun. 24, 2022.
International Search Report and Written Opinion for International Application No. PCT/IB2022/000772 dated May 23, 2023.

BENZODIAZEPINE DERIVATIVES AND USES THEREOF

RELATED APPLICATIONS

This application is a continuation of U.S. patent application Ser. No. 16/425,237, filed May 29, 2019, which claims the benefit of U.S. Provisional Application No. 62/677,498, filed May 29, 2018, the contents of each of which are fully incorporated by reference herein.

BACKGROUND

Antibody-drug conjugates (ADCs) are emerging as a powerful class of anti-tumor agents with efficacy across a range of cancers. ADCs commonly include three distinct features: a cell-binding agent or targeting moiety; a linker; and a cytotoxic agent. The linker component of an ADC is an important feature in developing targeted anti-cancer agents that possess a desirable target-specificity, i.e., high activity in tumor cells, but with low activity in healthy cells. The use of targeting moieties in combination with cytotoxic agents that, if untargeted, could harm healthy tissue also changes the calculus of desirable features for such cytotoxic agents. Therefore, there is a need for improved linkers and cytotoxic agents useful for preparing ADCs.

SUMMARY OF THE INVENTION

In certain aspects, provided herein are compounds having the structure of Formula (I):

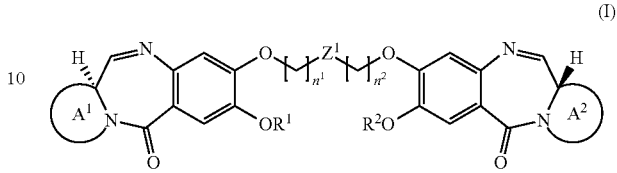

or a pharmaceutically acceptable salt thereof,
wherein:
$A^1$ and $A^2$ each independently represent a heterocyclic ring, preferably a five- or six-membered ring, optionally fused to or substituted with one or more aryl or heteroaryl rings;
$R^1$ and $R^2$ are each independently an alkyl group, preferably a lower alkyl group;
$Z^1$ is methylene or a linking group; and
$n^1$ and $n^2$ are each independently an integer having a value of 1 to 5.

In some embodiments, the compound of Formula (I) is selected from:

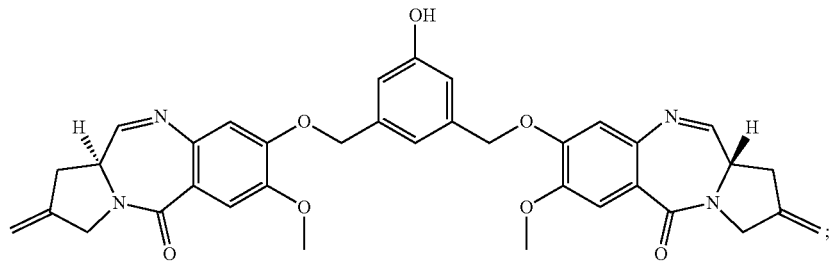

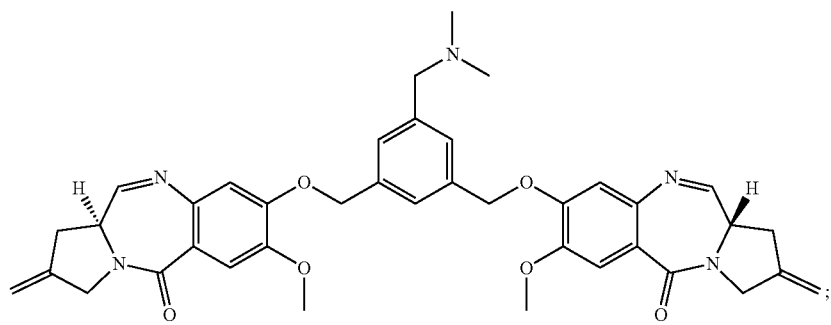

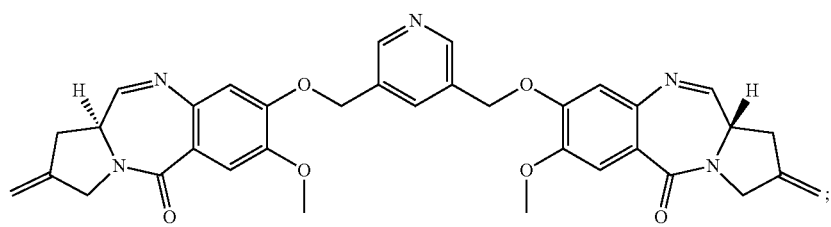

-continued
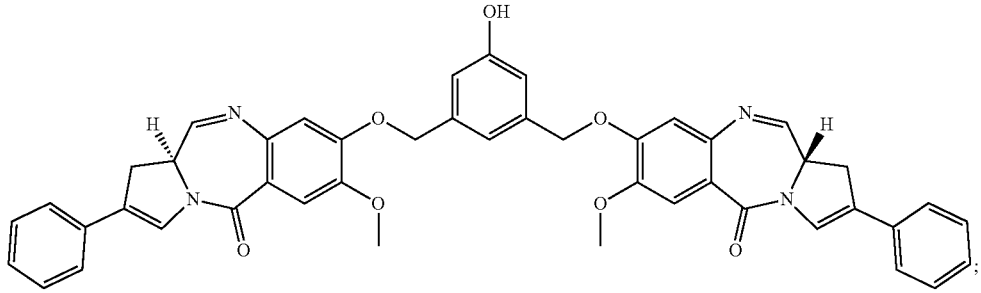
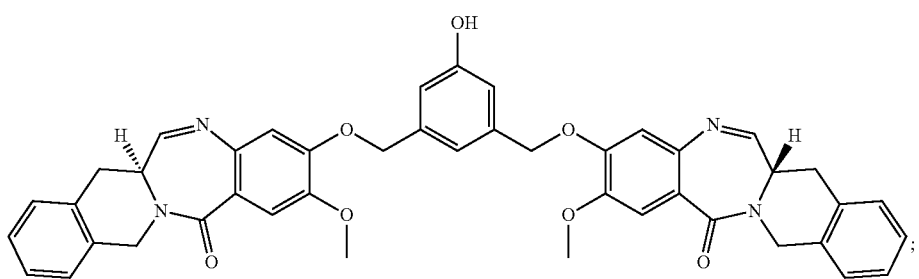
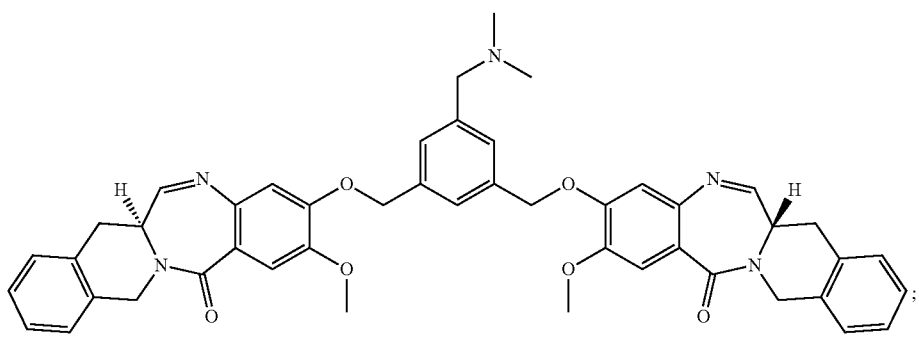
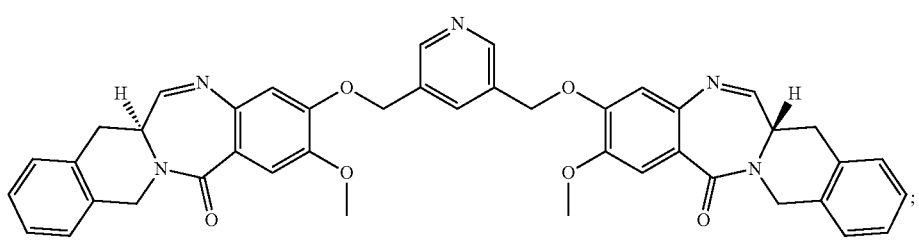
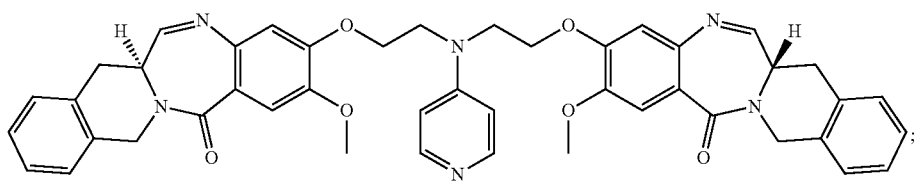
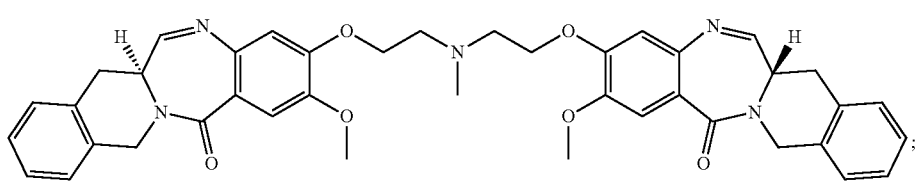

-continued
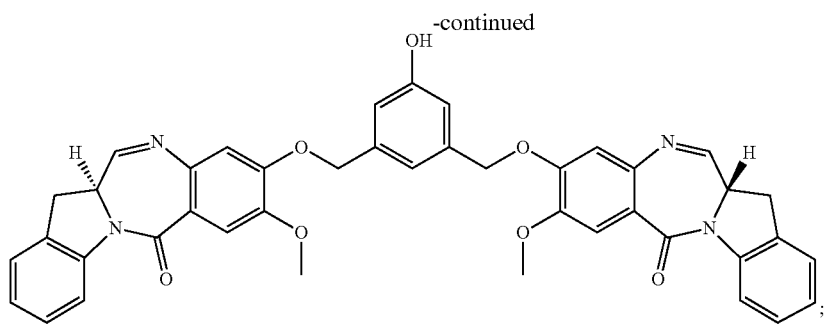
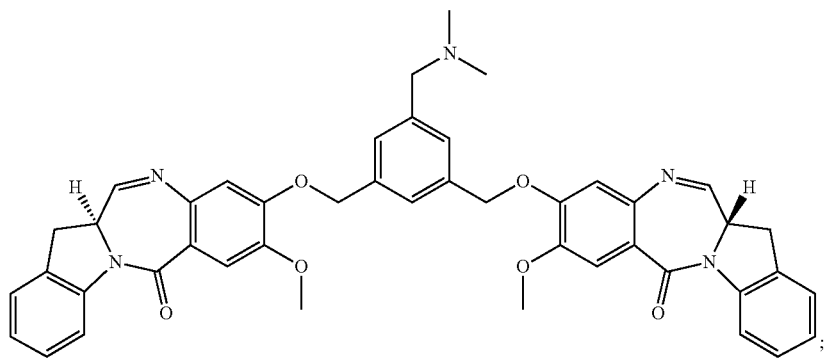
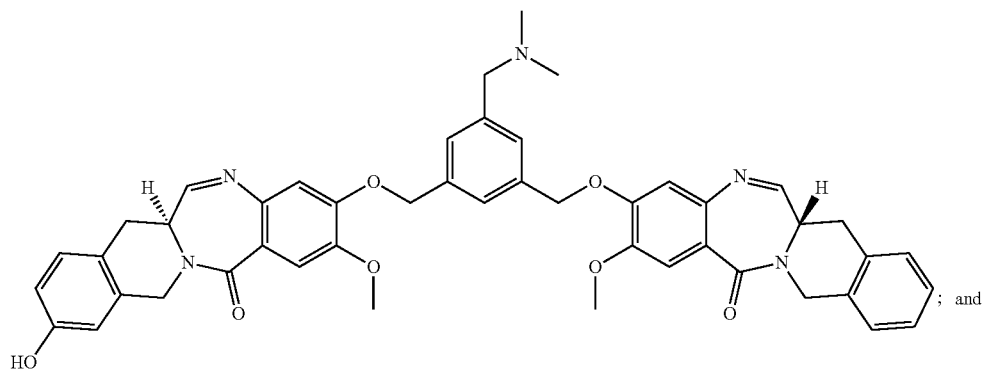
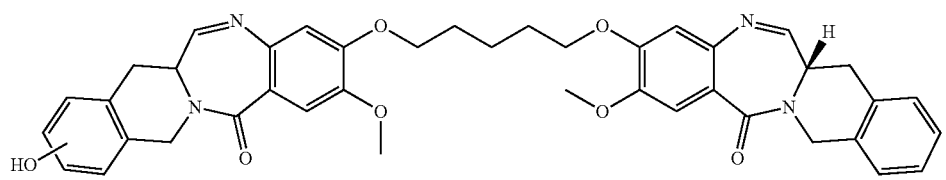
or a pharmaceutically acceptable salt thereof.
In certain aspects, provided herein are conjugates comprising a compound of Formula (I), a cleavable linker, and a targeting agent, wherein the cleavable linker cleavably links the compound to the active agent targeting agent. In preferred embodiments, the targeting agent is a cell-binding agent.

In certain aspects, provided herein are compounds having the structure of Formula (II), (IIa), and (IIb):

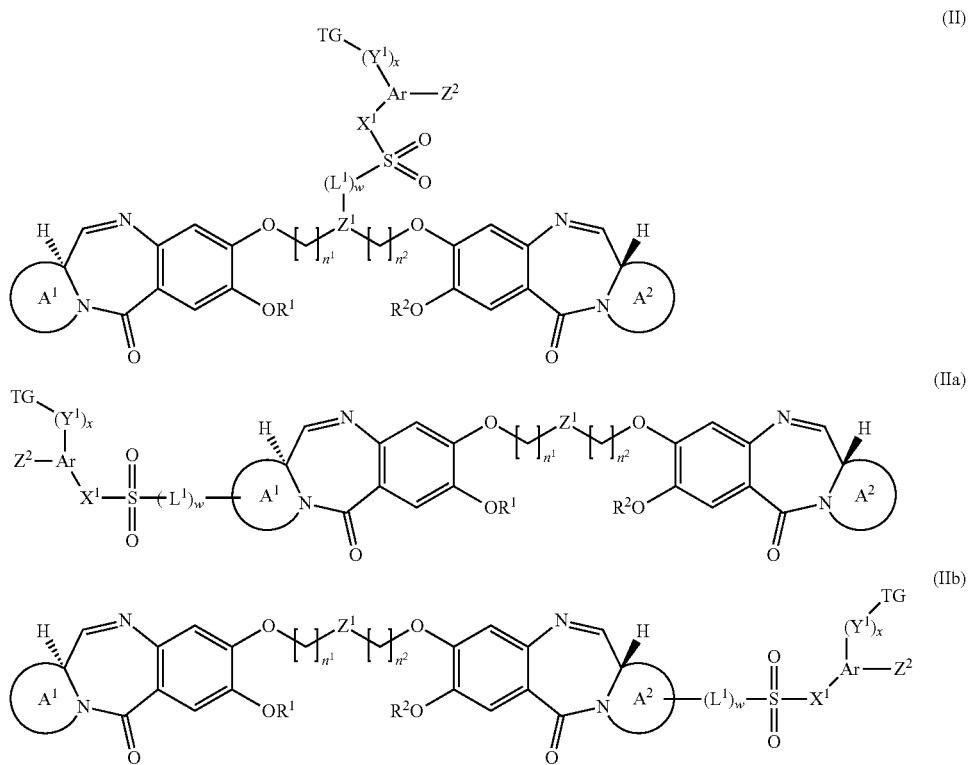

or a pharmaceutically acceptable salt thereof,
wherein:
$A^1$ and $A^2$ each independently represent a heterocyclic ring, preferably a five- or six-membered ring, optionally fused to or substituted with one or more aryl or heteroaryl rings;
$R^1$ and $R^2$ are each independently an alkyl group;
$Z^1$ is a linking group;
$Z^2$ is absent or a linking group;
$L^1$ is a linking group attached to the $SO_2$ via a heteroatom selected from O, S, and N, preferably O or N, and is selected such that cleavage of the bond between $L^1$ and $SO_2$ promotes cleavage of the bond between $L^1$ and $Z^1$ to release the active agent;
$X^1$ is —O—, —$CR^b{}_2$—, or —$NR^a$—, preferably —O—;
Ar represents a ring, such as aryl, heteroaryl, cycloalkyl, or heterocycloalkyl, preferably aryl or heteroaryl;
$Y^1$ is —$(CR^b{}_2)_y N(R^a)$—, —$(CR^b{}_2)_y O$—, or —$(CR^b{}_2)_y S$—, positioned such that the N, O, or S atom is attached to TG if y is 1 to 5; wherein $X^1$ and $Y^1$ are positioned on adjacent atoms of Ar;
TG is a triggering group that, when activated, generates an N, O, or S atom capable of reacting with the $SO_2$ to displace $Z^2$ and form a 5-6-membered ring including X—$SO_2$ and the intervening atoms of Ar;
each $R^a$ is hydrogen or lower alkyl; and
each $R^b$ is independently hydrogen or lower alkyl; or
two $R^b$, together with the carbon atom to which they are attached, form a 3-5-membered ring, preferably a 3-4-membered ring;
$n^1$ and $n^2$ are each independently an integer having a value of 1 to 5;

w and x are each independently an integer having a value of 0 or 1; and
y is an integer having a value of 0 to 5.

In certain aspects, provided herein are conjugates having the structure of Formula (III):

$$(D\text{-}L)_{dl}\text{-}LG\text{-}(CB)_{cb} \quad\quad (III)$$

or a pharmaceutically acceptable salt thereof,
wherein:
LG is a linking group;
CB is a cell-binding agent;
cb and dl are each independently integers having a value of 1 to about 20, preferably from 1 to about 10, such as 1; and
each D-L independently is a group having the structure of a compound of Formula (I) or (II).

The present disclosure also relates to compositions (e.g., pharmaceutical compositions) comprising a compound of Formula (I), (II), (IIa), (IIb), or a conjugate of Formula (III), and a carrier (e.g., a pharmaceutically acceptable carrier).

In certain aspects, the present disclosure provides methods of delivering an active agent to a cell comprising administering a conjugate of Formula (III) or a pharmaceutical composition thereof, wherein the targeting moiety is selected to bind to a molecule associated with a target cell. In certain aspects, the invention provides conjugates of Formula (III) and pharmaceutical compositions thereof, for use in a method for delivering an active agent to a cell, wherein the targeting moiety is selected to bind to a molecule associated with a target cell. In particular, the present compounds, conjugates, and compositions may be useful for inhibiting abnormal cell growth or treating a proliferative disorder in a mammal (e.g., a human), such as where the target cell is a cancer cell and the targeting moiety is selected to bind to a molecule associated with the cancer cell (and not associated with healthy cells, or at least preferentially associated with tumor cells rather than healthy cells).

The conjugates of Formula (III) and pharmaceutical compositions thereof may be useful for treating conditions such as cancer, rheumatoid arthritis, multiple sclerosis, graft versus host disease (GVHD), transplant rejection, lupus, myositis, infection, immune deficiency such as AIDS, and inflammatory diseases in a mammal (e.g., human).

DETAILED DESCRIPTION OF THE INVENTION

Figure 1:
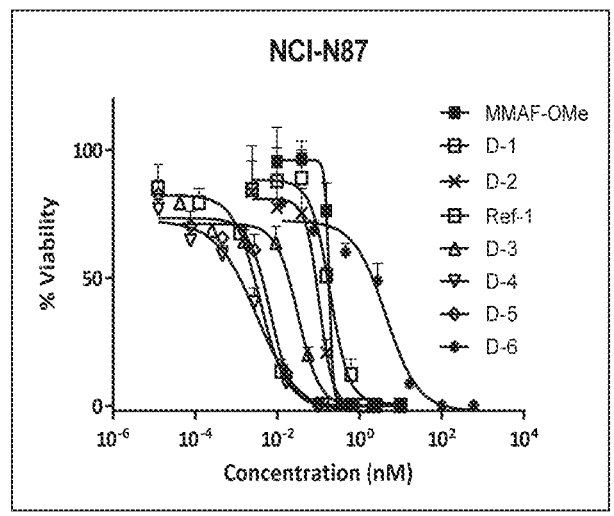
FIG. 1 shows the in vitro cytotoxic activity of compounds D-1, D-2, D-3, D-4, D-5, and D-6 against NCI-N87.
Figure 2:
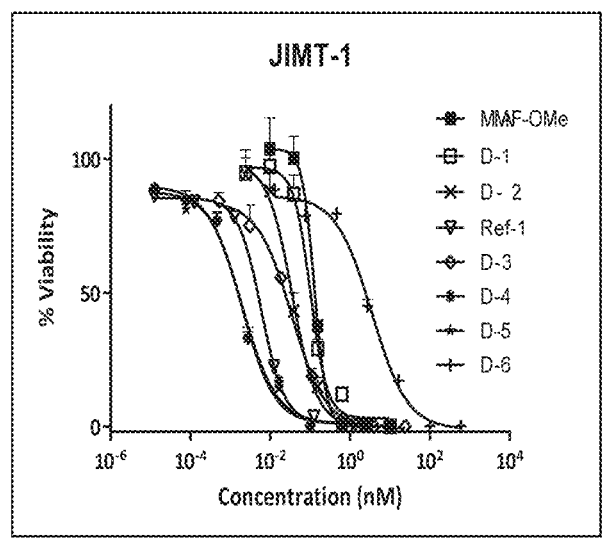
FIG. 2 shows the in vitro cytotoxic activity of compounds D-1, D-2, D-3, D-4, D-5, and D-6 against JIMT-1.
Figure 3:
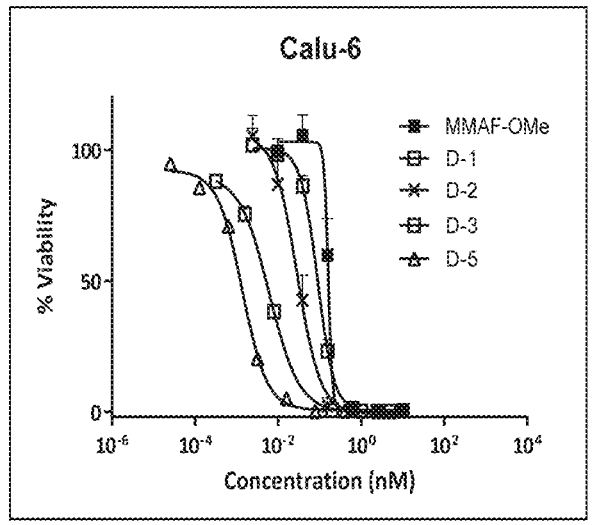
FIG. 3 shows the in vitro cytotoxic activity of compounds D-1, D-2, D-3, and D-5 against Calu-6.
Figure 4:
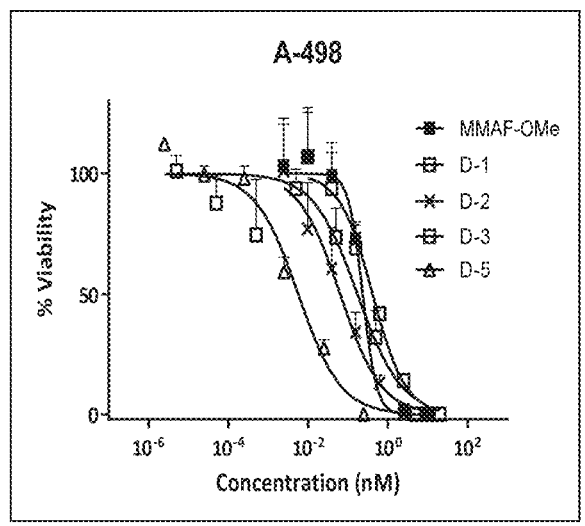
FIG. 4 shows the in vitro cytotoxic activity of compounds D-1, D-2, D-3, and D-5 against A-498
Figure 5:
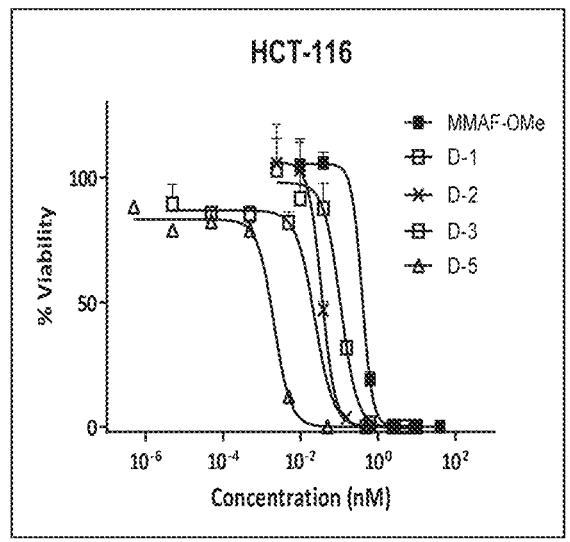
FIG. 5 shows the in vitro cytotoxic activity of compounds D-1, D-2, D-3, and D-5 against HCT-116.
Figure 6:
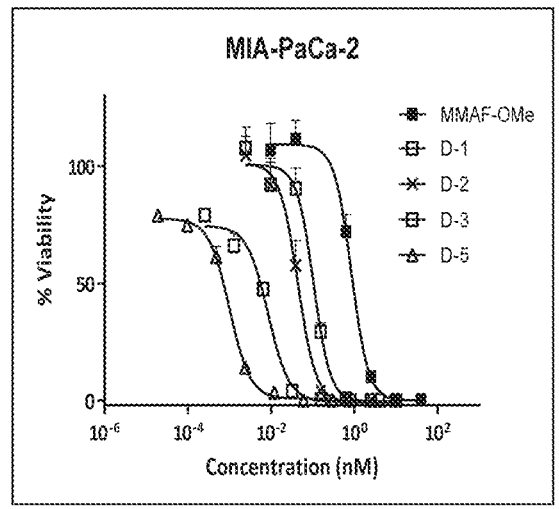
FIG. 6 shows the in vitro cytotoxic activity of compounds D-1, D-2, D-3, and D-5 against MIA-PaCa-2.
Figure 7:
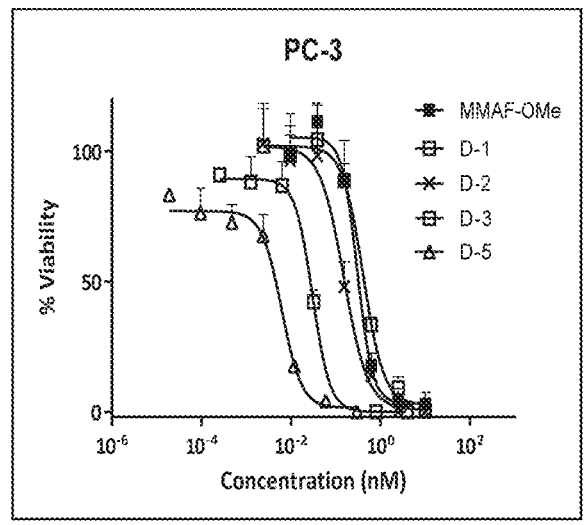
FIG. 7 shows the in vitro cytotoxic activity of compounds D-1, D-2, D-3, and D-5 against PC-3.
Figure 8:
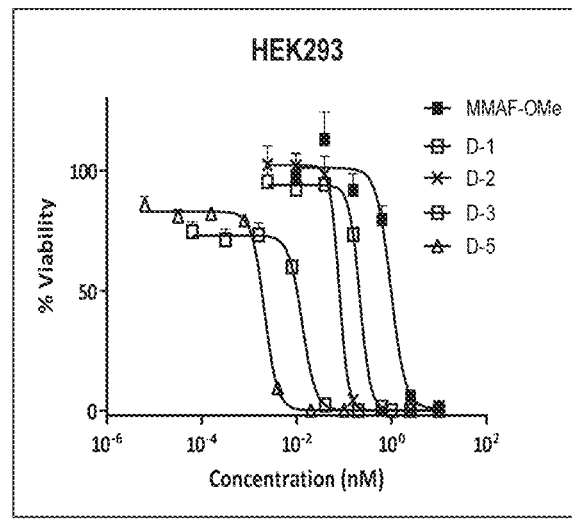
FIG. 8 shows the in vitro cytotoxic activity compounds D-1, D-2, D-3, and D-5 against HEK-293E.
Figure 9:
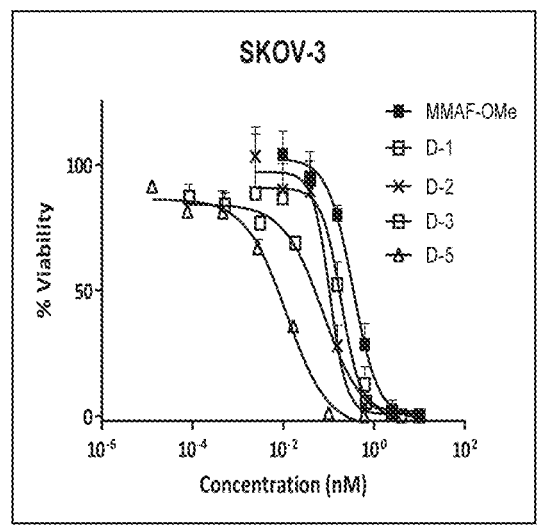
FIG. 9 shows the in vitro cytotoxic activity of compounds D-1, D-2, D-3, and D-5 against SK-OV-3.

Some pyrrolobenzodiazepines (PBDs) have the ability to recognize and bond to specific sequences of DNA; the preferred sequence is PuGPu. The first PBD antitumor antibiotic, anthramycin, was discovered in 1965 (Leimgruber et al, J. Am. Chem. Soc, 87:5793-5795 (1965); Leimgruber et al, J. Am. Chem. Soc., 87:5791-5793 (1965)). Since then, a number of naturally occurring PBDs have been reported, and over 10 synthetic routes have been developed to a variety of analogues (Thurston et al, Chem. Rev. 1994:433-465 (1994)). Family members include abbeymycin (Hochlowski et al, J. Antibiotics, 40:145-148 (1987)), chicamycin (Konishi et al, J. Antibiotics, 37:200-206 (1984)), DC-81 (Japanese Patent 58-180 487; Thurston et al, Chem. Brit, 26:161-112 (1990); Bose et al, Tetrahedron, 48:751-758 (1992)), mazethramycin (Kuminoto et al, J. Antibiotics, 33:665-667 (1980)), neothramycins A and B (Takeuchi et al, J. Antibiotics, 29:93-96 (1976)), porothramycin (Tsunakawa et al, J. Antibiotics, 41:1366-1373 (1988)), prothracarcin (Shimizu et al, J. Antibiotics, 29:2492-2503 (1982); Langley and Thurston, J. Org. Chem., 52:91-97 (1987)), sibanomicin (DC-102) (Hara et al, J. Antibiotics, 41:702-704 (1988); Itoh et al, J. Antibiotics, 41:1281-1284 (1988)), sibiromycin (Leber et al, J. Am. Chem. Soc, 110:2992-2993 (1988)) and tomamycin (Arima et al, J. Antibiotics, 25:437-444 (1972)).

PBDs are of the general structure:

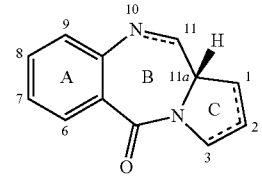

They differ in the number, type and position of substituents, in both their aromatic A rings and pyrrolo C rings, and in the degree of saturation of the C ring. In the B-ring there is either an imine (N═C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral CI la position which provides them with a right-handed twist when viewed from the C ring towards the A ring.

This gives them the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, Acc. Chem. Res., 19:230-237 (1986)). Their ability to form an adduct in the minor groove, enables them to interfere with DNA processing, hence their use as antitumor agents.

Indolinobenzodiazepines (IBDs) differ from PBDs, in that the PBD C ring is replaced by an indolino ring. For the sake of convenience, certain A ring and B ring positions in the IBDs adopt the same nomenclature as those in the PBDs, such as the C6-C9, N10, and C11 positions.

Provided herein are compounds and conjugates thereof comprising a PBD or an IBD compound and, optionally, a cleavable linker, and uses thereof. In certain embodiments, the compounds and conjugates disclosed herein comprise an active agent (e.g., a compound of Formula (I)) comprise a functional group that undergoes a chemical reaction (e.g., a physicochemical reaction and/or a biological reaction) under predetermined conditions to release a nucleophilic heteroatom, and an $SO_2$ functional group positioned proximal to the nucleophilic heteroatom so that it can react with the nucleophilic heteroatom in an intramolecular cyclization reaction to release the active agent. In some embodiments, the compounds and conjugates disclosed herein further comprise a targeting moiety (e.g., oligopeptide, polypeptide, antibody, etc.) having binding specificity for a desired target receptor or other molecule associated with a target cell.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g., "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

All of the above, and any other publications, patents and published patent applications referred to in this application are specifically incorporated by reference herein. In case of conflict, the present specification, including its specific definitions, will control.

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "amide", as used herein, refers to a group

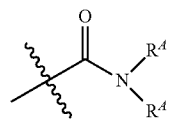

wherein each $R^A$ independently represents a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

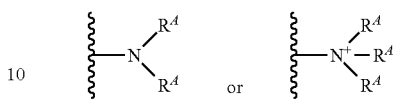

wherein each $R^A$ independently represents a hydrogen or a hydrocarbyl group, or two $R^A$ are taken together with the N atom to which they are attached complete a heterocycle having from 4 to 8 atoms in the ring structure.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The terms "halo" and "halogen" as used herein means halogen and includes chloro, fluoro, bromo, and iodo.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by Formula I. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts of compounds of Formula I are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds of Formula I for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by Formula I or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixtures and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of formula I). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of Formula I. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The terms "abnormal cell growth" and "proliferative disorder" are used interchangeably in this application. "Abnormal cell growth," as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or over-expression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

Compounds and Conjugates of the Invention

Compounds of Formula (I)

The present disclosure provides compounds having the structure of Formula (I):

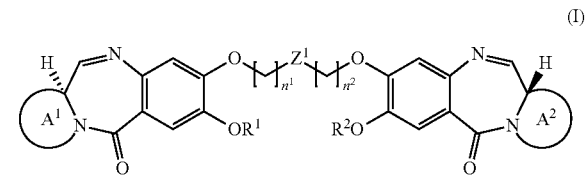

or a pharmaceutically acceptable salt thereof,
wherein:
$A^1$ and $A^2$ each independently represent a heterocyclic ring, preferably a five-membered ring, optionally fused to one or more aryl or heteroaryl rings;
$R^1$ and $R^2$ are each independently an alkyl group, preferably a lower alkyl group;
$Z^1$ is methylene or a linking group; and
$n^1$ and $n^2$ are each independently an integer having a value of 1 to 5.

In some embodiments, $A^1$ is selected from:

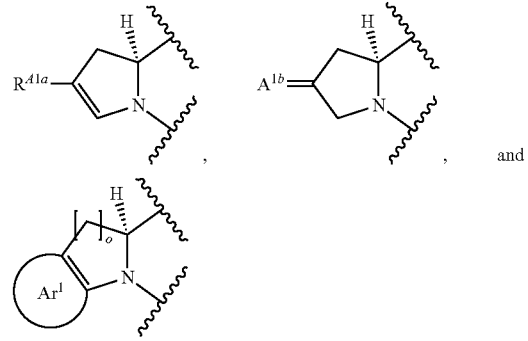

, , and wherein:
$R^{A1a}$ is H, alkyl, alkenyl, cycloalkyl, heterocycloalkyl, aryl, or heteroaryl;
$R_{A1b}$ is $CHR^{A1ba}$;
$R^{A1ba}$ is H, halogen, alkyl, —$CO_2$-alkyl, CHO, or $CO_2H$;
$Ar^1$ is aryl or heteroaryl, preferably a six-membered aryl or heteroaryl, optionally substituted one or more times with halogen, hydroxyl, cyano, nitro, alkyl, haloalkyl, cycloalkyl, carboxyl, amino, aryl, or heteroaryl; and
o is an integer having a value of 1 or 2; and
p is an integer having a value from 0 to 5.

In some such embodiments, $Ar^1$ is aryl or heteroaryl optionally substituted with one or more of $R^{A1c}$, wherein $R^{A1c}$ is halogen, OH, CN, $NO_2$, alkyl, alkoxy, $CO_2H$, $CO_2$-alkyl, or $(CH_2)_pN(R^{A1ca})_2$; each $R^{A1ca}$ is independently selected from H or alkyl; and p is an integer having a value from 0 to 5.

In some embodiments, $A^1$ is

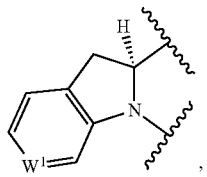

wherein $W^1$ is $CR^{W1}$ or N; and $R^{W1}$ is H, alkyl, or cycloalkyl.

In some embodiments, $A^1$ is

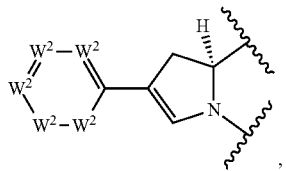

wherein each $W^2$ is independently $CR^{A1aa}$ or N; and $R^{A1aa}$ is H, OH, alkyl, alkoxy, alkylamino, or dialkylamino. In some such embodiments, $A^1$ is

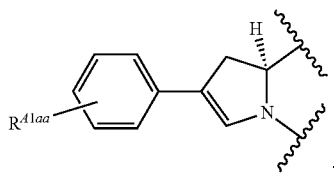

In preferred such embodiments, $A^1$ is

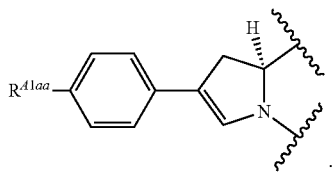

In some embodiments, $A^2$ is

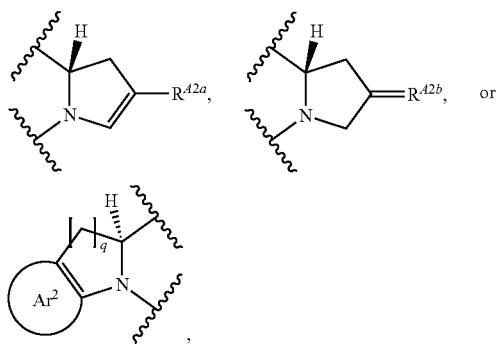

wherein:
$R^{A2a}$ is H, alkyl, alkenyl, cycloalkyl, heterocycloalkyl, aryl, or heteroaryl;
$R^{A2b}$ is $CHR^{A2ba}$.
$R^{A2ba}$ is H, halogen, alkyl, —$CO_2$-alkyl, CHO, or $CO_2H$;
$Ar^2$ is aryl or heteroaryl, preferably a six-membered aryl or heteroaryl, optionally substituted with one or more of $R^{A2c}$.
$R^{A2c}$ is halogen, OH, CN, $NO_2$, alkyl, alkoxy, $CO_2H$, $CO_2$-alkyl, or $(CH_2)_rN(R^{A2ca})_2$;
each $R^{A2ca}$ is independently selected from H or alkyl;
q is an integer having a value of 1 or 2; and
r is an integer having a value from 0 to 5.

In some embodiments, $A^2$ is

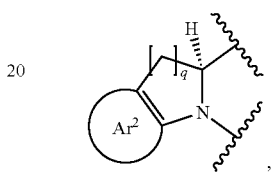

selected from

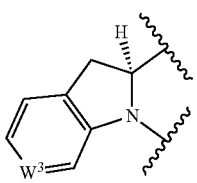 and 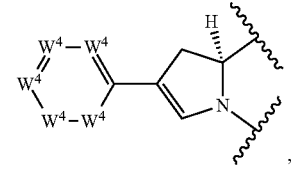

wherein
$W^3$ is $CR^{W3}$ or N, provided that no more than three $W^4$ are N, and preferably no more than one $W^4$ is N;
$R^{W3}$ is H, alkyl, or cycloalkyl;
each $W^4$ is independently $CR^{A2aa}$ or N; and
$R^{A2aa}$ is H, OH, alkyl, alkoxy, alkylamino, or dialkylamino.

In some such embodiments, $A^2$ is

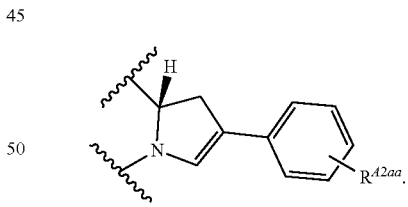

In preferred such embodiments, $A^2$ is

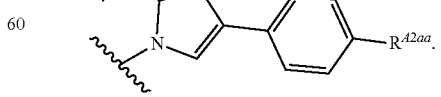

In certain embodiments, the compound of Formula (I) is a compound having the structure of Formula (Ia), (Ib), or (Ic):

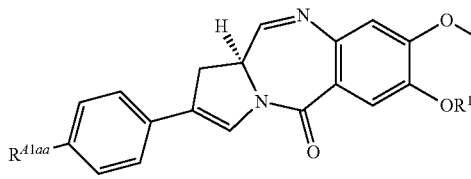
(Ia)

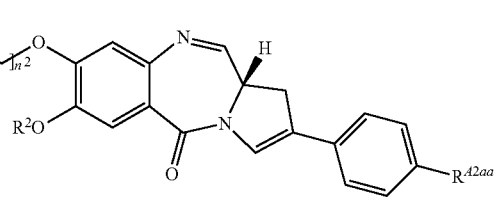
(Ib)

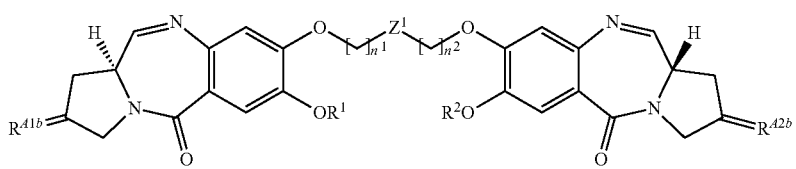
(Ic)

or a pharmaceutically acceptable salt thereof, wherein:
$R^{A1aa}$ and $R^{A2aa}$ are each independently H, OH, alkyl, alkoxy, alkylamino, or dialkylamino;
$R^{A1b}$ is $CHR^{A1ba}$.
$R^{A1ba}$ is H, halogen, alkyl, —$CO_2$-alkyl, CHO, or $CO_2H$;
$R^{A2b}$ is $CHR^{A2ba}$.
$R^{A2ba}$ is H, halogen, alkyl, —$CO_2$-alkyl, CHO, or $CO_2H$;
$Ar^1$ is aryl or heteroaryl, preferably a six-membered aryl or heteroaryl, optionally substituted one or more times with halogen, hydroxyl, cyano, nitro, alkyl, haloalkyl, cycloalkyl, carboxyl, amino, aryl, or heteroaryl;
$R^{A1c}$ is halogen, OH, CN, $NO_2$, alkyl, alkoxy, $CO_2H$, $CO_2$-alkyl, or $(CH_2)_pN(R^{A1ca})_2$;
each $R^{A1ca}$ is independently selected from H or alkyl;
$Ar^2$ is aryl or heteroaryl, preferably a six-membered aryl or heteroaryl, optionally substituted one or more times with halogen, hydroxyl, cyano, nitro, alkyl, haloalkyl, cycloalkyl, carboxyl, amino, aryl, or heteroaryl;
$R^{A2c}$ is halogen, OH, CN, $NO_2$, alkyl, alkoxy, $CO_2H$, $CO_2$-alkyl, or $(CH_2)_rN(R^{A2ca})_2$;
each $R^{A2ca}$ is independently selected from H or alkyl;
o and q are integers each independently having a value of 1 or 2.

In some such embodiments, $Ar^1$ is aryl or heteroaryl optionally substituted with one or more of $R^{A1c}$, wherein $R^{A1c}$ is halogen, OH, CN, $NO_2$, alkyl, alkoxy, $CO_2H$, $CO_2$-alkyl, or $(CH_2)_pN(R^{A1ca})_2$; each $R^{A1ca}$ is independently selected from H or alkyl; and p is an integer having a value from 0 to 5. Similarly, in certain embodiments, $Ar^2$ is aryl or heteroaryl optionally substituted with one or more of $R^{A1c}$, wherein $R^{A2c}$ is halogen, OH, CN, $NO_2$, alkyl, alkoxy, $CO_2H$, $CO_2$-alkyl, or $(CH_2)_rN(R^{A2ca})_2$; each $R^{A2ca}$ is independently selected from H or alkyl; and r is an integer having a value from 0 to 5.

In some embodiments, $R^1$ and $R^2$ are the same. In preferred embodiments, $R^1$ and $R^2$ are methyl.

In some embodiments, $Z^1$ provides an amine or a phenol for conjugation. Thus, in certain such embodiments, for example, $Z^1$ comprises amino, hydroxy-substituted aryl, or nitrogen-containing heteroaryl, and may optionally be further substituted. In other such embodiments, $R^{Y1a}$ or $R^{Z1a}$ provide an amine or a phenol for conjugation. For example, $R^{Z1a}$ may be selected from amino (e.g., alkyl-substituted amino), hydroxy-substituted aryl, or nitrogen-containing heteroaryl, and may optionally be further substituted.

In certain embodiments, $Z^1$ is methylene.

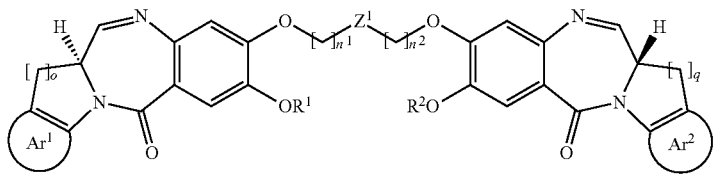

In other embodiments, $Z^1$ is wherein:
$Y^1$ is $CR^{Y1}$ or N, preferably wherein only one $Y^1$ is N;
$R^{Y1}$ is H, hydroxyl, amino, amido, or $(CH_2)_y(R^{Y1a})$;
$R^{Y1a}$ is amino (e.g., secondary or tertiary amino), aryl, or heteroaryl;
y is an integer having a value of 1 to about 10. In preferred embodiments, $Z^1$ is

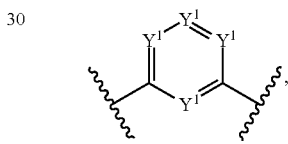

wherein $R^{Z1}$ is absent, hydroxyl, amino, amido, or $(CH_2)_z(R^{Z1a})$; and $R^{Z1a}$ is amino (e.g., secondary or tertiary amino), aryl, or heteroaryl; and z is an integer having a value of 0 to about 10.

In more preferred embodiments, $Z^1$ is

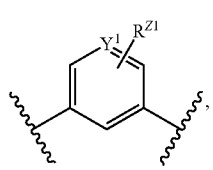 ; 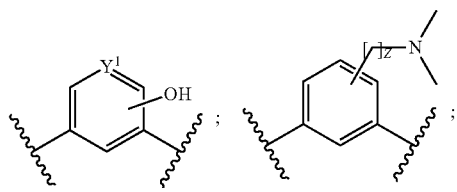 ;

-continued
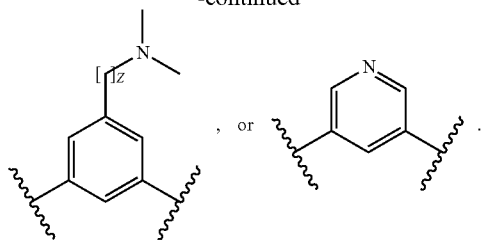
In still other embodiments, $Z^1$ is
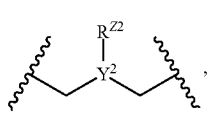
wherein:
$Y^2$ is $CR^{Y2}$ or N;
$R^{Y2}$ is H or alkyl, preferably lower alkyl;
$R^{Z2}$ is $(CH_2)_z R^{Z2a}$;
$R^{Z2a}$ is amino (e.g., secondary or tertiary amino), aryl, or heteroaryl; and
z is an integer having a value of 0 to about 10.
In certain preferred embodiments, $Z^1$ is
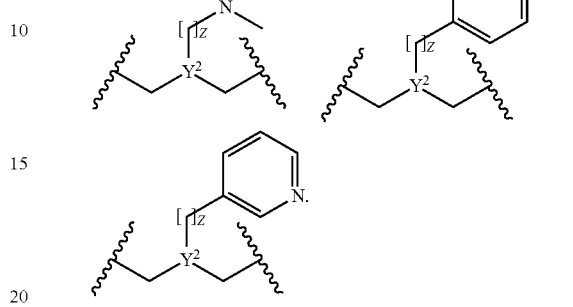
In certain embodiments, the compound of Formula (I) is selected from:
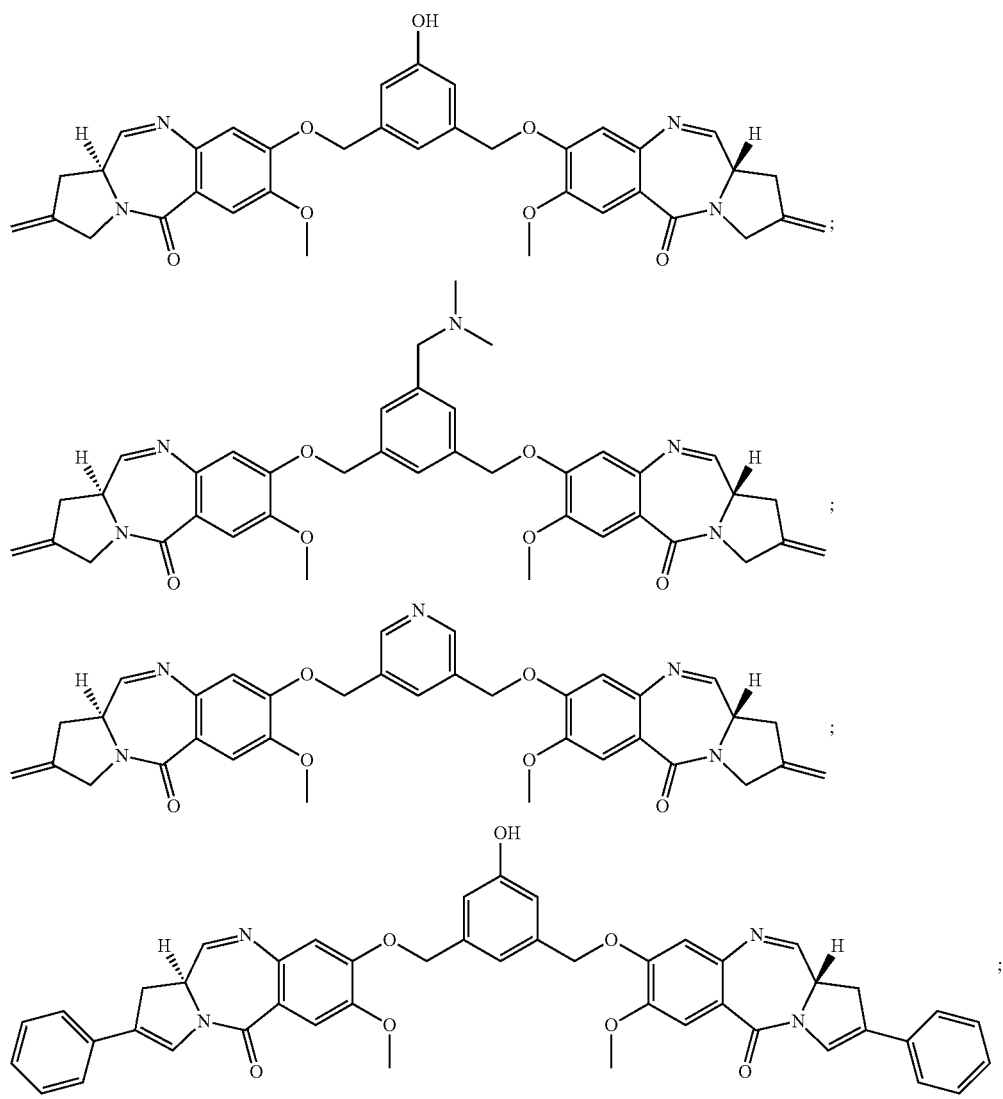

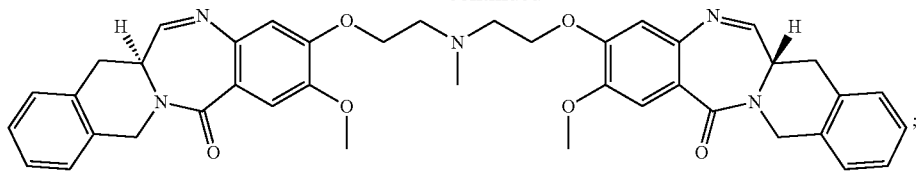
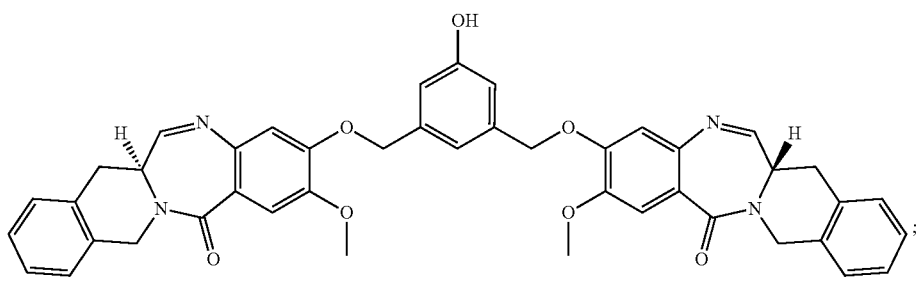
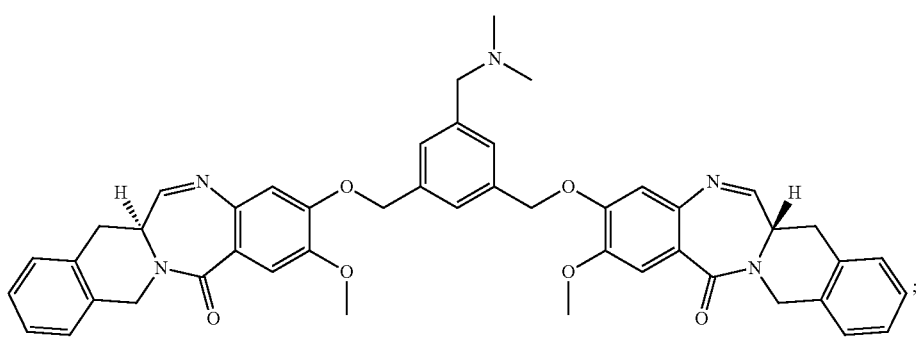
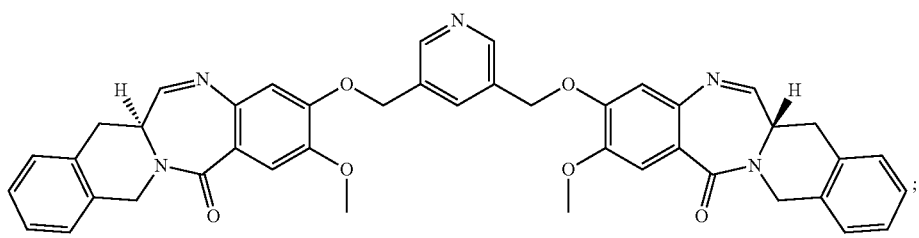
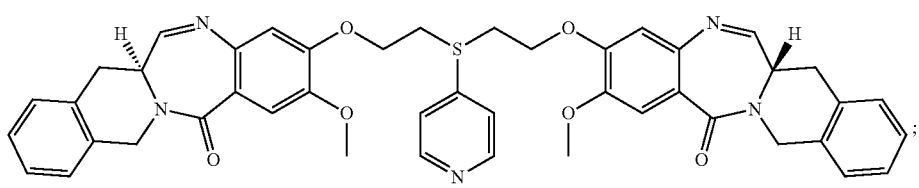
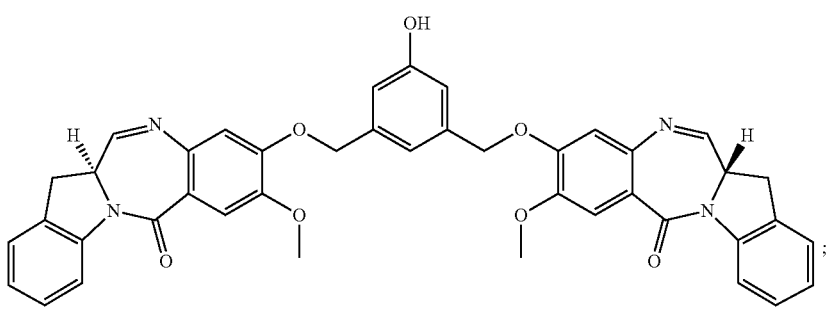

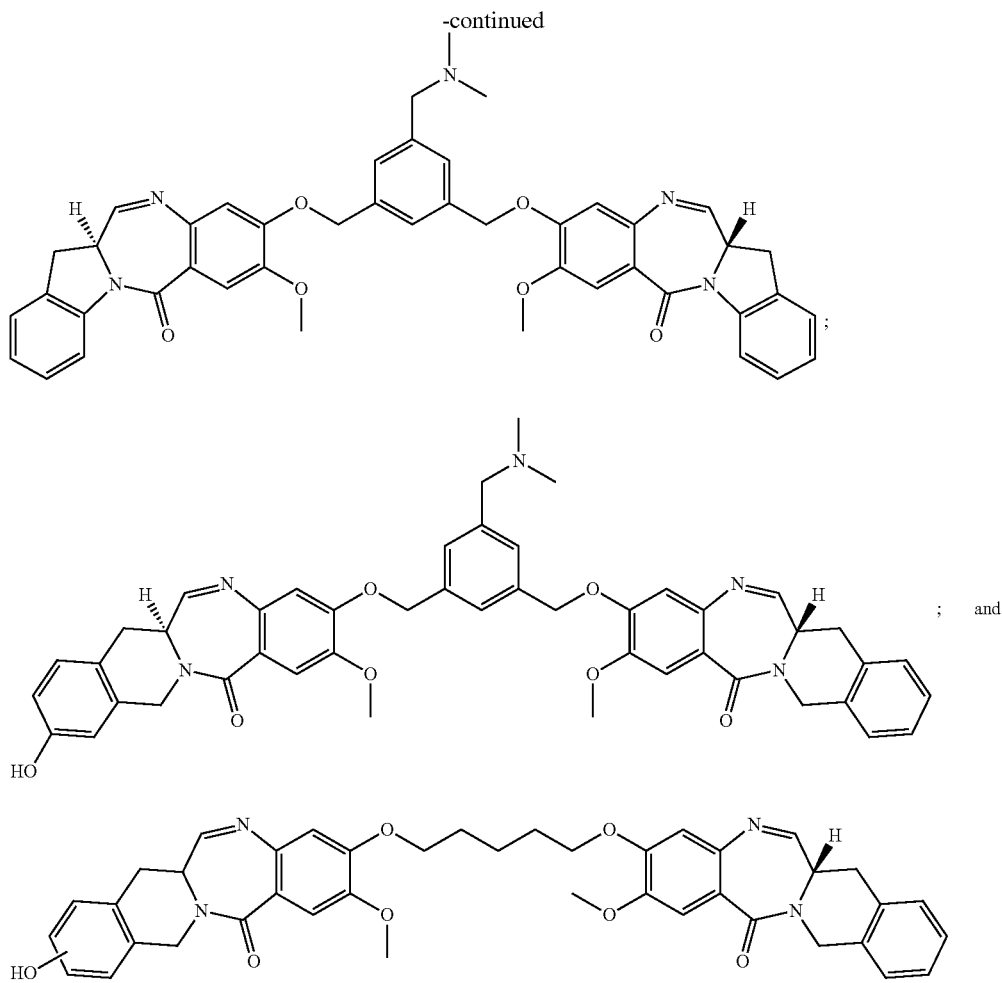

or a pharmaceutically acceptable salt thereof.

Conjugates of Formula (I)

In some embodiments, provided herein are conjugates comprising compounds of Formula (I), a cleavable linker, and targeting agent, wherein the cleavable linker cleavably links the compound to the targeting agent. In preferred embodiments, the targeting agent is a cell-binding agent. In some embodiments, the linker comprises a functional group that undergoes a chemical reaction (e.g., a physicochemical reaction and/or a biological reaction) under predetermined conditions to release a nucleophilic heteroatom, and an $SO_2$ functional group positioned proximal to a nucleophilic heteroatom. In preferred embodiments, the $SO_2$ functional group reacts with the nucleophilic heteroatom in an intramolecular cyclization reaction to release the active agent. In some embodiments, the conjugates further comprises a targeting moiety (e.g., oligopeptide, polypeptide, antibody, etc.) having binding specificity for a desired target receptor or other molecule associated with a target cell.

Compounds of Formula (II), (IIa), and (IIb)

Also provided herein are compounds having the structure of Formula (II), (IIa), and (IIb)

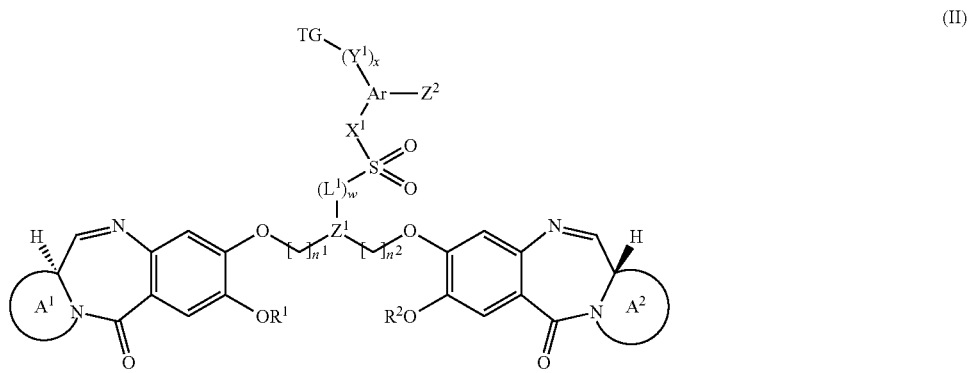

(II)

-continued

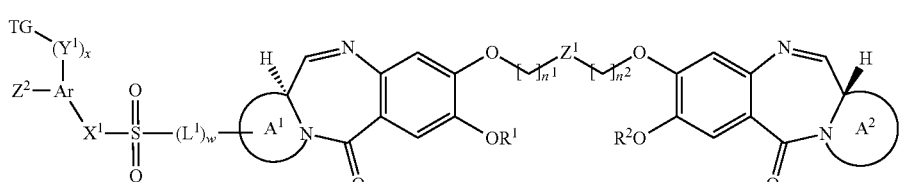
(IIa)

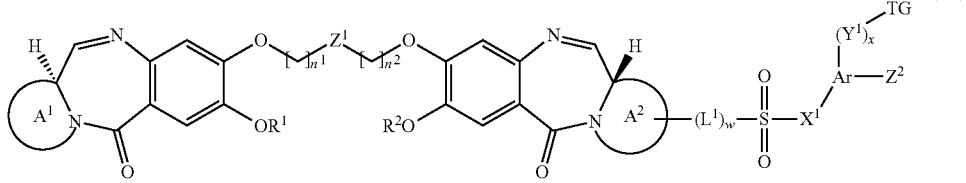
(IIb)

or a pharmaceutically acceptable salt thereof,
wherein:
$A^1$ and $A^2$ each independently represent a heterocyclic ring, preferably a five- or six-membered ring, optionally fused to or substituted with an aryl or heteroaryl ring;
$R^1$ and $R^2$ are each independently an alkyl group;
$Z^1$ is a linking group; and
$n^1$ and $n^2$ are each independently an integer having a value of 1 to 5.
$Z^2$ is absent or a linking group;
$L^1$ is a linking group attached to the $SO_2$ via a heteroatom selected from O, S, and N, preferably O or N, and is selected such that cleavage of the bond between $L^1$ and $SO_2$ promotes cleavage of the bond between $L^1$ and $Z^1$ to release the active agent;
$X^1$ is —O—, —$CR^b{}_2$—, or —$NR^a$—, preferably —O—;
Ar represents a ring, such as aryl, heteroaryl, cycloalkyl, or heterocycloalkyl, preferably aryl or heteroaryl;
$Y^1$ is —$(CR^b{}_2)_y N(R^a)$—, —$(CR^b{}_2)_y O$—, or —$(CR^b{}_2)_y S$—, positioned such that the N, O, or S atom is attached to TG if y is 1; wherein $X^1$ and $Y^1$ are positioned on adjacent atoms of Ar;
TG is a triggering group that, when activated, generates an N, O, or S atom capable of reacting with the $SO_2$ to displace Z and form a 5-6-membered ring including X—$SO_2$ and the intervening atoms of Ar;
w and x are each independently an integer having a value of 0 or 1;
each $R^a$ is hydrogen or lower alkyl;
each $R^b$ is independently hydrogen or lower alkyl; or
two $R^b$, together with the carbon atom to which they are attached, form a 3-5-membered ring, preferably a 3-4-membered ring; and
y is an integer having a value of 1 to about 10.
In some embodiments, $X^1$ is —O—.
In other embodiments, Ar is aryl. In preferred embodiments, phenyl or naphthyl.
In yet other embodiments, $Z^2$ is a linking group comprising one or more groups selected from isocyanide, isothiocyanide, 2-pyridyl disulfide, haloacetamide (—NHC(O)CH$_2$-halo), maleimide, diene, alkene, halide, tosylate (TsO$^-$), aldehyde, sulfonate (R—SO$_3{}^-$),

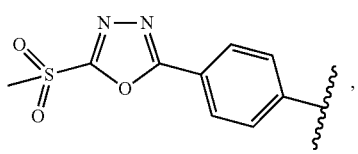

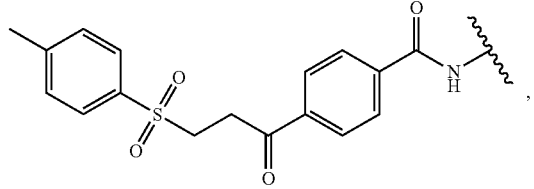

phosphonic acid (—P(=O)(OH)$_2$), ketone, $C_8$-$C_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—$R^a$), and dihydrogen phosphate (—OP(=O)(OH)$_2$).

In still other embodiments, x is 0.

In various embodiments, the variables of Formula (II), (IIa), and (IIb) are the same as defined in Formula (I) above.

Additional embodiments of conjugates, linking groups, triggering groups, and the like are provided in U.S. Provisional Application No. 62/597,226, which is hereby incorporated by reference in its entirety.

Release of the Active Agent

As described above, in certain embodiments, the compounds and conjugates disclosed herein are capable of dissociating one or more active agents represented by Formula (II) through an intramolecular cyclization reaction following a chemical reaction that activates the triggering group. In certain embodiments, the chemical reaction is a physicochemical reaction and/or a biochemical reaction.

In some embodiments, the compounds and conjugates disclosed herein comprise a nucleophilic functional group (Y or Y') introduced at an adjacent atom on Ar with respect to X (e.g., O). Typically, the nucleophilic functional group is masked by a triggering group (TG), as further detailed below. Upon activation, the triggering group releases the nucleophilic functional group to react with the nearby $SO_2$ moiety in an intramolecular cyclization, ultimately releasing the one or more compounds of Formula (II), (IIa), or (IIb). In some such embodiments, one or more active agents are released through an intramolecular cyclization reaction after a chemical reaction, a physicochemical reaction and/or a biochemical reaction (see, for example, Reaction Scheme 1), or the active agent is released through 1,6-elimination or 1,4-elimination after the intramolecular cyclization reaction (see, for example, Reaction Scheme 2).

As an example, when Y is —Y'-TG and Q is directly conjugated to the SO² group, the active agent may be released by the mechanism shown in Reaction Scheme 1:

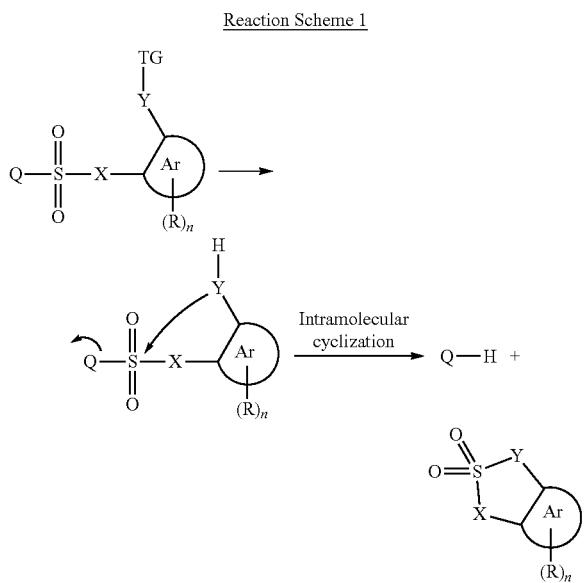

When Q is

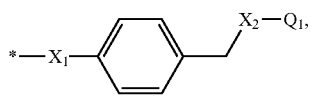

$Q^1$ may be released by the mechanism shown in Reaction Scheme 2:

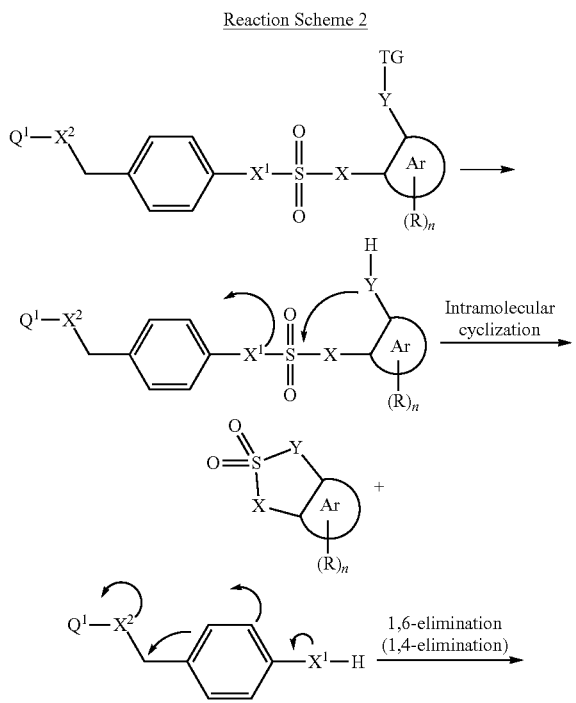

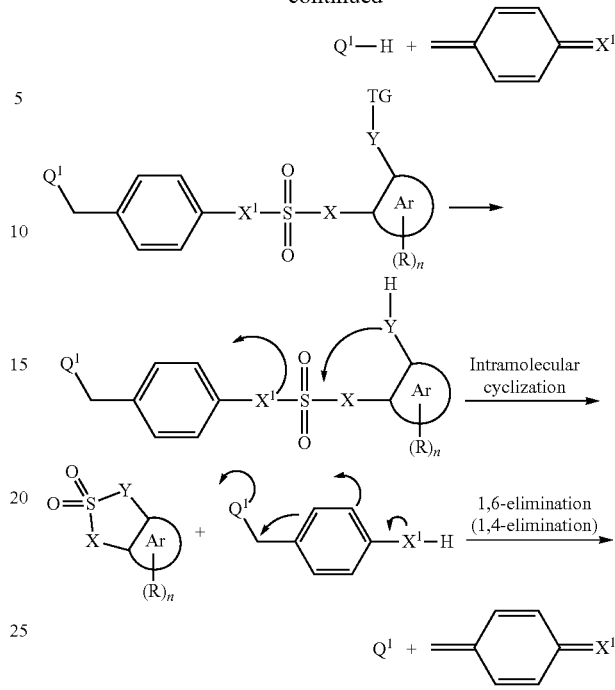

In some embodiments, $Q^1$ when released is an active agent comprising at least one functional group selected from —OH, —NH—, —SH and —COOH. According to these embodiments, as further described herein, $Q^1$ is conjugated to a compound as described herein by the —OH, —NH—, —SH and —COOH, for instance through a functional group selected from ester, amide, thioester, carbamate, urea, oxime, hydrazone, etc. In some such embodiments, $Q^2$ is used in place of $Q^1$, and $Q^2$ is an amine group-containing drug. In other embodiments, $Q^2$ is an active agent capable of binding with an ammonium unit. In still other embodiments, $Q^2$ is capable of being dissociated in its original form having an amine group upon release of $Q^2$ release, wherein the active agent may be a drug, a toxin, an affinity ligand, a probe for detection, or a combination thereof.

In some embodiments, the compounds and conjugates disclosed herein are chemically and physiologically stable. In some such embodiments, the compounds and conjugates disclosed herein reach a desired target cell in a state wherien there is little dissociation of the active agent in the blood, thereby selectively releasing the drug.

Triggering Groups (TGs)

In some embodiments, the conjugates of the present invention include a triggering group (TG). TGs are groups capable of being cleaved, preferably selectively cleaved, by a chemical reaction, such as a biological reaction. Generally, triggering groups serve to mask the nucleophilic nature of the Y or Y' group, thereby providing stability (e.g., by preventing self-immolation or intramolecular cyclization prior to the conjugate reaching a target location or experiencing a predetermined trigger condition) to the compounds and conjugates disclosed herein. Upon activation, the triggering group releases the nucleophilic Y group and allows for self-immolation or intramolecular cyclization to occur, as described above.

In some embodiments, the TG comprises a sequence (such as a peptide sequence) or a moiety recognized by TEV, trypsin, thrombin, cathepsin B, cathespin D, cathepsin K, caspase 1, matrix metalloproteinase (MMP), and the like, which can be hydrolyzed by an enzyme (e.g., an oxidoreductase, a transferase, a hydrolase, a lyase, an isomerase, a ligase, etc.) and/or may include a moiety selected from a phosphodiester, a phospholipid, an ester, a β-galactose, a β-glucose, a fucose, an oligosugar, and the like.

In some embodiments, the TG comprises a reactive chemical moiety or functional group that can be cleaved under nucleophilic reagent conditions (e.g., a silyl ether, a 2-N-acyl nitrobenzenesulfonamide, an unsaturated vinyl sulfide, a sulfonamide after activation, a malondialdehyde-indole derivative, a levulinoyl ester, a hydrazone, or an acyl hydrazone).

In some embodiments, the TG may comprise a reactive chemical moiety or functional group that can be cleaved under basic reagent conditions (e.g., a 2-cyanoethyl ester, an ethylene glycolyl disuccinate, a 2-sulfonylethyl ester, an alkyl thioester, or a thiophenyl ester).

In some embodiments, the TG may comprise a reactive chemical moiety or functional group that can be cleaved by photo-irradiation (e.g., 2-nitrobenzyl derivative, phenacyl ester, 8-quinolinyl benzenesulfonate, coumarin, phosphotriester, bis-arylhydrazone, or bimane bi-thiopropionic acid derivative).

In some embodiments, the TG may comprise a reactive chemical moiety or functional group that can be cleaved by reducing agent conditions (e.g., hydroxylamine, disulfide, levulinate, nitro, or 4-nitrobenzyl derivative).

In some embodiments, the TG may comprise a reactive chemical moiety or a functional group that can be cleaved using acidic conditions (e.g., saccharides, tert-butylcarbamate analogue, dialkyl or diaryl dialkoxysilane, orthoester, acetal, aconityl, hydrazone, 3-thiopropionate, phosphoramidate, imine, trityl, vinyl ether, polyketal, and alkyl 2-(diphenylphosphino)benzoate derivative; alkyl ester, 8-hydroxyquinoline ester, and picolinate ester).

In some embodiments, the TG may comprise a reactive chemical moiety or functional group that can be cleaved under oxidative conditions (e.g., a boronate, a vicinal diol, paramethoxybenzyl derivative, or a selenium compound).

In certain preferred embodiments, the TG comprises a saccharide, which can be cleaved under acidic or enzymatic conditions. In certain preferred embodiments, the triggering group is —$NO_2$, which can be cleaved under reducing conditions. In certain preferred embodiments, the triggering group is a boronate, which can be cleaved under oxidative conditions. In certain preferred embodiments, the triggering group is an ester, which can be cleaved under acidic, basic, or enzymatic conditions. In certain preferred embodiments, the triggering group is a hydrazone, which can be cleaved under nucleophilic conditions or under acidic conditions. In certain preferred embodiments, the triggering group is a hydroxylamine, which can be cleaved under reducing conditions.

Saccharide Triggering Groups

In some embodiments, the compounds and conjugates disclosed herein comprise a saccharide triggering group, for instance a triggering group selected from:

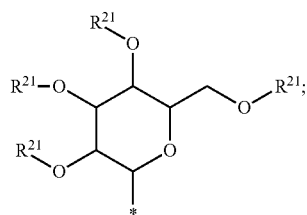

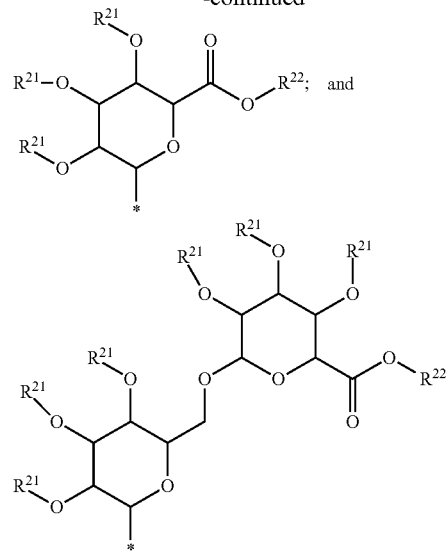

wherein each $R^{21}$ is independently hydrogen or is selected such that O—$R^{21}$ is a hydroxy protecting group (e.g., acetyl); and $R^{22}$ is hydrogen or lower alkyl (e.g., $C_1$-$C_6$-alkyl). In certain embodiments, the hydroxy protecting group is capable of being used in organic synthesis, including but not limited to: methyl ether, methoxymethyl ether, methylthiomethyl ether, 2-methoxyethoxymethyl ether, bis (2-chloroethoxy)methyl ether, tetrahydropyranyl ether, tetrahydrothiopyranyl ether, 4-methoxytetrahydropyranyl ether, 4-methoxytetrahydrothiopyranyl ether, tetrahydrofuranyl ether, 1-ethoxyethyl ether, 1-methyl-1-methoxyethyl ether, 2-(phenylselenyl)ethyl ether, t-butyl ether, allyl ether, benzyl ether, o-nitrobenzyl ether, triphenyl methyl ether, α-naphthyldiphenyl methyl ether, p-methoxyphenyldiphenylmethyl ether, 9-(9-phenyl-10-oxo)anthryl ether, trimethylsilyl ether, isopropyldimethylsilyl ether, t-butyldimethylsilyl ether, t-butyldiphenylsilyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethylbenzoate ester, methyl carbonate, 2,2,2-trichloroethyl carbonate, allyl carbonate, p-nitrophenyl carbonate, benzyl carbonate, p-nitrobenzyl carbonate, S-benzylthiocarbonate, N-phenylcarbamate, nitrate ester, 2,4-dinitrophenylsulfenate ester, etc., but is not limited thereto.

Protecting Groups as Triggering Groups

In some embodiments, TG is a group that is capable of being cleaved by a chemical reaction, a physicochemical reaction, and/or a biological reaction. In certain embodiments, TG is a protecting group. In some such embodiments, the protecting group is an amine group protecting group, an alcohol protecting group, or a thiol protecting group.

Amine Protecting Groups

In certain embodiments, the amine protecting group is a general protecting group that is capable of being used in organic synthesis, including but not limited to: m-nitrophenyl carbamate, 3,5-dimethoxybenzyl carbamate, o-nitrobenzyl carbamate, phenyl(o-nitrophenyl)methyl carbamate, alkyl carbamate, 9-fluorenylmethyl carbamate, 2,2,2-trichloroethyl carbamate, 2-trimethylsilylethyl carbamate (Teoc), t-butyl carbamate (Boc), vinyl carbamate (Voc), allyl carbamate (Alloc), 1-isopropylallyl carbamate (Ipaoc), 8-quinolyl carbamate, N-hydroxypiperidinyl carbamate, benzyl carbamate, p-methoxybenzyl carbamate, p-nitrobenzyl carbamate, diphenyl methyl carbamate, acetamide, chloroacetamide, trichloroacetamide, phenylacetamide, benzamide, N-phthalimide, N-2,3-diphenylmaleimide, N-2,5-dimethylpyrrole, N-1,1-dimethylthiomethyleneamine, N-benzylideneamine, benzenesulfenamide, o-nitrobenzenesulfenamide, triphenylmethylsulfenamide, p-toluenesulfonamide, methanesulfonamide, etc., but is not limited thereto.

Alcohol Protecting Groups

In certain embodiments, the alcohol protecting group is a general protecting group that is capable of being used in organic synthesis, including but not limited to: methyl ether, methoxymethyl ether (MOM ether), benzyloxymethyl ether (BOM ether), 2-(trimethylsilyl)ethoxymethyl ether (SEM ether), phenylthiomethyl ether (PTM ether), 2,2-dichloro-1,1-difluoroethyl ether, p-bromophenacyl ether, chloropropylmethyl ether, isopropyl ether, cyclohexyl ether, 4-methoxybenzyl, 2,6-dichlorobenzyl ether, 4-(dimethylaminocarbonyl)benzyl ether, 9-anthrylmethyl ether, 4-picolyl ether, methylthiomethyl ether (MTM ether), 2-methoxyethoxymethyl ether (MEM ether), bis(2-chloroethoxy)methyl ether, tetrahydropyranyl ether (THP ether), tetrahydrothiopyranyl ether, 4-methoxytetrahydropyranyl ether, 4-methoxytetrahydrothiopyranyl ether, tetrahydrofuranyl ether, 1-ethoxyethyl ether, 1-methyl-1-methoxyethyl ether, 2-(phenylselenyl)ethyl ether), t-butyl ether, allyl ether, benzyl ether, o-nitrobenzyl ether, triphenylmethyl ether, α-naphthyldiphenylmethyl ether, p-methoxyphenyldiphenylmethyl ether, 9-(9-phenyl-10-oxo)anthryl ether, trimethylsilyl ether (TMS ether), isopropyldimethylsilyl ether, t-butyldimethylsilyl ether (TBDMS ether), t-butyldiphenyl silyl ether, tribenzylsilyl ether, triisopropylsilyl ether, formate ester, acetate ester, trichloroacetate ester, phenoxyacetate ester, isobutyrate ester, pivaloate ester, adamantoate ester, benzoate ester, 2,4,6-trimethylbenzoate (Mesitoate) ester, methyl carbonate, 2,2,2-trichloroethyl carbonate, allyl carbonate, p-nitrophenyl carbonate, benzyl carbonate, p-nitrobenzyl carbonate, S-benzyl thiocarbonate, N-phenylcarbamate, nitrate ester, 2,4-dinitrophenylsulfenate ester, dimethylphosphinyl ester (DMP ester), dimethylthiophosphinyl ester (MPT ester), aryl methanesulfonate, aryl toluenesulfonate, etc., but is not limited thereto.

Thiol Protecting Groups

In certain embodiments, the thiol protecting group is capable of being used in organic synthesis, including but not limited to: S-benzyl thioether, S-p-methoxybenzyl thioether, S-o- or p-hydroxyl or acetoxybenzyl thioether, S-p-nitrobenzyl thioether, S-4-picolyl thioether, S-2-picolyl N-oxide thioether, S-9-anthrylmethyl thioether, S-9-fluorenylmethyl thioether, S-methoxymethyl monothioacetal, A-acetyl derivative, S-benzoyl derivative, S—(N-ethylcarbamate), S—(N-methoxymethylcarbamate), etc., but is not limited thereto.

Linking Group

In some embodiments, the compounds and conjugates disclosed herein comprise a linking group connecting each CB and Ar through a covalent bond. Typical linking groups are stable, non-hydrolyzable moieties, such as, for example a $C_{10}$-$C_{100}$ linear or branched, saturated or unsaturated alkylene. In certain embodiments, the linking unit satisfies at least two, and more preferably at least three, out of four of the following criteria:

(i) at least one —$CH_2$— in the alkylene moiety is substituted with (i.e., is replaced by) one or more heteroatoms selected from —NH—, —C(=O)—, —O—, —S— and —P—;

(ii) at least one heteroarylene is included in the alkylene moiety;

(iii) at least one amino acid moiety, sugar bond, peptide bond, or amide bond is included in the alkylene moiety; and (iv) the alkylene may be further substituted with one or more substituents selected from the group consisting of $C_1$-$C_{20}$ alkyl, $C_6$-$C_{20}$ aryl $C_1$-$C_8$ alkyl, —$(CH_2)_s$COOH, and —$(CH_2)_p$$NH_2$, wherein s is an integer having a value of 0 to 10, and p is an integer having a value of 1 to about 10.

In certain embodiments, the linking unit comprises at least two, and more preferably at least three, of the following:

(i) at least one heteroatom selected from —NH—, —C(=O)—, —O—, —S— and —P—;

(ii) at least one heteroarylene;

(iii) at least one amino acid moiety, sugar bond, peptide bond, or amide bond; and (iv) the alkylene may be further substituted with one or more substituents selected from the group consisting of $C_1$-$C_{20}$ alkyl, $C_6$-$C_{20}$ aryl $C_1$-$C_8$ alkyl, —$(CH_2)_s$COOH, and —$(CH_2)_p$$NH_2$, wherein s is an integer having a value of 0 to 10, and p is an integer having a value of 1 to about 10.

In other embodiments, the linking group connecting each CB and Ar comprises a functional group produced through a click chemical reaction.

In alternative embodiments, the linking unit comprises a reactive functional group capable of participating in a click chemical reaction.

A click chemical reaction is a reaction that can be performed under mild conditions, and is extremely selective for functional groups that are not commonly found in biological molecules (e.g., an azide group, an acetylene group, etc.). Accordingly, this reaction can be carried out in the presence of complex triggering groups, targeting moieties, etc. Further, click chemistry has high reaction specificity. For example, the click chemical reaction between an azide group and an acetylene group proceeds selectively without interference from other functional groups present in the molecule. For example, azide-acetylene click chemistry may afford a triazole moiety in high yield.

Thus, in some embodiments, the linking group connecting each CB and Ar comprises

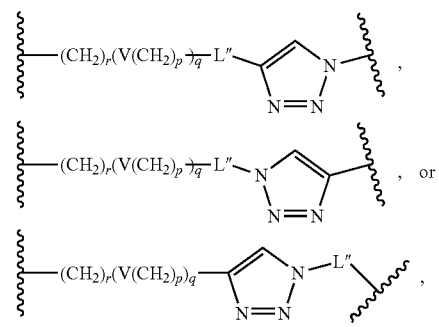

V may be a single bond, —O—, —S—, —$NR^{21}$—, —C(O)$NR^{22}$—, —$NR^{23}$C(O)—, —$NR^{24}SO_2$—, or —$SO_2NR^{25}$—, $R^{21}$ to $R^{25}$ may be each independently hydrogen, $(C_1$-$C_6)$ alkyl, $(C_1$-$C_6)$alkyl$(C_6$-$C_{20})$aryl, or $(C_1$-$C_6)$alkyl$(C_3$-$C_{20})$heteroaryl, r may be an integer having a value of 1 to about 10, p may be an integer having a value of 0 to about 10, q may be an integer having a value of 1 to about 10, and L" may be a single bond.

In other embodiments, the linking unit connecting each CB and Ar is a linking group represented by Formula (A):

$$**-L^c-W^{b1}-(CH_2)_b-W^{a3}-(P^1)_a-Y^2-W^{a2}-Y^1-W^{a1}-* \quad (A)$$

wherein:
* is the point of attachment to CB;
** is point of attachment to Ar;
$W^{a1}$, $W^{a2}$, and $W^{a3}$ are each independently —NH—, —C(=O)—, or (—CH$_2$—)$_b$;
$W^{b1}$ is an amide bond or triazolylene;
$P^1$ is a linker connecting $W^{a3}$ and $Y^2$, and is an amino acid moiety, a peptide bond, or an amide bond;
$L^c$ is alkylene;
$Y^2$ is a single bond, —W$^{a4}$—(CH$_2$)$_c$—W$^{b2}$—(CH$_2$)$_d$—W$^{a5}$—, or —W$^{a6}$—(CH$_2$)$_e$—CR$^e$R$^f$—X—;
$R^e$ is $C_1$-$C_8$ alkyl or CB—W$_{a7}$—Y$_3$—W$_{c1}$—(CH$_2$)$_f$—;
$R^f$ is B—W$^{a7}$—Y$^3$—W$^{c1}$—(CH$_2$)$_f$—;
X is —NHC(=O)—(CH$_2$)$_g$—W$^{a8}$— or —C(=O)NH—(CH$_2$)$_h$—W$^{a9}$—;
$W^{a4}$, $W^{a5}$, $W^{a6}$, $W^{a7}$, $W^{a8}$, and $W^{a9}$ are each independently —NH—, —C(=O)—, or —CH$_2$—;
$W^{b2}$ is an amide bond or triazolylene;
$W^{c1}$ is —NHC(=O)— or —C(=O)NH—;
$Y^3$ is —(CH$_2$)$_i$—(X'CH$_2$CH$_2$)$_j$—(CH$_2$)$_k$—;
X' is —O—, —S—, —NH—, or —CH$_2$—;
CB is the same as defined above;
b, c, d, e, f, g, h, i, and j are each independently an integer having a value of 1 to about 10;
k and y are each independently an integer having a value of 0 to about 10;
$Y^1$ is —(CH$_2$)$_q$—(CH$_2$CH$_2$X")$_o$— or —(CH$_2$)$_q$—(X"CH$_2$CH$_2$)$_o$—;
X" is —O—, —S—, —NH—, or —CH$_2$—; and
o and q are an integer having a value of 1 to about 10.

In some embodiments, $P^1$ comprises at least one unit represented by Formula (B) or (C):

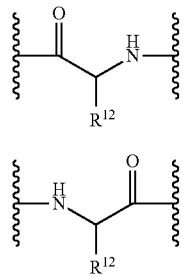

(B)

(C)

wherein:
$R^{12}$ is hydrogen, $C_1$-$C_8$-alkyl, an amino acid side chain, such as a natural amino acid side chain (e.g., H, methyl, isopropyl, isobutyl, sec-butyl, S-methyl thioether, benzyl, indole, pyrollidine, pyrroline, hydroxymethyl, tyrosyl, lysyl, imidazole, glycyl, glutamyl, carbamoylbutanoic acid, carboxamide, aspartic acid, 1-hydroxyethyl, and 2-hydroxyethyl), —(CH$_2$)$_s$COR$^{13}$ or —(CH$_2$)$_p$NR$^{14}$R$^{15}$;
$R^{13}$ is OH or —NH(CH$_2$)$_s$(X"CH$_2$CH$_2$)$_{s''}$Z;
$R^{14}$ and $R^{15}$ are each independently hydrogen or —(C(O)(CH$_2$)$_s$(X"CH$_2$CH$_2$)$_{s''}$Z)$_m$—CB;
X" is —O—, —S—, —NH—, or —CH$_2$—;
Z and CB are the same as defined above;
p is an integer having a value of 1 to about 10;

s and s" are an integer having a value of 0 to about 10;
s' is an integer having a value of 1 to about 10; and
m is an integer having a value of 0 or 1.

In some embodiments of formula (B) or (C):
$R^{12}$ is hydrogen, alkyl, an amino acid side chain, —(CH$_2$)$_s$C(O)R$^{13}$ or —(CH$_2$)$_p$NR$^{14}$R$^{15}$;
p is an integer having a value of 1 to about 10;
s is an integer having a value of 0 to about 10;
$R^{13}$ is OH or —NH(CH$_2$)$_s$(X'''CH$_2$CH$_2$)$_{s''}$Z"—(CB)$_m$;
$R^{14}$ and $R^{15}$ are each independently hydrogen or —C(O)(CH$_2$)$_s$(X'''CH$_2$CH$_2$)$_{s''}$Z"—(CB)$_m$;
s" is an integer having a value of 0 to about 10;
s' is an integer having a value of 1 to about 10;
m is an integer having a value of 0 or 1;
X''' is —O—, —S—, —NH—, or —CH$_2$—; and
Z" is a linking group connecting CB to the remainder of $R^{14}$ or $R^{15}$; or Z" is a linking group comprising a reactive group.

In some such embodiments of formula (B) or (C):
$R^{13}$ is OH or —NH(CH$_2$)$_s$(X'''CH$_2$CH$_2$)$_{s''}$Z";
$R^{14}$ and $R^{15}$ are each independently hydrogen or —C(O)(CH$_2$)$_s$(X'''CH$_2$CH$_2$)$_{s''}$Z"; and
Z" is a reactive precursor of a linking unit selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

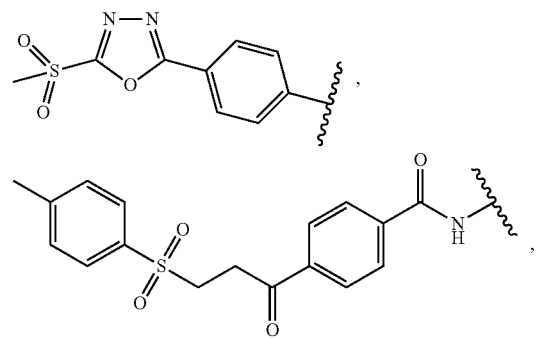

phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In other such embodiments of formula (B) or (C):
$R^{13}$ is OH or —NH(CH$_2$)$_s$(X'''CH$_2$CH$_2$)$_{s''}$Z"CB;
$R^{14}$ and $R^{15}$ are each independently hydrogen or —C(O)(CH$_2$)$_s$(X'''CH$_2$CH$_2$)$_{s''}$Z"CB; and
Z" is a linking unit connecting CB to the remainder of $R^{14}$ or $R^{15}$ formed from a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

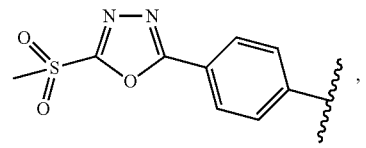

-continued

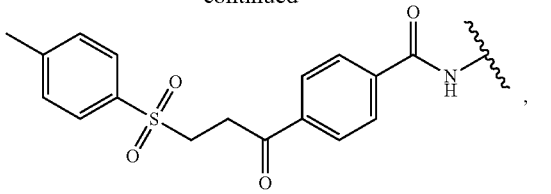

phosphonic acid (—P(=O)(OH)$_2$), ketone, $C_8$-$C_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is $C_1$-$C_{10}$-alkyl), and dihydrogen phosphate (—OP(=O)(OH)$_2$).

In some embodiments, Y$^2$ is a single bond or is selected from:

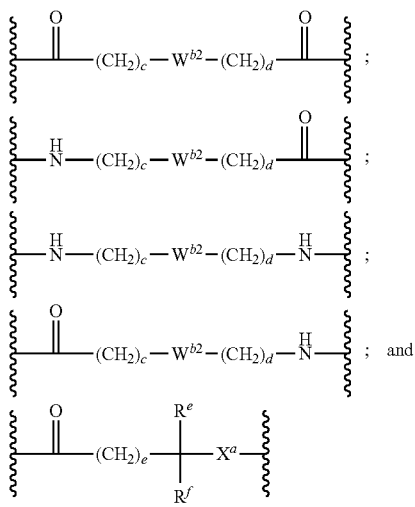

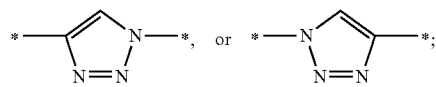

wherein:
W$^{b2}$ is —C(O)NH—, —NHC(O)—,

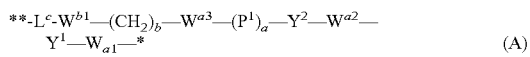

R$^e$ is $C_1$-$C_8$-alkyl or -(L$^{1'}$-Z—)$_m$CB;
R$^f$ is B—W$_{b2'}$—(CH$_2$)$_i$—(X"CH$_2$CH$_2$)$_j$—NH—C(=O)—(CH$_2$)$_f$—;
X$^a$ is —NHC(=O)—(CH$_2$)$_g$—NH— or —C(O)NH—(CH$_2$)$_h$—NH—;
W$^{b2'}$ is —C(O)NH— or —NHC(=O)—;
c, d, e, f, g, h, i, and j are each independently an integer having a value of 1 to about 10;
X" is —O—, —S—, —NH—, or —CH$_2$—; and
L$^{1'}$, Z, m, and B are the same as defined above.

In certain embodiments, the linking unit connecting each CB and Ar is a linking group comprising (CH$_2$)$_b$, L$^c$, (P$^1$)$_a$, W$^{a1}$, W$^{a2}$, W$^{a3}$, Y$^1$, and Y$^2$ groups connected to each other by covalent bonds, wherein:
W$^{a1}$, W$^{a2}$, and W$^{a3}$ are each independently —NH—, —C(O)—, or —CH$_2$—;
W$^{b1}$ is an amide bond or triazolylene;
P$^1$ is an amide bond, an amino acid residue, or a peptide;
L$^c$ is alkylene;
Y$^1$ is —(CH$_2$)$_q$—(CH$_2$CH$_2$X")$_o$— or —(CH$_2$)$_q$—(X"CH$_2$CH$_2$X")$_o$—;
X" is —O—, —S—, —NH— or —CH$_2$—;

Y$^2$ is a single bond or a group selected from:

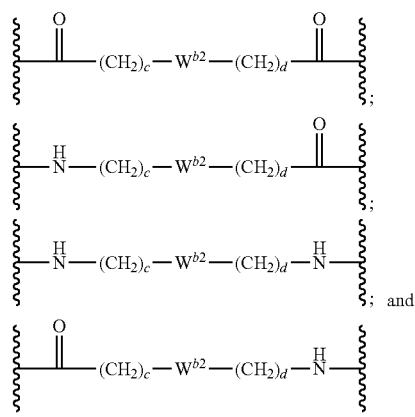

W$^{b2}$ is an amide bond or triazolylene;
a is 0 to 10;
b, c, and d are each independently an integer having a value of 1 to about 10; and
o and q are each independently an integer having a value of 1 to about 10.

In some embodiments, R$^{12}$ is a natural amino acid side chain. In other embodiments, R$^{12}$ is non-natural amino acid side chain.

In some embodiments, the linking unit connecting each CB and Ar is a linking group represented by Formula (A):

$$**\text{-L}^c\text{-W}^{b1}—(CH_2)_b—W^{a3}—(P^1)_a—Y^2—W^{a2}—Y^1—W_{a1}—*$$ (A)

wherein:
* is the point of attachment to CB; and
** is point of attachment to Ar.
In some such embodiments, P$^1$ is

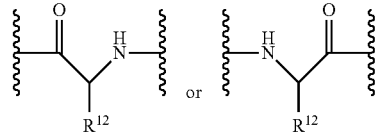

wherein:
R$^{12}$ is hydrogen, alkyl, an amino acid side chain, —(CH$_2$)$_s$COOH or —(CH$_2$)$_p$NH$_2$;
p is an integer having a value of 1 to about 10; and
s and s" are each independently an integer having a value of 0 to about 10.

In some embodiments P$^1$ is

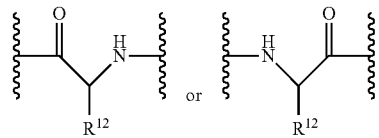

wherein:
R$^{12}$ is hydrogen, alkyl, an amino acid side chain, —(CH$_2$)$_s$C(O)R$^{13}$ or —(CH$_2$)$_p$NR$^{14}$R$^{15}$;
p is an integer having a value of 1 to about 10;
s is an integer having a value of 0 to about 10;
R$^{13}$ is OH or —NH(CH$_2$)$_s$(X'"CH$_2$CH$_2$)$_{s"}$Z"—(CB)$_m$;
R$^{14}$ and R$^{15}$ are each independently hydrogen or —C(O)(CH$_2$)$_s$(X'"CH$_2$CH$_2$)$_{s"}$Z"—(CB)$_m$;

s" is an integer having a value of 0 to about 10;
s' is an integer having a value of 1 to about 10;
m is an integer having a value of 0 or 1;
X''' is —O—, —S—, —NH—, or —CH$_2$—; and
Z" is a linking group connecting CB to the remainder of R$^{14}$ or R$^{15}$; or Z" is a linking group comprising a reactive group.

In some such embodiments of P$^1$:
R$^{13}$ is OH or —NH(CH$_2$)$_s$(X'''CH$_2$CH$_2$)$_{s''}$Z";
R$^{14}$ and R$^{15}$ are each independently hydrogen or —C(O)(CH$_2$)$_s$(X'''CH$_2$CH$_2$)$_{s''}$Z"; and
Z" is a reactive precursor of a linking unit selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

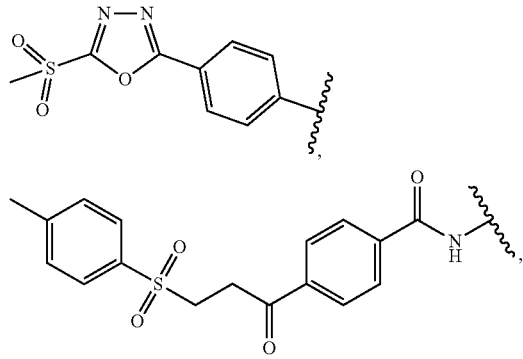

phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In other such embodiments of P$^1$:
R$^{13}$ is OH or —NH(CH$_2$)$_s$(X'''CH$_2$CH$_2$)$_{s''}$Z"CB;
R$^{14}$ and R$^{15}$ are each independently hydrogen or —C(O)(CH$_2$)$_s$(X'''CH$_2$CH$_2$)$_{s''}$Z"CB; and
Z" is a linking unit connecting CB to the remainder of R$^{14}$ or R$^{15}$ formed from a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

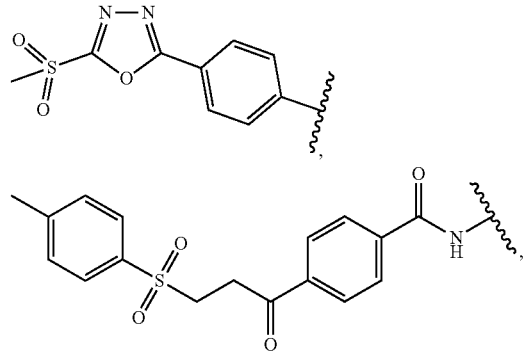

phosphonic acid (—P(=O)(OH)$_2$), ketone, C$_8$-C$_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is C$_1$-C$_{10}$-alkyl), and dihydrogen phosphate (—OP(=O)(OH)$_2$).

In alternative embodiments, the linking unit connecting CB and Ar is a linking group represented by Formula (IIIb), (IIIc), (IIId), (IIIe), (IIIf), (IIIh), (IIIh), or (IIIj):

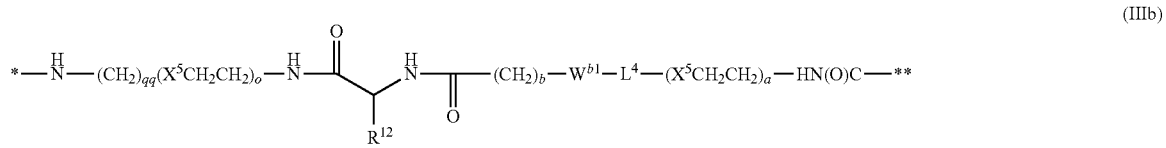
(IIIb)

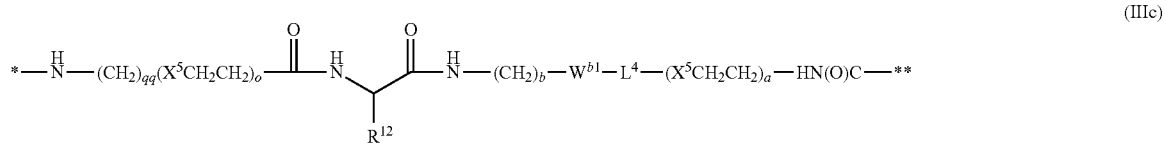
(IIIc)

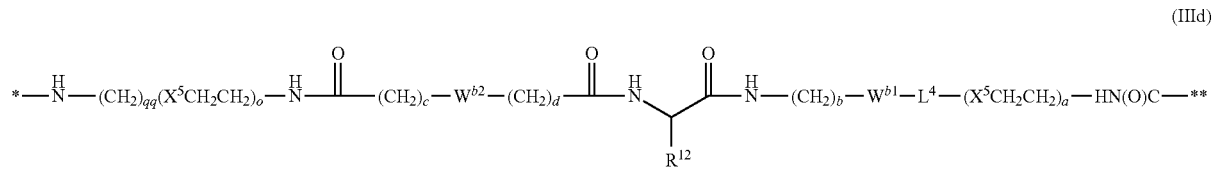
(IIId)

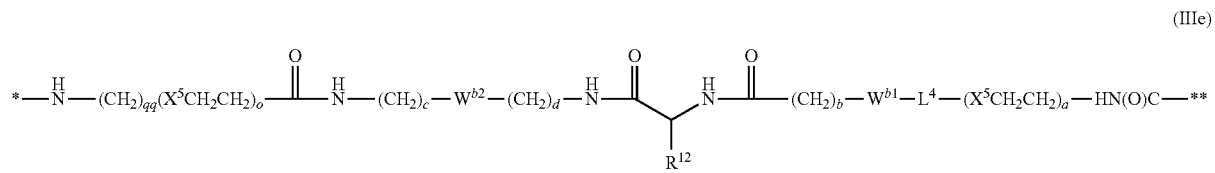
(IIIe)

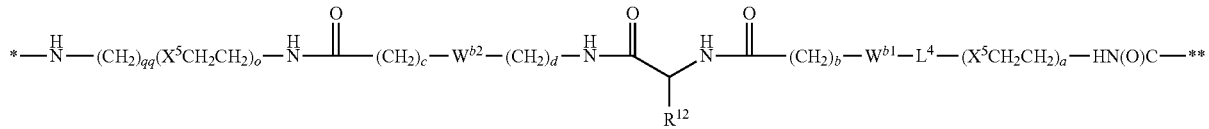

(IIIf)

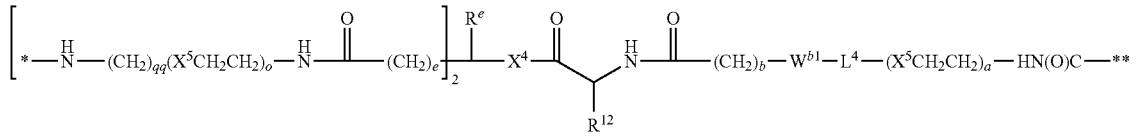

(IIIg)

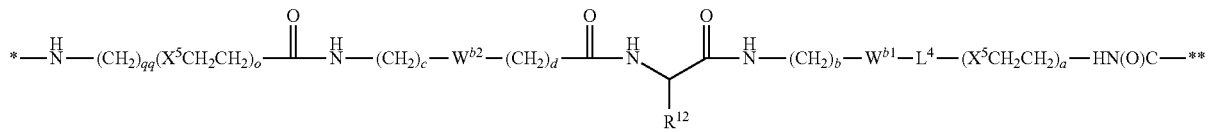

(IIIh)

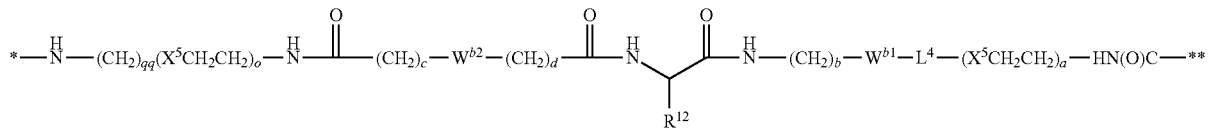

(IIIj)

wherein:

$R^e$ is alkyl;

$X^5$ is —O—, —S—, —NH—, or —CH$_2$—;

$W^{b1}$ and $W^{b2}$ are each independently —C(O)NH—, —NHC(O)—,

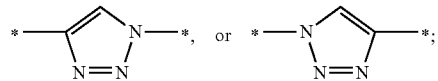

$R^{12}$ is hydrogen, alkyl, an amino acid side chain, —(CH$_2$)$_s$C(O)R$^{13}$ or —(CH$_2$)$_p$NR$^{14}$R$^{15}$;

$R^{13}$ is OH or —NH(CH$_2$)$_s$(X$^4$CH$_2$CH$_2$)$_{s''}$Z''—(CB)$_m$;

$R^{14}$ and $R^{15}$ are each independently hydrogen or —C(O)(CH$_2$)$_s$(X'''CH$_2$CH$_2$)$_{s''}$Z''—(CB)$_m$;

s and s'' are each independently an integer having a value of 0 to about 10;

m is an integer having a value of 0 or 1;

$X^4$ and $X^5$ are each independently —O—, —S—, —NH—, or —CH$_2$—; and b, c, d, e, g, h, o, and q are each independently an integer having a value of 1 to about 10.

In some such embodiments of Formula (IIIb), (IIIc), (IIId), (IIIe), (IIIf), (IIIh), (IIIh), or (IIIj):

$R^{13}$ is OH or —NH(CH$_2$)$_s$(X'''CH$_2$CH$_2$)$_{s''}$Z''CB;

$R^{14}$ and $R^{15}$ are each independently hydrogen or —C(O)(CH$_2$)$_s$(X'''CH$_2$CH$_2$)$_{s''}$Z''CB; and Z'' is a linking unit connecting CB to the remainder of $R^{14}$ or $R^{15}$ formed from a precursor selected from isocyanide, isothiocyanide, 2-pyridyl disulfide, haloacetamide (—NHC(O)CH$_2$-hal), maleimide, diene, alkene, halide, tosylate (TsO$^-$), aldehyde, sulfonate (R—SO$_3^-$),

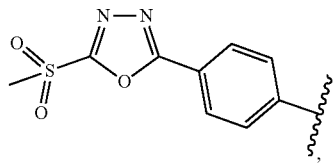

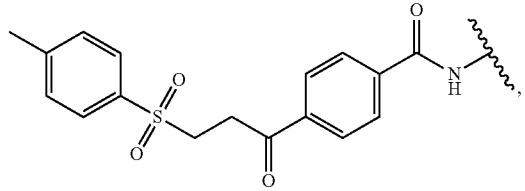

phosphonic acid (—P(=O)(OH)$_2$), ketone, $C_8$-$C_{10}$ cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡C—R$^a$, wherein R$^a$ is $C_1$-$C_{10}$-alkyl), and dihydrogen phosphate (—OP(=O)(OH)$_2$).

Targeting Moieties

The compounds and conjugates of the present invention can further comprise a ligand or targeting moiety, CB. In some embodiments, the ligand or targeting moiety is any molecular recognition element, which can undergo a specific interaction with at least one other molecular through, e.g., noncovalent bonding such as hydrogen bonding, metal coordination, hydrophobic forces, van der Waals forces, π-π interactions, halogen bonding, electrostatic, and/or electromagnetic effects. In certain embodiments, CB is selected from a nanoparticle, an immunoglobulin, a nucleic acid, a protein, an oligopeptide, a polypeptide, an antibody, a fragment of an antigenic polypeptide, a repebody, and the like.

The compounds and conjugates of the present invention may comprise one or more targeting moieties. That is, the variable cb may have an integer value selected from 1, 2, 3, 4, 5, 1-10, or 1-20.

In some embodiments, CB comprises two or more independently selected natural amino acids or non-natural amino acids conjugated by covalent bonds (e.g., peptide bonds), and the peptide may include 2, 3, 4, 5, 6, 7, 8, 9, 10, 11, 12, 13, 14, 15, 16, 17, 18, 19, 20, or more natural amino acids or non-natural amino acids that are conjugated by peptide bonds. In some embodiments, the ligand comprises shorter amino acid sequences (e.g., fragments of natural proteins or synthetic polypeptide fragments) as well as full-length proteins (e.g., pre-engineered proteins).

In some embodiments, CB is selected from an antibody, a hormone, a drug, an antibody analogue (e.g., non-IgG), protein, an oligopeptide, a polypeptide, etc., which bind to a receptor. In certain embodiments, CB selectively targets the drug in a specific organ, tissue, or cell. In other embodiments, CB specifically binds to a receptor over-expressed in cancer cells as compared to normal cells, and may be classified into a monoclonal antibody (mAb) or an antibody fragment and a low-molecular non-antibody. Preferably, CB is selected from peptides, tumor cell-specific peptides, tumor cell-specific aptamers, tumor cell-specific carbohydrates, tumor cell-specific monoclonal antibodies, polyclonal antibodies, and antibody fragments that are identified in a library screen.

Exemplary ligands or targeting moieties include, but are not limited to, carnitine, inositol, lipoic acid, pyridoxal, ascorbic acid, niacin, pantothenic acid, folic acid, riboflavin, thiamine, biotin, vitamin $B_{12}$, other water-soluble vitamins (vitamin B), fat-soluble vitamins (vitamin A, D, E, K), RGD (Arg-Gly-Asp), NGR (Asn-Gly-Arg), transferein, VIP (vasoactive intestinal peptide) receptor, APRPG (Ala-Pro-Arg-Pro-Gly) peptide, TRX-20 (thioredoxin-20), integrin, nucleolin, aminopeptidase N (CD13), endoglin, vascular epithelial growth factor receptor, low density lipoprotein receptor, transferrin receptor, somatostatin receptor, bombesin, neuropeptide Y, luteinizing hormone releasing hormone receptor, folic acid receptor, epidermal growth factor receptor, transforming growth factor, fibroblast growth factor receptor, asialoglycoprotein receptor, galectin-3 receptor, E-selectin receptor, hyaluronic acid receptor, prostate-specific membrane antigen (PSMA), cholecystokinin A receptor, cholecystokinin B receptor, discoidin domain receptor, mucin receptor, opioid receptor, plasminogen receptor, bradykinin receptor, insulin receptor, insulin-like growth factor receptor, angiotensin AT1 receptor, angiotensin AT2 receptor, granulocyte macrophage colony stimulating factor receptor (GM-CSF receptor), galactosamine receptor, sigma-2 receptor, delta-like 3 (DLL-3), aminopeptidase P, melanotransferrin, leptin, tetanus toxin Tet1, tetanus toxin G23, RVG (Rabies Virus Glycoprotein) peptide, HER2 (human epidermal growth factor receptor 2), GPNMB (glycoprotein non-metastatic b), Ley, CA6, CanAng, SLC44A4 (Solute carrier family 44 member 4), CEACAM5 (Carcinoembryonic antigen-related cell adhesion molecule 5), Nectin-4, Carbonic Anhydrase 9, TNNB2, 5T4, CD30, CD37, CD74, CD70, PMEL17, EphA2 (EphrinA2 receptor), Trop-2, SC-16, Tissue factor, ENPP-3 (AGS-16), SLITRK6 (SLIT and NTRK like family member 6), CD27, Lewis Y antigen, LIV1, GPR161 (G Protein-Coupled Receptor 161), PBR (peripheral-type benzodiazeoine receptor), MERTK (Mer receptor tyrosine kinase) receptor, CD71, LLT1 (Lectin-like transcript 1 or CLED2D), interleukin-22 receptor, sigma 1 receptor, peroxisome proliferator-activated receptor, DLL3, C4.4a, cKIT, EphrinA, CTLA4 (Cytotoxic T-Lymphocyte Associated Protein 4), FGFR2b (fibroblast growth factor receptor 2b), N-acetylcholine receptor, gonadotropin releasing hormone receptor, gastrin-releasing peptide receptor, bone morphogenetic protein receptor-type 1B (BMPR1B), E16 (LAT1, SLC7A5), STEAP1 (six transmembrane epithelial antigen of prostate), 0772P (CA125, MUC16), MPF (MSLN, mesothelin), Napi3b (SLC34A2), Sema5b (semaphorin 5b), ETBR (Endothelin type B receptor), MSG783 (RNF124), STEAP2 (six transmembrane epithelial antigen of prostate 2), TrpM4 (transient receptor potential cation 5 channel, subfamily M, member 4), CRIPTO (teratocarcinoma-derived growth factor), CD21, CD79b, FcRH2 (IFGP4), HER2 (ErbB2), NCA (CEACM6), MDP (DPEP1), IL20R-alpha (IN20Ra), Brevican (BCAN), EphB2R, ASLG659 (B7h), CD276, PSCA (prostate stem cell antigen precursor), GEDA, BAFF-R (BR3), CD22 (BL-CAM), CD79a, CXCR5, HLA-DOB, P2X5, CD72, LY64, FcRH1, IRTA2, TENB2, SSTR2, SSTR5, SSTR1, SSTR3, SSTR4, ITGAV (Integrin, alpha 5), ITGB6 (Integrin, beta 6), MET, MUC1, EGFRvIII, CD33, CD19, IL2RA (interleukin 2 receptor, alpha), AXL, BCMA, CTA (cancer tetis antigens), CD174, CLEC14A, GPR78, CD25, CD32, LGR5 (GPR49), CD133 (Prominin), ASG5, ENPP3 (ectonucleotide Pyrophosphatase/Phosphodiesterase 3), PRR4 (proline-rich protein 4), GCC (guanylate cyclase 2C), Liv-1 (SLC39A6), CD56, CanAg, TIM-1, RG-1, B7-H4, PTK7, CD138, Claudins, Her3 (ErbB3), RON (MST1R), CD20, TNC (Tenascin C), FAP, DKK-1, CD52, CS1 (SLAMF7), Annexin A1, V-CAM, gp100, MART-1, MAGE-1 (melanoma antigen-encoding gene-1), MAGE-3 (melanoma-associated antigen 3), BAGE, GAGE-1, MUM-1 (multiple myeloma oncogene 1), CDK4, TRP-1 (gp75), TAG-72 (tumor-associated glycoprotein-72), ganglioside GD2, GD3, GM2, GM3, VEP8, VEP9, Myl, VIM-D5, D156-22, OX40, RNAK, PD-L1, TNFR1, TNFR2, etc.

Targets

In some embodiments, the target or targets of the molecular recognition element are specifically associated with one or more particular cell or tissue types. In some embodiments, targets are specifically associated with one or more particular disease states. In some embodiments, targets are specifically associated with one or more particular developmental stages. For example, a cell type specific marker is typically expressed at levels at least 2 fold greater in that cell type than in a reference population of cells. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1,000 fold greater than its average expression in a reference population. Detection or measurement of a cell type specific marker may make it possible to distinguish the cell type or types of interest from cells of many, most, or all other types. In some embodiments, a target can comprise a protein, a carbohydrate, a lipid, and/or a nucleic acid, as described herein.

In some embodiments, a substance is considered to be "targeted" if it specifically binds to a targeting moiety, such as a nucleic acid targeting moiety. In some embodiments, a targeting moiety, such as a nucleic acid targeting moiety, specifically binds to a target under stringent conditions.

In certain embodiments, the conjugates and compounds described herein comprise a targeting moiety that specifically binds to one or more targets (e.g., antigens) associated with an organ, tissue, cell, extracellular matrix component, and/or intracellular compartment. In some embodiments, the conjugates and compounds described herein comprise a targeting moiety that specifically binds to targets associated with a particular organ or organ system. In some embodiments, the conjugates and compounds described herein comprise a targeting moiety that specifically binds to one or more intracellular targets (e.g., organelle, intracellular protein). In some embodiments, the conjugates and compounds described herein comprise a targeting moiety which specifically binds to targets associated with diseased organs, tissues, cells, extracellular matrix components, and/or intracellular compartments. In some embodiments, the conjugates and compounds described herein comprise a targeting moiety that specifically binds to targets associated with particular cell types (e.g., endothelial cells, cancer cells, malignant cells, prostate cancer cells, etc.).

In some embodiments, the conjugates and compounds described herein comprise a targeting moiety that binds to a target that is specific for one or more particular tissue types (e.g., liver tissue vs. prostate tissue). In some embodiments, the conjugates and compounds described herein comprise a targeting moiety that binds to a target that is specific for one or more particular cell types (e.g., T cells vs. B cells). In some embodiments, the conjugates and compounds described herein comprise a targeting moiety that binds to a target that is specific for one or more particular disease states (e.g., tumor cells vs. healthy cells). In some embodiments, the conjugates and compounds described herein comprise a targeting moiety that binds to a target that is specific for one or more particular developmental stages (e.g., stem cells vs. differentiated cells).

In some embodiments, a target may be a marker that is exclusively or primarily associated with one or a few cell types, with one or a few diseases, and/or with one or a few developmental stages. A cell type specific marker is typically expressed at levels at least 2 fold greater in that cell type than in a reference population of cells which may consist, for example, of a mixture containing cells from a plurality (e.g., 5-10 or more) of different tissues or organs in approximately equal amounts. In some embodiments, the cell type specific marker is present at levels at least 3 fold, at least 4 fold, at least 5 fold, at least 6 fold, at least 7 fold, at least 8 fold, at least 9 fold, at least 10 fold, at least 50 fold, at least 100 fold, or at least 1000 fold greater than its average expression in a reference population. Detection or measurement of a cell type specific marker may make it possible to distinguish the cell type or types of interest from cells of many, most, or all other types.

In some embodiments, a target comprises a protein, a carbohydrate, a lipid, and/or a nucleic acid. In some embodiments, a target comprises a protein and/or characteristic portion thereof, such as a tumor marker, integrin, cell surface receptor, transmembrane protein, intercellular protein, ion channel, membrane transporter protein, enzyme, antibody, chimeric protein, glycoprotein, etc. In some embodiments, a target comprises a carbohydrate and/or characteristic portion thereof, such as a glycoprotein, sugar (e.g., monosaccharide, disaccharide, polysaccharide), glycocalyx (i.e., the carbohydrate-rich peripheral zone on the outside surface of most eukaryotic cells), etc. In some embodiments, a target comprises a lipid and/or characteristic portion thereof, such as an oil, fatty acid, glyceride, hormone, steroid (e.g., cholesterol, bile acid), vitamin (e.g., vitamin E), phospholipid, sphingolipid, lipoprotein, etc. In some embodiments, a target comprises a nucleic acid and/or characteristic portion thereof, such as a DNA nucleic acid; RNA nucleic acid; modified DNA nucleic acid; modified RNA nucleic acid; nucleic acid that includes any combination of DNA, RNA, modified DNA, and modified RNA.

Numerous markers are known in the art. Typical markers include cell surface proteins, e.g., receptors. Exemplary receptors include, but are not limited to, the transferrin receptor; LDL receptor; growth factor receptors such as epidermal growth factor receptor family members (e.g., EGFR, Her2, Her3, Her4) or vascular endothelial growth factor receptors, cytokine receptors, cell adhesion molecules, integrins, selectins, and CD molecules. The marker can be a molecule that is present exclusively or in higher amounts on a malignant cell, e.g., a tumor antigen.

Antibody-Drug Conjugates (ADCs) In some embodiments, CB is an antibody, and Q is a drug. Accordingly, the compounds and conjugates disclosed herein may be used to conjugate an antibody to a drug moiety to form an antibody-drug conjugate (ADC). Antibody-drug conjugates (ADCs) may increase therapeutic efficacy in treating disease, e.g., cancer, due to the ability of the ADC to selectively deliver one or more drug moiety(s) to target tissues, such as a tumor-associated antigen. Thus, in certain embodiments, the invention provides ADCs for therapeutic use, e.g., treatment of cancer.

ADCs of the invention comprise an antibody linked to one or more drug moieties. The specificity of the ADC is defined by the specificity of the antibody. In one embodiment, an antibody is linked to one or more cytotoxic drug(s), which is delivered internally to a cancer cell.

Examples of drugs that may be used in the ADC of the invention are provided below. The terms "drug", "agent", and "drug moiety" are used interchangeably herein. The terms "linked" and "conjugated" are also used interchangeably herein and indicate that the antibody and moiety are covalently linked.

In certain aspects, the present disclosure is directed to ADCs, compositions comprising ADCs, methods of treating, and methods of formulating ADC compositions. ADCs comprise an antibody, or an antibody fragment, conjugated to a cytotoxic compound. In some embodiments, the cytotoxic compound is conjugated to an antibody via a linker. In other embodiments, the cytotoxic compound is linked directly to the antibody. The types of antibodies, linkers, and cytotoxic compounds encompassed by this disclosure are described below.

In some embodiments, the ADC has the following formula (Formula (III)):

(D-L)$_{dl}$-LG-(CB)$_{cb}$        (III)

or a pharmaceutically acceptable salt thereof,
wherein:
LG is a linking group;
CB is a cell-binding agent;
cb and dl are each independently integers having a value of 1 to about 20, preferably from 1 to about 10; and
each D-L independently is a group having the structure of a compound of Formula (I) or (II).

Antibodies

The antibody of an ADC may be any antibody that binds, typically but not necessarily specifically, an antigen expressed on the surface of a target cell of interest. The antigen need not, but in some embodiments, is capable of internalizing an ADC bound thereto into the cell. Target cells of interest may include cells where induction of apoptosis is desirable. Target antigens may be any protein, glycoprotein, polysaccharide, lipoprotein, etc. expressed on the target cell of interest, but will typically be proteins that are either uniquely expressed on the target cell and not on normal or healthy cells, or that are over-expressed on the target cell as compared to normal or healthy cells, such that the ADCs selectively target specific cells of interest, such as, for example, tumor cells. As will be appreciated by skilled artisans, the specific antigen, and hence antibody, selected will depend upon the identity of the desired target cell of interest. In specific embodiments, the antibody of the ADC is an antibody suitable for administration to humans.

Antibodies (Abs) and immunoglobulins (Igs) are glycoproteins having the same structural characteristics. While antibodies exhibit binding specificity to a specific target, immunoglobulins include both antibodies and other antibody-like molecules which lack target specificity. Native antibodies and immunoglobulins are usually heterotetrameric glycoproteins of about 150,000 daltons, composed of two identical light (L) chains and two identical heavy (H) chains. Each heavy chain has at one end a variable domain (VH) followed by a number of constant domains. Each light chain has a variable domain at one end (VL) and a constant domain at its other end.

References to "VH" refer to the variable region of an immunoglobulin heavy chain of an antibody, including the heavy chain of an Fv, scFv, or Fab. References to "VL" refer to the variable region of an immunoglobulin light chain, including the light chain of an Fv, scFv, dsFv or Fab.

The term "antibody" herein is used in the broadest sense and refers to an immunoglobulin molecule that specifically binds to, or is immunologically reactive with, a particular antigen, and includes polyclonal, monoclonal, genetically engineered and otherwise modified forms of antibodies, including but not limited to murine, chimeric antibodies, humanized antibodies, heteroconjugate antibodies (e.g., bispecific antibodies, diabodies, triabodies, and tetrabodies), and antigen binding fragments of antibodies, including e.g., Fab', F(ab')2, Fab, Fv, rIgG, and scFv fragments. The term "scFv" refers to a single chain Fv antibody in which the variable domains of the heavy chain and the light chain from a traditional antibody have been joined to form one chain.

Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "antibody fragment" refers to a portion of a full-length antibody, generally the target binding or variable region. Examples of antibody fragments include Fab, Fab', F(ab')2 and Fv fragments. An "Fv" fragment is the minimum antibody fragment that contains a complete target recognition and binding site. This region consists of a dimer of one heavy and one light chain variable domain in a tight, non-covalent association (VH-VL dimer). It is in this configuration that the three CDRs of each variable domain interact to define a target binding site on the surface of the VH-VL dimer. Often, the six CDRs confer target binding specificity to the antibody. However, in some instances even a single variable domain (or half of an Fv comprising only three CDRs specific for a target) can have the ability to recognize and bind target. "Single-chain Fv" or "scFv" antibody fragments comprise the VH and VL domains of an antibody in a single polypeptide chain. Generally, the Fv polypeptide further comprises a polypeptide linker between the VH and VL domains which enables the scFv to form the desired structure for target binding. "Single domain antibodies" are composed of a single VH or VL domains which exhibit sufficient affinity to the target. In a specific embodiment, the single domain antibody is a camelized antibody (see, e.g., Riechmann, 1999, Journal of Immunological Methods 231:25-38).

The Fab fragment contains the constant domain of the light chain and the first constant domain (CH1) of the heavy chain. Fab' fragments differ from Fab fragments by the addition of a few residues at the carboxyl terminus of the heavy chain CH1 domain including one or more cysteines from the antibody hinge region. F(ab') fragments are produced by cleavage of the disulfide bond at the hinge cysteines of the F(ab')2 pepsin digestion product. Additional chemical couplings of antibody fragments are known to those of ordinary skill in the art.

Both the light chain and the heavy chain variable domains have complementarity determining regions (CDRs), also known as hypervariable regions. The more highly conserved portions of variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The CDRs in each chain are held together in close proximity by the FR regions and, with the CDRs from the other chain, contribute to the formation of the target binding site of antibodies (see Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al., unless otherwise indicated.

In certain embodiments, the antibodies of the ADCs of the present disclosure are monoclonal antibodies. The term "monoclonal antibody" (mAb) refers to an antibody that is derived from a single copy or clone, including e.g., any eukaryotic, prokaryotic, or phage clone, and not the method by which it is produced. Preferably, a monoclonal antibody of the disclosure exists in a homogeneous or substantially homogeneous population. Monoclonal antibody includes both intact molecules, as well as, antibody fragments (such as, for example, Fab and F(ab')2 fragments), which are capable of specifically binding to a protein. Fab and F(ab')2 fragments lack the Fc fragment of intact antibody, clear more rapidly from the circulation of the animal, and may have less non-specific tissue binding than an intact antibody (Wahl et al., 1983, *J. Nucl. Med* 24:316). Monoclonal antibodies useful with the present disclosure can be prepared using a wide variety of techniques known in the art including the use of hybridoma, recombinant, and phage display technologies, or a combination thereof. The antibodies of the disclosure include chimeric, primatized, humanized, or human antibodies.

While in most instances antibodies are composed of only the genetically-encoded amino acids, in some embodiments non-encoded amino acids may be incorporated at specific. Examples of non-encoded amino acids that may be incorporated into antibodies for use in controlling stoichiometry and attachment location, as well as methods for making such modified antibodies are discussed in Tian et al., 2014, *Proc Nat'l Acad Sci USA* 111(5):1766-1771 and Axup et al., 2012, *Proc Nat'l Acad Sci USA* 109(40):16101-16106 the entire contents of which are incorporated herein by reference.

In certain embodiments, the antibody of the ADCs described herein is a chimeric antibody. The term "chimeric" antibody as used herein refers to an antibody having variable sequences derived from a non-human immunoglobulin, such as rat or mouse antibody, and human immunoglobulin constant regions, typically chosen from a human immunoglobulin template. Methods for producing chimeric antibodies are known in the art. See, e.g., Morrison, 1985, *Science* 229(4719):1202-7; Oi et al., 1986, *BioTechniques* 4:214-221; Gillies et al., 1985, *J. Immunol. Methods* 125:191-202; U.S. Pat. Nos. 5,807,715; 4,816,567; and 4,816,397, which are incorporated herein by reference in their entireties.

In certain embodiments, the antibody of the ADCs described herein is a humanized antibody. "Humanized" forms of non-human (e.g., murine) antibodies are chimeric immunoglobulins, immunoglobulin chains or fragments thereof (such as Fv, Fab, Fab', F(ab')2 or other target-binding subdomains of antibodies), which contain minimal sequences derived from non-human immunoglobulin. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody can also comprise at least a portion of an immunoglobulin constant region (Fc), typically that of a human immunoglobulin consensus sequence. Methods of antibody humanization are known in the art. See, e.g., Riechmann et al., 1988, *Nature* 332:323-7; U.S. Pat. Nos. 5,530,101; 5,585,089; 5,693,761; 5,693,762; and 6,180,370 to Queen et al.; EP239400; PCT publication WO 91/09967; U.S. Pat. No. 5,225,539; EP592106; EP519596; Padlan, 1991, *Mol. Immunol.*, 28:489-498; Studnicka et al., 1994, *Prot. Eng.* 7:805-814; Roguska et al., 1994, *Proc. Natl. Acad Sci. USA* 91:969-973; and U.S. Pat. No. 5,565,332, all of which are hereby incorporated by reference in their entireties.

In certain embodiments, the antibody of the ADCs described herein is a human antibody. Completely "human" antibodies can be desirable for therapeutic treatment of human patients. As used herein, "human antibodies" include antibodies having the amino acid sequence of a human immunoglobulin and include antibodies isolated from human immunoglobulin libraries or from animals transgenic for one or more human immunoglobulin and that do not express endogenous immunoglobulins. Human antibodies can be made by a variety of methods known in the art including phage display methods using antibody libraries derived from human immunoglobulin sequences. See U.S. Pat. Nos. 4,444,887, 4,716,111, 6,114,598, 6,207,418, 6,235,883, 7,227,002, 8,809,151 and U.S. Published Application No. 2013/189218, the contents of which are incorporated herein by reference in their entireties. Human antibodies can also be produced using transgenic mice which are incapable of expressing functional endogenous immunoglobulins, but which can express human immunoglobulin genes. See, e.g., U.S. Pat. Nos. 5,413,923; 5,625,126; 5,633,425; 5,569,825; 5,661,016; 5,545,806; 5,814,318; 5,885,793; 5,916,771; 5,939,598; 7,723,270; 8,809,051 and U.S. Published Application No. 2013/117871, which are incorporated by reference herein in their entireties. In addition, companies such as Medarex (Princeton, N.J.), Astellas Pharma (Deerfield, Ill.), and Regeneron (Tarrytown, N.Y.) can be engaged to provide human antibodies directed against a selected antigen using technology similar to that described above. Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1988, *Biotechnology* 12:899-903).

In certain embodiments, the antibody of the ADCs described herein is a primatized antibody. The term "primatized antibody" refers to an antibody comprising monkey variable regions and human constant regions. Methods for producing primatized antibodies are known in the art. See, e.g., U.S. Pat. Nos. 5,658,570; 5,681,722; and 5,693,780, which are incorporated herein by reference in their entireties.

In certain embodiments, the antibody of the ADCs described herein is a bispecific antibody or a dual variable domain antibody (DVD). Bispecific and DVD antibodies are monoclonal, often human or humanized, antibodies that have binding specificities for at least two different antigens. DVDs are described, for example, in U.S. Pat. No. 7,612,181, the disclosure of which is incorporated herein by reference.

In certain embodiments, the antibody of the ADCs described herein is a derivatized antibody. For example, but not by way of limitation, derivatized antibodies are typically modified by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to, specific chemical cleavage, acetylation, formylation, metabolic synthesis of tunicamycin, etc. Additionally, the derivative can contain one or more non-natural amino acids, e.g., using ambrx technology (see, e.g., Wolfson, 2006, *Chem. Biol.* 13(10):1011-2).

In certain embodiments, the antibody of the ADCs described herein has a sequence that has been modified to alter at least one constant region-mediated biological effector function relative to the corresponding wild type sequence. For example, in some embodiments, the antibody can be modified to reduce at least one constant region-mediated biological effector function relative to an unmodified antibody, e.g., reduced binding to the Fc receptor (FcR). FcR binding can be reduced by mutating the immunoglobulin constant region segment of the antibody at particular regions necessary for FcR interactions (see, e.g., Canfield and Morrison, 1991, *J. Exp. Med* 173:1483-1491; and Lund et al., 1991, *J. Immunol.* 147:2657-2662).

In certain embodiments, the antibody of the ADCs described herein is modified to acquire or improve at least one constant region-mediated biological effector function relative to an unmodified antibody, e.g., to enhance FcγR interactions (see, e.g., US 2006/0134709). For example, an antibody with a constant region that binds FcγRIIA, FcγRIIB and/or FcγRIIIA with greater affinity than the corresponding wild type constant region can be produced according to the methods described herein.

In certain specific embodiments, the antibody of the ADCs described herein is an antibody that binds tumor cells, such as an antibody against a cell surface receptor or a tumor-associated antigen (TAA). In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to the surface of the no-cancerous cells. Such cell surface receptor and tumor-associated antigens are known in the art, and can prepared for use in generating antibodies using methods and information which are well known in the art.

Exemplary Cell Surface Receptors and TAAs

Examples of cell surface receptor and TAAs to which the antibody of the ADCs described herein may be targeted include, but are not limited to, the various receptors and TAAs listed below in Table 1. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to the listed cell surface receptors and TAAs are available in public databases such as GenBank.

TABLE I 4-1BB
5AC
5T4
Alpha-fetoprtein
angiopoietin 2
ASLG659
TCL1
BMPR1B
Brevican (BCAN, BEHAB)
C2-42 antigen
C5
CA-125
CA-125 (imitation)
CA-IX (Carbonic anhydrase 9)
CCR4
CD140a
CD152
CD19
CD20
CD200
CD21 (C3DR) 1)
CD22 (B-cell receptor CD22-B isoform)
CD221
CD23 (gE receptor)
CD28
CD30 (TNFRSF8)
CD33
CD37
CD38 (cyclic ADP ribose hydrolase)
CD4
CD40
CD44 v6
CD51
CD52
CD56
CD70
CD72 (Lyb-2, B-cell differentiation antigen CD72)
CD74
CD79a (CD79A, CD79α, immunoglobulin-associated alpha) Genbank accession No. NP_001774.10)
CD79b (CD79B, CD79β, B29)
CD80

TABLE I-continued

CEA
CEA-related antigen
ch4D5
CLDN18.2
CRIPTO (CR, CR1, CRGF, TDGF1 teratocarcinoma-derived growth factor)
CTLA-4
CXCR5
DLL4
DR5
E16 (LAT1, SLC7A5) EGFL7
EGFR
EpCAM
EphB2R (DRT, ERK, Hek5, EPHT3, Tyro5)
Episialin
ERBB3
ETBR (Endothelin type B receptor)
FCRH1 (Fc receptor-like protein 1)
FcRH2 (IFGP4, IRTA4, SPAP1, SPAP1B, SPAP1C, SH2 domain containing phosphatase anchor protein
Fibronectin extra domain-B
Folate receptor 1
Frizzled receptor
GD2
GD3 ganglioside
GEDA
GPNMB
HER1
HER2 (ErbB2)
HER2/neu
HER3
HGF
HLA-DOB
HLA-DR
Human scatter factor receptor kinase
IGF-1 receptor
IgG4
IL-13
IL20Rα (IL20Ra, ZCYTOR7)
IL-6
ILGF2
ILFR1R
integrin α
integrin α5β1
integrin αvβ3
IRTA2 (Immunoglobulin superfamily receptor translocation associated 2, Gene Chromosome 1q21)
Lewis-Y antigen
LY64 (RP105)
MCP-1
MDP (DPEP1)
MPF (MSLN, SMR, mesothelin, megkaryocyte potentiating factor)
MS4A1
MSG783 (RNF124, hypothetical protein FLJ20315)
MUC1
Mucin CanAg
Napi3 (NAPI-3B, NPTIIb, SLC34A2, type II sodium-dependent phosphate transporter 3b)
NCA (CEACAM6)
P2X5 (Purinergic receptor P2X ligand-gated ion channel 5)
PD-1
PDCD1
PDGF-R α
Prostate specific membrane antigen
PSCA (Prostate stem cell antigen precursor)
PSCA hlg
RANKL
RON
SDC1
Sema 5b
SLAMF7 (CS-1)
STEAP1
STEAP2 (HGNC_8639, PCANAP1, STAMP1, STEAP2, STMP, prostate cancer associated gene 1)
TAG-72
TEM1
Tenascin C
TENB2, (TMEFF2, tomoregulin, TPEF, HPP1, TR)
TGF-β

TABLE I-continued

TRAIL-E2
TRAIL-R1
TRAIL-R2
TrpM4 (BR22450, FLJ20041, TRPM4, TRPM4B, transient receptor potential cation channel subfmlily M, member 4)
TA CTAA16.88
TWEAK-R
TYRP1 (glycoprotein 75)
VEGF
VEGF-A
EGFR-1
VEGFR-2
Vimentin Exemplary Antibodies Exemplary antibodies to be used with ADCs of the disclosure include but are not limited to 3F8 (GD2), Abagovomab (CA-125 (imitation)), Adecatumumab (EpCAM), Afutuzumab (CD20), Alacizumab pegol (VEGFR2), ALD518 (IL-6), Alemtuzumnab (CD52), Altumomab pentetate (CEA), Amatuximab (Mesothelin), Anatumomnab mafenatox (TAG-72), Apolizumab (HLA-DR), Arcitumomab (CEA), Bavituximab (Phosphatidylserine), Bectumomab (CD22), Belimumab (BAFF), Besilesomab (CEA-related antigen), Bevacizumab (VEGF-A), Bivatuzumab mertansine (CD44 v6), Blinatumomab (CD19), Brentuximab vedotin ((CD30 (TNFRSF8)), Cantuzumab mertansine (Mucin CanAg), Cantuzumab ravtansine (MUC1), Capromab pendetide (Prostatic carcinoma cells), Carlumab (MCP-1), Catumaxomab (EpCAM, CD3), CC49 (Tag-72), cBR96-DOX ADC (Lewis-Y antigen), Cetuximab (EGFR), Citatuzumab bogatox (EpCAM), Cixutumumab (IGF-1 receptor), Clivatuzumab tetraxetan(MUC1), Conatumumab (TRAIL-E2), Dacetuzumab (CD40), Dalotuzumab (Insulin-like growth factor 1 receptor), Deratumumab ((CD38 (cyclic ADP ribose hydrolase)), Demcizumab (DLL4), Denosumab (RANKL), Detumomab (B-lymphoma cell), Drozitumab (DR5), Dusigitumab (ILGF2), Ecromeximab (D3 ganglioside), Eculizumab ($C_5$), Edrecolomab (EpCAM), Elotuzumab (SLAMF7), Elsilimomab (IL-6), Enavatuzumab (TWEAK receptor), Enoticumab (DLL4), Ensituximab (5AC), Epitumomab cituxetan (Episialin), Epratuzumab (CD22), Ertumaxomab ((HER2/neu, CD3)), Etancizumab (Integrin αvβ3), Farletuzumab (Folate receptor 1), FBTA05 (CD20), Ficlatuzumab (HGF), Figitumumab (IGF-1 receptor), Flanvotumab ((TYRP1 (glycoprotein 75)), Fresolimumab (TGF-1), Galiximab (CD80), Ganitumab (IGF-I), Gemtuzumab ozogamicin (CD33), Girentuximab ((Carbonic anhydrase 9 (CA-IX)), Glembatumumab vedotin (GPNMB), Ibritumomab tiuxetan (CD20) Icrucumab (VEGFR-1), Igovomab (CA-125), IMAB362 (CLDN18.2), Imgatuzumab (EGFR), Indatuximab ravtansine (SDC1), Intetumumab (CD51), Inotuzumab ozogamicin (CD22), Ipilimumab (CD152), Iratumumab ((CD30 (TNFRSF8)), Labetuzumab (CEA), Lambrolizumab (PDCD1), Lexatumumab (TRAIL-R2), Lintuzumab (CD33), Lorvotuzumab mertansine (CD56), Lucatumumab (CD40), Lumiliximab ((CD23 (IgE receptor)), Mapatumumab (TRAIL-R1), Margetuximab (ch4DS), Matuzumab (EGFR), Milatuzumab (CD74), Mitumomab (GD3 ganglioside), Mogamulizumab (CCR4), Moxetumomab pasudotox (CD22), Nacolomab tafenatox ($C_2$-42 antigen), Naptumomab estafenatox (5T4), Narnatumab (RON), Natalizumab (integrin α4), Necitumumab (EGFR), Nesvacumab (angiopoietin 2), Nimotuzumab (EGFR), Nivolumab (IgG4), Ocaratuzumab (CD20), Ofatumumab (CD20), Olaratumab (PDGF-R α), Onartuzumab (Human scatter factor receptor kinase), Ontuxizumab (TEM1), Oportuzumab monato (EpCAM), Oregovomab (CA-125), Otlertuzumab (CD37), Panitumumab (EGFR) Pankomab (Tumor specific glycosylation of MUC1), Parsatuzumab (EGFL7), Patritumab (HER3), Pemtumomab (MUC1), Pertuzumab (HER2/neu), Pidilizumab (PD-1), Pinatuzumab vedotin (CD22), Pritumumab (Vimentin), Racotumomab (N-glycolylneuraminic acid), Radretumab (Fibronectin extra domain-B), Ramucirumab (VEGFR2), Rilotumumab (HGF), Rituximab (CD20), Robatumumab (IGF-1 receptor), Samalizumab (CD200), Satumomab pendetide (TAG-72), Seribantumab (ERBB3), Sibrotuzumab (FAP), SGN-CD19A (CD19), SGN-CD33A (CD33), Siltuximab (IL-6), Solitomab (EpCAM), Sonepcizumab (Sphingosine-1-phosphate), Tabalumb (BAFF), Tacatuzumab tetraxetan (Alpha-fetoprotein), Taplitumomab paptox (CD19), Tenatumomab (Tenascin C), Teprotumumab (CD221), TGN1412 (CD28), Ticilimumab (CTLA-4), Tigatuzumab (TRAIL-R2), TNX-650 (IL-13), Tovetumab (CD40a), Trastuzumab (HER2/neu), TRBS07 (GD2), Tremelimumab (CTLA-4), Tucotuzumab celmoleukin (EpCAM), Ublituximab (MS4A), Urelumab (4-1BB), Vandetanib (VEGF), Vantictumab (Frizzled receptor), Volociximab (integrin α5β1), Vorsetuzumab mafodotin (CD70), Votumumab (Tumor antigen CTAA16.88), Zalutumumab (EGFR), Zanolimumab (CD4), and Zatuximab (HER1).

Methods of Making Antibodies

The antibody of an ADC can be prepared by recombinant expression of immunoglobulin light and heavy chain genes in a host cell. For example, to express an antibody recombinantly, a host cell is transfected with one or more recombinant expression vectors carrying DNA fragments encoding the immunoglobulin light and heavy chains of the antibody such that the light and heavy chains are expressed in the host cell and, optionally, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Molecular Cloning; A Laboratory Manual, Second Edition (Sambrook, Fritsch and Maniatis (eds), Cold Spring Harbor, N.Y., 1989), Current Protocols in Molecular Biology (Ausubel, F. M. et al., eds., Greene Publishing Associates, 1989) and in U.S. Pat. No. 4,816,397.

In one embodiment, the Fc variant antibodies are similar to their wild-type equivalents but for changes in their Fc domains. To generate nucleic acids encoding such Fc variant antibodies, a DNA fragment encoding the Fc domain or a portion of the Fc domain of the wild-type antibody (referred to as the "wild-type Fe domain") can be synthesized and used as a template for mutagenesis to generate an antibody as described herein using routine mutagenesis techniques; alternatively, a DNA fragment encoding the antibody can be directly synthesized.

Once DNA fragments encoding wild-type Fc domains are obtained, these DNA fragments can be further manipulated by standard recombinant DNA techniques, for example, to convert the constant region genes to full-length antibody chain genes. In these manipulations, a CH-encoding DNA fragment is operatively linked to another DNA fragment encoding another protein, such as an antibody variable region or a flexible linker. The term "operatively linked," as used in this context, is intended to mean that the two DNA fragments are joined such that the amino acid sequences encoded by the two DNA fragments remain in-frame.

To express the Fc variant antibodies, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. A variant antibody light chain gene and the antibody heavy chain gene can be inserted into separate vectors or, more typically, both genes are inserted into the same expression vector.

The antibody genes are inserted into the expression vector by standard methods (e.g., ligation of complementary restriction sites on the antibody gene fragment and vector, or blunt end ligation if no restriction sites are present). Prior to insertion of the variant Fc domain sequences, the expression vector can already carry antibody variable region sequences. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel, Gene Expression Technology: Methods in Enzymology 185 (Academic Press, San Diego, Calif., 1990). It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al., and U.S. Pat. No. 4,968,615 by Schaffner et al.

In addition to the antibody chain genes and regulatory sequences, the recombinant expression vectors can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all to Axel et al.). For example, typically the selectable marker gene confers resistance to drugs, such as G418, puromycin, blasticidin, hygromycin or methotrexate, on a host cell into which the vector has been introduced. Suitable selectable marker genes include the dihydrofolate reductase (DHFR) gene (for use in DHFR− host cells with methotrexate selection/amplification) and the neo gene (for G418 selection). For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, lipofection, calcium-phosphate precipitation, DEAE-dextran transfection, and the like.

It is possible to express the antibodies in either prokaryotic or eukaryotic host cells. In certain embodiments, expression of antibodies is performed in eukaryotic cells, e.g., mammalian host cells, for optimal secretion of a properly folded and immunologically active antibody. Exemplary mammalian host cells for expressing the recombinant antibodies include Chinese Hamster Ovary (CHO cells) (including DHFR− CHO cells, described in Urlaub and Chasin, 1980, Proc. Natl. Acad. Sci. USA 77:4216-4220, used with a DHFR selectable marker, e.g., as described in Kaufman and Sharp, 1982, Mol. Biol. 159:601-621), NSO myeloma cells, COS cells, 293 cells and SP2/0 cells. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods. Host cells can also be used to produce portions of intact antibodies, such as Fab fragments or scFv molecules.

In some embodiments, the antibody of an ADC can be a bifunctional antibody. Such antibodies, in which one heavy and one light chain are specific for one antigen and the other heavy and light chain are specific for a second antigen, can be produced by crosslinking an antibody to a second antibody by standard chemical crosslinking methods. Bifunctional antibodies can also be made by expressing a nucleic acid engineered to encode a bifunctional antibody.

In certain embodiments, dual specific antibodies, i.e. antibodies that bind one antigen and a second, unrelated antigen using the same binding site, can be produced by mutating amino acid residues in the light chain and/or heavy chain CDRs. Exemplary second antigens include a proinflammatory cytokine (such as, for example, lymphotoxin, interferon-γ, or interleukin-1). Dual specific antibodies can be produced, e.g., by mutating amino acid residues in the periphery of the antigen binding site (see, e.g., Bostrom et al., 2009, Science 323:1610-1614). Dual functional antibodies can be made by expressing a nucleic acid engineered to encode a dual specific antibody.

Antibodies can also be produced by chemical synthesis (e.g., by the methods described in Solid Phase Peptide Synthesis, 2nd ed., 1984 The Pierce Chemical Co., Rockford, Ill.). Antibodies can also be generated using a cell-free platform (see, e.g., Chu et al., Biochemia No. 2, 2001 (Roche Molecular Biologicals)).

Methods for recombinant expression of Fc fusion proteins are described in Flanagan et al., Methods in Molecular Biology, vol. 378: Monoclonal Antibodies: Methods and Protocols.

Once an antibody has been produced by recombinant expression, it can be purified by any method known in the art for purification of an immunoglobulin molecule, for example, by chromatography (e.g., ion exchange, affinity, particularly by affinity for antigen after Protein A or Protein G selection, and sizing column chromatography), centrifugation, differential solubility, or by any other standard technique for the purification of proteins.

Once isolated, an antibody can, if desired, be further purified, e.g., by high performance liquid chromatography (see, e.g., Fisher, *Laboratory Techniques In Biochemistry And Molecular Biology* (Work and Burdon, eds., Elsevier, 1980)), or by gel filtration chromatography on a Superdex™ 75 column (Pharmacia Biotech AB, Uppsala, Sweden).

Methods of Treatment

Target-Oriented Treatments

The targeting moiety of the conjugate may be recognized by a cell, thereby providing a so-called target-oriented treatment.

In some embodiments, the conjugates described herein comprise an active agent as described herein, for example an active agent of formula (I). In some such embodiments, the active agent is:

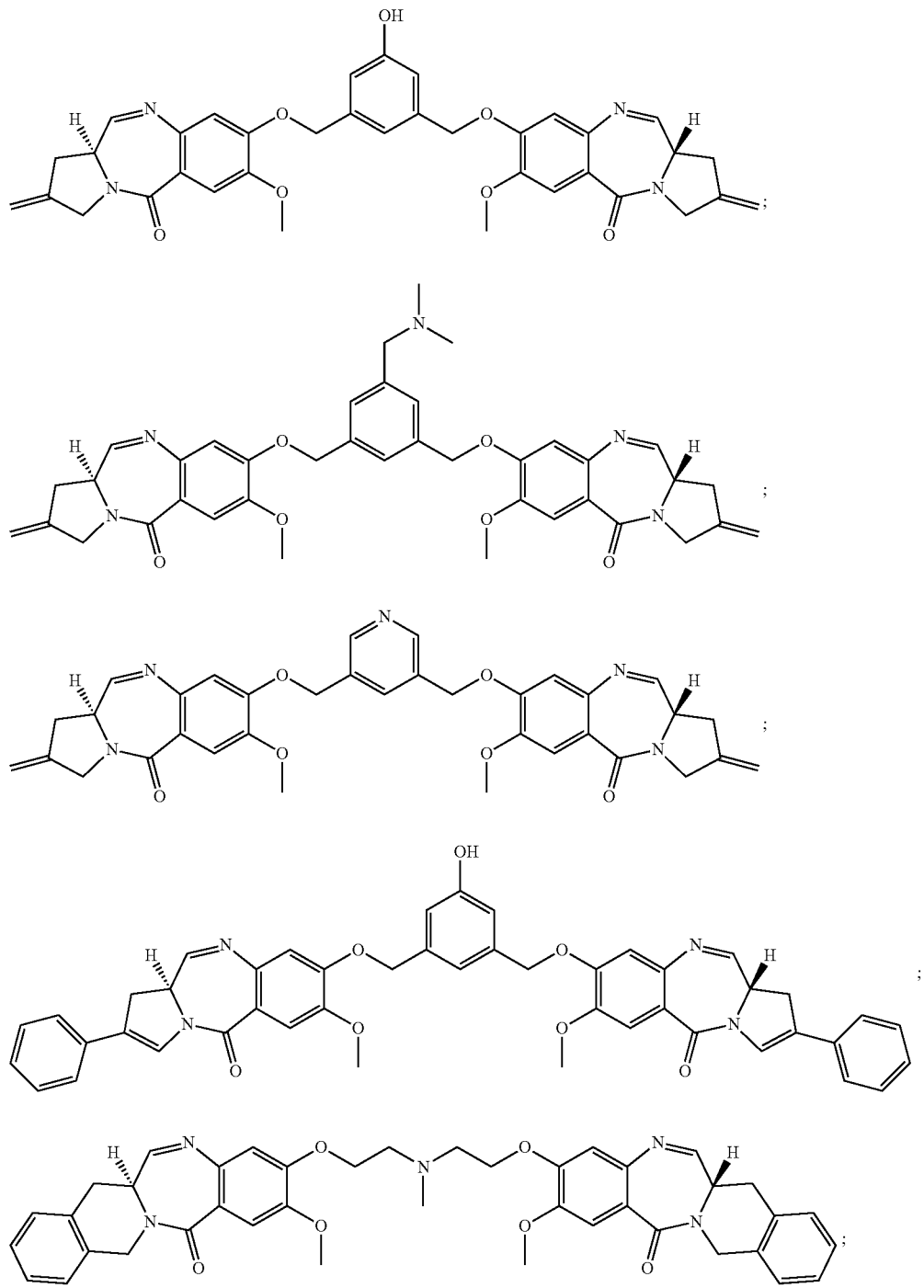

-continued
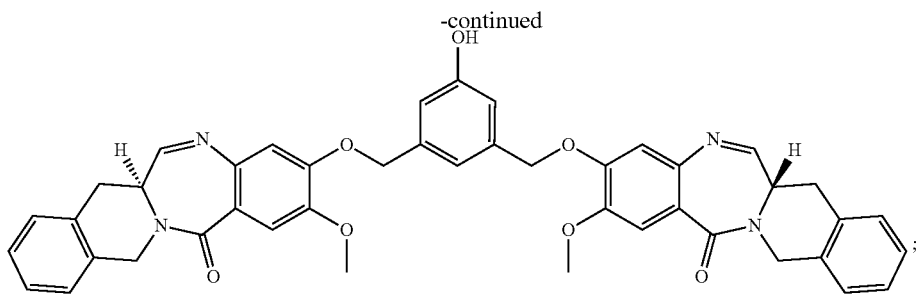
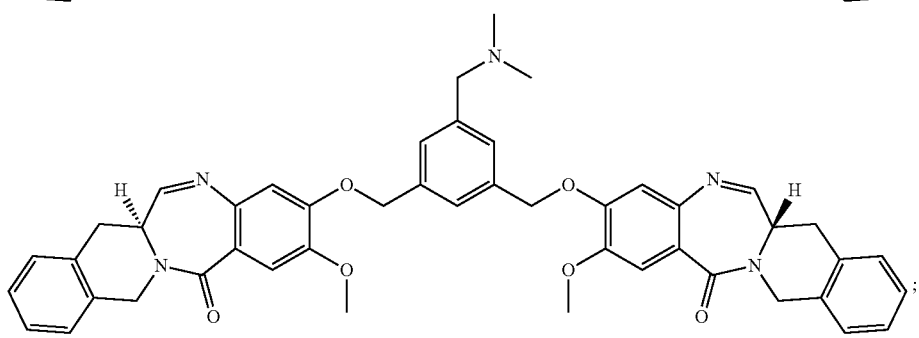
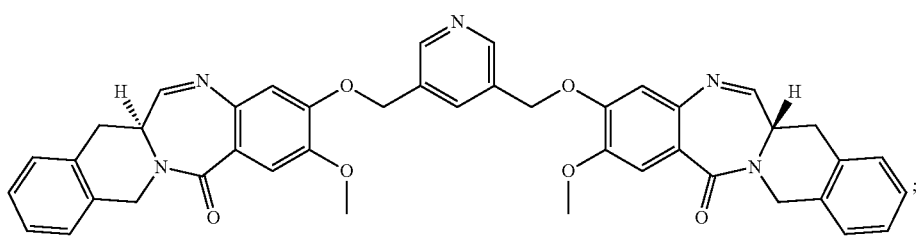
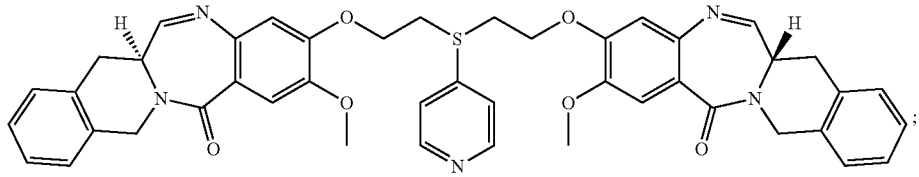
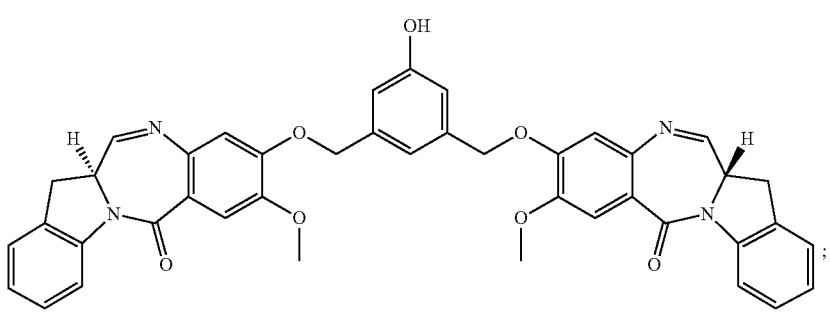
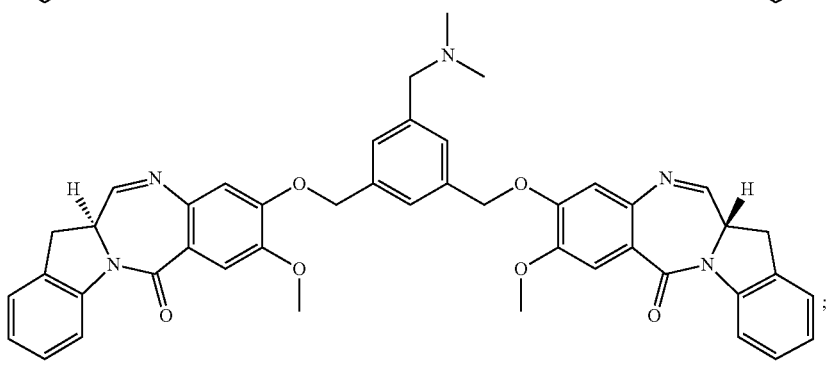

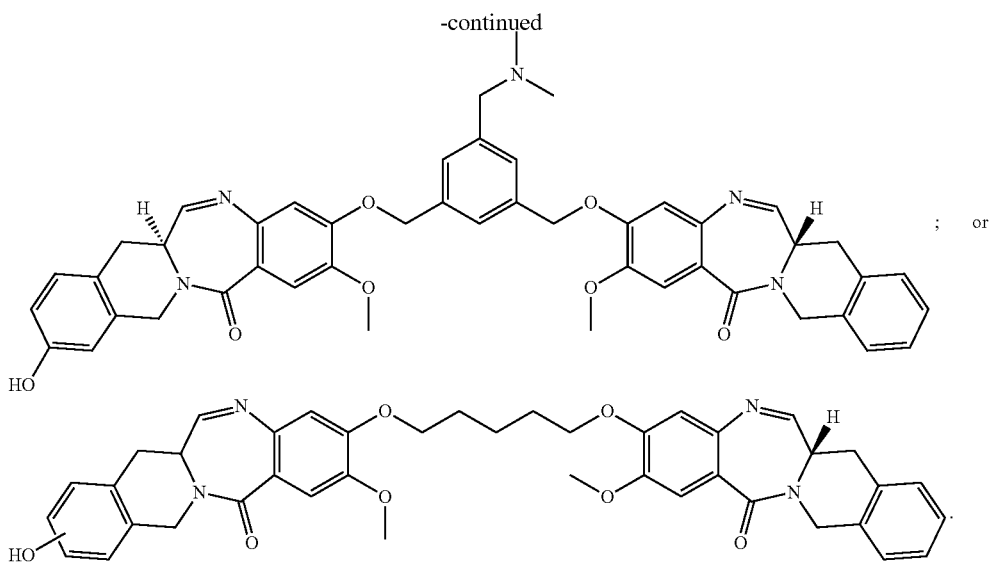
; or

Cellular Proliferation and Apoptosis

The compounds and conjugates disclosed herein may be used in methods to induce apoptosis in cells.

Dysregulated apoptosis has been implicated in a variety of diseases, including, for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., breast cancer, lung cancer), viral infections (e.g., herpes, papilloma, or HIV), and other conditions, such as osteoarthritis and atherosclerosis. The compounds, conjugates, and compositions described herein may be used to treat or ameliorate any of these diseases. Such treatments generally involve administering to a subject suffering from the disease an amount of a compound, conjugate, or composition described herein sufficient to provide therapeutic benefit. The identity of the antibody of the compound, conjugate, or composition administered will depend upon the disease being treated-thus the antibody should bind a cell-surface antigen expressed in the cell type where inhibition would be beneficial. The therapeutic benefit achieved will also depend upon the specific disease being treated. In certain instances, the compounds and compositions disclosed herein may treat or ameliorate the disease itself, or symptoms of the disease, when administered as monotherapy. In other instances, the compounds and compositions disclosed herein may be part of an overall treatment regimen including other agents that, together with the inhibitor or the compounds and compositions disclosed herein, treat or ameliorate the disease being treated, or symptoms of the disease. Agents useful to treat or ameliorate specific diseases that may be administered adjunctive to, or with, the compounds and compositions disclosed herein will be apparent to those of skill in the art.

Although absolute cure is always desirable in any therapeutic regimen, achieving a cure is not required to provide therapeutic benefit. Therapeutic benefit may include halting or slowing the progression of the disease, regressing the disease without curing, and/or ameliorating or slowing the progression of symptoms of the disease. Prolonged survival as compared to statistical averages and/or improved quality of life may also be considered therapeutic benefit.

One particular class of diseases that involve dysregulated apoptosis and that are significant health burden world-wide are cancers. In a specific embodiment, the the compounds and compositions disclosed herein may be used to treat cancers. The cancer may be, for example, solid tumors or hematological tumors. Cancers that may be treated with the compounds and compositions disclosed herein include, but are not limited to bladder cancer, brain cancer, breast cancer, bone marrow cancer, cervical cancer, chronic lymphocytic leukemia, colorectal cancer, esophageal cancer, hepatocellular cancer, lymphoblastic leukemia, follicular lymphoma, lymphoid malignancies of T-cell or B-cell origin, melanoma, myelogenous leukemia, myeloma, oral cancer, ovarian cancer, non-small cell lung cancer, chronic lymphocytic leukemia, myeloma, prostate cancer, small cell lung cancer and spleen cancer. The compounds and compositions disclosed herein may be especially beneficial in the treatment of cancers because the antibody can be used to target the tumor cell specifically, thereby potentially avoiding or ameliorating undesirable side-effects and/or toxicities that may be associated with systemic administration of unconjugated inhibitors. One embodiment pertains to a method of treating a disease involving dysregulated intrinsic apoptosis, comprising administering to a subject having a disease involving dysregulated apotosis an amount of a compound and composition disclosed herein effective to provide therapeutic benefit, wherein the ligand of the compounds and compositions disclosed herein binds a cell surface receptor on a cell whose intrinsic apoptosis is dysregulated. One embodiment pertains to a method of treating cancer, comprising administering to a subject having cancer a compound and composition disclosed herein, wherein the ligand is capable of binding a cell surface receptor or a tumor associated antigen expressed on the surface of the cancer cells, in an amount effective to provide therapeutic benefit.

In the context of tumorigenic cancers, therapeutic benefit, in addition to including the effects discussed above, may also specifically include halting or slowing progression of tumor growth, regressing tumor growth, eradicating one or more tumors and/or increasing patient survival as compared to statistical averages for the type and stage of the cancer being treated. In one embodiment, the cancer being treated is a tumorigenic cancer.

The compounds and conjugates disclosed herein may be administered as monotherapy to provide therapeutic benefit, or may be administered adjunctive to, or with, other chemotherapeutic agents and/or radiation therapy. Chemotherapeutic agents to which the compounds and compositions disclosed herein may be utilized as adjunctive therapy may be targeted (for example, ADCs, protein kinase inhibitors, etc.) or non-targeted (for example, non-specific cytotoxic agents such as radionucleotides, alkylating agents and intercalating agents). Non-targeted chemotherapeutic agents with which the compounds and compositions disclosed herein may be adjunctively administered include, but are not limited to, methotrexate, taxol, L-asparaginase, mercaptopurine, thioguanine, hydroxyurea, cytarabine, cyclophosphamide, ifosfamide, nitrosoureas, cisplatin, carboplatin, mitomycin, dacarbazine, procarbizine, topotecan, nitrogen mustards, Cytoxan, etoposide, 5-fluorouracil, BCNU, irinotecan, camptothecins, bleomycin, doxorubicin, idarubicin, daunorubicin, dactinomycin, plicamycin, mitoxantrone, asperaginase, vinblastine, vincristine, vinorelbine, paclitaxel, calicheamicin, and docetaxel.

The compounds and conjugates disclosed herein that may not be effective as monotherapy to treat cancer may be administered adjunctive to, or with, other chemotherapeutic agents or radiation therapy to provide therapeutic benefit. One embodiment pertains to a method in which a compound or composition disclosed herein is administered in an amount effective to sensitize the tumor cells to standard chemotherapy and/or radiation therapy. Accordingly, in the context of treating cancers, "therapeutic benefit" includes administering the compounds and compositions disclosed herein adjunctive to, or with, chemotherapeutic agents and/ or radiation therapy, either in patients who have not yet begin such therapy or who have but have not yet exhibited signs of resistance, or in patients who have begun to exhibit signs of resistance, as a means of sensitizing the tumors to the chemo and/or radiation therapy.

Pharmaceutical Compositions and Administration Thereof

The compounds and conjugates disclosed herein may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a disclosed compound and a pharmaceutically acceptable carrier.

Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection, or the like. The composition can also be present in a transdermal delivery system, e.g., a skin patch. The composition can also be present in a solution suitable for topical administration, such as an ointment or cream.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compounds, conjugates, or compositions thereof may also be administered as a bolus, electuary, or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697, and 2005/004074; and U.S. Pat. No. 6,583,124, the contents of which are incorporated herein by reference. If desired, liquid ophthalmic formulations have properties similar to that of lacrimal fluids, aqueous humor or vitreous humor or are compatible with such fluids.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to about 99.5% (more preferably, about 0.5 to about 90.0%) of active ingredient in combination with a pharmaceutically acceptable carrier.

In some embodiments of the invention, a compound of the invention is conjointly administered with one or more additional compounds/agents.

In certain such embodiments, the conjoint administration is simultaneous. In certain such embodiments, the compound of the invention is co-formulated with the one or more additional compounds. In certain other such embodiments, the compound of the invention is administered separately but simultaneously with the one or more additional compounds. In certain such embodiments, the conjoint administration is sequential, with administration of the compound of the invention preceding or following the administration of the one or more additional compound by minutes or hours.

Methods of introduction of a compound of the invention may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound, conjugate or combination of compounds and/or conjugates employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. "Therapeutically effective amount" refers to the concentration of a compound that is sufficient to elicit the desired therapeutic effect. It is generally understood that the effective amount of the compound will vary according to the weight, sex, age, and medical history of the subject. Other factors that influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound or conjugate may be administered as one, two, three, four, five, six, or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds or conjugates disclosed herein may be used alone or conjointly administered with another type of therapeutic agent. As used herein, the phrase "conjoint administration" refers to any form of administration of two or more different therapeutic compounds or conjugates such that the second compound or conjugate is administered while the previously administered therapeutic compound or conjugate is still effective in the body (e.g., the two compounds or conjugates are simultaneously effective in the patient, which may include synergistic effects of the two compounds or conjugates). For example, the different therapeutic compounds or conjugates can be administered either in the same formulation or in a separate formulation, either concomitantly or sequentially. In certain embodiments, the different therapeutic compounds or conjugates can be administered within one hour, 12 hours, 24 hours, 36 hours, 48 hours, 72 hours, a week, or more of one another. Thus, an individual who receives such treatment can benefit from a combined effect of different therapeutic compounds or conjugates.

This invention includes the use of pharmaceutically acceptable salts of compounds or conjugates disclosed herein. In certain embodiments, contemplated salts of the invention include, but are not limited to, alkyl, dialkyl, trialkyl, or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn, or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Examples

The invention now being generally described, it will be more readily understood by reference to the following examples, which are included merely for purposes of illustration of certain aspects and embodiments of the present invention, and are not intended to limit the invention.

Synthetic Protocols

Abbreviations
AcO: acetyl
AcOH: acetic acid
EA: ethyl acetate
DCM: dichloromethane m-CPBA: meta-chloroperoxybenzoic acid
TBDMSOTf: tert-butyldimethylsilyl triflate
TBDMS: tert-Butyldimethylsilyl
DMF: Dimethylformamide
EDCI: 1-Ethyl-3-(3-dimethylaminopropyl)carbodiimide
HOBt: 1-Hydroxybenzotriazole hydrate
ACN: Acetonitrile
TBDMS-Cl: tert-Butyldimethylsilyl chloride
DBU: 1,8-Diazabicyclo[5.4.0]undec-7-ene
THF: Tetrahydrofuran
DCC: N,N'-Dicyclohexylcarbodiimide
DMAP: 4-Dimethylaminopyridine
NHS: N-Hydroxysuccinimide
DIPEA: Diisopropylethylamine
TEA: triethylamine
DEAD: diethyl azodicarboxylate
Boc: tert-butyloxycarbonyl
LAH: lithium aluminium hydride
CDI: 1,1'-Carbonyldiimidazole
BEMP: 2-tert-Butylimino-2-diethylamino-1,3-dimethylperhydro-1,3,2-diazaphosphorine
TPSCl: Triphenylchlorosilane
tfa: Trifluoroacetyl
PyBop: benzotriazol-1-yl-oxytripyrrolidinophosphonium hexafluorophosphate
HBTU: N,N,N',N'-Tetramethyl-O-(1H-benzotriazol-1-yl) uronium hexafluorophosphate
TFA: Trifluoroacetic acid
DIC: N,N'-Diisopropylcarbodiimide
DMPA: 2,2-Dimethoxy-2-phenylacetophenone
TBAF: Tetra-n-butylammonium fluoride
AgOTf: Silver trifluoromethanesulfonate
(BimC4A)$_3$: Tripotassium 5,5',5"-[2,2',2"-nitrilotris(methylene)tris(1H-benzimidazole-2,1-diyl)]tripentanoate hydrate

TABLE A

| Compound No. | Structure |
|---|---|
| Pyrrolo-BenzoDiazepine (PBD) Type Compounds | |
| D-1 | 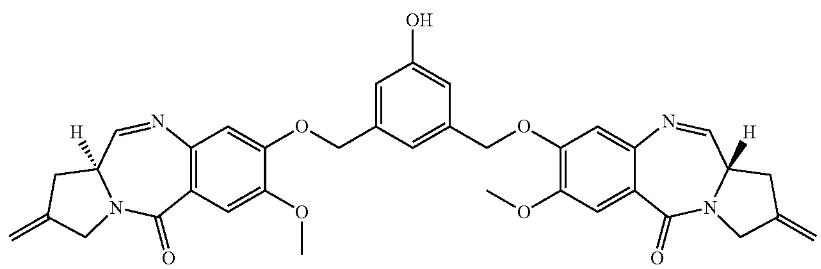 |
| D-2 | 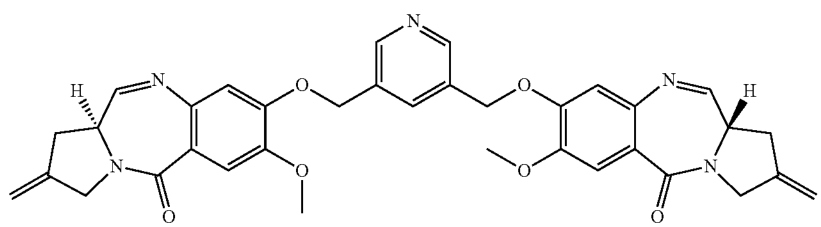 |
| D-10 | 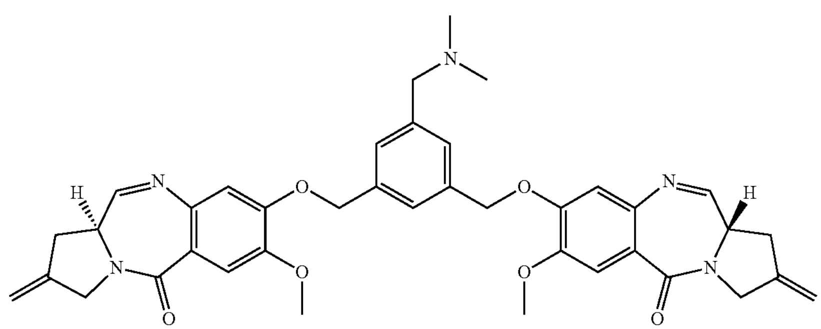 |
| D-11 | 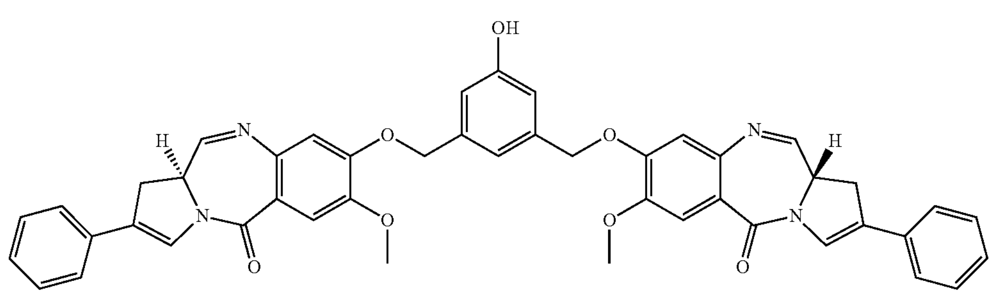 [SMILES: COc1cc2c(cc1OCc1cc(O)cc(COc3cc4c(cc3OC)C(=O)N3C=C(c5ccccc5)C[C@H]3C=N4)c1)N=C[C@@H]1CC(c3ccccc3)=CN1C2=O] |

TABLE A-continued

| Compound No. | Structure |
|---|---|
| D-14 | R = H, OH, or OMe |
| D-15 | 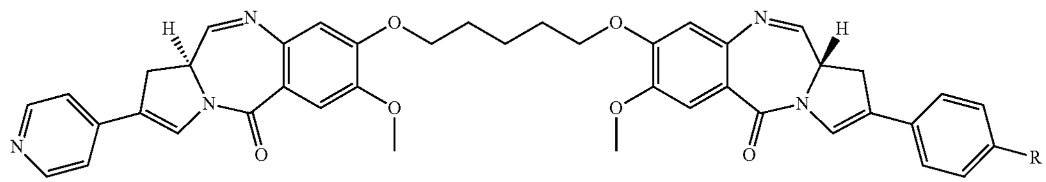 |
| D-7 | 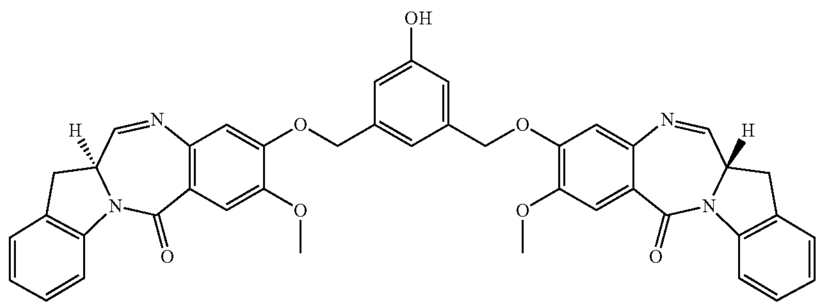 [SMILES: COc1cc2c(cc1OCc1cc(O)cc(COc3cc4c(cc3OC)C(=O)N3c5ccccc5C[C@H]3C=N4)c1)N=C[C@@H]1Cc3ccccc3N1C2=O] |
| D-8 | 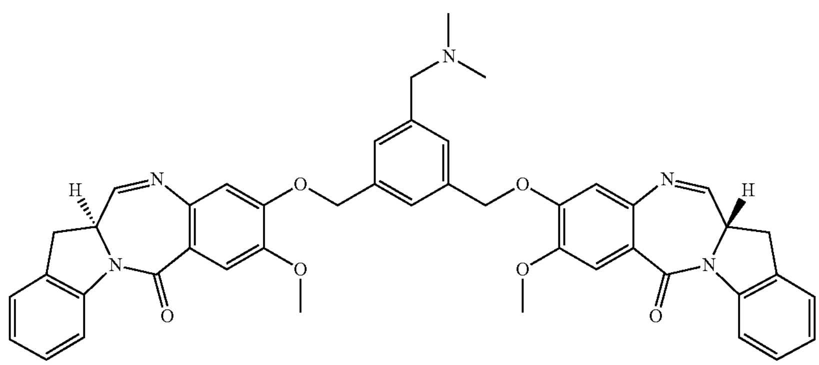 [SMILES: COc1cc2c(cc1OCc1cc(COc3cc4c(cc3OC)C(=O)N3c5ccccc5C[C@H]3C=N4)cc(CN(C)C)c1)N=C[C@@H]1Cc3ccccc3N1C2=O] |

Tetrahydroisoquinoline-BenzoDiazepine TBD Type Compounds

| | |
|---|---|
| D-3 | |

TABLE A-continued
| Compound No. | Structure |
| --- | --- |
| D-4 | 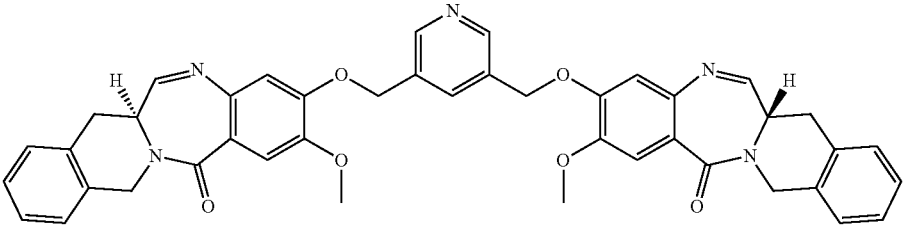 [SMILES: COc1cc2c(cc1OCc1cncc(COc3cc4c(cc3OC)C(=O)N3Cc5ccccc5C[C@H]3C=N4)c1)N=C[C@@H]1Cc3ccccc3CN1C2=O] |
| D-5 | 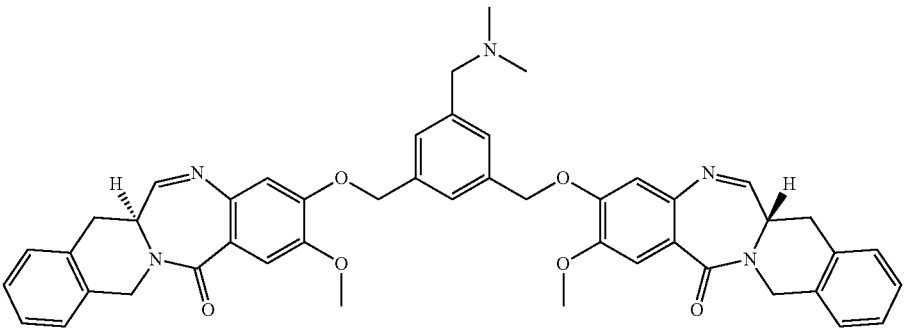 [SMILES: COc1cc2c(cc1OCc1cc(COc3cc4c(cc3OC)C(=O)N3Cc5ccccc5C[C@H]3C=N4)cc(CN(C)C)c1)N=C[C@@H]1Cc3ccccc3CN1C2=O] |
| D-6 | 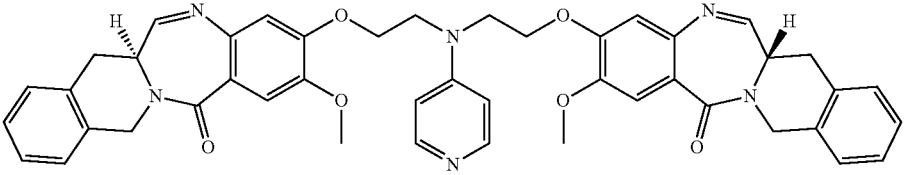 [SMILES: COc1cc2c(cc1OCCN(CCOc1cc3c(cc1OC)C(=O)N1Cc4ccccc4C[C@H]1C=N3)c1ccncc1)N=C[C@@H]1Cc3ccccc3CN1C2=O] |
| D-9 | 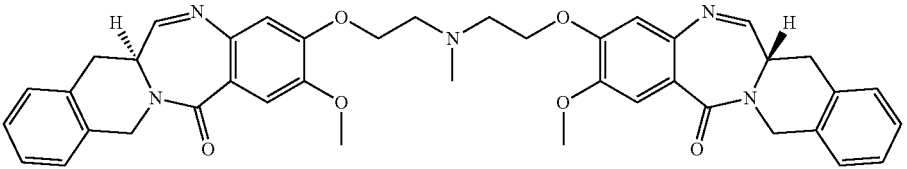 [SMILES: COc1cc2c(cc1OCCN(C)CCOc1cc3c(cc1OC)C(=O)N1Cc4ccccc4C[C@H]1C=N3)N=C[C@@H]1Cc3ccccc3CN1C2=O] |
| Ref 1 | 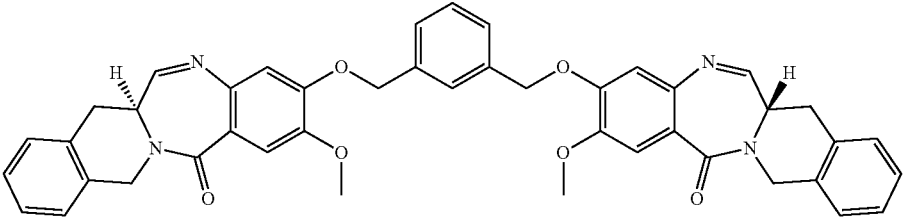 [SMILES: COc1cc2c(cc1OCc1cccc(COc3cc4c(cc3OC)C(=O)N3Cc5ccccc5C[C@H]3C=N4)c1)N=C[C@@H]1Cc3ccccc3CN1C2=O] |
| Ref 2 | 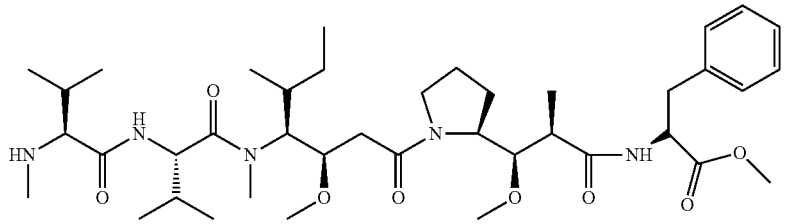<br>(MMAF-OMe) |

Preparation of Linker

Example 1: Preparation of Compound L-1

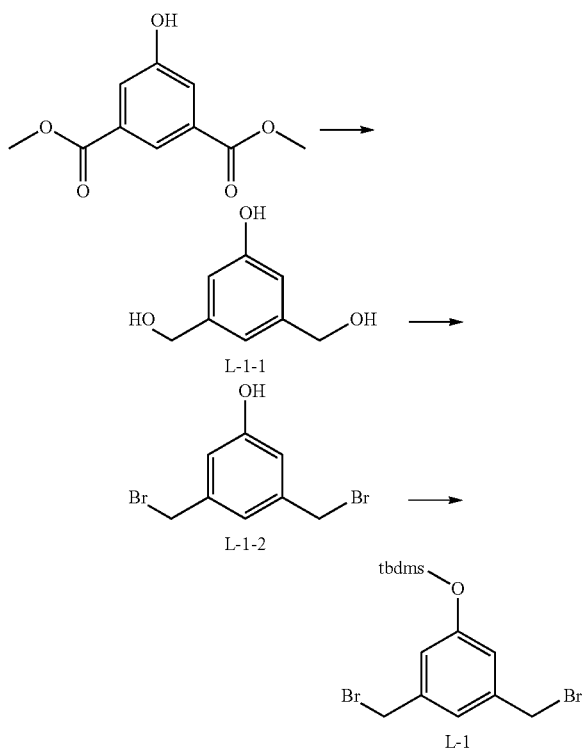

Preparation of Compound L-1-1

To solution of dimethyl 5-hydroxyisophthalate (5 g, 23.79 mmol) in dry THF (300 mL) was added LAH (3.6 g, 95.15 mmol) dropwise at −78° C. under $N_2$ atmosphere. The reaction mixture was stirred at room temperature for 17 hours. After the reaction was completed, 15% NaOH solution (4 mL), $H_2O$ (8 mL) and EA (100 mL) were added and then the reaction mixture was stirred for 1 hour. The mixture was filtered and concentrated under reduced pressure. The residue was purified by column chromatography to obtain compound L-1-1 (3.02 g, 82%).

$^1$H NMR (400 MHz, DMSO-d6) δ 6.66 (s, 1H), 6.58 (s, 2H), 4.38 (s, 4H).

Preparation of Compound L-1-2

To a solution of compound L-1-1 (2 g, 12.97 mmol) was dissolved in HBr (5.0 mL, 33% in AcOH) under $N_2$ atmosphere. After stirring at 60° C. for 18 hours, the reaction was quenched by addition of $NaHCO_3$ solution (pH-8). And then distilled water (50 mL) and EA (100 mL×2) were added in reaction mixture. The organic layer was dried over anhydrous $Na_2SO_4$, filtered and concentrated under reduced pressure. The residue was purified by column chromatography to obtain compound L-1-2 (2.9 g, 80%).

$^1$H NMR (400 MHz, $CDCl_3$) δ 6.99 (s, 1H), 6.81 (s, 2H), 4.85 (s, 2H), 4.41 (s, 2H).

Preparation of Compound L-1

To a solution of compound L-1-2 (100 mg, 0.36 mmol) in dry DCM (3 mL) was added imidazole (27 mg, 0.39 mmol) and TBDMS-Cl (59 mg, 0.39 mmol) at room temperature under $N_2$ atmosphere. After stirring for 16 hours, distilled water (50 mL) and EA (100 mL) were added in the reaction mixture. The organic layer was dried over anhydrous $Na_2SO_4$, filtered and concentrated under reduced pressure. The residue was purified by column chromatography to obtain compound L-1 (110 mg, 79%).

$^1$H NMR (400 MHz, $CDCl_3$) δ 7.00 (s, 1H), 6.80 (s, 2H), 4.41 (s, 4H), 0.99 (s, 9H), 0.21 (s, 6H).

Example 2: Preparation of Compound L-2

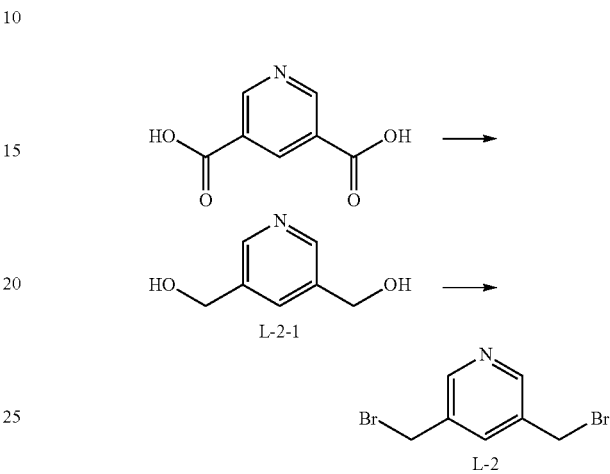

Preparation of Compound L-2-1

To a solution of 3,5-pyridinedicarboxylic acid (1.0 g, 5.98 mmol) in anhydrous THF (50 mL) at 0° C. under $N_2$ atmosphere was added boron trifluoride tetrahydrofuran complex (30.0 mL, 30.0 mmol, 1M THF). The reaction was allowed to warm up to room temperature and stirred for 18 hours. The mixture was quenched with 2N HCl till pH 2 and extracted with distilled water (20 mL) and EA (50 mL×2). The organic layer was dried over anhydrous $Na_2SO_4$, filtered and concentrated under reduced pressure. The residue was purified by preparative TLC to obtain compound L-2-1 (363 mg, 48%).

$^1$H NMR (400 MHz, DMSO-$d_6$) δ 8.38 (s, 2H), 7.99 (s, 1H), 5.59 (t, J=4.0 Hz, 2H), 4.61 (d, J=5.2 Hz, 2H).

Preparation of Compound L-2

A mixture of L-2-1 (100 mg, 0.72 mmol) and HBr (1.5 mL, 48% in AcOH) was stirred at 120° for 3 hours. The reaction was quenched with $NaHCO_3$ solution till pH-8. The distilled water (20 mL) and EA (50 mL×2) were added thereto. The organic layer was dried over anhydrous $Na_2SO_4$, filtered and concentrated under reduced pressure. The residue was purified by preparative TLC to obtain compound L-2 (123.5 mg, 65%).

$^1$H NMR (400 MHz, $CDCl_3$) δ 8.56 (s, 2H), 7.77 (s, 1H), 4.47 (s, 2H).

Example 3: Preparation of Compound L-3

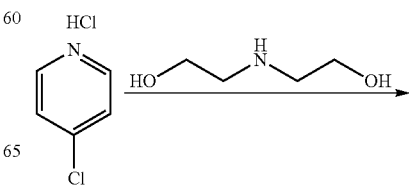

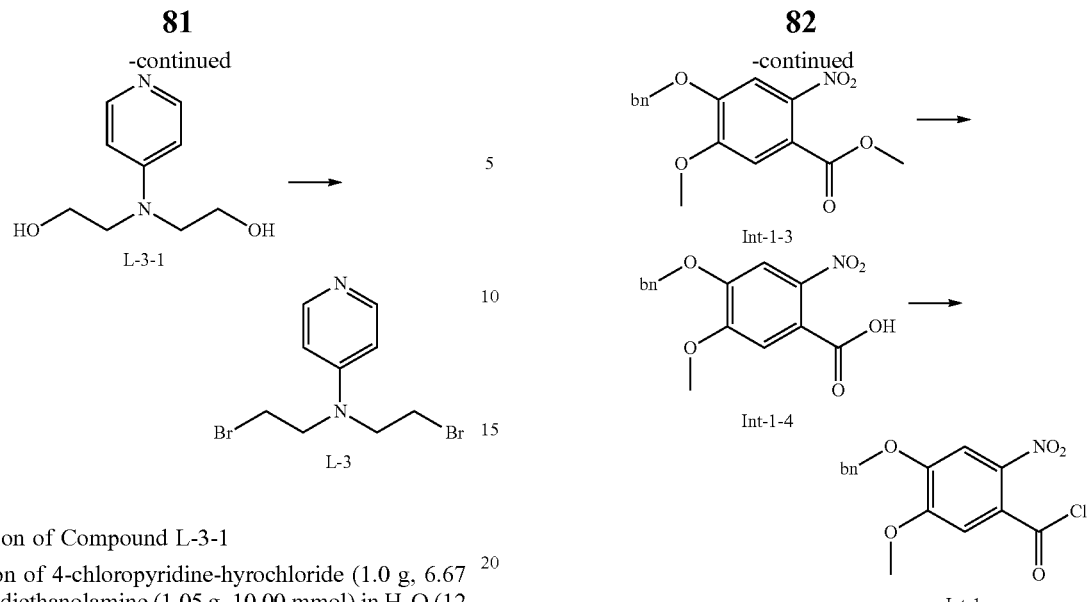

Preparation of Compound L-3-1

A solution of 4-chloropyridine-hyrochloride (1.0 g, 6.67 mmol) and diethanolamine (1.05 g, 10.00 mmol) in H$_2$O (12 mL) at room temperature under N$_2$ atmosphere was treated NaOH (1.07 g, 26.67 mmol) and heated to 110° C. for 1 hour using microwave reactor. After the reaction was quenched with distilled water (18 mL)/methanol (10 mL) and extracted with EA (200 mL). The organic layer was dried over anhydrous Na$_2$SO$_4$, filtered and concentrated under reduced pressure. The residue was purified by column chromatography to obtain compound L-3-1 (160 mg, 13%).

$^1$H NMR (400 MHz, DMSO-d6) δ 8.10 (d, J=5.6 Hz, 2H), 6.83 (d, J=6.0 Hz, 2H), 4.91 (br s, 2H), 3.57 (s, 8H). EI-MS m/z: 183 (M$^+$+1).

Preparation of Compound L-3

A mixture of compound L-3-1 (10 mg, 0.05 mmol) and HBr (2.0 mL, 48% in H$_2$O) was reacted in microwave at 150° C. for 3 hours. After the mixture was concentrated under reduced pressure, the compound L-3 was used directly in the next step without further purification. (20 mg). EI-MS m/z: 309 (M$^+$+1).

Example 4: Preparation of Compound Int-1

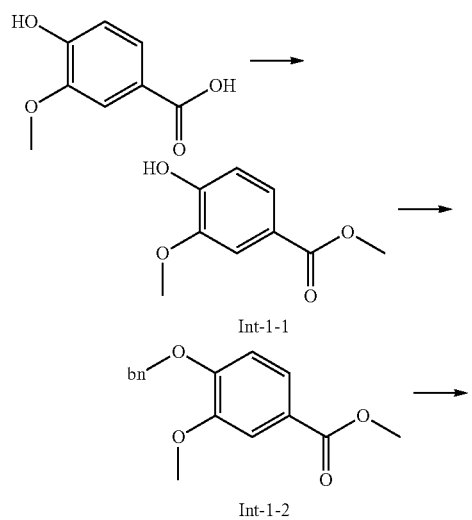

Preparation of Compound Int-1-1

To a solution of vanillic acid (50.0 g, 0.30 mol) in MeOH (700 mL) was added dropwise SOCl$_2$ (207 mL, 2.85 mol) and stirred at 0° C. under N$_2$ atmosphere. The reaction mixture was allowed warm up to room temperature and stirred overnight. The mixture was concentrated under reduced pressure and the pH was adjusted to 7-8. The mixture was extracted with distilled water (100 mL) and EA (200 mL×2). The organic layer was dried over anhydrous Na$_2$SO$_4$, filtered and concentrated under reduced pressure. The residue was purified by column chromatography to obtain compound Int-1-1 (54.2 g, quant)

$^1$H NMR (400 MHz, CDCl$_3$) δ 7.64 (dd, J=6.4, 1.6 Hz, 1H), 7.55 (s, 1H), 6.94 (d, J=8.4 Hz, 1H), 6.05 (s, 1H), 3.95 (s, 3H), 3.89 (s, 3H).

Preparation of Compound Int-1-2

To a solution of compound Int-1-1 (54.2 g, 0.30 mol) in DMF (200 mL) was added K$_2$CO$_3$ (61.6 g, 0.45 mol) and benzyl bromide (39.0 mL, 0.33 mol) under N$_2$ atmosphere. After stirring for 6 h at 100° C., the mixture was cooled to room temperature and diluted with distilled water (100 mL) and EA (200 mL×2). The organic layer was dried over anhydrous Na$_2$SO$_4$, filtered and concentrated under reduced pressure. The residue was purified by column chromatography to obtain compound Int-1-2 (79.8 g, 98%).

$^1$H NMR (400 MHz, CDCl$_3$) δ 7.60 (dd, J=6.4, 2.0 Hz, 1H), 7.56 (d, J=2.0 Hz, 1H), 7.44-7.31 (m, 5H), 6.89 (d, J=8.4 Hz, 1H), 5.22 (s, 2H), 3.94 (s, 3H), 3.88 (s, 3H).

Preparation of Compound Int-1-3

To a solution of compound Int-1-2 (79.8 g, 0.29 mol) in acetic anhydride (550 mL) under N$_2$ atmosphere at 0° C. was added copper (II) nitrate hemi-(pentahydrate) (75.0 g, 0.32 mol). The mixture was stirred at 0° C. for 6 h, the reaction was quenched with ice water (800 mL) and a solid precipitated out. The solid was filtered and washed with distilled water (100 mL) and hexane (200 mL×2) to obtain compound Int-1-3 (85.5 g, 92%).

$^1$H NMR (400 MHz, CDCl$_3$) δ 7.52 (s, 1H), 7.45-7.35 (m, 5H), 7.08 (s, 1H), 5.22 (s, 2H), 3.98 (s, 3H), 3.91 (s, 3H).

Preparation of Compound Int-1-4

To a solution of compound Int-1-3 (85.5 g, 0.27 mol) in THF (800 mL) and MeOH (300 mL) was added 2N NaOH (404 mL, 0.81 mol). After stirring for 5 hr at 65° C., the reaction was cooled to room temperature and adjusted to pH 2 by addition of 2N HCl solution, and then extracted with distilled water (100 mL) and EA (300 mL×2). The organic layer was dried over anhydrous Na$_2$SO$_4$, filtered and concentrated under reduced pressure. The residue solid was collected and washed with hexane to obtain compound Int-1-4 (79.2 g, 97%).

$^1$H NMR (400 MHz, DMSO-d6) δ 7.69 (s, 1H), 7.47-7.35 (m, 5H), 7.03 (s, 1H), 5.24 (s, 2H), 3.91 (s, 3H).

Preparation of Compound Int-1

To a solution of compound Int-1-4 (100 mg, 0.33 mmol) in anhydrous THF (500 μL) and anhydrous DCM (1.5 mL) were slowly added dropwise oxalyl chloride (42.4 μL) and added 1 drop of DMF at 0° C. under N$_2$ atmosphere. After stirring for 30 min, the reaction mixture was concentrated under reduced pressure. The compound Int-1 was used directly in the next step without further purification.

Example 5: Preparation of Compound L-4

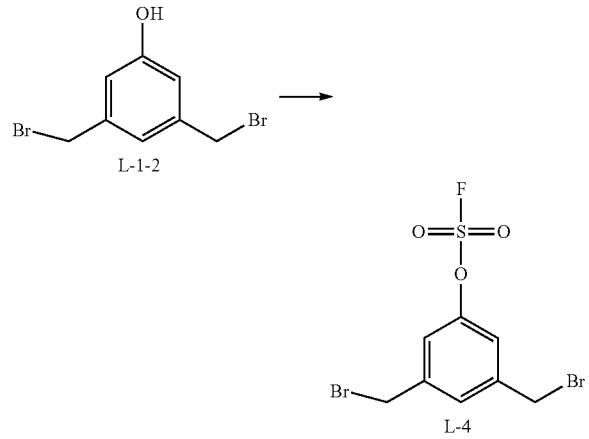

To a solution of compound L-1-2 (1.0 g, 3.57 mmol) in DCM (35 mL) was added TEA (0.45 mL, 3.21 mmol) at room temperature under N$_2$ atmosphere. SO$_2$F$_2$ gas was introduced via balloon, and the mixture was stirred at room temperature for 1 hours. Then mixture was washed with DCM (50 mL) and water (30 mL) were added. The organic layer was washed with NaHCO$_3$ aqueous solution, dried over anhydrous Na$_2$SO$_4$, filtered, and concentrated under reduced pressure. The residue was purified by column chromatography to obtain compound L-4 (941.7 mg, 73%).

$^1$H NMR (400 Hz, CDCl$_3$) δ 7.47 (s, 1H), 7.32 (s, 2H), 4.46 (s, 4H).

Example 6: Preparation of Compound L-5

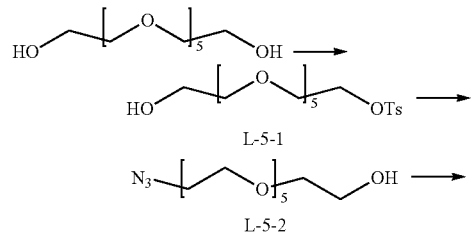

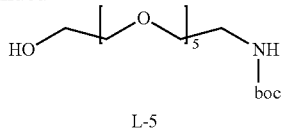

Preparation of Compound L-5-1

To a solution of hexaethylene glycol (5.0 g, 17.71 mmol) in anhydrous DCM (178 mL) were added KI (294 mg, 1.77 mmol) and Ag$_2$O (4.92 g, 19.48 mmol) under N$_2$ atmosphere. The mixture was stirred overnight at room temperature. After the reaction was completed, the mixture was filtered through Celite and washed with DCM (100 mL). The filtrate was concentrated under reduced pressure. The residue was purified by column chromatography to obtain compound L-5-1 (5.98 g, 73%).

1H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.71-3.58 (m, 22H), 2.88 (br, 1H), 2.45 (s, 3H).

Preparation of Compound L-5-2

To a solution of compound L-5-1 (5.98 g, 13.7 mmol) in DMF (30 mL) was added NaN$_3$ (1.34 g, 20.55 mmol) under N$_2$ atmosphere. The mixture was stirred at 110° C. for 1 h and concentrated under reduced pressure. The residue was purified by column chromatography to obtain compound L-5-2 (4.1 g, 97%).

$^1$H NMR (400 Hz, CDCl$_3$) δ 3.72-3.60 (m, 22H), 3.39 (t, J=4.8 Hz, 2H), 2.78 (br, 1H).

Preparation of Compound L-5

5% Pd/C (1.04 g, 0.49 mmol) was added to a stirred solution of L-5-2 (1.0 g, 3.25 mmol) in EtOH (5 mL) at room temperature. Hydrogen gas was bubbled through the reaction mixture for 4 h. The mixture was filtered through Celite to remove Pd/C, and concentrated under reduced pressure. After the residue was dissolved in DCM (25 mL), BOC$_2$O (852.1 mg, 3.9 mmol) was added thereto. The mixture was stirred at room temperature for 3 hours. The mixture was concentrated under reduced pressure. The residue was purified by column chromatography to produce compound L-5 (330 mg, 28%).

$^1$H NMR (400 Hz, CDCl$_3$) δ 5.19 (br s, 1H), 3.73 (t, J=4.8 Hz, 2H), 3.67 (s, 12H), 3.63-3.60 (m, 6H), 3.54 (t, J=5.2 Hz, 2H), 3.34-3.27 (m, 1H), 1.44 (s, 9H).

EI-MS m/z: 382 (M$^+$+1).

Example 7: Preparation of Compound L-6

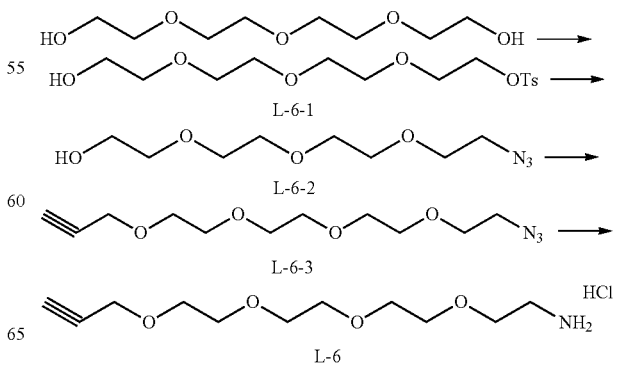

Compound L-6 was synthesized by a similar synthetic route as described in Journal of Polymer Science, Part A: Polymer Chemistry, 2012, 50(19), 3986-3995, incorporated herein by reference.

Preparation of compound L-6-1

Yield 30%

$^1$H NMR (400 Hz, CDCl3) δ 7.80 (d, J=8.4 Hz, 2H), 7.34 (d, J=8.4 Hz, 2H), 4.16 (t, J=4.8 Hz, 2H), 3.74-3.58 (m, 14H), 2.45 (s, 3H).

Preparation of Compound L-6-2

Yield 68%

$^1$H NMR (400 Hz, CDCl3) δ 3.74-3.61 (m, 14H), 3.40 (t, J=4.8 Hz, 2H), 2.45 (t, J=6.0 Hz, 2H).

Preparation of compound L-6-3

Yield 63%

$^1$H NMR (400 Hz, CDCl3) δ 4.21 (d, J=2.4 Hz, 2H), 3.72-3.67 (m, 14H), 3.39 (t, J=5.2 Hz, 2H), 2.43 (t, J=2.4 Hz, 1H).

Preparation of Compound L-6

Yield 76%

$^1$H NMR (400 Hz, CDCl3) δ 4.20 (d, J=2.4 Hz, 2H), 3.71-3.61 (m, 12H), 3.51 (t, J=4.8 Hz, 2H), 2.87 (t, J=5.6 Hz, 2H), 2.43 (t, J=2.4 Hz, 1H).

Example 8: Preparation of Compound L-7

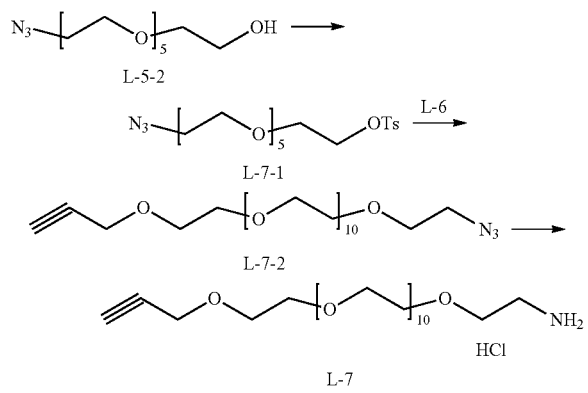

Preparation of Compound L-7-1

Compound L-5-2 (1.9 g, 6.18 mmol) was dissolved in DCM (20 mL) under N$_2$ atmosphere. Triethylamine (2.0 mL, 14.22 mmol) and p-TsCl (2.4 g, 12.36 mmol) were added thereto, and the mixture was stirred overnight at room temperature. After the reaction was completed, the mixture was concentrated under reduced pressure. The residue was purified by column chromatography to obtain a compound L-7-1 (2.58 g, 91%).

$^1$H NMR (400 Hz, CDCl$_3$) δ 7.80 (d, J=8.4 Hz, 2H), 7.35 (d, J=8.4 Hz, 2H), 4.16 (t, J=4.8 Hz, 2H), 3.70-3.61 (m, 16H), 3.56 (s, 1H), 3.39 (t, J=4.8 Hz, 2H), 2.45 (s, 3H).

EI-MS m/z: 462 (M$^+$+1).

Preparation of Compound L-7-2

A homogeneous solution of L-6 (1.1 g, 3.4 mmol) in anhydrous THF (30 mL) under N$_2$ atmosphere was treated with NaH (60% dispersion in mineral oil, 135 mg, 3.4 mmol) and cooled to 0° C. After the mixture was stirred at 0° C. for 20 min, L-7-1 (1.56 g, 3.4 mmol) was added thereto. The reaction was allowed to warm up to room temperature and stirred overnight.

The reaction was allowed to cool, quenched with MeOH (5 mL) and concentrated under reduced pressure. The residue was purified by column chromatography to obtain a compound L-7-2 (1.91 g, 93%).

EI-MS m/z: 610 (M$^+$+1).

Preparation of Compound L-7

At 0° C., to a solution of compound L-7-2 (906.7 mg, 1.49 mmol) in EA (4 mL) and ether (4 mL) under N$_2$ atmosphere was slowly added 5% HCl solution (8 mL) and triphenylphosphine (390 mg, 1.49 mmol). The mixture was stirred at 0° C. overnight. The mixture was diluted with DCM (10 mL). The aqueous layer was extracted with DCM (10 mL×3). The aqueous phase was concentrated under high vacuum to obtain compound L-7 (495 mg, 54%).

EI-MS m/z: 584 (M$^+$+1).

Example 9: Preparation of Compound L-8

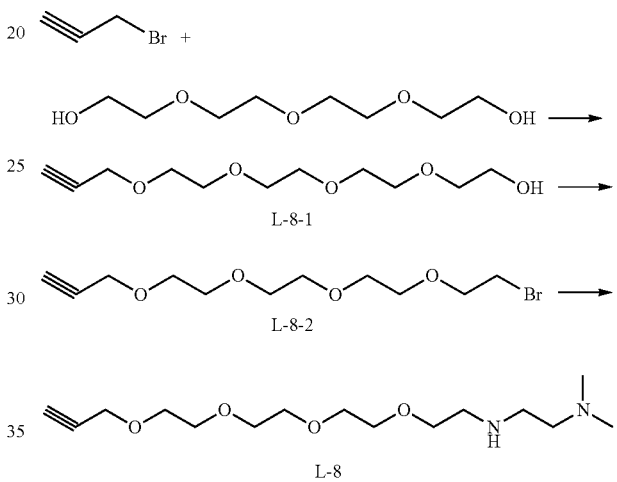

Preparation of Compound L-8-1

At −20° C. under N$_2$ atmosphere, to a solution of KOtBu (943 mg, 8.41 mmol) in dry THF (50 mL) was added tetraethylene glycol (4.35 mL, 25.22 mmol) followed by propargyl bromide (1.0 g, 8.41 mL) The reaction was allowed to warm up to room temperature and stirred for 17 hours. The reaction was quenched by the addition of MeOH (1 mL) and H$_2$O (50 mL) with cooling in an ice bath and extracted with EA (100 mL). The organic layer was dried over anhydrous Na$_2$SO$_4$, filtered and concentrated under reduced pressure. The residue was purified by column chromatography to obtain compound L-8-1 (1.46 g, 75%).

$^1$H NMR (400 MHz, CDCl$_3$) δ 4.26-4.20 (m, 2H), 3.78-3.60 (m, 16H), 2.42-2.40 (m, 1H).

Preparation of Compound L-8-2

To a solution of CBr$_4$ (1.43 g, 4.31 mmol) in dry DCM (20 mL) cooled in an ice bath was added triphenylphosphine (1.13 g, 4.31 mmol) followed by L-8-1 (500 mg, 2.15 mmol). The mixture was allowed to warm up to room temperature and stirred for 18 hours. The reaction was diluted with water (50 mL) and extracted with DCM (100 mL). The organic layer was dried over anhydrous Na$_2$SO$_4$, filtered and concentrated under reduced pressure. The residue was purified by column chromatography to obtain compound L-8-2 (410 mg, 65%).

$^1$H NMR (400 Hz, CDCl$_3$) δ 4.21 (s, 2H), 3.82 (t, J=6.4 Hz, 2H), 3.74-3.64 (m, 12H), 3.45 (t, J=6.4 Hz, 2H), 2.45-2.42 (m, 1H).

Preparation of Compound L-8

To a solution of compound L-8-2 (300 mg, 1.02 mmol) in DMF (10 mL) was added N, N-dimethylethylenediamine (555 µL, 5.08 mmol) at room temperature under N₂ atmosphere. The mixture was stirred at room temperature for 5 hours. After the reaction was completed, the mixture was concentrated under reduced pressure. The residue was purified by column chromatography to obtain compound L-8 (218 mg, 71%).

EI-MS m/z: 303 (M$^{+1}$).

Example 10: Preparation of Compound L-9

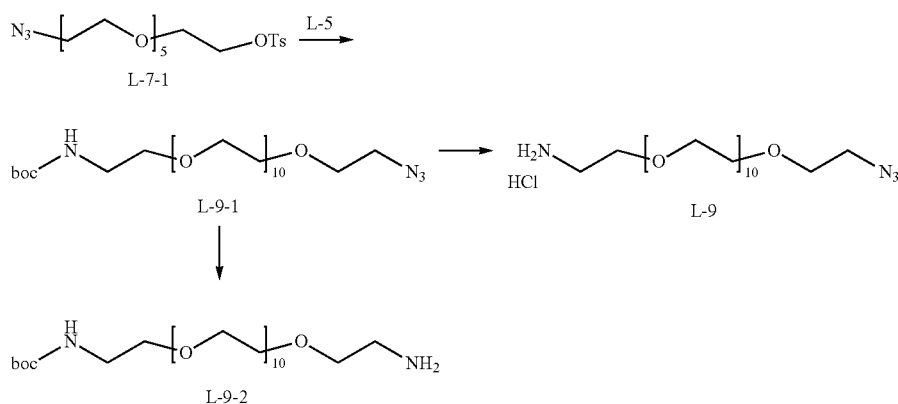

Preparation of Compound L-9-1

At 0° C. under N₂ atmosphere, to a solution of L-5 (450 mg, 1.18 mmol) in anhydrous THF (10 mL) was added NaH (60% dispersion in mineral oil, 47.2 mg, 1.18 mmol) followed by L-7-1 (544.5 mg, 1.18 mmol). The reaction was allowed warm up to room temperature and stirred overnight then cooled in an ice bath and MeOH (5 mL) was added dropwise. After the mixture was concentrated under reduced pressure, the residue was purified by column chromatography to obtain a compound L-9-1 (582.9 mg, 74%).

EI-MS m/z: 671 (M$^{+}$+1).

Preparation of Compound L-9-2

A cloudy solution of L-9-1 (112.3 mg, 0.17 mmol) in ether (1.5 mL), THF (3.0 mL) and H₂O (1.5 mL) at 0° C. under N₂ atmosphere was treated with triphenylphosphine (44 mg, 0.17 mmol, 1.0 eq.) and stirred overnight at room temperature. The mixture was diluted with water (20 mL) and extract with DCM (100 mL×3). The aqueous layer was concentrated under reduced pressure to obtain compound L-9-2 (107 mg, quant.) as colorlessness oil.

EI-MS m/z: 645 (M$^{+}$+1).

Preparation of Compound L-9

To a solution of compound L-9-1 (582.9 mg, 0.87 mmol) in DCM (3 mL) was added 4M-HCl (in 1,4-dioxane, 1 mL) at 0° C. under N₂ atmosphere. The mixture was stirred at room temperature for 2 h. The mixture was concentrated to obtain compound L-9 (527.6 mg, quant).

EI-MS m/z: 571 (M$^{+}$+1).

Example 11: Preparation of Compound L-10

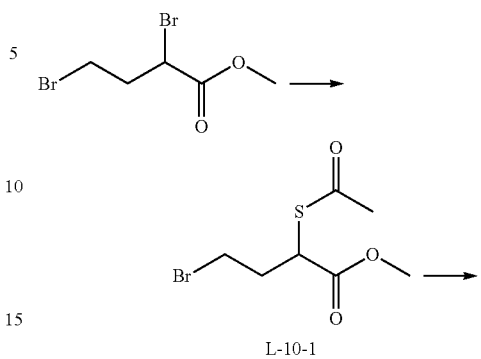

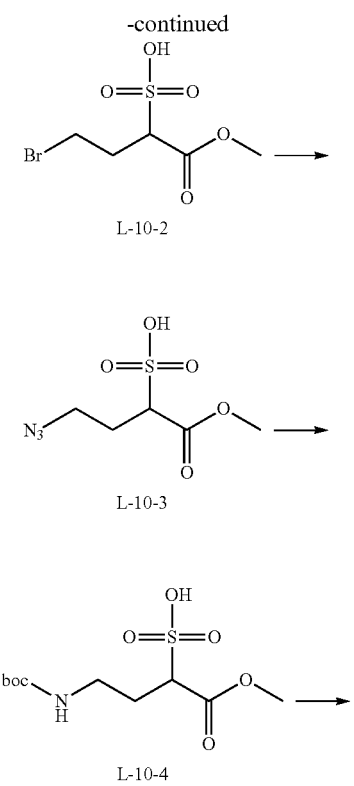

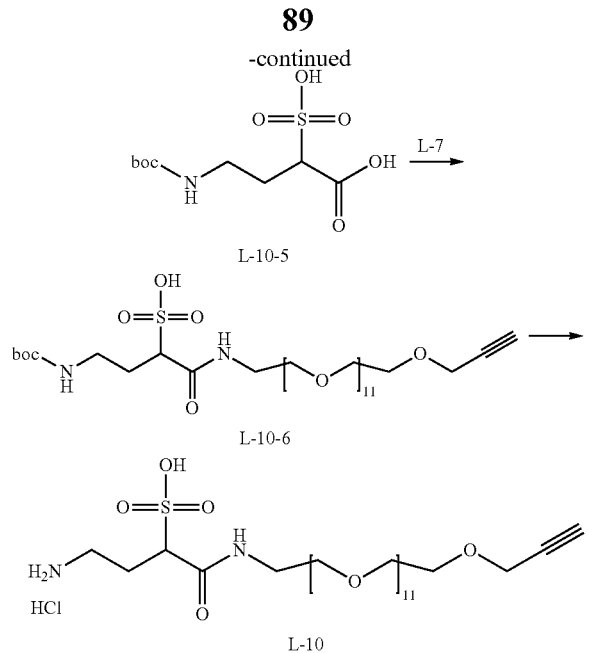

Preparation of Compound L-10-1

A homogeneous solution of methyl 2,4-dibromobutyrate (10 g, 38.47 mmol) in dry THE (100 mL) at room temperature under $N_2$ atmosphere was added dropwise the mixture of thioacetic acid (2.75 mL, 38.47 mmol, 1.0 eq.) and DIPEA (8.5 mL, 48.9 mmol, 1.3 eq.) in dry THE (50 mL) for 1.5 hour. After stirring for 4 hours at −20° C. under $N_2$ atmosphere, the mixture was concentrated, diluted with water (100 mL) and extract with EA (200 mL×3). The organic layer was dried over anhydrous $Na_2SO_4$, filtered, and concentrated under reduced pressure. The residue was purified by column chromatography (Hex:EA=12:1) to obtain compound L-10-1 (9.67 g, 98%) as white solid.

$^1$H NMR (600 MHz, CDCl$_3$) δ 4.38 (t, J=7.6 Hz, 1H), 3.46-3.39 (m, 2H), 2.56-2.47 (m, 1H), 2.36 (s, 3H), 2.32-2.23 (m, 1H).

Preparation of Compound L-10-2

L-10-1 (9.67 g, 37.90 mmol) in AcOH (80 mL) at room temperature under $N_2$ atmosphere was added 35% hydrogen peroxide (40 mL). The mixture was stirred overnight, then concentrated, diluted with water (20 mL), neutralized with NaHCO$_3$ and washed with EA/Hex (1/1, 30 mL×2). The aqueous layer was concentrated under reduced pressure. The residue was purified by column chromatography (DCM: MeOH:AcOH=8:1:0.01 to 5:1:0.01) to obtain compound L-10-2 (7.0 g, 71%) as white solid.

$^1$H NMR (600 MHz, D$_2$O) δ 4.11 (dd, J=5.4, 4.8 Hz, 1H), 3.82 (s, 3H), 3.65-3.62 (m, 1H), 3.52-3.47 (m, 1H), 2.62-2.48 (m, 2H).

Preparation of Compound L-10-3

To a solution of L-10-2 (7.0 g, 26.81 mmol) in DMF (20 mL) was added NaN$_3$ (4.5 g, 69.71 mmol, 2.6 eq) under $N_2$ atmosphere, and the mixture was stirred overnight at room temperature. After the reaction was completed, the mixture was concentrated under reduced pressure. The residue was purified by column chromatography (DCM:MeOH: AcOH=7:1:0.01 to 5:1:0.01) to obtain compound L-10-3 (5.4 g, 90%) as white solid.

$^1$H NMR (600 MHz, D$_2$O) δ 3.82 (dd, J=4.2, 6.0 Hz, 1H), 3.63 (s, 3H), 3.36-3.26 (m, 2H), 2.29-2.02 (m, 2H).

Preparation of Compound L-10-4

In a 50 mL round-bottled flask was added L-10-3 (500 mg, 2.24 mmol), 10 mL of MeOH, 5% Pd/C (715 mg, 0.34 mmol, 0.15 eq.) and Boc$_2$O (538 mg, 2.46 mmol, 1.1 eq). After sucked out air, the mixture was stirred at room temperature under H$_2$ for 15 hours. The catalyst was filtered through Celite, and the Celite was washed with MeOH (20 mL×2). The solvent was removed by rotary evaporator and the residue was purified by column chromatography (DCM: MeOH:AcOH=7:1:0.01 to 5:1:0.01) to obtain compound L-10-4 (450.2 mg, 68%) as white solid.

$^1$H NMR (600 MHz, DMSO-d6) δ 6.79 (s, 1H), 4.13 (br s, 1H), 3.55 (s, 3H), 2.88-2.80 (m, 2H), 1.96-1.88 (m, 2H), 1.36 (s, 9H).

Preparation of Compound L-10-5

A homogeneous solution of L-10-4 (100 mg, 0.34 mmol) in THF/water (4 mL/8 mL) at room temperature under $N_2$ was treated with LiOH (21.2 mg, 0.50 mmol, 1.5 eq.) and stirred for 8 hours. The reaction mixture was neutralized with 2N HCl solution and concentrated under reduced pressure. The compound L-10-5 was used directly in the next step without further purification.

EI-MS m/z: 284 (M$^+$+1).

Preparation of Compound L-10-6

A homogeneous solution of L-10-5 (0.34 mmol), N-hydroxysuccinimide (77.4 mg, 0.67 mmol, 2.0 eq.) and EDCI-HCl (260.7 mg, 1.36 mmol, 4.0 eq.) in DMF (2 mL) at room temperature under $N_2$ atmosphere was stirred overnight. The mixture was treated with L-7 (210.8 mg, 0.34 mmol, 1.0 eq.), DIPEA (177.6 uL, 1.02 mmol, 3.0 eq.) and stirred overnight. The reaction was concentrated under reduced pressure. The residue was purified by column chromatography (DCM:MeOH:AcOH=12:1:0.01 to 5:1:0.01) to obtain compound L-10-6 (159.1 mg, 55%) as yellow oil.

EI-MS m/z: 850 (M$^+$+1).

Preparation of Compound L-10

A homogeneous solution of L-10-6 (100 mg 0.12 mmol) in 1,4-dioxane (2 mL) at room temperature under $N_2$ atmosphere was treated with c-HCl (500 uL) and stirred for 30 minutes. The reaction mixture was concentrated under reduced pressure to obtain compound L-10 (92 mg, 99%) as yellow oil.

EI-MS m/z: 749 (M$^+$+1).

Example 12: Preparation of Compound L-11

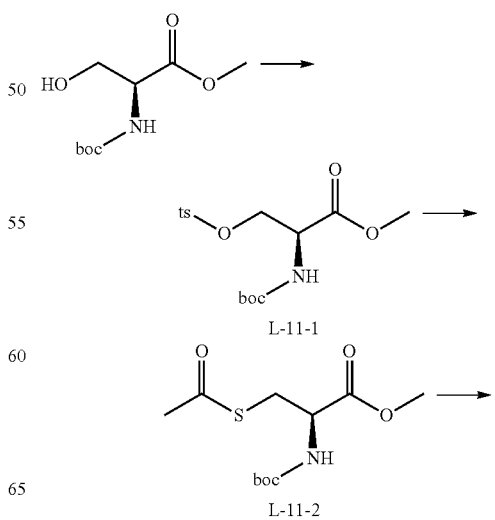

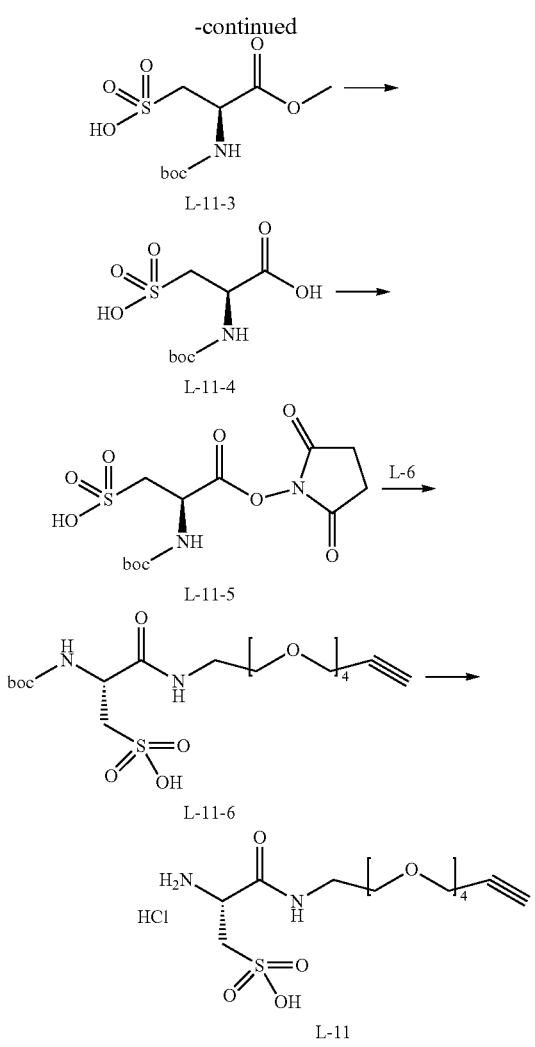

Preparation of Compound L-11-1

A homogeneous solution of Boc-L-serine methyl ester (5.0 g, 22.8 mmol) in DCM (30 mL) at room temperature under $N_2$ atmosphere was treated with pyridine (8 mL), P-toluene sulfonyl chloride (5.22 g, 27.4 mmol, 1.2 eq.) and stirred overnight. The reaction was quenched by addition of water (50 mL) and extract with EA (100 mL×3). The combined organic layer was dried over anhydrous $Na_2SO_4$, filtered, and concentrated under reduced pressure. The residue was purified by column chromatography (Hex:EA=9:1 to 2:1) to obtain compound L-11-1 (7.0 g, 82%) as white solid.

$^1$H NMR (600 MHz, $CDCl_3$) δ 7.76 (d, J=8.4 Hz, 2H), 7.35 (d, J=7.8 Hz, 2H), 5.29 (S, 1H), 4.53-4.47 (m, 1H), 4.39 (dd, J=2.4, 7.8 Hz, 1H), 4.29 (d, J=7.2, 2.4 Hz, 1H), 3.69 (s, 3H), 2.45 (s, 3H).

Preparation of Compound L-11-2

A suspension of $CsCO_3$ (1.05 g, 3.21 mmol, 0.6 eq.) in DMF (12 mL) at room temperature under $N_2$ atmosphere was treated with thioacetic acid (498 uL, 6.96 mmol, 1.3 eq.) and L-11-1 (2.0 g, 5.36 mmol) in DMF (8 mL) and stirred overnight. The mixture was quenched by addition of water (50 mL) and extracted of with EA (100 mL×3). The organic layer was dried over anhydrous $Na_2SO_4$, filtered, and concentrated under reduced pressure. The residue was purified by column chromatography (Hex:EA=5:1) to obtain compound L-11-2 (1.4 g, 95%) as white solid.

$^1$H NMR (600 MHz, $CDCl_3$) δ 5.24 (s, 1H), 4.53-4.49 (m, 1H), 3.75 (s, 3H), 2.45 (s, 3H), 4.41-4.31 (m, 2H).

Preparation of Compound L-11-3

L-11-2 (1.2 g, 4.33 mmol) in AcOH (10 mL) at room temperature under $N_2$ atmosphere was added 35% hydrogen peroxide (4 mL). The mixture was stirred for 7 hours, then concentrated under reduced pressure. The residue was diluted with water (5 mL) and basified using saturated aqueous solution of $NaHCO_3$ at 0° C. to a pH of 9. $Boc_2O$ (1.4 g, 6.49 mmol, 1.5 eq.) was added and the resultant mixture was stirred overnight. The mixture was neutralized with 2N HCl at 0° C. and concentrated under reduced pressure. The residue was purified by column chromatography (DCM:MeOH:AcOH=8:1:0.01 to 5:1:0.01) to obtain compound L-11-3 (521.5 mg, 42%) as white solid.

$^1$H NMR (400 MHz, DMSO-d6) δ 6.96 (d, J=7.2 Hz, 1H), 4.20 (q, J=6.8, 4.8 Hz, 1H), 3.58 (s, 3H), 2.84 (dd, J=14, 6.4 Hz, 1H), 2.76 (dd, J=9.2, 4.4 Hz, 1H), 1.37 (s, 9H).

Preparation of Compound L-11-4

A homogeneous solution of L-11-3 (71 mg, 0.25 mmol) in $THF/H_2O$ (2.0 mL/4.0 mL) at room temperature under $N_2$ atmosphere was treated with LiOH (17.3 mg, 0.41, 1.5 eq.) and stirred for 3 hours. The mixture was neutralized with 2N HCl at 0° C. and concentrated under reduced pressure to obtain compound L-11-4 (67 mg, 99%) as white solid.

$^1$H NMR (400 MHz, DMSO-d6) δ 6.40 (d, J=7.2 Hz, 1H), 3.96 (q, J=6.4, 5.6 Hz, 1H), 2.88-2.78 (m, 2H), 1.36 (s, 9H).

Preparation of Compound L-11-5

L-11-4 (35 mg, 0.13 mmol), N-hydroxysuccinimide (22.4 mg, 0.19 mmol, 1.5 eq.) and EDCI-HCl (50 mg, 0.26 mmol, 2.0 eq.) were dissolved in DMF (2 mL) at room temperature under $N_2$ atmosphere. After the mixture was stirred overnight, the compound L-11-5 was used directly in the next step without further purification.

EI-MS m/z: 367 ($M^+$+1).

Preparation of Compound L-11-6

To a stirred solution of L-11-5 (0.13 mmol) in DMF (2 mL) at room temperature under $N_2$ atmosphere was added N-hydroxysuccinimide (22.4 mg, 0.19 mmol, 1.5 eq.) and EDCI-HCl (50 mg, 0.26 mmol, 2.0 eq.). The mixture was stirred overnight at room temperature. After the resulting mixture was concentrated under reduced pressure, the residue was purified by column chromatography (DCM:MeOH:AcOH=12:1:0.01 to 5:1:0.01) to obtain compound L-11-6 (34.8 mg, 64%) as yellow oil.

EI-MS m/z: 483 ($M^+$+1).

Preparation of Compound L-11 c-HCl (300 uL) was added to a stirred solution of L-11-6 (29.6 mg 0.061 mmol in 1,4-dioxane (1.2 mL) at room temperature under $N_2$ atmosphere and the mixture stirred for 30 minutes. The mixture was concentrated under reduced pressure to obtain compound L-11 (25.4 mg, 99%) as yellow oil.

EI-MS m/z: 382 ($M^+$+1).

Example 13: Preparation of Compound L-12

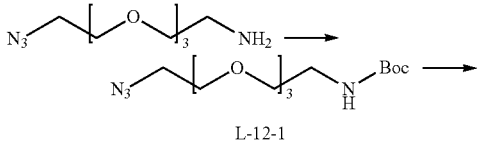

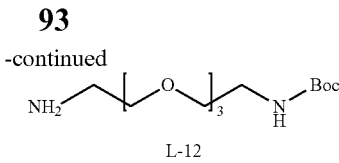

Preparation of Compound L-12-1

A clear solution of 11-azido-3,6,9-trioxaundecan-1-amine (Aldrich, CAS 134179-38-7, 5.0 g, 22.9 mmol) in 1,4-dioxane (100 mL) and H$_2$O (25 mL) at room temperature under N$_2$ atmosphere was treated with NaHCO$_3$ (3.8 g, 45.8 mmol, 2.0 eq.) and BOC$_2$O (6.0 g, 27.5 mmol, 1.2 eq.) and then stirred for 6 hours. The reaction was quenched with water (50 mL) and extracted with DCM (100 mL×3). The organic layer was dried over anhydrous Na$_2$SO$_4$, filtered, and concentrated under reduced pressure. The residue was purified by column chromatography (1% to 3% MeOH in DCM) to obtain compound L-12-1 (7.2 g, 99%) as colorlessness oil.

$^1$H NMR (400 MHz, CDCl$_3$) δ 5.03 (br s, 1H), 3.72-3.60 (m, 10H), 3.98-3.52 (m, 1H), 3.43-3.36 (m, 1H), 3.35-3.24 (m, 1H), 1.26 (s, 9H).

EI-MS m/z: 319 (M$^+$+1).

Preparation of Compound L-12

A clear solution of L-12-1 (7.2 g, 22.6 mmol) in THF (30 mL), Ether (15 mL) and H$_2$O (15 mL) at room temperature under N$_2$ atmosphere was treated with triphenylphosphine (6.5 g, 24.9 mmol, 1.1 eq.) and then stirred overnight. The reaction mixture was diluted with water (10 mL) and extract with DCM (60 mL×3). The water layer was concentrated under reduced pressure to obtain compound L-12-1 (6.3 g, 95%) as colorlessness oil.

EI-MS m/z: 293 (M$^+$+1)

Example 14: Preparation of Compound L-13

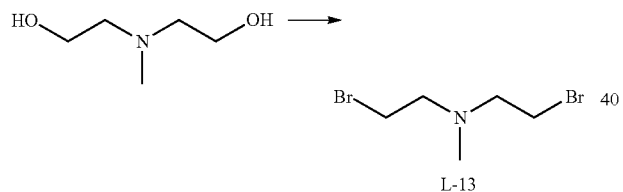

A homogeneous solution of N-methyldiethanolamine (50 mg, 0.42 mmol) in DCM (3.0 mL) at 0° C. under N$_2$ atmosphere was treated with 1M PBr$_3$ (2.0 mL, 2.10 mmol, 5.0 eq.) and stirred overnight at 37° C. The reaction mixture was extracted with DCM (50 mL) and washed with saturated NaHCO$_3$ (50 mL) and water (50 mL). After the organic layer was dried over anhydrous Na$_2$SO$_4$, filtered and N$_2$ bubbled to remove the solvent, the compound L-13 was used directly in the next step without further purification.

EI-MS m/z: 245 (M$^+$+1).

Example 15: Preparation of Compound Int-2

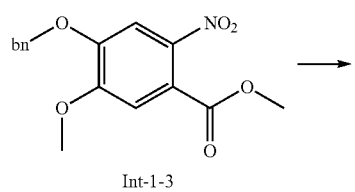

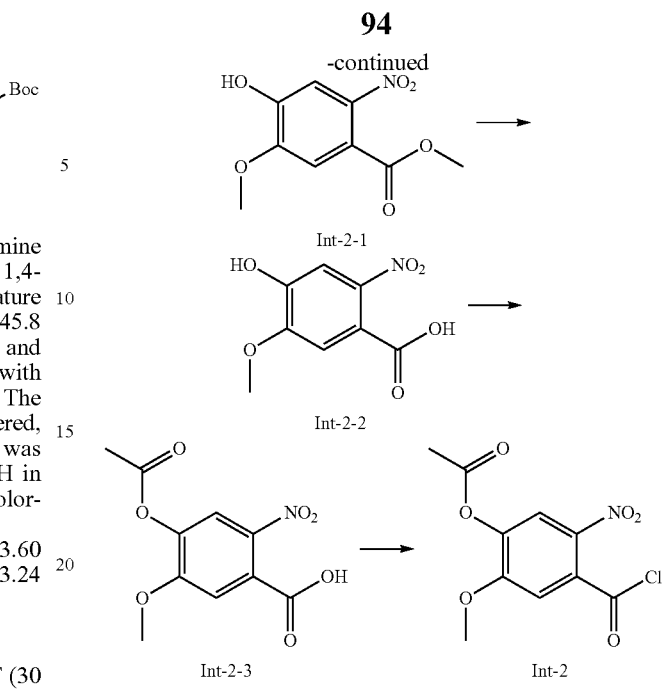

Preparation of Compound Int-2-1

To a brown solution of compound Int-1-3 (24.8 g, 78.2 mmol) in DCM (500 mL) at −78° C. under N$_2$ atmosphere was added 1M BCl$_3$ in DCM (93.8 mL, 93.8 mmol, 1.2 eq.) and stirred for 3 hours. After the reaction was quenched with MeOH (100 mL), the mixture was allowed to warm up to room temperature and then concentrated under reduced pressure. The resultant residue was dissolved in DCM (600 mL). The resultant mixture was washed with saturated NaHCO$_3$ (100 mL) and brine (100 mL), then dried over anhydrous Na$_2$SO$_4$, filtered. Removal of solvent gave Int-2-1 (17.5 g, 98%) as yellow solid.

$^1$H NMR (400 MHz, CDCl$_3$) δ 7.47 (s, 1H), 7.14 (s, 1H), 6.03 (s, 1H), 4.02 (s, 3H), 3.90 (s, 3H).

Preparation of Compound Int-2-2

A brown solution of compound Int-2-1 (17.5 g, 77.03 mmol) in 1,4-dioxane (250 mL) at room temperature under N$_2$ atmosphere was treated with 6N NaOH (38.5 mL, 231.0 mmol). After stirring for 5 hours at 40° C., the mixture was allowed to cool to 0° C. and acidified with 2N HCl. The mixture was diluted with H$_2$O (150 mL) and extracted with EA (300 mL×3). The combined organic layer was dried over anhydrous Na$_2$SO$_4$, filtered and concentrated under reduced pressure. The resultant precipitate was collected by filtration, washed with hexane, and dried under vacuum to obtain compound Int-2-2 (15.9 g, 97%) as yellow solid.

$^1$H NMR (400 MHz, DMSO-d6) δ 10.6 (br s, 1H), 7.31 (s, 1H), 7.25 (s, 1H), 3.90 (s, 3H), 3.57 (s, 3H).

Preparation of Compound Int-2-3

A brown solution of compound Int-2-2 (15.9 g, 74.6 mmol) in anhydrous THF (370 mL) at room temperature under N$_2$ atmosphere was treated with DMAP (1.8 g, 14.92 mmol, 0.2 eq.), acetic anhydride (8.5 mL, 87.5 mmol, 1.2 eq) and TEA (15.6 mL, 111.9 mmol, 1.5 eq) and stirred for 6 hours. The reaction mixture was diluted with water (150 mL) and extract with EA (300 mL×2). The combined organic layer was dried over anhydrous Na$_2$SO$_4$, filtered, and concentrated under reduced pressure to obtain compound Int-2-3 (18 g, 95%) as yellow solid.

$^1$H NMR (400 MHz, DMSO-d$_6$) δ 7.99 (s, 1H), 7.46 (s, 1H), 3.94 (s, 3H), 2.30 (s, 3H).

Preparation of Compound Int-2

A brown solution of compound Int-2-3 (14.4 g, 56.43 mmol) in anhydrous THF (15 mL) and anhydrous DCM (40 mL) at 0° C. under N$_2$ atmosphere was treated with oxalyl chloride (7.6 mL, 84.64 mmol, 1.5 eq) and DMF (2 drops) and stirred for 6 hours. The reaction mixture was concentrated under reduced pressure. The compound Int-2 was used directly in the next step without further purification.

Example 16: Preparation of BGal-Br (Hereinafter "Int-TG")

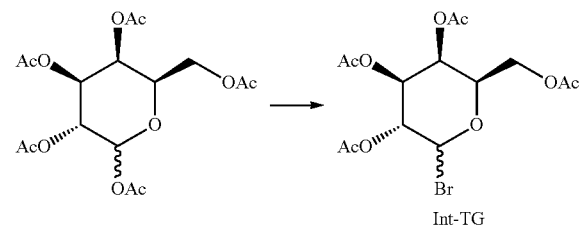 [SMILES: CC(=O)OC[C@H]1OC(OC(C)=O)[C@H](OC(C)=O)[C@@H](OC(C)=O)[C@H]1OC(C)=O ; CC(=O)OC[C@H]1OC(Br)[C@H](OC(C)=O)[C@@H](OC(C)=O)[C@H]1OC(C)=O]

β-D-galactose pentaacetate (Alfa, CAS 4163-60-4, 5.0 g, 12.81 mmol) was dissolved in 33% HBr in AcOH (20 mL) at 0° C. under N$_2$ atmosphere. The mixture was allowed to warm up to room temperature and stirred for 4 hours. All volatile materials were removed by rotary evaporator. The resultant residue was quenched with saturated sodium bicarbonate (1000 mL) and extracted with EA (1000 mL). The organic layer was dried over anhydrous Na$_2$SO$_4$, filtered, and concentrated under reduced pressure. The residue was purified by column chromatography to obtain compound Int-TG (5.2 g, 99%).

$^1$H NMR (400 Hz, CDCl$_3$) δ 6.70 (d, J=4.0 Hz, 1H), 5.52 (d, J=2.4 Hz, 1H), 5.41 (dd, J=7.6, 2.8 Hz, 1H), 5.05 (dd, J=6.4, 4.0 Hz, 1H), 4.49 (t, J=6.4 Hz, 1H), 4.22-4.09 (m, 2H), 2.16-2.01 (m, 12H).

Example 17: Preparation of Compound Int-TG1 and Int-TG2

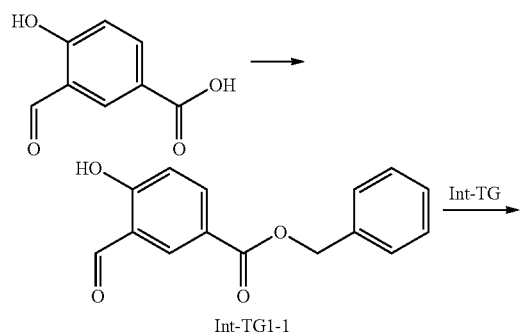

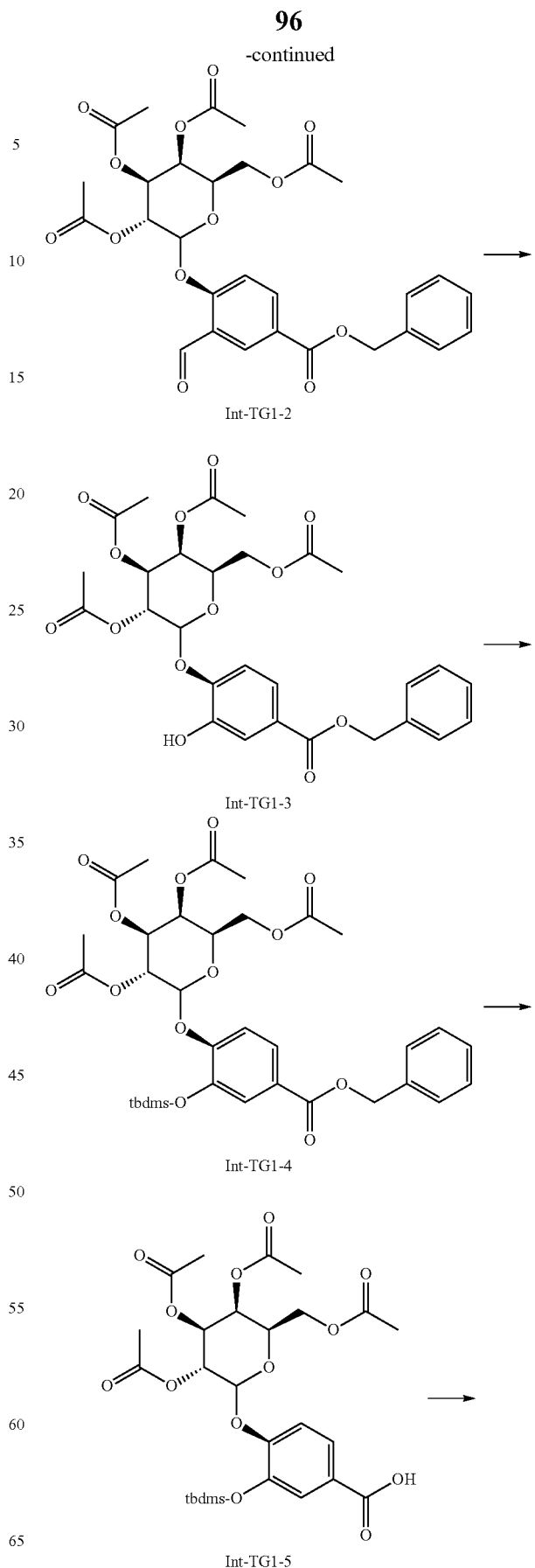

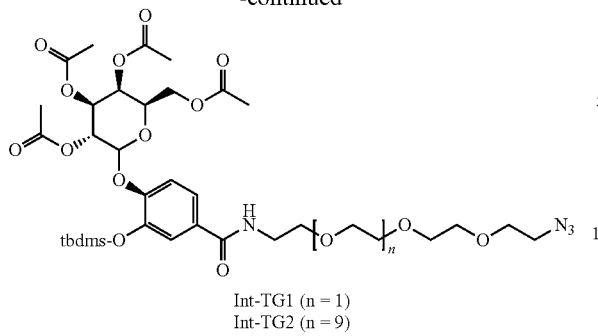

Int-TG1 (n = 1)
Int-TG2 (n = 9)

Preparation of Compound Int-TG1-1

To a solution of the 3-formyl-4-hydroxybenzoic acid (5 g, 43.06 mmol) in DMIF (100 mL) was added benzyl bromide (5.1 mL, 43.06 mmol) and NaHCO$_3$ (2.53 g, 43.06 mmol) at room temperature under N$_2$ atmosphere. The mixture was stirred overnight at room temperature under N$_2$ atmosphere. The reaction was diluted with water (100 mL) and extracted with EA (200 mL×2). The obtained organic layer was dried over anhydrous Na$_2$SO$_4$, filtered, and concentrated under reduced pressure. The residue was purified by column chromatography to obtain compound Int-TG1-1 (2.56 g, 39%).

$^1$HNMR (400 Hz, CDCl$_3$) δ 11.41 (s, 1H), 9.95 (s, 1H), 8.34 (d, J=2.0 Hz, 1H), 8.23 (dd, J=6.4 Hz, 2.4 Hz, 1H), 7.46-7.35 (m, 5H), 7.04 (d, J=9.2 Hz, 1H), 5.37 (s, 2H).

Preparation of Compound Int-TG1-2

To a solution of compound Int-TG-1 (1.0 g, 3.90 mmol) and compound Int-TG (1.6 g, 3.90 mmol) in anhydrous ACN (30 mL) was added molecular sieve (8 g) and Ag$_2$O (3.62 g, 15.61 mmol) at room temperature under N$_2$ atmosphere. After stirring for 1 hour, the mixture was diluted with ACN (30 mL) and filtered through Celite. The filtrate was concentrated under reduced pressure and purified by column chromatography to obtain compound Int-TG1-2 (2.1 g, 92%).

$^1$H NMR (400 Hz, CDCl$_3$) δ 10.34 (s, 1H), 8.55 (d, J=2.0 Hz, 1H), 8.26 (dd, J=6.8, 2.0 Hz, 1H), 7.45-7.35 (m, 5H), 7.17 (d, J=8.8 Hz, 1H), 5.63-5.60 (m, 1H), 5.50 (d, J=3.6 Hz, 1H), 5.37 (s, 2H), 5.23 (d, J=8.0 Hz, 1H), 5.16 (dd, J=7.2, 3.6 Hz, 1H) 4.24-4.10 (m, 4H), 2.20 (s, 3H), 2.10-2.03 (m, 9H).

Preparation of Compound Int-TG1-3

To a solution of compound Int-TG1-2 (2.1 g, 3.58 mmol) in DCM (30 mL) was added m-CPBA (2.65 g, 10.74 mmol) at 0° C. under N$_2$ atmosphere. After stirring for 7 hours at 0° C., the mixture was quenched by addition of saturated sodium bicarbonate (40 mL×2). The mixture was separated and the organic layers were washed with brine, dried over Na$_2$SO$_4$, filtered, and concentrated under reduced pressure. The residue was dissolved in DCM (5 mL) then cooled in an ice bath and hydrazine-hydrate (261 µL, 5.37 mmol) was added. After stirring at 0° C. for 1 hour, the reaction was quenched with 1M HCl (10 mL) and extracted with EA (30 mL×2). The organic layer was dried over anhydrous Na$_2$SO$_4$, filtered and concentrated under reduced pressure to obtain compound Int-TG1-3 (1.1 g, 55%).

EI-MS m/z: 574 (M$^+$+Na)

Preparation of Compound Int-TG1-4

To a solution of compound Int-TG1-3 (280 mg, 0.49 mmol) in DCM (5 mL) was added TBDMS-OTf (224 µL, 0.97 mmol) and Et$_3$N (207 µL, 1.46 mmol) at 0° C. under N$_2$ atmosphere. The mixture was stirred for 1.5 hours at room temperature, and then quenched by addition of citric acid (20 mL). The organic layer was washed with brine (20 mL) and water (20 mL), dried over Na$_2$SO$_4$, filtered, and concentrated under reduced pressure. The residue was purified by column chromatography to obtain compound Int-TG1-4 (246.3 mg, 68%).

$^1$H NMR (400 Hz, CDCl$_3$) δ 7.67 (d, J=8.4 Hz, 1H), 7.57 (s, 1H), 7.44-7.34 (m, 5H), 7.02 (d, J=8.4 Hz, 1H), 5.49-5.44 (m, 2H), 5.30 (s, 2H), 5.19 (d, J=7.6 Hz, 1H), 5.10 (dd, J=6.8, 3.2 Hz, 1H) 4.20-4.11 (m, 2H), 4.05 (t, J=6.8 Hz, 2H), 2.19 (s, 3H), 2.04 (s, 3H), 2.01 (d, J=6.0 Hz, 6H), 1.02 (s, 9H), 0.20 (d, J=15.6 Hz, 6H).

Preparation of Compound Int-TG1-5

Palladium on carbon, 5% Pd/C (87.5 mg, 0.04 mmol) was added to a stirred solution of Int-TG1-4 (283.2 mg, 0.41 mmol) in EA (5 mL) under N$_2$ atmosphere. The flask was flushed by bubbling hydrogen gas through the solution at room temperature. The mixture was stirred at the same temperature for 1 hours. The mixture was diluted with EA (30 mL), filtered through Celite, the Celite plug washed with EA (50 mL×2). The filtrate was concentrated under reduced pressure. The compound Int-TG1-5 was used directly in the next step without further purification (246 mg, quant).

$^1$H NMR (400 Hz, CDCl$_3$) δ 7.67 (d, J=8.8 Hz, 1H), 7.57 (s, 1H), 7.05 (d, J=8.4 Hz, 1H), 5.49-5.45 (m, 2H), 5.22 (d, J=7.6 Hz, 1H), 5.12 (dd, J=7.2, 3.6 Hz, 1H) 4.20-4.06 (m, 4H), 2.19 (s, 3H), 2.05 (s, 3H), 2.02 (d, J=7.6 Hz, 6H), 1.01 (s, 9H), 0.21 (d, J=15.2 Hz, 6H).

Preparation of Compound Int-TG1

To a solution of compound Int-TG1-5 (243.2 mg, 0.41 mmol) and 11-azido-3,6,9-trioxaundecan-1-amine (Aldrich, CAS 134179-38-7, 89.5 mg, 0.41 mmol) in DMF (5 mL) were added PyBOP (275 mg, 0.53 mmol) and DIPEA (176 uL, 1.02 mmol) at room temperature under N$_2$ atmosphere. The mixture was stirred for 2 hours at room temperature under N$_2$ atmosphere. The reaction was distilled water (10 mL) and extracted with EA (30 mL×2). The obtained organic layer was dried over anhydrous Na$_2$SO$_4$, filtered, and concentrated under reduced pressure. The residue was purified by column chromatography to obtain compound Int-TG1 (272.8 mg, 84%).

$^1$H NMR (400 Hz, CDCl$_3$) δ 7.34 (s, 1H), 7.31 (d, J=9.2 Hz, 1H), 7.02 (d, J=8.0 Hz, 1H), 6.73 (s, 1H), 5.48-5.44 (m, 2H), 5.19 (d, J=7.6 Hz, 1H), 5.10 (dd, J=6.4, 3.6 Hz, 1H), 4.20-4.10 (m, 2H), 4.06 (t, J=6.4 Hz, 2H), 3.66 (s, 14H), 3.38 (t, J=4.4 Hz, 2H), 2.19 (s, 3H), 2.02 (t, J=8.4 Hz, 9H), 1.00 (s, 9H), 0.20 (d, J=14.4 Hz, 6H).

EI-MS m/z: 799 (M$^+$+1).

Preparation of Compound Int-TG2

To a solution of compound Int-TG1-5 (246 mg, 0.41 mmol) and L-9 (249.5 mg, 0.41 mmol) in DMF (3 mL) were added PyBOP (278 mg, 0.53 mmol) and DIPEA (179 uL, 1.02 mmol) at room temperature under N$_2$ atmosphere. After the mixture was stirred for 2 hours, the reaction mixture was subjected to preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain a compound Int-TG2 (384.6 mg, 81%). EI-MS m/z: 1152 (M$^{+1}$).

Example 18: Preparation of Compound Int-TG3
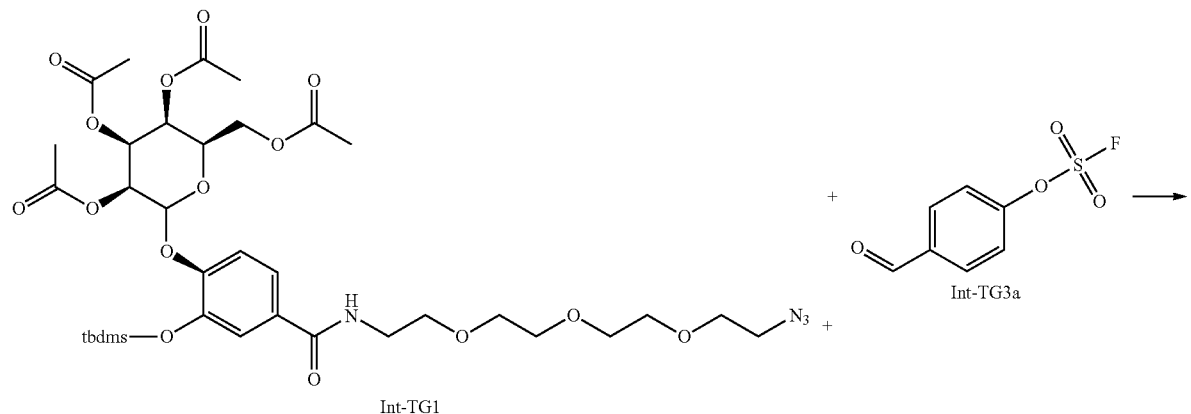
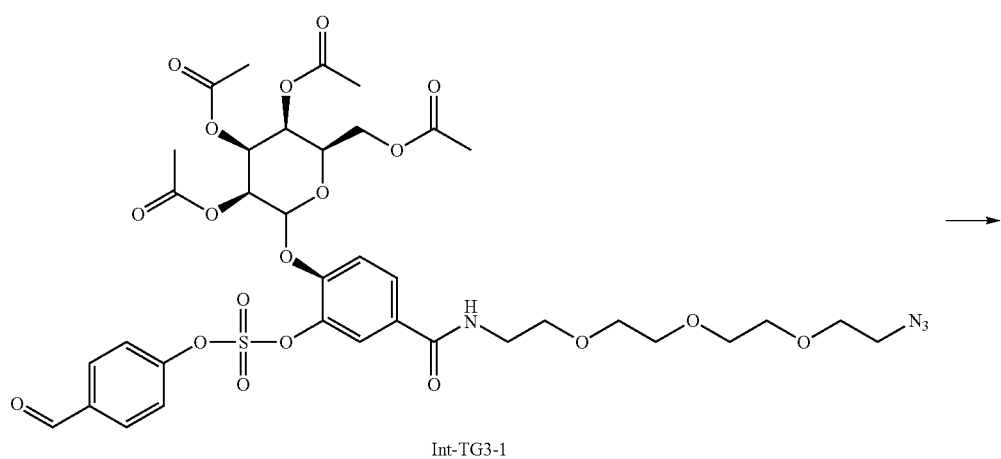
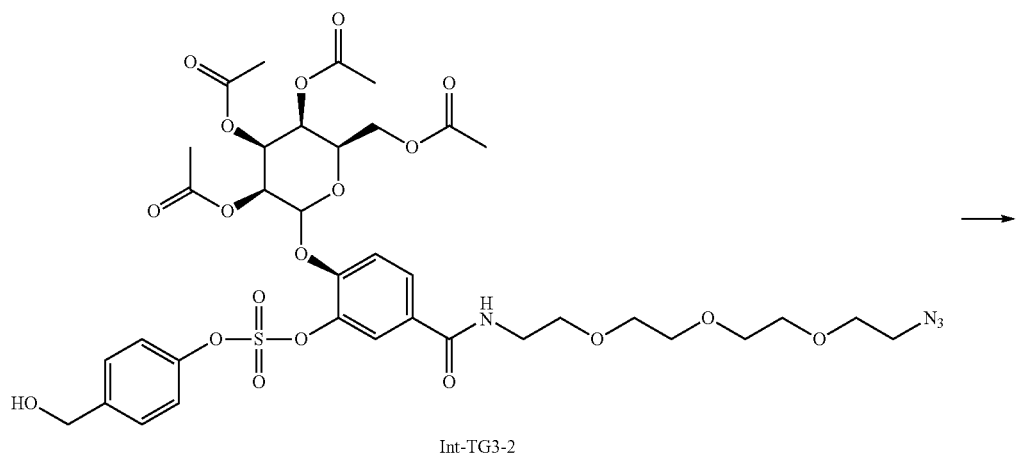

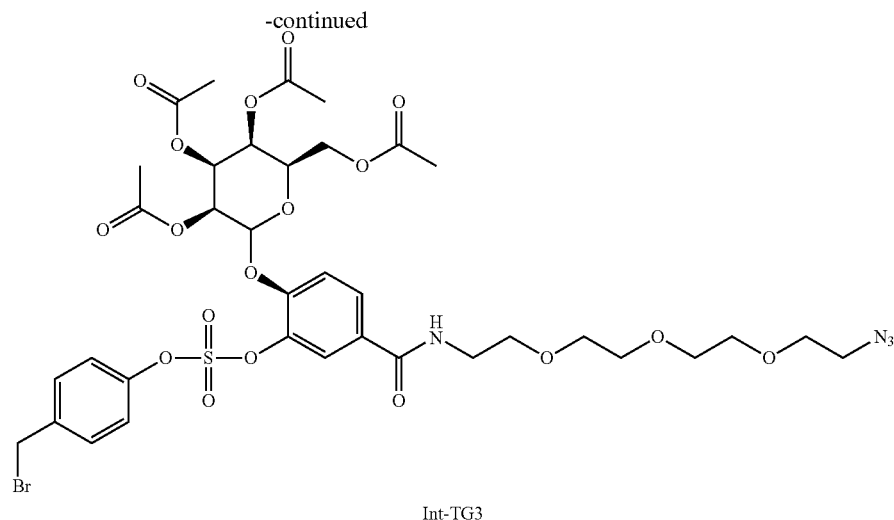

Int-TG3

Preparation of Compound Int-TG3a

To a solution of 4-hydroxybenzaldehyde (1 g, 8.19 mmol) in DCM (3 mL) was added Et$_3$N (2.28 mL, 16.38 mmol) at room temperature under N$_2$ atmosphere. SO$_2$F$_2$ gas was introduced via balloon, and the mixture was stirred at room temperature for 2 hours. The mixture was extracted with DCM (30 mL×3) and brine (30 mL), the organic layer was dried over anhydrous Na$_2$SO$_4$, filtered and concentrated under reduced pressure. The residue was purified by column chromatography to obtain compound Int-TG3a (790 mg, 63%).

$^1$H NMR (400 Hz, CDCl$_3$) δ 10.06 (s, 1H), 8.05 (d, J=8.0 Hz, 2H), 7.55 (d, J=8.8 Hz, 2H).

Preparation of Compound Int-TG3-1

To a solution of compound Int-TG1 (100 mg, 0.13 mmol) and compound Int-TG3a (26 mg, 0.13 mmol) in anhydrous ACN (3 mL) was added DBU (4 µL, 25 µmol). The mixture was stirred at room temperature for 1 hour, washed with distilled water (10 mL) and extracted with EA (15 mL×2). The organic layer was dried over anhydrous Na$_2$SO$_4$, filtered and concentrated under reduced pressure. The residue was purified by column chromatography to obtain compound Int-TG3-1 (103 mg, 94%).

EI-MS m/z: 869 (M$^+$+1).

Preparation of Compound Int-TG3-2

To a solution of compound Int-TG3-1 (103 mg, 0.12 mmol) in THF (8 mL) was added NaBH$_4$ (9 mg, 0.24 mmol) at 0° C. under N$_2$ atmosphere. After stirring for 2 hours, the reaction was quenched with distilled water (10 mL) and extracted with EA (10 mL×2). The organic layer was dried over anhydrous Na$_2$SO$_4$, filtered and concentrated under reduced pressure to obtain compound Int-TG3-2 (101 mg, 98%).

EI-MS m/z: 871 (M$^+$+1).

Preparation of Compound Int-TG3

To a solution of compound Int-TG3-2 (320.5 mg, 0.0.37 mmol) in DCM (3 ml) was added 1M PBr$_3$ in DCM (165 ul, 0.19 mmol) at 0° C. under N$_2$ atmosphere. After stirring for 2 hours, the mixture was quenched by addition of saturated sodium bicarbonate (8 mL×2). The organic layers were washed with brine, dried over Na$_2$SO$_4$, filtered, and concentrated under reduced pressure. The residue was purified by column chromatography to produce compound Int-TG3 (202.6 mg, 59%)

EI-MS m/z: 934 (M$^+$+1).

Example 19: Preparation of Compound Int-TG4

Int-TG1 ⟶

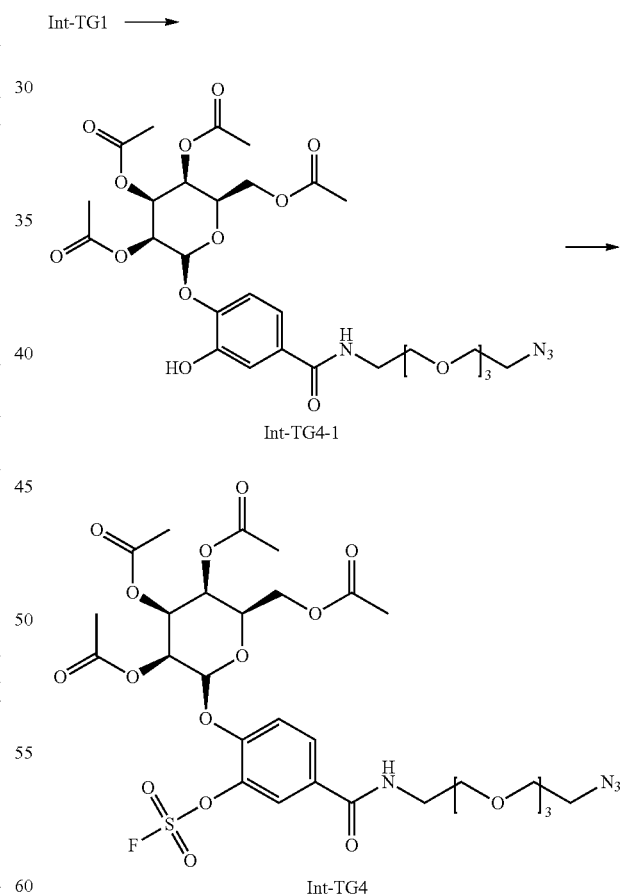

Int-TG4-1

Int-TG4

Preparation of Compound Int-TG4-1

A homogeneous solution of compound Int-TG1 (210 mg, 0.26 mmol) in dry THF (2 mL) at room temperature under N$_2$ atmosphere was treated with 1M TBAF in THF (315 µL, 0.32 mmol, 1.2 eq.) and stirred for 1 hour. The reaction mixture was diluted with water (100 mL) and extract with EA (200 mL×2). The organic layer was dried over anhydrous $Na_2SO_4$, filtered, and concentrated under reduced pressure. The residue was purified by column chromatography (Hex: EA=2:1) to obtain compound Int-TG4-1 (151 mg, 84%) as white foam solid.

$^1$H NMR (400 Hz, $CDCl_3$) δ 7.36-7.33 (m, 2H), 7.00 (d, J=7.6 Hz, 1H), 6.72-6.64 (m, 1H), 6.05 (s, 1H), 5.52-5.44 (m, 2H), 5.18-5.12 (m, 1H), 4.98 (d, J=8.0 Hz, 1H), 4.28-4.07 (m, 3H), 3.70-3.62 (m, 14H), 3.36 (t, J=4.8 Hz, 2H), 2.22 (s, 3H), 2.12 (s, 3H), 2.0 (s, 3H), 2.03 (s, 3H); EI-MS m/z: 685 (M$^+$+1).

Preparation of Compound Int-TG4

A homogeneous solution of compound Int-TG4-1 (151 mg, 0.22 mmol) in DCM (5 mL) at room temperature under $N_2$ atmosphere was treated TEA (92.4 μL, 0.66 mmol, 3.0 eq.), $SO_2F_2$ gas was introduced via balloon, and stirred for 16 hours. Then mixture was extracted with EA (100 mL) and water (100 mL). The organic layer was dried over anhydrous $Na_2SO_4$, filtered, and concentrated under reduced pressure. The residue was purified by column chromatography (Hex: EA=1:1) to obtain compound Int-TG4 (137 mg, 81%) as white foam solid.

$^1$H NMR (400 Hz, $CDCl_3$) δ 7.88 (s, 1H), 7.68 (d, J=8.8 Hz, 1H), 7.30 (d, J=8.8 Hz, 1H), 7.05 (br s, 1H), 5.62-5.56 (m, 1H), 5.48 (d, J=2.8 Hz 1H), 5.17 (d, J=8.0 Hz, 1H), 5.12 (dd, J=7.2, 3.2 Hz, 1H), 4.26-4.08 (m, 3H), 3.72-3.60 (m, 14H), 3.36 (t, J=4.8 Hz, 2H), 2.20 (s, 3H), 2.08 (s, 6H), 2.02 (s, 3H); EI-MS m/z: 767 (M$^+$+1).

Example 20: Preparation of Compound Int-TG5 and TG-6

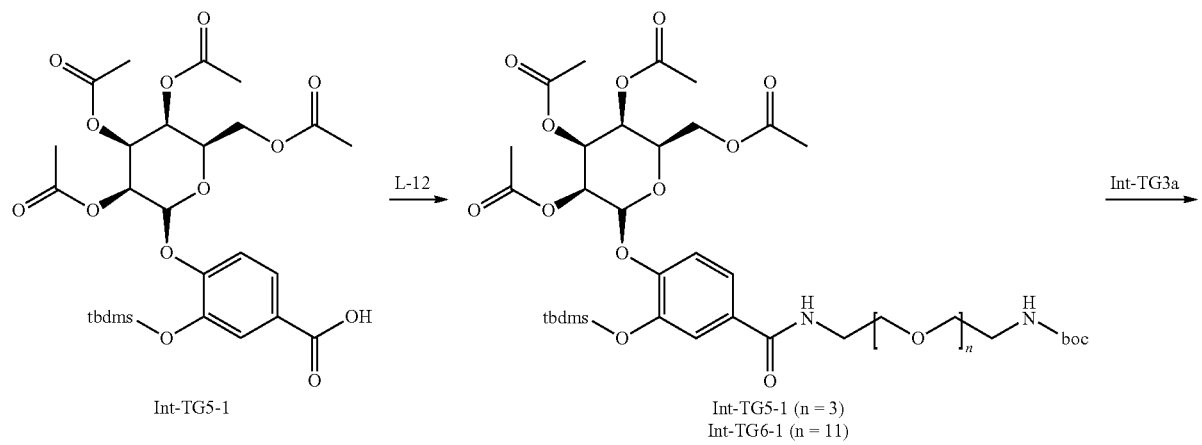

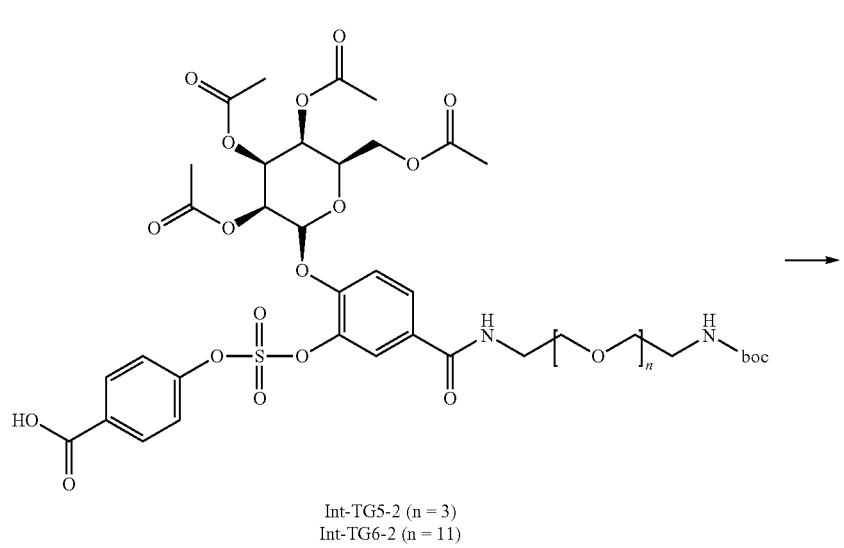

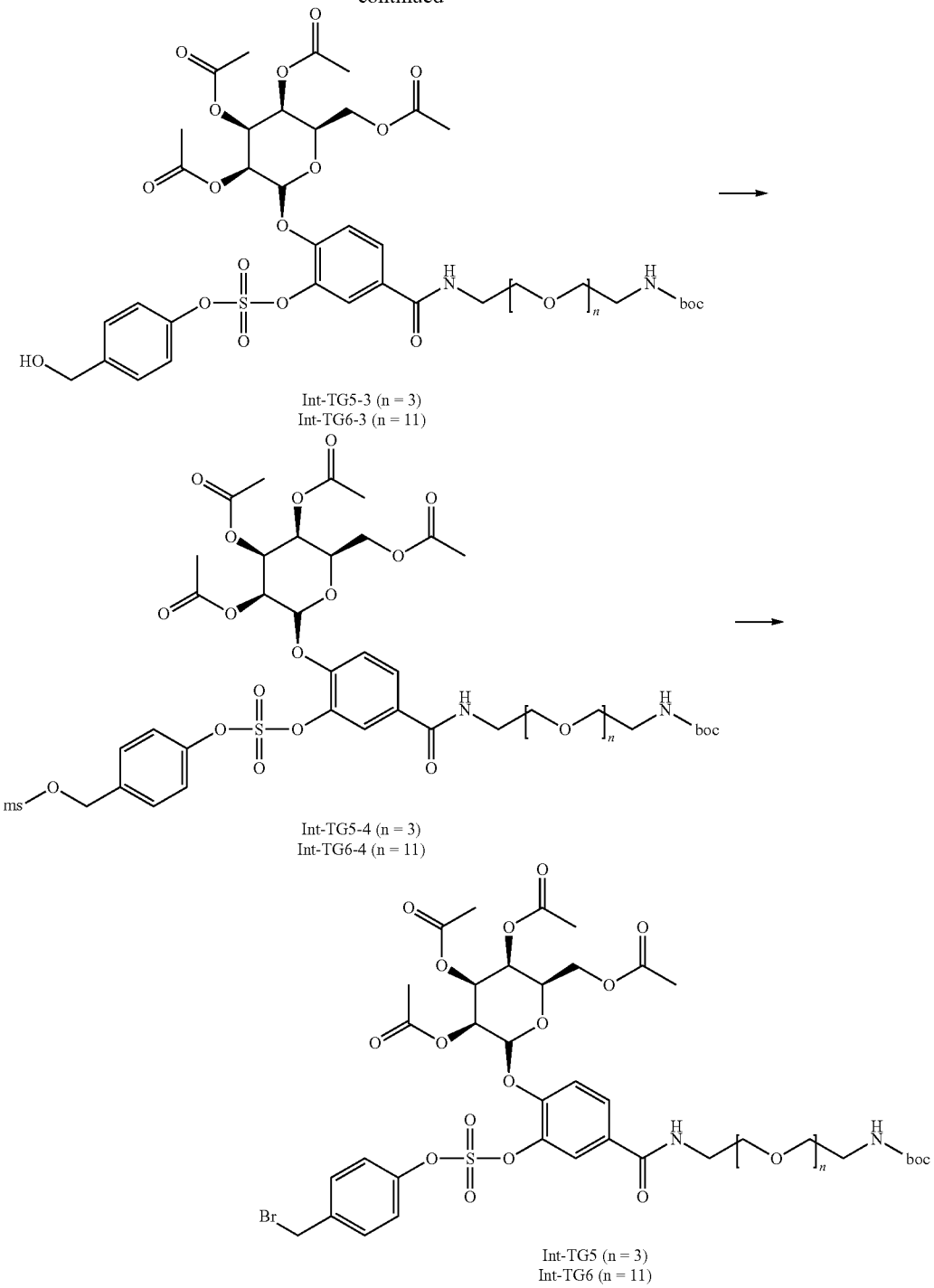

Int-TG5-3 (n = 3)
Int-TG6-3 (n = 11)

Int-TG5-4 (n = 3)
Int-TG6-4 (n = 11)

Int-TG5 (n = 3)
Int-TG6 (n = 11)

Preparation of Compound Int-TG5-1

A homogeneous solution of compound Int-TG1-5 (1.0 g, 0.26 mmol) and L-12 (586 mg, 2.0 mmol, 1.2 eq.) in DMF (10 mL) at room temperature under $N_2$ atmosphere was treated with PyBOP (1.13 g, 2.17 mmol, 1.3 eq.), DIPEA (873 uL, 5.01 mmol, 3.0 eq.) and stirred for 4 hours. The reaction was quenched with water (20 mL) and extracted with EA (30 mL×2). The organic layer was dried over anhydrous $Na_2SO_4$, filtered and concentrated under reduced pressure. The residue was purified by column chromatography (Hex:EA=1:1 to 1:3) to obtain compound Int-TG5-1 (1.05 g, 72%) as white foam solid.

EI-MS m/z: 874 (M$^+$+1).

Preparation of Compound Int-TG5-2

A homogeneous solution of compound Int-TG5-1 (500 mg, 0.57 mmol) and compound Int-TG3a (140 mg, 0.69 mmol, 1.2 eq.) in anhydrous ACN (10 mL) at room temperature under $N_2$ atmosphere was treated with BEMP (66.3 μL, 0.23 mmol, 0.4 eq.) and stirred for 4 hours. The reaction was quenched with water (20 mL) and extracted with EA (30 mL×2). The organic layer was dried over anhydrous Na$_2$SO$_4$, filtered, and concentrated under reduced pressure. The residue was purified by column chromatography (4% MeOH in DCM) to obtain compound Int-TG5-2 (495 mg, 85%) as white foam solid.

EI-MS m/z: 869 (M$^+$+1).

Preparation of Compound Int-TG5-3

To a solution of compound Int-TG5-2 (495 mg, 0.52 mmol) in anhydrous THF (5.0 mL) at 0° C. under N$_2$ atmosphere was treated with NaBH$_4$ (39.7 mg, 1.05 mmol, 2.0 eq.) and stirred for 2 hours. The reaction was quenched with water (20 mL) and extracted with EA (30 mL×2). The organic layer was dried over anhydrous Na$_2$SO$_4$, filtered, and concentrated under reduced pressure. The residue was purified by column chromatography (2% to 3% MeOH in DCM) to obtain compound Int-TG5-3 (418 mg, 91%) as white foam solid.

EI-MS m/z: 945 (M$^+$+1).

Preparation of Compound Int-TG5-4

To a solution of compound Int-TG5-3 (214.2 mg, 0.23 mmol) in anhydrous THF (5.0 mL) at 0° C. under N$_2$ atmosphere was treated with methane sulfonyl chloride (24.6 uL, 0.32 mmol, 1.4 eq.) and TEA (79.2 uL, 0.57 mmol, 1.5 eq.) and stirred overnight at room temperature. The reaction was quenched with water (10 mL) and extracted with DCM (20 mL×2). The organic layer was dried over anhydrous Na$_2$SO$_4$, filtered, and concentrated under reduced pressure. The residue was purified by column chromatography (100% DCM to 5% MeOH in DCM) to obtain compound Int-TG5-4 (164 mg, 70%) as white foam solid.

EI-MS m/z: 1024 (M$^+$+1).

Preparation of Compound Int-TG5

To a solution of compound Int-TG5-4 (164 mg, 0.16 mmol) in anhydrous THF (10 mL) at room temperature under N$_2$ atmosphere was treated with LiBr (69.6 mg, 0.80 mmol, 5.0 eq.) and stirred for 3 hours. The reaction was diluted with water (10 mL) and extracted with DCM (20 mL×2). The organic layer was dried over anhydrous Na$_2$SO$_4$, filtered, and concentrated under reduced pressure. The residue was purified by column chromatography (3% to 5% MeOH in DCM) to obtain compound Int-TG5 (161 mg, 99%) as white foam solid.

EI-MS m/z: 1008 (M$^+$+1).F

Compound Int-6 was synthesized via a similar manner to the preparation method of the compound Int-5.

Preparation of Compound Int-TG6-1
Yield 72%, colorlessness oil
EI-MS m/z: 1226 (M$^+$+1).

Preparation of Compound Int-TG6-2
Yield 82%, colorlessness oil
EI-MS m/z: 1296 (M$^+$+1).

Preparation of Compound Int-TG6-3
Yield 75%, colorlessness oil
EI-MS m/z: 1298 (M$^+$+1).

Preparation of Compound Int-TG6-4
Yield 82%, colorlessness oil
EI-MS m/z: 1376 (M$^+$+1).

Preparation of Compound Int-TG6
Yield 82%, colorlessness oil
EI-MS m/z: 1361 (M$^+$+1).

Example 21: Preparation of Compound MPS-D1

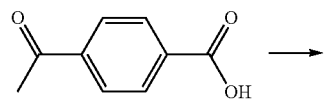

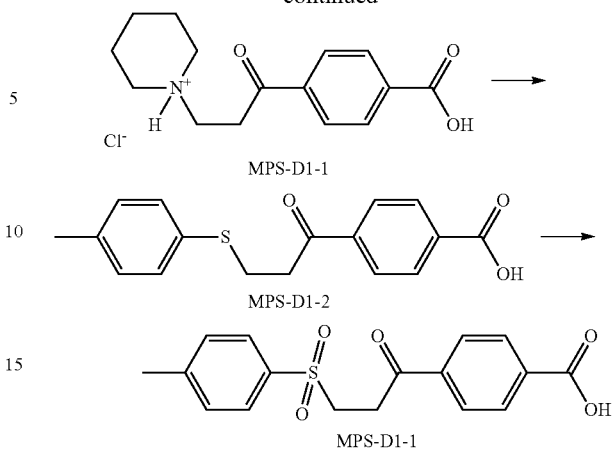

Preparation of Compound MPS-D1-1

To a solution of 4-acetylbenzoic acid (9 g, 54.82 mmol) in EtOH (50 mL) was added piperidine hydrochloride (6.66 g, 54.82 mmol), paraformaldehyde (4.95 g, 164.5 mmol), and conc. HCl (0.6 mL) at room temperature under N$_2$ atmosphere. After stirring 100° C. for 16 hours, the mixture was then cooled to room temperature, added dropwise acetone (90 mL). The mixture was stirred at 0° C. for 1 hour. The solid was filtered and washed with diethyl ether (30 mL×2) to obtain compound MPS-D1-1 (6.11 g, 38%).

$^1$H NMR (400 Hz, DMSO-d$_6$) δ 8.08 (s, 4H), 5.73 (s, 1H), 3.65 (t, J=7.2 Hz, 2H), 3.35 (t, J=7.2 Hz, 2H), 3.31 (m, 6H), 1.74 (s, 4H).

Preparation of Compound MPS-D1-2

To a solution of MPS-D1-1 (6.11 g, 20.52 mmol) in EtOH (40 mL) and MeOH (26 mL) was added 4-methoxybenzenethiol (2.55 g, 20.52 mmol) and piperidine (0.3 mL, 3.08 mmol) at room temperature. After stirring at 100° C. for 16 hours, the mixture was cooled to 0° C. and additionally stirred for 1 hour. The solid was filtered and washed with ether (30 mL×2) to obtain compound MPS-D1-2 (5.56 g, 90%).

$^1$H NMR (400 Hz, CDCl$_3$) δ 8.04-7.99 (m, 4H), 7.27 (d, J=8.4 Hz, 2H), 7.15 (d, J=7.6 Hz, 2H), 3.39-3.36 (m, 2H), 3.25-3.21 (m, 2H), 2.27 (s, 3H).

Preparation of Compound MPS-D1

To a solution of MPS-D1b (5.56 g, 18.51 mmol) in MeOH (90 mL) and distilled water (90 mL) was added oxone (25.03 g, 40.72 mmol) at 0° C. under N$_2$ atmosphere. After stirring at room temperature for 14 hours, the mixture was quenched with distilled water (100 mL) and chloroform (150 mL×3). The organic layer was washed with brine (200 mL), dried over anhydrous Na$_2$SO$_4$, filtered and concentrated under reduced pressure to obtain compound MPS-D1 (5.29 g, 86%).

$^1$H NMR (400 Hz, CDCl$_3$) δ 8.04-7.99 (m, 4H), 7.81 (d, J=8.4 Hz, 2H), 7.46 (d, J=8.4 Hz, 2H), 3.63 (t, J=7.2 Hz, 2H), 3.41 (t, J=7.2 Hz, 2H), 2.44 (s, 3H). EI-MS m/z: 333 (M$^+$+1).

Example 22: Preparation of Compound MPS-D2

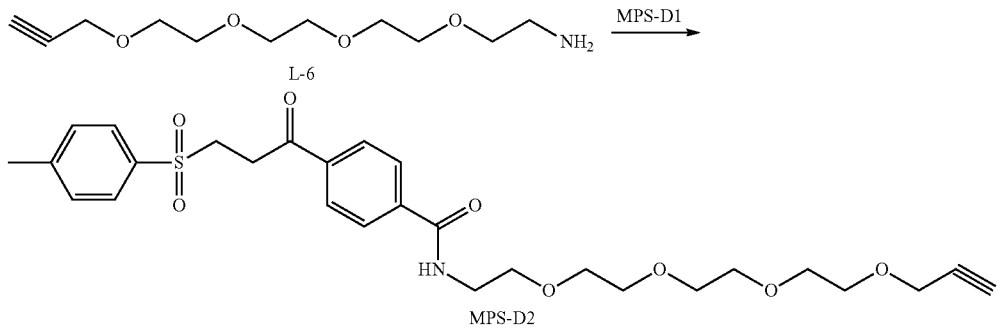

Preparation of Compound MPS-D2

Compound MPS-D1 (652.4 mg, 1.96 mmol) and compound L-6 (500 mg, 1.96 mmol) were dissolved in DMF (5 mL) under $N_2$ atmosphere. HBTU (893.3 mg, 2.36 mmol) and DIPEA (0.684 mL, 3.93 mmol) were added thereto, and the mixture was stirred at room temperature for 3 hours. The mixture was diluted with $H_2O$ (20 mL) and extracted with EA (30 mL×2). The organic layer was dried over anhydrous $Na_2SO_4$, filtered, and concentrated under reduced pressure. The residue was purified by column chromatography to obtain compound MPS-D2 (854.1 mg, 80%).

$^1$H NMR (400 Hz, $CDCl_3$) δ 8.11-7.94 (m, 4H), 7.83 (d, J=7.6 Hz, 2H), 7.44 (br s, 1H), 7.38 (d, J=8.0 Hz, 2H), 4.15 (s, 2H), 3.69-3.65 (m, 14H), 3.58-3.48 (m, 4H), 2.80 (s, 1H), 2.46 (s, 3H). EI-MS m/z: 546 ($M^+$+1).

Example 23: Preparation of Compound MPS-D3

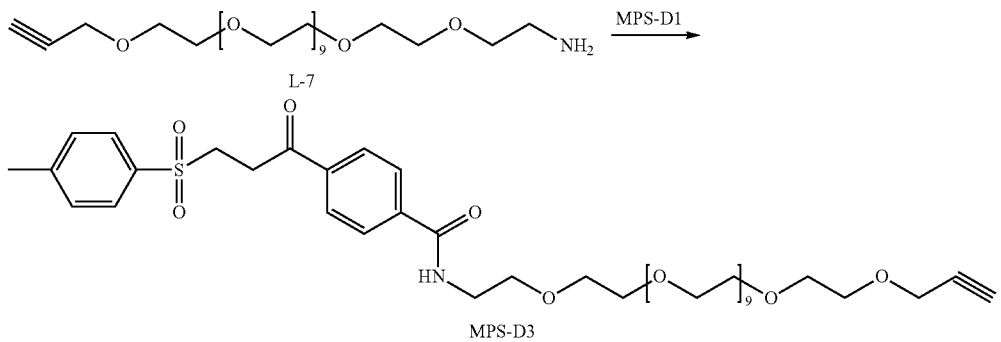

Compound MPS-D3 was synthesized via a similar synthetic route as described in Example 22.
Yield 72%
EI-MS m/z: 899 ($M^+$+1).

Example 24: Preparation of Compound MPS-D4

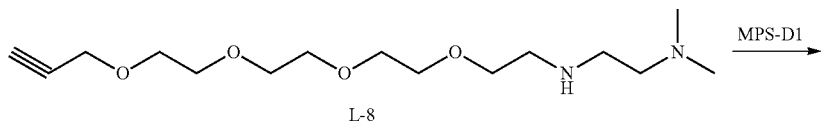

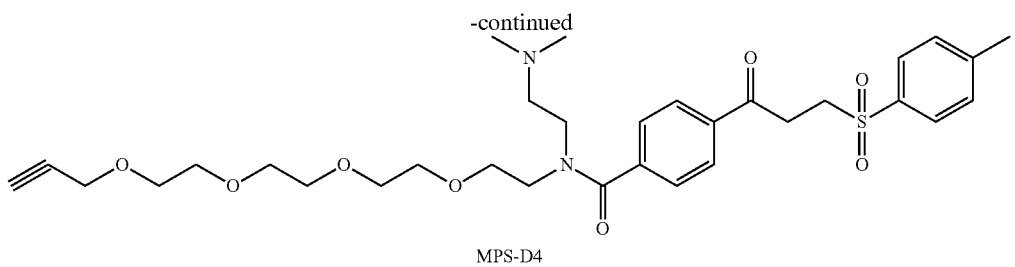

MPS-D4

To solution of compound L-8 (60 mg, 0.20 mmol) in DMF (1 mL) were added MPS-D1 (79 mg, 0.0.24 mmol), HBTU (90 mg, 0.24 mmol) and DIPEA (103 µL, 0.59 mmol) at 0° C. under $N_2$ atmosphere. The reaction mixture was stirred at room temperature for 2 days. The mixture was diluted with $H_2O$ (50 mL) and extracted with EA (100 mL). The organic layer was dried over anhydrous $Na_2SO_4$, filtered and concentrated under reduced pressure. The residue was purified by column chromatography to obtain compound MPS-D4 (59 mg, 48%). EI-MS m/z: 617 ($M^+$+1).

Example 25: Preparation of Compound POS-D1

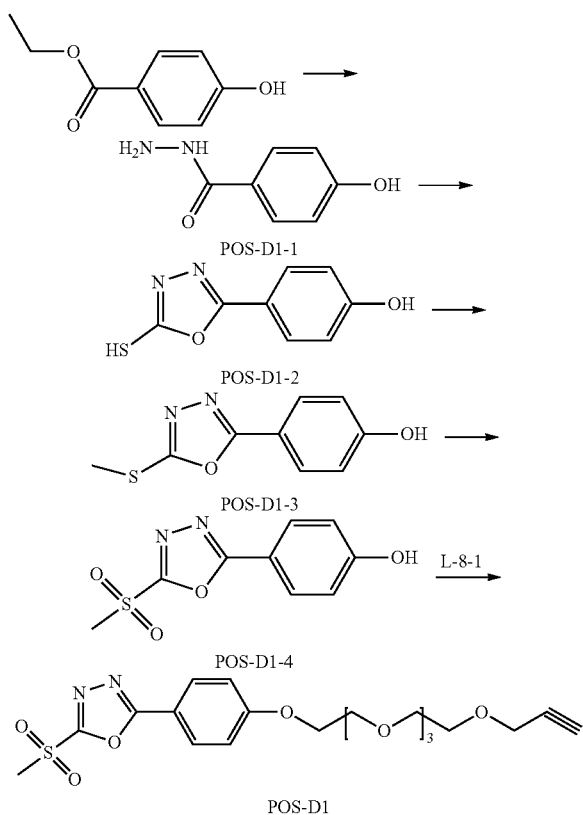

Preparation of compound POS-D1-1

To a solution of ethyl 4-hydrobenzoate (20 g, 120.35 mmol) in EtOH (60 mL) was added $NH_2NH_2 \cdot H_2O$ (88 mL, 1805.4 mmol) under $N_2$ atmosphere. The mixture was stirred overnight at reflux. The mixture was cooled to room temperature, and concentrated under reduced pressure, followed by EtOH trituration, thereby obtaining compound POS-D1-1 (17.54 g, 96%).

$^1$H NMR (400 Hz, DMSO-$d_6$) δ 9.50 (s, 1H), 7.68 (d, J=8.4 Hz, 2H), 6.78 (d, J=8.8 Hz, 2H), 4.37 (s, 2H). EI-MS m/z: 431 ($M^+$+1).

Preparation of Compound POS-D1-2

To a solution of compound POS-D1-1 (17.54 g, 115.28 mmol) in EtOH (200 mL) and DMF (100 mL) was added $CS_2$ (45 mL, 749.32 mmol) and KOH (6.5 g, 115.28 mmol) under $N_2$ atmosphere. After stirring at 85° C. for 18 hours, the reaction mixture was adjusted to pH 4 by addition of 1M HCl solution and diluted with distilled water (500 mL) and EA (500 mL2). The organic layer was washed with $H_2O$ (500 mL), and brine (500 mL), dried over anhydrous $Na_2SO_4$, filtered and concentrated under reduced pressure. The residue was subjected to ether/Hex trituration to obtain compound POS-D1-2 (20.7 g, 93%).

$^1$H NMR (400 Hz, DMSO-$d_6$) δ 10.44 (s, 1H), 7.72 (d, J=8.4 Hz, 2H), 6.94 (d, J=8.0 Hz, 2H). EI-MS m/z: 195 ($M^+$+1).

Preparation of Compound POS-D1-3

To a solution of compound POS-D1-2 (5 g, 25.75 mmol) in THE (100 mL) was added dropwise $Et_3N$ (4.3 mL, 30.9 mmol) and MeI (1.76 mL, 28.33 mmol) at 0° C. After stirring at 0° C. for 10 minutes, the mixture was allowed to warm up to room temperature stirred for 2 hours. The mixture was diluted with $H_2O$ (150 mL) and extracted with EA (100 mL×2). The organic layer was dried over anhydrous $Na_2SO_4$, filtered and concentrated under reduced pressure. The residue was subjected to ether trituration to obtain compound POS-D1-3 (5.15 g, 96%).

$^1$H NMR (400 Hz, DMSO-$d_6$) δ 7.80 (d, J=8.4 Hz, 2H), 6.94 (d, J=8.4 Hz, 2H), 2.74 (s, 3H). EI-MS m/z: 209 ($M^+$+1).

Preparation of Compound POS-D1-4

To a solution of compound POS-D1-3 (3.2 g, 15.37 mmol) in EtOH (150 mL) was added 70% m-CPBA (11.4 g, 46.11 mmol) at 0° C. under $N_2$ atmosphere. After stirring at room temperature for 5 hours, 70% m-CPBA (11.4 g, 46.11 mmol) was further added. Then the mixture was stirred overnight at room temperature and quenched with $H_2O$ (500 mL), saturated $NaHCO_3$ (300 mL) and extracted with EA (500 mL×2). The organic layer was washed with brine (300 mL), dried over anhydrous $Na_2SO_4$, filtered and concentrated under reduced pressure. The residue was subjected to Hex/EA=1:1 (100 mL) trituration to obtain compound POS-D1-4 (3.2 g, 89%).

$^1$H NMR (400 Hz, DMSO-$d_6$) δ 7.95 (d, J=8.8 Hz, 2H), 7.01 (d, J=8.8 Hz, 2H), 3.69 (4s, 3H). EI-MS m/z: 241 ($M^+$+1).

Preparation of Compound POS-D1

To a solution of POS-D1-4 (310 mg, 1.29 mmol) and L-8-1 (660 mg, 2.84 mmol) in THE (8 mL) and DMF (0.8 mL) was added $PPh_3$ (667 mg, 2.58 mmol). The mixture was cooled to 0° C. and DEAD (1.17 mL, 2.58 mmol) was added thereto, and the mixture was stirred at 0° C. for 3 hours. The mixture was diluted with water (15 mL) and extracted with EA (15 mL×2). The obtained organic layer was dried over anhydrous $Na_2SO_4$, filtered and concentrated under reduced pressure to obtain compound POS-D1 (205 mg, 30%).

EI-MS m/z: 455 ($M^+$+1).

Example 26: Preparation of Compound MPS-D5

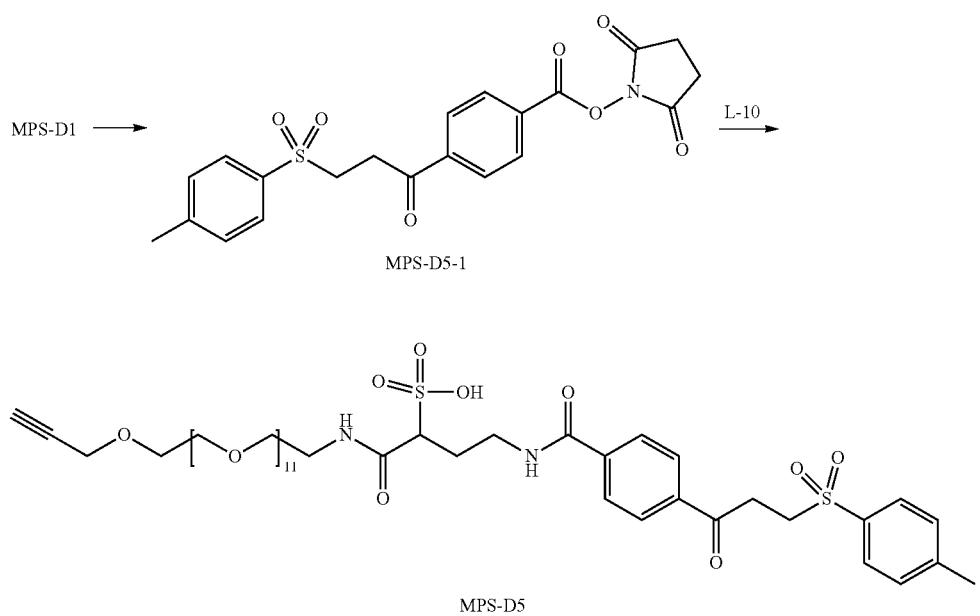

Preparation of Compound MPS-D5-1

MPS-D1 (100 mg, 0.30 mmol) was dissolved in DMF (1 mL) at room temperature under $N_2$ atmosphere followed by N-hydroxysuccinimide (41.6 mg, 0.36 mmol, 1.2 eq.) and then EDCI-HCl (115.4 mg, 0.60 mmol, 2.0 eq.). After the mixture was stirred overnight, the compound MPS-D5-1 was used directly in the next step without further purification.

EI-MS m/z: 430 (M$^+$+1).

Preparation of Compound MPS-D5

A homogeneous solution of L-10 (38.2 mg, 0.05 mmol) and MPS-D5-1 (23 mg, 0.54 mmol, 1.1 eq.) in DMF (1 mL) at room temperature under $N_2$ atmosphere was treated with DIPEA (25.4 uL, 0.15 mmol, 3.0 eq.) and stirred for 2 hours. The mixture was purified by preparative HPLC (Column: Innoval ODS-2 10 um, 100 Å, 21.2×250 mm; flow rate: 40 mL/min, A buffer 0.1% Formic acid in water/B buffer 0.1% Formic acid in ACN, method gradient, solvent A:solvent B 95:5 to 5:95, 1 hour, wavelength 214 nm) to obtain compound MPS-D5 (10.3 mg, 20%) as yellow oil.

EI-MS m/z: 1064 (M$^+$+1).

Example 27: Preparation of Compound MPS-D6, MPS-D7, MPS-D8, and MPS-D9

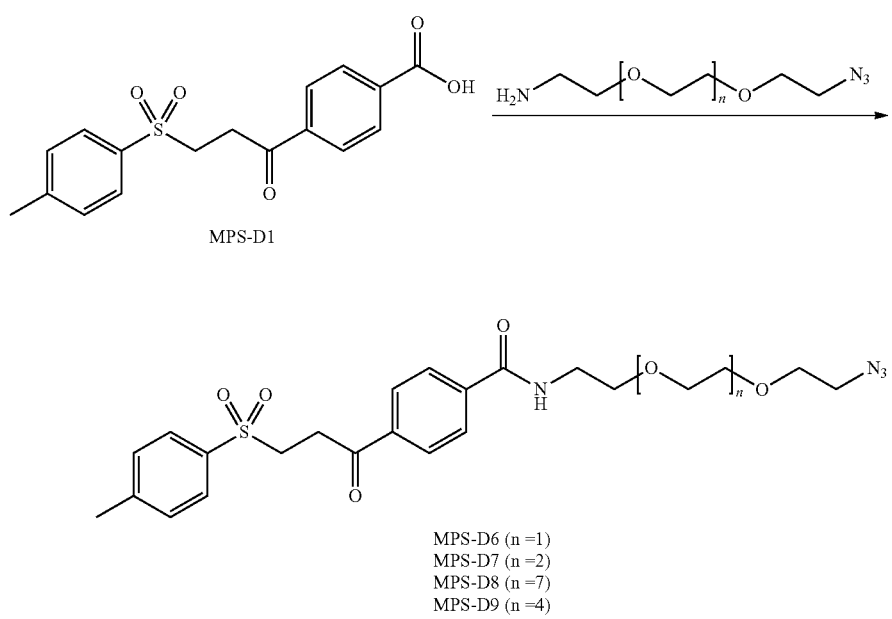

Compound MPS-D6, MPS-D7, MPS-D8, and MPS-D9 were synthesized via a similar synthetic route as described in Example 22.

Preparation of Compound MPS-D6

Yield 53%, light yellow solid $^1$H NMR (400 MHz, CDCl$_3$) δ 7.98 (d, J=8.4 Hz, 2H), 7.88 (d, J=8.4 Hz, 2H), 7.83 (d, J=8.0 Hz, 2H), 7.38 (d, J=8.0 Hz, 2H), 6.75 (br s, 1H), 3.74-3.66 (m, 10H), 3.58-3.48 (m, 4H), 3.37 (t, J=5.2 Hz, 2H), 2.46 (s, 3H); EI-MS m/z: 489 (M$^+$+1).

Preparation of Compound MPS-D7

Yield 52%, yellow solid $^1$H NMR (400 MHz, CDCl$_3$) δ 7.98 (d, J=8.4 Hz, 2H), 7.90 (d, J=8.4 Hz, 2H), 7.83 (d, J=8.0 Hz, 2H), 7.38 (d, J=8.0 Hz, 2H), 6.93 (br s, 1H), 3.74-3.62 (m, 14H), 3.58-3.47 (m, 4H), 3.34 (t, J=5.2 Hz, 2H), 2.46 (s, 3H); EI-MS m/z: 533 (M$^+$+1).

Preparation of Compound MPS-D8

Yield 53%, yellow oil

EI-MS m/z: 753 (M$^+$+1).

Preparation of Compound MPS-D9

Yield 84%, light yellow oil

EI-MS m/z: 621 (M$^+$+1).

Example 28: Preparation of Compound mMPS-D1

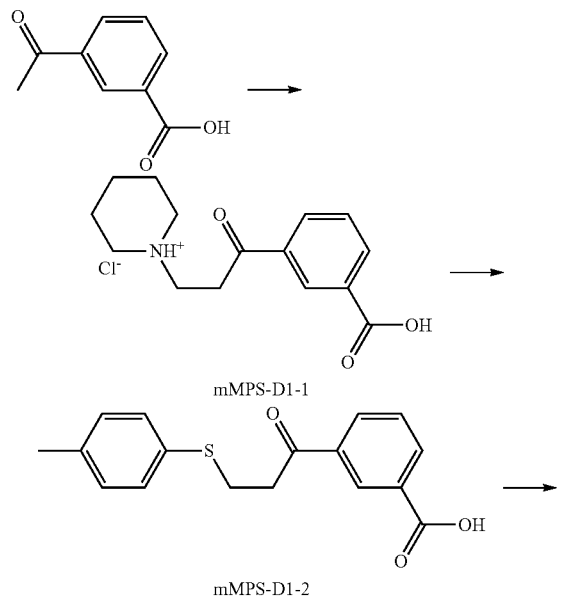

-continued

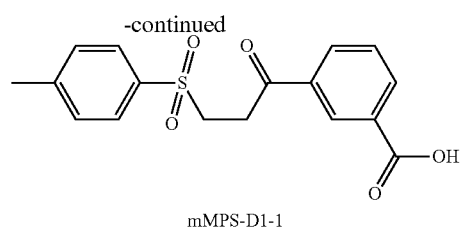

mMPS-D1-1

Preparation of Compound mMPS-D1-1

A mixture of 3-acetyl benzoic acid (3 g, 18.28 mmol), piperidine HCl (2.22 g, 18.28 mmol, 1 eq.) and paraformaldehyde (1.65 g, 54.83 mmol, 3 eq.) in EtOH (18 mL) at room temperature under N$_2$ atmosphere was treated with conc. HCl (0.2 mL) and heated to reflux overnight. The mixture was allowed to cool to room temperature, quenched with acetone (30 mL) and stirred at 0° C. for 1 hour. The solid were collected by filtration, washed with diethyl ether (70 mL) and dried under high vacuum to obtain compound mMPS-D1-1 (2.78 g, 51%) as white solid.

EI-MS m/z: 262 (M$^+$+1).

Preparation of Compound mMPS-D1-2

A cloudy mixture of mMPS-D1-1 (1.45 g, 4.87 mmol) and 4-methylbenzenethiol (605 mg, 4.87 mmol, 1 eq.) in EtOH (11 mL) and MeOH (7.5 mL) at room temperature under N$_2$ atmosphere was treated with piperidine (72 uL, 0.73 mmol, 0.15 eq.) and heated to reflux for 6 hours. The reaction mixture was allowed to cool to 0° C. for 1 hour to give a white solid. Diethyl ether was added to precipitate out more solid, which was collected by filtration, washed with diethyl ether (70 mL) and dried under high vacuum to obtain compound mMPS-D1-2 (1.05 g, 72%) as white solid.

$^1$H NMR (600 Hz, DMSO-d$_6$) δ 8.40 (s, 1H), 8.18-8.15 (m, 2H), 7.66-7.63 (m, 1H), 7.26 (d, J=7.8 Hz, 2H), 7.14 (d, J=7.8 Hz, 2H), 3.40-3.37 (m, 2H), 3.26-3.23 (m, 2H), 2.27 (s, 3H).

EI-MS m/z: 301 (M$^+$+1).

Preparation of Compound mMPS-D1

A cloudy solution of mMPS-D1-2 (500 mg, 1.67 mmol) in MeOH (30 mL) and H$_2$O (30 mL) at 0° C. under N$_2$ atmosphere was treated with oxone (2.25 g, 3.66 mmol, 2.2 eq.). The mixture was allowed to warm up to room temperature and stirred overnight. The reaction mixture was quenched with H$_2$O (120 mL) and extracted with CHCl$_3$ (100 mL×3). The combined organic extracts were washed with brine (200 mL), dried over anhydrous Na$_2$SO$_4$, filtered and concentrated in vacuum to obtain compound mMPS-D1 (258 mg, 47%) as yellowish solid.

$^1$H NMR (600 Hz, DMSO-d6) δ 8.37-8.36 (m, 1H), 8.20-8.16 (m, 2H), 7.81 (d, J=7.8 Hz, 2H), 7.68-7.65 (m, 1H), 7.46 (d, J=8.4 Hz, 2H), 3.66-3.63 (m, 2H), 3.44-3.41 (m, 2H), 2.41 (s, 3H).

EI-MS m/z: 333 (M$^+$+1).

Example 29: Preparation of Compound mMPS-D2 and mMPS-D3

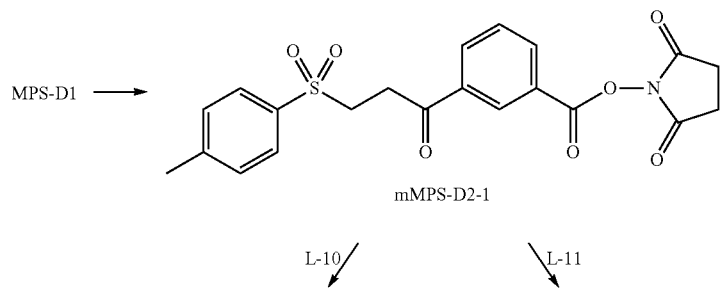

mMPS-D2-1

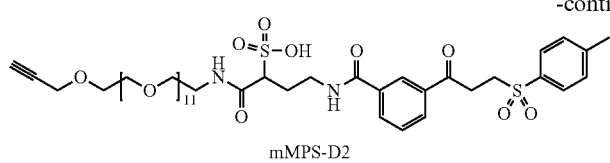
mMPS-D2

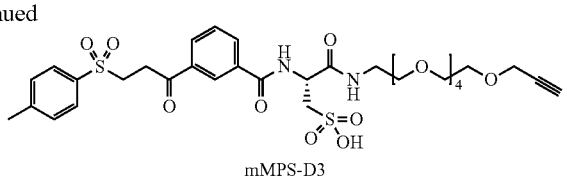
mMPS-D3

Preparation of Compound mMPS-D2-1

A cloudy solution of mMPS-D1 (50 mg, 0.15 mmol) in DMF (1 mL) at room temperature under $N_2$ atmosphere was treated with N-hydroxysuccinimide (21 mg, 0.18 mmol, 1.2 eq.) and EDCI-HCl (58 mg, 0.30 mmol, 2.0 eq.). After the mixture was stirred overnight, the compound mMPS-D2-1 was used directly in the next step without further purification.

EI-MS m/z: 430 ($M^+1$).

Preparation of Compound mMPS-D2

A homogeneous solution of L-10 (35.3 mg, 0.045 mmol) and mMPS-D2-1 (21.3 mg, 0.05 mmol, 1.1 eq.) in DMF (1 mL) at room temperature under $N_2$ atmosphere was treated with DIPEA (23.4 uL, 0.135 mmol, 3.0 eq) and stirred for 2 hours. The reaction mixture was purified by preparative HPLC (Column: Innoval ODS-2 10 um, 100 Å, 21.2×250 mm; flow rate: 40 mL/min, A buffer 0.1% Formic acid in water/B buffer 0.1% Formic acid in ACN, method gradient, solvent A:solvent B 95:5 to 5:95, 1 hour, wavelength 214 nm) to obtain compound mMPS-D2 (10.8 mg, 22%) as yellow oil.

EI-MS m/z: 1064 ($M^++1$).

Preparation of Compound mMPS-D3

A homogeneous solution of L-11 (10 mg, 0.024 mmol) and mMPS-D2-1 (11.3 mg, 0.026 mmol, 1.1 eq.) in DMF (1 mL) at room temperature under $N_2$ atmosphere was treated with DIPEA (20.8 uL, 0.12 mmol, 5.0 eq.) and stirred overnight. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound mMPS-D3 (10.8 mg, 22%) as yellow oil.

EI-MS m/z: 697 ($M^++1$).

Example 30: Preparation of Compound mMPS-D4

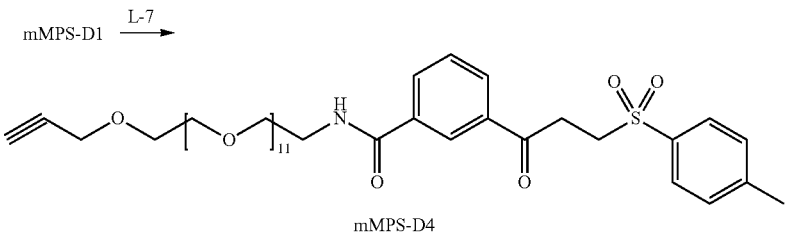
mMPS-D4

A homogeneous solution of mMPS-D1 (124.6 mg, 0.37 mmol) and L-7 (120.4 mg, 0.45 mmol, 1.2 eq.) in anhydrous DMF at room temperature under $N_2$ atmosphere was treated with DIPEA (0.13 mL, 0.75 mmol, 2 eq.) and HBTU (178.6 mg, 0.45 mmol, 1.2 eq.) and stirred for 3.5 hours. The reaction was quenched with $H_2O$ (40 mL) and extracted with DCM (50 mL×3). The combined organic layer was washed with $H_2O$ (40 mL×2), brine (40 mL), dried over anhydrous $Na_2SO_4$, filtered and concentrated in vacuo. The residue was purified by flash chromatography (Hex:EA=1:1 to 1:5) to obtain compound mMPS-D4 (123.1 mg, 60%) as white solid.

EI-MS m/z: 546 ($M^++1$).

Example 31: Preparation of Compound mMPS-D5

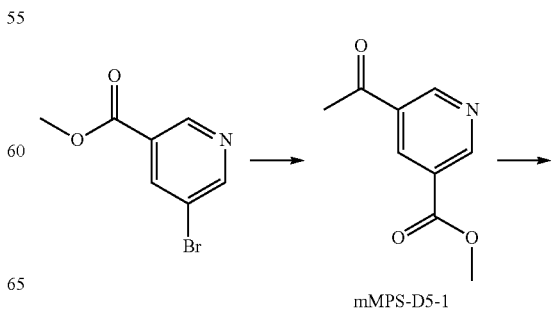
mMPS-D5-1

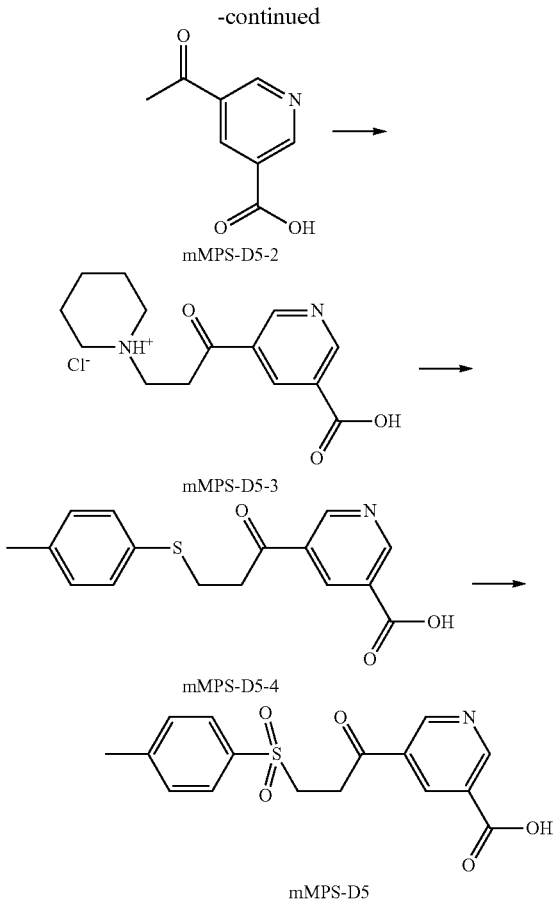

Preparation of Compound mMPS-D5-1

A solution of methyl 5-bromonicotinate (3 g, 13.89 mmol), PdCl$_2$(PPh$_3$)$_2$ (487 mg, 0.96 mmol, 0.05 eq) and tributyl(1-ethoxyvinyl)tin (5.86 mL, 17.36 mmol, 1.25 eq.) in anhydrous toluene (60 mL) at room temperature under N$_2$ atmosphere was heated to reflux for 3 hours. After the mixture was cooled to 0° C., filtered through Celite and washed with MeOH (100 mL). The filtrate was concentrated under reduced pressure. The residue dissolved in MeOH (30 mL) and 10M HCl (30 mL) at room temperature under N$_2$ atmosphere was allowed to stand for 2 hours. The reaction was quenched with saturated Na$_2$CO$_3$ (120 mL) and extracted with EA (150 mL×3). The organic layer was washed with brine (250 mL), dried over anhydrous Na$_2$SO$_4$, filtered and concentrated under reduced pressure. The residue was purified by flash chromatography (EA:HEX=1:2) to obtain compound mMPS-D5-1 (2.22 g, 89%) as a white solid.

$^1$H NMR (400 MHz, CDCl$_3$) δ 9.37 (s, 1H), 9.31 (s, 1H), 8.79 (s, 1H), 4.00 (s, 3H), 2.69 (s, 3H).

Preparation of Compound mMPS-D5-2

A homogeneous solution of mMPS-D5-1 (636 mg, 3.55 mmol) in MeOH (11 mL) at room temperature under N$_2$ atmosphere was treated with 1N NaOH (10.64 mL) and stirred for 1 hour. After the mixture was concentrated in under reduced pressure, the reaction was quenched with 1N HCl (pH 2) and extracted with EA (80 mL×3). The organic layer was washed with brine (150 mL), dried over anhydrous Na$_2$SO$_4$, filtered and concentrated under reduced pressure to obtain compound mMPS-D5-2 (crude) as a white solid.

$^1$H NMR (400 MHz, DMSO-d$_6$) δ 9.31 (s, 1H), 9.25 (s, 1H), 8.64 (s, 1H), 2.69 (s, 3H).

Compound mMPS-D5-3, mMPS-D5-4, and mMPS-D5 were synthesized via a similar manner to the preparation method of the compound MPS-D1 of Example 21.

Preparation of Compound mMPS-D5-3

Yield 30%, white solid.

EI-MS m/z: 264 (M$^+$+1).

Preparation of compound mMPS-D5-4

Yield 11%, white solid.

$^1$H NMR (400 Hz, DMSO-d$_6$) δ 9.26 (d, J=2 Hz, 1H), 9.23 (d, J=2 Hz, 1H), 8.58 (m, 1H), 7.26 (d, J=8 Hz, 2H), 7.13 (d, J=8.4 Hz, 2H), 3.46 (t, J=7.2 Hz, 2H), 3.24 (d, J=7.2 Hz, 2H), 2.26 (s, 3H); EI-MS m/z: 302 (M$^+$+1).

Preparation of Compound mMPS-D5

Yield 43%, white solid.

EI-MS m/z: 334 (M$^+$+1).

Example 32: Preparation of Compound mMPS-D5

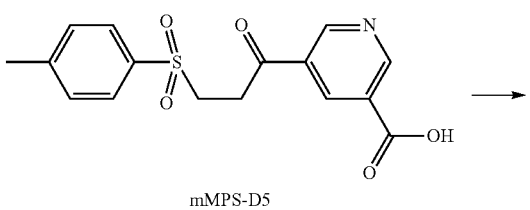

mMPS-D5

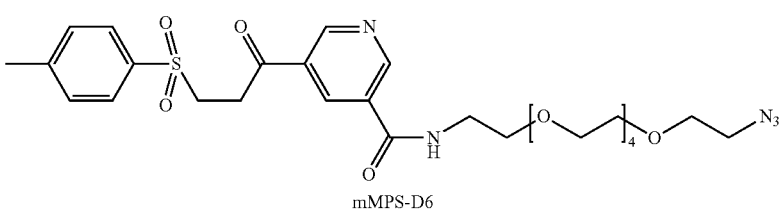

mMPS-D6

Compound mMPS-D6 was synthesized via a similar manner to the preparation method of the compound MPS-D9 of Example 27.
Yield 13%, yellowish oil.
EI-MS m/z: 622 (M+1).

Example 33: Preparation of Compound BCN-PNP

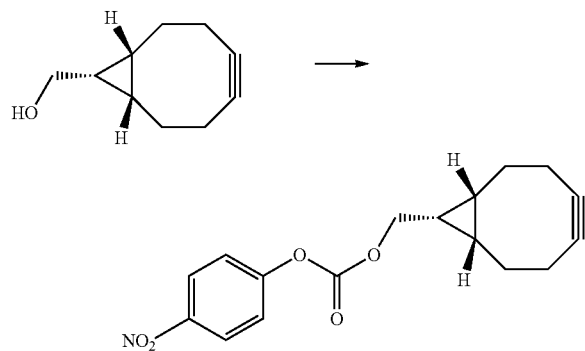

BCN-PNP (1R,8S,9s)-Bicyclo[6.1.0]non-4-yn-9-ylmethanol (800 mg, 5.3 mmol) was dissolved in DCM (125 mL) at room temperature under $N_2$ atmosphere. Pyridine (1.22 mL, 15.9 mmol, 3.0 eq.) and 4-nitrophenyl chloroformate (1.75 g, 8.74 mmol, 1.6 eq.) were added thereto. After the mixture was stirred for 4 hours at the same temperature, the reaction was quenched by the addition of saturated $NH_4Cl$ solution (100 mL) and extracted with EA (100 mL×4). The organic layer was dried over $Na_2SO_4$, filtered and concentrated in vacuo. The residue was purified by column chromatography (Hex:EA=10:1) to obtain compound BCN-PNP (1.34 g, 84%) as white solid.

$^1$H NMR (600 MHz, CDCl$_3$) δ 8.29 (d, J=9 Hz, 2H), 7.39 (d, J=9 Hz, 2H), 4.41 (d, J=8.4 Hz, 2H), 2.36-2.24 (m, 6H), 1.62-1.55 (m, 2H), 1.53-1.49 (m, 1H), 1.07 (t, J=10.2 Hz, 2H).

Example 34: Preparation of Compound MPS-D10 and MPS-D11

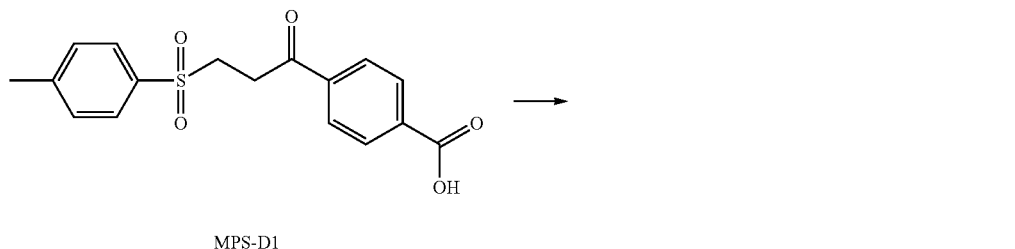

MPS-D1

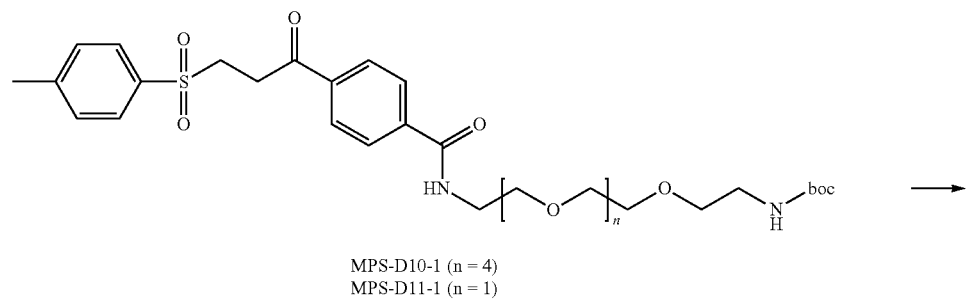

MPS-D10-1 (n = 4)
MPS-D11-1 (n = 1)

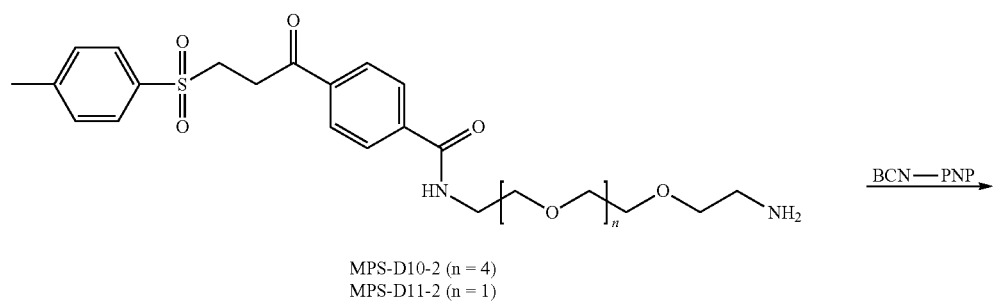

MPS-D10-2 (n = 4)
MPS-D11-2 (n = 1)

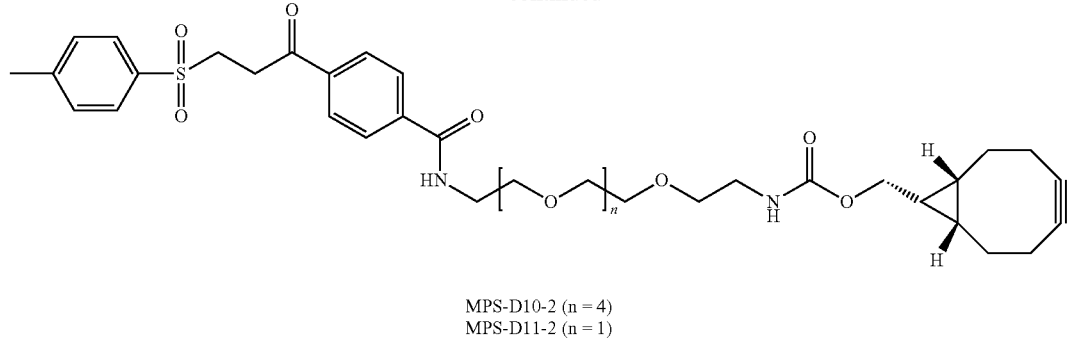

MPS-D10-2 (n = 4)
MPS-D11-2 (n = 1)

Compound MPS-D10-1 and MPS-D11-1 were synthesized via a similar manner to the preparation method of the compound MPS-D2 of Example 22.

Preparation of compound MPS-D10-1

Yield 71%, light yellow oil $^1$H NMR (400 MHz, CDCl$_3$) δ 7.99-7.93 (m, 4H), 7.83 (d, J=8.0 Hz, 2H), 7.39 (d, J=8.0 Hz, 2H), 7.30 (br s, 1H), 5.01 (br s, 1H), 3.74-3.46 (m, 26H), 3.34-3.26 (m, 2H), 2.46 (s, 3H), 1.43 (s, 9H); EI-MS m/z: 695 (M$^+$+1).

Preparation of Compound MPS-D11-1

Yield 71%, light yellow oil $^1$H NMR (400 MHz, CDCl$_3$) δ 8.02-7.86 (m, 4H), 7.83 (d, J=7.6 Hz, 2H), 7.38 (d, J=8.0 Hz, 2H), 6.91 (br s, 1H), 4.98 (br s, 1H), 3.72-3.44 (m, 10H), 3.36-3.24 (m, 2H), 2.46 (s, 3H), 1.43 (s, 9H); EI-MS m/z: 563 (M$^+$+1).

Compound MPS-D10-2 and MPS-D11-2 were synthesized via a similar manner to the preparation method of the compound L-9 of Example 10.

Preparation of Compound MPS-D10-2

Yield 99%, light yellow oil.

$^1$H NMR (400 MHz, DMSO-D6) δ 8.74 (t, J=8.0 Hz, 1H), 7.98 (dd, J=12, 8.4 Hz, 2H), 7.82 (d, J=8.4 Hz, 2H), 7.46 (d, J=8.0 Hz, 2H), 3.68-3.36 (m, 24H), 3.01-2.94 (m, 2H), 2.22 (s, 3H); EI-MS m/z: 595 (M$^+$+1).

Preparation of Compound MPS-D11-2

Yield quant., light yellow oil.

EI-MS m/z: 463 (M$^+$+1).

Preparation of Compound MPS-D10

A homogeneous solution of MPS-D10-2 (63 mg, 0.10 mmol) and BCN-PNP (31.5 mg, 0.10 mmol, 1.0 eq.) in anhydrous DMF (2.0 mL) at room temperature under N$_2$ atmosphere was treated with DIPEA (52 uL, 0.3 mmol, 3 eq.) and HBTU (57 mg, 0.15 mmol, 1.5 eq.) and stirred for 2 hours. The reaction was quenched with H$_2$O (20 mL) and extracted with EA (30 mL×3). The combined organic layer was washed with brine (10 mL), dried over anhydrous Na$_2$SO$_4$, filtered and concentrated under reduced pressure. The residue was purified by preparative TLC to obtain compound mMPS-D10 (57 mg, 74%). EI-MS m/z: 771 (M$^+$+1).

Preparation of Compound MPS-D11

Compound MPS-D11 was synthesized via a similar manner to the preparation method of the compound MPS-D10.

Yield 82%, light yellow oil.

EI-MS m/z: 639 (M$^+$+1).

Preparation of Monomers

Example 35: Preparation of Pyrrolo-Benzodiazepine Monomer (Hereinafter "PBD-Monomer")

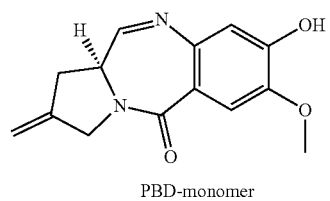

PBD-monomer

PBD monomer was obtained by performing a reaction in a similar method described in EP20071813614.

Example 36: Preparation of Tetrahydroisoquinolino-Benzodiazepine Monomer (Hereinafter "TBD-Monomer")

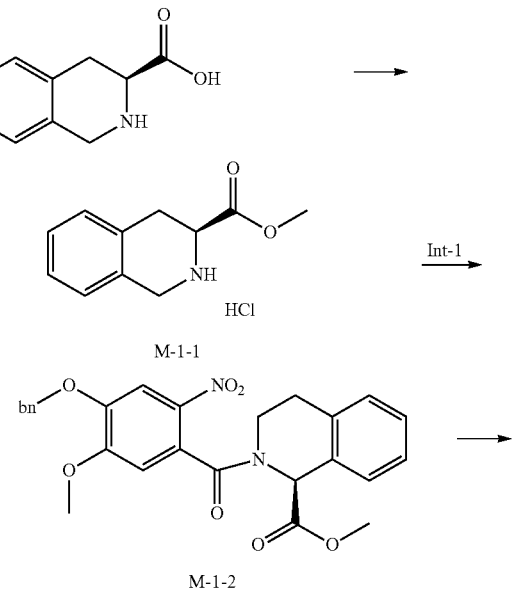

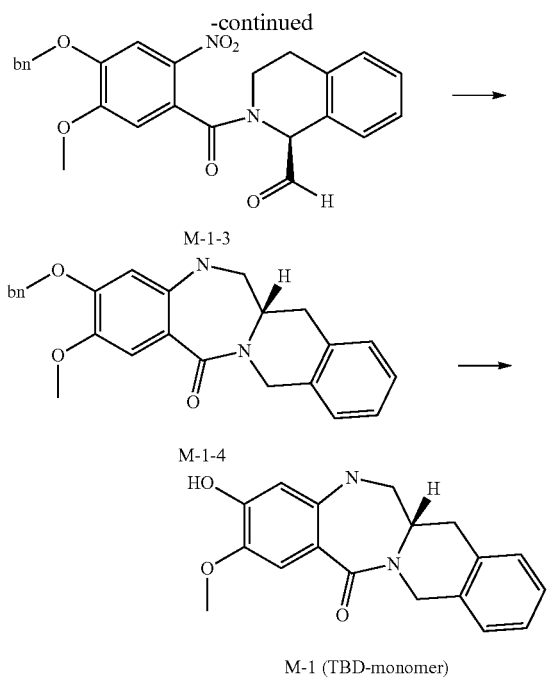

Preparation of Compound M-1-1

To a solution of (s)-(−)-1, 2, 3, 4-tetrahydroisoquinoline-3-carboxylic acid (5.0 g, 28.22 mmol) in MeOH (140 mL) was added dropwise $SOCl_2$ (2.30 mL, 31.04 mmol) to 0° C. under $N_2$ atmosphere. After stirring for 21 hours at 40° C., the mixture was concentrated under reduced pressure. Diethyl ether (50 mL) was added to give a precipitate, which was filtered with diethyl ether to obtain compound M-1-1 (6.42 g, yield 99%).

$^1$H NMR (400 MHz, DMSO-d6) δ 10.02 (s, 2H), 7.27 (s, 4H), 4.60-4.56 (m, 1H), 4.39-4.29 (m, 2H), 3.82 (s, 3H), 3.19-3.12 (m, 2H); EI-MS m/z: 192 (M$^+$+1).

Preparation of Compound M-1-2

To a solution of compound Int-1 (9.07 g, 28.22 mmol) in anhydrous THF (50 ml) was added compound M-1-1 (6.42 g, 28.22 mmol) in THF (100 mL) and TEA (7.9 mL, 56.43 mmol) at 0° C. After stirring for 2 hours at room temperature, the reaction was diluted with distilled water (500 mL) and extracted with EA (800 mL). The organic layer was dried over anhydrous $Na_2SO_4$, filtered and concentrated under reduced pressure. The residue was purified by column chromatography to obtain compound M-1-2 (12.01 g, 90%). EI-MS m/z: 477 (M$^+$+1).

Preparation of Compound M-1-3

To a solution of compound M-1-2 (4 g, 8.39 mmol) in anhydrous DCM (18 mL) and toluene (52 mL) was added dropwise DIBAL (16.8 mL, 16.79 mmol, 1.0M in toluene) at −78° C. under $N_2$ atmosphere. After stirring for 4 hours at −78° C., the reaction was quenched with MeOH (0.4 mL) and 2N HCl (25 mL) at −78° C. The mixture was diluted with water (100 mL) and extracted with EA (500 mL). The organic layer was dried over anhydrous $Na_2SO_4$, filtered and concentrated under reduced pressure. The residue was purified by column chromatography to obtain compound M-1-3 (3.07 g, 82%). EI-MS m/z: 447 (M$^+$+1).

Preparation of Compound M-1-4

To a solution of compound M-1-3 (3 g, 6.72 mmol) in THF (130 mL) and distilled water (86 mL) was added $Na_2S_2O_4 \cdot 2H_2O$ (11.3 g, 53.76 mmol) at room temperature. After stirring for 5 h, the reaction was concentrated under reduced pressure four times by using toluene as a co-solvent, thereby removing water. Then, the obtained yellow solid was dissolved in anhydrous MeOH (220 mL) and acetyl chloride (4.8 mL, 67.19 mmol) was added thereto. After stirring 15 minutes, the reaction mixture was adjusted to pH 7 by addition of saturated $NaHCO_3$ solution and diluted with distilled water (100 mL) and extracted with EA (250 mL×2). The organic layer was dried over anhydrous $Na_2SO_4$, filtered and concentrated under reduced pressure. The residue was purified by column chromatography to obtain compound M-1-4 (2.48 g, 93%).

$^1$H NMR (400 MHz, CDCl$_3$) δ 7.55 (s, 1H), 7.45-7.27 (m, 10H), 6.84 (s, 1H), 5.24-5.15 (m, 2H), 5.00 (d, J=15.2, 1H), 4.56 (d, J=15.6, 1H), 3.97 (s, 3H), 3.93-3.92 (m, 1H), 3.31-3.12 (m, 2H). EI-MS m/z: 399 (M$^+$+1).

Preparation of Compound M-1

To a solution of compound M-1-4 (1 g, 2.51 mmol) in anhydrous DCM (10 mL) was added the methane sulfonic acid (5 mL) in DCM (10 mL) at 0° C. After stirring for 3 h at 0° C., the mixture was quenched with $NaHCO_3$ solution, water (100 mL) and extracted with EA (400 mL). The organic layer was dried over anhydrous $Na_2SO_4$, filtered and concentrated under reduced pressure. The residue was purified by column chromatography to obtain compound M-1 (703 mg, 91%).

$^1$H NMR (400 MHz, CDCl$_3$) δ 7.54 (s, 1H), 7.48 (d, J=4.8 Hz, 1H), 7.37-7.26 (m, 4H), 6.88 (s, 1H), 6.03 (s, 1H), 5.00 (d, J=15.6 Hz, 1H), 4.56 (d, J=15.6 Hz, 1H), 3.98 (s, 3H), 3.95-3.90 (m, 1H), 3.30-3.13 (m, 2H). EI-MS m/z: 309 (M$^+$+1).

Example 37: Preparation of Indolino-Benzodiazepine Monomer (Hereinafter "IBD-Monomer")

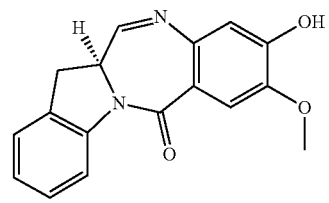

IBD-monomer

IBD monomer was obtained by performing a reaction in a similar synthetic method described in WO2010091150.

$^1$H NMR (400 MHz, CDCl$_3$) δ 8.27 (d, J=7.6 Hz, 1H), 7.88 (d, J=4.4 Hz, 1H), 7.56 (s, 1H), 7.33-7.30 (m, 1H), 7.11 (t, J=7.6 Hz, 1H), 6.92 (s, 1H), 4.50-4.46 (m, 1H), 3.99 (s, 3H), 3.78-3.67 (m, 1H), 3.53-3.50 (m, 1H). EI-MS m/z: 295 (M$^+$+1).

Example 38: Preparation of PBD Compound Bearing C2-Aryl Substituents

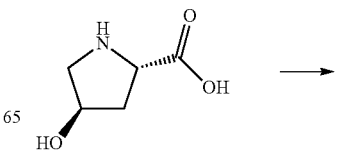

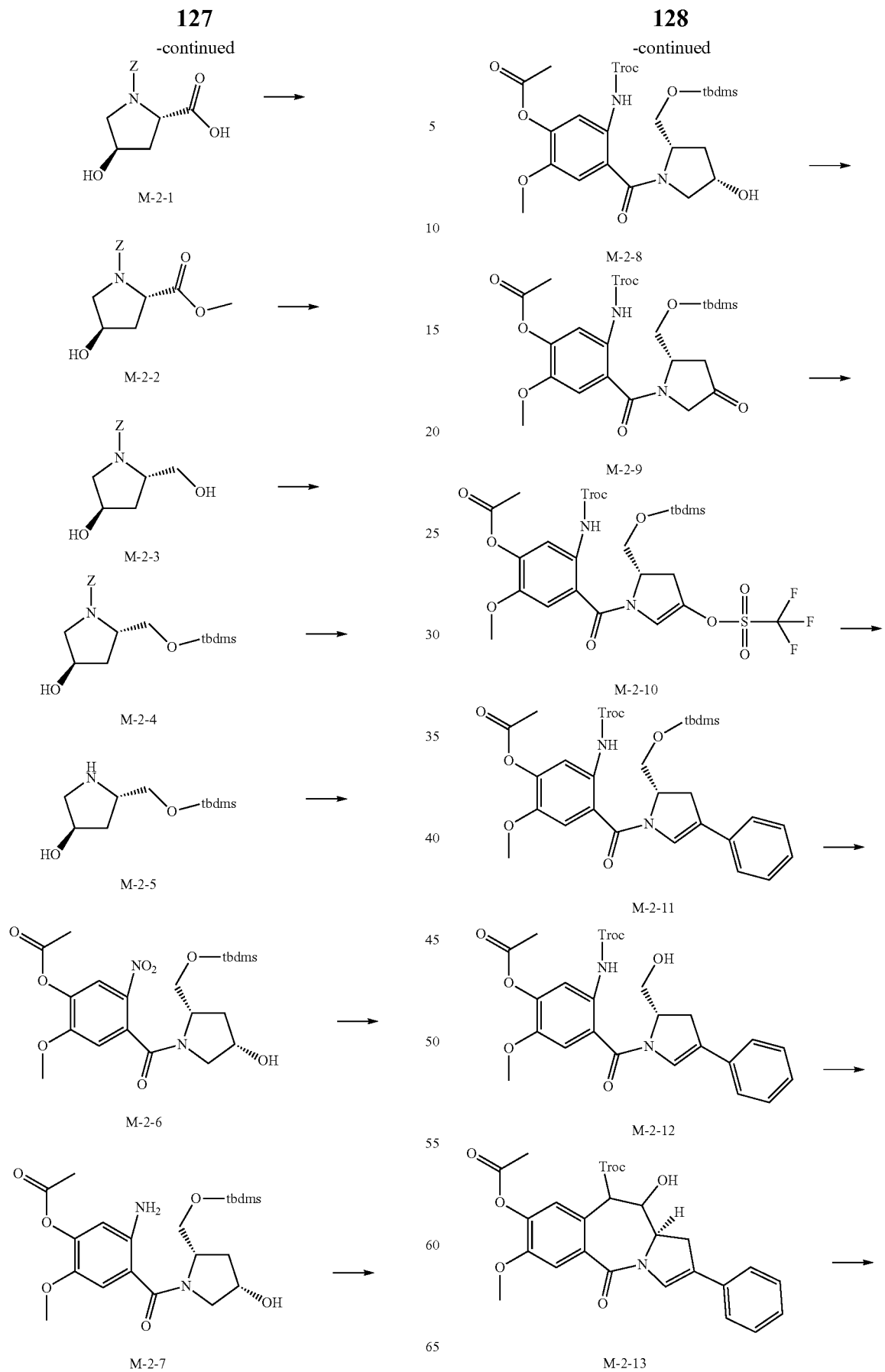

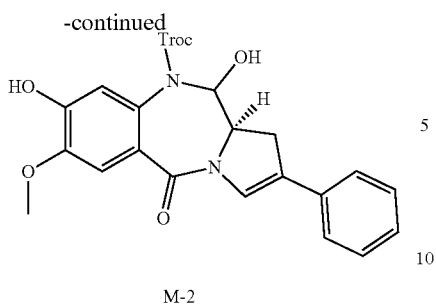

M-2

Preparation of Compound M-2-1

To a stirred solution of trans-4-hydroxy-L-proline (30 g, 230 mmol) and NaHCO$_3$ (43 g, 570 mmol, 2.5 eq.) in H$_2$O/toluene (500 mL/120 mL) at room temperature under N$_2$ atmosphere was added Cbz-Cl (37.4 mL, 260 mmol, 1.15 eq.) After addition, the mixture was stirred at this temperature overnight. The mixture was extracted with EA (500 mL×3). The organic layer was washed with water (500 mL×2) and dried over anhydrous Na$_2$SO$_4$, filtered and concentrated under reduced pressure to obtain compound M-2-1 (57.5 g, 95%) as light brown oil.

$^1$H NMR (400 MHz, DMSO-d6) δ 12.7 (br s, 1H), 7.40-7.28 (m, 5H), 5.18-5.02 (m, 2H), 4.31-4.24 (m, 2H), 3.51-3.35 (m, 2H), 2.23-2.10 (m, 1H), 2.00-1.87 (m, 1H); EI-MS m/z: 266 (M$^+$+1).

Preparation of Compound M-2-2

A brown solution of compound M-2-1 (57.5 g, 220 mmol) in MeOH (400 mL) at 0° C. under N$_2$ atmosphere was treated with thionyl chloride (45.3 mL, 610 mmol, 2.8 eq.). The reaction mixture was allowed to warm up to room temperature and stirred overnight. The mixture was concentrated under reduced pressure to obtain compound M-2-2 (60.5 g, quant.) as light brown oil.

$^1$H NMR (400 MHz, CDCl$_3$) δ 7.38-7.28 (m, 5H), 5.23-5.09 (m, 2H), 4.56-4.47 (m, 2H), 3.80 (s, 1H), 3.76-3.66 (m, 2H), 3.58-3.52 (m, 1H) 2.38-2.26 (m, 1H), 2.16-2.08 (m, 1H); EI-MS m/z: 270 (M$^+$+1).

Preparation of Compound M-2-3

A brown solution of compound M-2-2 (60.5 g, 220 mmol) in anhydrous THE (500 mL) at 0° C. under N$_2$ atmosphere was treated with LiBH$_4$ (3.9 g, 180 mmol, 0.8 eq) and stirred for 30 minutes. And then the mixture was stirred at room temperature for further 2 days. The mixture was quenched with water (200 mL) and 2N HCl (100 mL). The organic solvent was removed by rotary evaporator. The residue was extract with EA (500 mL×3) and then the organic layer was dried over anhydrous Na$_2$SO$_4$, filtered and concentrated under reduced pressure to obtain compound M-2-3 (54.6 g, 98%) as light brown oil.

1H NMR (400 MHz, CDCl$_3$) δ 7.39-7.30 (m, 5H), 5.21-5.12 (m, 2H), 4.66 (d, J=7.2 Hz, 1H), 4.39 (s, 1H), 4.21 (q, J=7.6, 7.2 Hz, 1H), 3.76 (t, J=9.6 Hz, 2H), 3.66-3.58 (m, 1H), 3.50 (dd, J=8.0, 4.0 Hz, 1H), 2.10-2.23 (m, 1H), 1.78-1.64 (m, 1H); EI-MS m/z: 252 (M$^+$+1).

Preparation of Compound M-2-4

A brown solution of M-2-3 (53 g, 210 mmol) in anhydrous DCM (500 mL) at room temperature under N$_2$ atmosphere was treated with t-butyldimethylsilyl chloride (25.4 g, 170 mmol, 0.8 eq.), TEA (30 mL, 210 mmol, 1.0 eq.) and DBU (6.3 mL, 42.2 mmol, 0.2 eq). After addition, the mixture was stirred overnight. The reaction mixture was washed with NH$_4$Cl (300 mL) followed by brine (300 mL), and then the organic layer was dried over anhydrous Na$_2$SO$_4$, filtered and concentrated under reduced pressure.

The residue was purified by column chromatography (Hex:EA=1:1) to obtain compound M-2-4 (48.2 g, 63%) as light brown oil.

$^1$H NMR (400 MHz, CDCl$_3$) δ 7.38-7.28 (m, 5H), 5.20-5.08 (m, 2H), 4.50 (s, 1H), 4.12-4.00 (m, 1H), 3.97 (dd, J=6.4, 4.0 Hz, 1H), 3.71 (dd, J=5.6, 4.8 Hz, 1H), 3.66-3.58 (m, 1H), 3.52-3.48 (m, 1H), 2.28-2.18 (m, 1H), 2.02-1.92 (m, 1H), 0.10-0.08 (m, 6H); EI-MS m/z: 366 (M$^+$+1).

Preparation of Compound M-2-5

Palladium on carbon, 5% Pd/C (1.3 g, 1.23 mmol, 0.03 eq.) was added to a stirred solution of M-2-4 (15 g, 41.0 mmol) in EA (50 mL) under N$_2$ atmosphere. The flask was flushed by bubbling hydrogen gas through the solution at room temperature. The mixture was stirred at the same temperature for 5 hours. The mixture was diluted with EA (30 mL), filtered through Celite, the Celite plug washed with EA (50 mL×2). The filtrate was concentrated under reduced pressure to obtain compound M-2-5 (9.5 g, quant.) as a light brown oil.

$^1$H NMR 400 MHz, CDCl$_3$) δ 4.41 (br s, 1H), 3.60-3.44 (m, 3H), 3.12 (dd, J=7.2 Hz, 4.8 Hz, 1H), 2.89 (d, J=12 Hz, 1H), 1.84-1.79 (m, 1H), 1.74-1.67 (m, 1H), 0.89 (s, 9H), 0.06 (s, 6H); EI-MS m/z: 232 (M$^+$+1).

Preparation of Compound M-2-6

A brown solution of compound M-2-5 (11.9 g, 51.42 mmol) and Int-2 (14.4 g, 56.6 mmol, 1.1 eq.) in anhydrous THE (400 ml) at 0° C. under N$_2$ atmosphere was treated with DIPEA (26.9 mL, 154.3 mmol, 3.0 eq.) and stirred for 5 hours. The reaction mixture was diluted with distilled water (50 mL) and extracted with EA (150 mL×2). The organic layer was dried over anhydrous Na$_2$SO$_4$, filtered and concentrated under reduced pressure. The residue was purified by column chromatography (Hex:EA=2:1 to 2:1) to obtain compound M-2-6 (20 g, 83%) as yellow form solid.

$^1$H NMR (400 MHz, CDCl$_3$) δ 7.95 (s, 1H), 6.87 (s, 1H), 4.60-4.51 (m, 1H), 4.49-4.41 (m, 1H), 4.24-4.08 (m, 1H), 3.91 (s, 3H), 3.80-3.68 (m, 1H), 3.37 (dd, J=7.6 Hz, 4.0 Hz, 1H), 3.14 (d, J=10.4 Hz, 1H), 2.35 (s, 3H), 2.18-2.08 (m, 1H), 0.91 (s, 9H), 0.1 (s 6H); EI-MS m/z: 469 (M$^+$+1).

Preparation of Compound M-2-7

Palladium on carbon, 5% Pd/C (9.1 g, 4.27 mmol, 0.1 eq.) was added to a stirred solution of M-2-6 (20 g, 42.68 mmol) in EA (213 mL) under N$_2$ atmosphere. The flask was flushed by bubbling hydrogen gas through the solution at room temperature. After stirring for 8 hours, the mixture was diluted with EA (50 mL), filtered through Celite, the Celite plug washed with EA (50 mL×2). The filtrate was concentrated under reduced pressure to obtain compound M-2-7 (18.5 g, 99%) as yellow form solid.

$^1$H NMR (400 MHz, CDCl$_3$) δ 6.81 (s, 1H), 6.44 (s, 1H), 5.79 (br s, 1H), 4.58-4.50 (m, 1H), 4.42-4.36 (m, 1H), 4.10 (br s, 1H), 3.79 (s, 3H), 3.59 (dd, J=8.4 Hz, 2.8 Hz, 1H), 3.50 (d, J=11.2 Hz, 1H), 2.30-2.24 (m, 1H), 2.06-2.01 (m, 1H), 0.89 (s, 9H), 0.05 (d, J=1.6 Hz, 6H); EI-MS m/z: 439 (M$^+$+1).

Preparation of Compound M-2-8

A yellow solution of M-2-7 (18.5 g, 42.18 mmol) in anhydrous DCM (210 mL) at 0° C. under N$_2$ atmosphere was treated with 2,2,2-trichloroethyl chloroformate (6.4 mL, 46.4 mmol, 1.1 eq.) and pyridine (6.9 mL, 87.4 mmol, 2.0 eq.) and then stirred for 3 hours. The mixture was washed with CuSO$_4$ solution (50 mL) and brine (100 mL×2). The organic layer was dried over anhydrous Na$_2$SO$_4$, filtered and concentrated under reduced pressure. The residue was purified by column chromatography (Hex:EA=2:1) to obtain compound M-2-8 (21.2 g, 82%) as brown form solid.

$^1$H NMR (400 MHz, CDCl$_3$) δ 8.87 (br s, 1H), 7.86 (s, 1H), 6.89 (s, 1H), 4.84 (d, J=12.8 Hz, 1H), 4.71 (d, J=10.8 Hz, 1H), 4.61 (br s, 1H), 4.45 (s, 1H), 4.20 (br s, 1H), 3.78 (s, 3H), 3.70-3.62 (m, 1H), 3.57 (s, 2H), 2.32 (s, 4H), 2.11-2.02 (m, 1H), 1.80 (s, 1H), 0.90 (s, 9H), 0.05 (s, 6H); EI-MS m/z: 615 (M$^+$+1).

Preparation of Compound M-2-9

A homogeneous solution of oxalyl chloride (21 mL, 24.4 mmol, 1.5 eq) in anhydrous DCM (50 mL) at −78° C. under of N$_2$ atmosphere was treated with DMSO (3.5 mL, 48.9 mmol, 3.0 eq) in anhydrous DCM (20 mL) and stirred for 1 hour. A solution of M-2-8 (10 g, 0.33 mmol) in anhydrous DCM (100 mL) was added dropwise to the reaction mixture and stirred for 2 hours. The reaction mixture was treated with TEA (22.7 mL, 162.9 mmol, 10 eq.) and stirred for 1 hour at room temperature. The mixture was extracted with NH$_4$Cl solution (30 mL) and DCM (100 mL×2). The organic layer was dried over anhydrous Na$_2$SO$_4$, filtered and concentrated under reduced pressure. The residue was purified by column chromatography (Hex:EA=4:1 to 1:1) to obtain compound M-2-9 (8.2 g, 83%) as brown form solid.

$^1$H NMR (400 MHz, CDCl$_3$) δ 8.68 (br s, 1H), 7.91 (s, 1H), 6.86 (s, 1H), 5.12 (br s, 1H), 4.80 (s, 2H), 4.13 (br s, 1H), 4.04 (d, J=17.2 Hz, 1H), 3.98-3.86 (m, 1H), 3.80 (s, 3H), 3.76-3.62 (m, 1H), 2.84-2.72 (m, 2H), 2.54 (d, J=17.2 Hz, 1H), 2.32 (s, 3H), 2.08-1.98 (m, 1H), 0.88 (s, 9H), 0.21 (s, 6H); EI-MS m/z: 612 (M$^+$+1).

Preparation of Compound M-2-10

A yellow solution of M-2-9 (2.0 g, 3.27 mmol) and 2,6-lutidine (4.6 mL, 12 eq) in anhydrous DCM (100 mL) at −10° C. under N$_2$ atmosphere was treated with triflic anhydride (5.5 mL, 32.68 mmol, 10 eq.) and stirred for 6 hours. The reaction mixture was allowed to warm up to room temperature and stirred for a further 1 hour. The mixture was diluted with distilled water (50 mL) and extracted with DCM (100 mL×2). The organic layer was dried over anhydrous Na$_2$SO$_4$, filtered and concentrated under reduced pressure. The residue was purified by column chromatography (Hex:EA=4:1) to obtain compound M-2-10 (502 mg, 21%) as yellow oil.

$^1$H NMR (400 MHz, CDCl$_3$) δ 8.78 (br s, 1H), 7.97 (s, 1H), 6.85 (s, 1H), 6.80 (s, 1H), 4.86-4.72 (m, 3H), 4.20-4.32 (m, 1H), 3.80 (s, 3H), 3.76-3.68 (m, 1H), 3.20-3.00 (m, 2H), 2.33 (s, 3H), 0.89 (s, 9H), 0.06 (d, J=10.6 Hz 6H); EI-MS m/z: 745 (M$^+$+1).

Preparation of Compound M-2-11

A yellow solution of M-2-10 (500 mg, 0.67 mmol) in toluene (4.0 mL), H$_2$O (0.6 mL) and ethanol (4.0 mL) at room temperature under N$_2$ atmosphere was treated with 4,4,5,5-tetramethyl-2-phenyl-1,3,2-dioxaborolane (164.6 mg, 0.81 mmol, 1.2 eq.), Pd(TPP)$_4$ (77.5 mg, 0.067 mmol, 0.1 eq) and TEA (234.2 uL, 1.68 mmol, 2.5 eq.) and then stirred for 3 hours. The mixture was diluted with distilled water (100 mL) and extracted with EA (100 mL). The organic layer was dried over anhydrous Na$_2$SO$_4$, filtered and concentrated under reduced pressure. The residue was purified by column chromatography (Hex:EA=3:1) to obtain compound M-2-11 (343 mg, 76%) as yellow form solid.

$^1$H NMR (400 MHz, CDCl$_3$) δ 8.76 (br s, 1H), 7.96 (s, 1H), 7.38-7.28 (m, 5H), 6.98 (s, 1H), 6.93 (s, 1H), 4.78-4.68 (m, 3H), 4.16-4.04 (m, 2H), 3.92-3.84 (m, 1H), 3.79 (s, 3H), 3.24-3.12 (m, 1H), 3.08-2.90 (m, 1H), 2.34 (s, 3H), 0.85 (s, 9H), 0.05 (s, 6H); EI-MS m/z: 673 (M$^+$+1).

Preparation of Compound M-2-12

A yellow solution of M-2-11 (340 mg, 0.505 mmol) in THF (4.0 mL) and H$_2$O (2.0 mL) at room temperature under N$_2$ atmosphere was treated with acetic acid (8.0 mL) and stirred for 20 hours. The mixture was diluted with distilled water (10 mL) and extracted with EA (20 mL×2). The organic layer was dried over anhydrous Na$_2$SO$_4$, filtered and concentrated under reduced pressure. The residue was purified by column chromatography (Hex:EA=2:1) to obtain compound M-2-12 (250 mg, 89%) as yellow form solid.

$^1$H NMR (400 MHz, CDCl$_3$) δ 8.86 (br s, 1H), 7.87 (s, 1H), 7.36-7.28 (m, 5H), 7.00 (s, 1H), 6.85 (s, 1H), 4.93 (br s, 1H), 4.75 (s, 2H), 4.16-4.10 (m, 3H), 3.82 (s, 3H), 3.64 (s, 1H), 3.33 (t, J=13.6, 5.6 Hz, 1H), 2.77 (d, J=17.2 Hz, 1H) 2.34 (s, 3H); EI-MS m/z: 558 (M$^+$+1).

Preparation of Compound M-2-13

A homogeneous solution of oxalyl chloride (58 uL, 0.67 mmol, 1.5 eq.) in anhydrous DCM (1.0 mL) at −78° C. under of N$_2$ atmosphere was treated with DMSO (80 uL, 1.12 mmol, 3.0 eq.) in anhydrous DCM (1.0 mL) and stirred for 15 minutes. A solution of M-2-12 (250 mg, 0.45 mmol) in anhydrous DCM (3.0 mL) was added dropwise to the reaction mixture and stirred for 3 hours followed by TEA (500 uL, 3.58 mmol, 8.0 eq.) and stirred for a further 30 minutes at room temperature. The reaction mixture was diluted with distilled water (5.0 mL) and extracted with EA (15 mL×2). The organic layer was dried over anhydrous Na$_2$SO$_4$, filtered and concentrated under reduced pressure. The residue was purified by column chromatography (Hex:EA=3:1) to obtain compound M-2-13 (202 mg, 81%) as yellow form solid.

$^1$H NMR (400 MHz, CDCl$_3$) δ 7.45 (s, 1H), 7.38 (s, 5H), 7.12 (s, 1H), 5.84 (br s, 1H), 5.18 (d, J=10.6 Hz, 1H), 4.31 (d, J=12.8 Hz, 1H), 4.18-4.06 (m, 3H), 3.84 (s, 3H), 3.72 (s, 1H), 3.43 (t, J=10.0 Hz, 1H), 3.12 (d, J=18.0 Hz, 1H), 2.32 (s, 3H); EI-MS m/z: 556 (M$^+$+1)

Preparation of Compound M-2

A yellow solution of M-2-13 (175 mg, 0.31 mmol) in MeOH (16 mL) and H$_2$O (3.0 mL) at room temperature under N$_2$ atmosphere was treated with K$_2$CO$_3$ (109 mg, 0.79 mmol, 2.5 eq.) and stirred for 2 hours. The mixture was diluted with water (5 mL) and extracted with EA (10 mL×2). The organic layer was dried over anhydrous Na$_2$SO$_4$, filtered and concentrated under reduced pressure. The residue was purified by column chromatography (Hex:EA=2:1) to obtain compound M-2 (135 mg, 85%) as yellow form solid.

$^1$H NMR (400 MHz, CDCl$_3$) δ 7.49 (s, 1H), 7.37 (s, 5H), 6.94 (s, 1H), 5.93 (br s, 1H), 5.88-5.82 (m, 1H), 5.14 (d, J=11.6 Hz, 1H), 4.32 (d, J=10.8 Hz, 1H), 4.18-4.00 (m, 2H), 3.97 (s, 3H), 3.41 (t, J=9.6 Hz, 1H), 3.10 (d, J=16.0 Hz, 1H); EI-MS m/z: 514 (M$^+$+1)

Example 39: Preparation of PBD Compound Bearing C2-Aryl Substituents

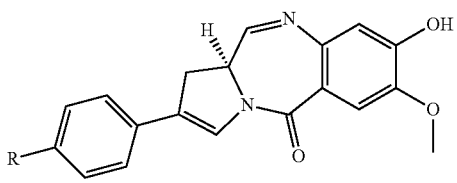

C2-aryl substituted PBD monomer

R = H or OMe or OH (including Br, or CN)

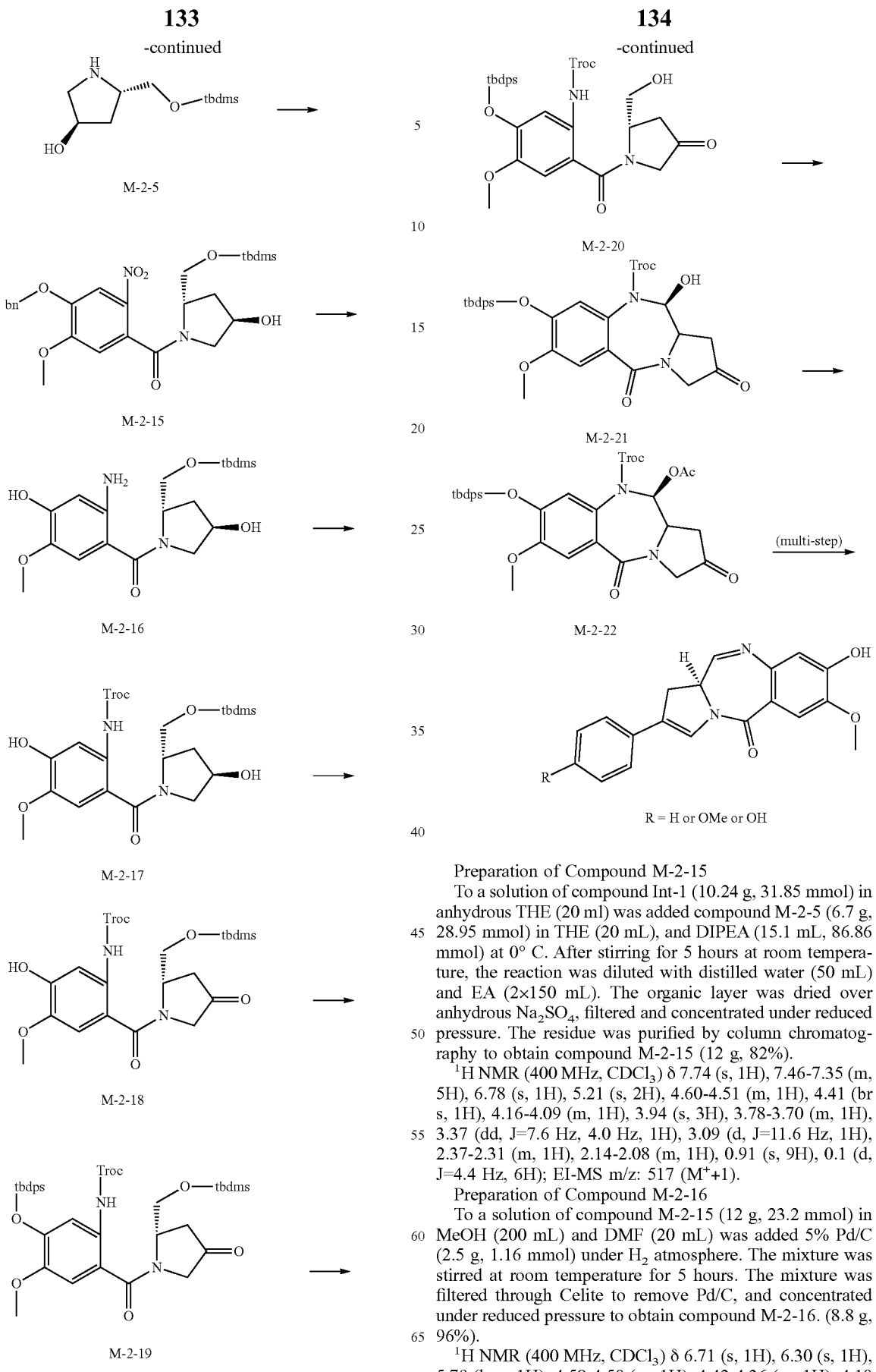

Preparation of Compound M-2-15

To a solution of compound Int-1 (10.24 g, 31.85 mmol) in anhydrous THE (20 ml) was added compound M-2-5 (6.7 g, 28.95 mmol) in THE (20 mL), and DIPEA (15.1 mL, 86.86 mmol) at 0° C. After stirring for 5 hours at room temperature, the reaction was diluted with distilled water (50 mL) and EA (2×150 mL). The organic layer was dried over anhydrous $Na_2SO_4$, filtered and concentrated under reduced pressure. The residue was purified by column chromatography to obtain compound M-2-15 (12 g, 82%).

$^1$H NMR (400 MHz, $CDCl_3$) δ 7.74 (s, 1H), 7.46-7.35 (m, 5H), 6.78 (s, 1H), 5.21 (s, 2H), 4.60-4.51 (m, 1H), 4.41 (br s, 1H), 4.16-4.09 (m, 1H), 3.94 (s, 3H), 3.78-3.70 (m, 1H), 3.37 (dd, J=7.6 Hz, 4.0 Hz, 1H), 3.09 (d, J=11.6 Hz, 1H), 2.37-2.31 (m, 1H), 2.14-2.08 (m, 1H), 0.91 (s, 9H), 0.1 (d, J=4.4 Hz, 6H); EI-MS m/z: 517 ($M^+$+1).

Preparation of Compound M-2-16

To a solution of compound M-2-15 (12 g, 23.2 mmol) in MeOH (200 mL) and DMF (20 mL) was added 5% Pd/C (2.5 g, 1.16 mmol) under $H_2$ atmosphere. The mixture was stirred at room temperature for 5 hours. The mixture was filtered through Celite to remove Pd/C, and concentrated under reduced pressure to obtain compound M-2-16. (8.8 g, 96%).

$^1$H NMR (400 MHz, $CDCl_3$) δ 6.71 (s, 1H), 6.30 (s, 1H), 5.79 (br s, 1H), 4.58-4.50 (m, 1H), 4.42-4.36 (m, 1H), 4.10

(br s, 1H), 3.79 (s, 3H), 3.59 (dd, J=8.4 Hz, 2.8 Hz, 1H), 3.50 (d, J=11.2 Hz, 1H), 2.30-2.24 (m, 1H), 2.06-2.01 (m, 1H), 0.89 (s, 9H), 0.05 (d, J=1.6 Hz, 6H); EI-MS m/z: 397 (M$^+$+1).

Preparation of Compound M-2-17

A solution of 2,2,2-trichloroethyl chloroformate (555 uL, 4.03 mmol) in anhydrous DCM (20 mL) was added dropwise to a solution of M-2-16 (2.0 g, 5.04 mmol) and pyridine (2.0 mL, 25.2 mmol) in anhydrous DCM (30 mL) at 0° C. After stirring for 1 hour at 0° C., the reaction was washed with CuSO$_4$ solution (50 mL) and brine (2×100 mL). The organic layer was dried over anhydrous Na$_2$SO$_4$, filtered and concentrated under reduced pressure. The residue was purified by column chromatography to obtain compound M-2-17 (1.23 g, 43%).

$^1$H NMR (400 MHz, CDCl$_3$) δ 9.05 (br s, 1H), 7.66 (s, 1H), 6.79 (s, 1H), 5.92 (s, 1H), 5.21 (s, 2H), 4.385 (d, J=12.4 Hz, 1H), 4.70 (d, J=11.6 Hz, 1H), 4.56 (br s, 1H), 4.30 (s, 1H), 4.14 (br s, 1H), 3.84 (s, 3H), 3.58 (s, 2H), 2.36-2.26 (m, 1H), 2.12-2.0 (m, 1H), 1.93 (br s, 1H), 0.90 (s, 9H), 0.04 (s, 6H); EI-MS m/z: 593 (M$^+$+1).

Preparation of Compound M-2-18

A solution of DMSO (485.2 uL, 6.45 mmol) in anhydrous DCM (5 mL) was added dropwise to a solution of oxalyl chloride (369 uL, 4.3 mmol) in anhydrous DCM (20 mL) at −78° C. After stirring for 1 hours at −78° C., a solution of M-2-17 (1.23 g, 2.15 mmol) in anhydrous DCM (20 mL) was added dropwise to the reaction mixture and stirred for 2 hours at −78° C. After 2 hours TEA (3 mL, 21.5 mmol) was added in reaction mixture and stirred for 1 hour at room temperature. The reaction mixture was extracted with NH$_4$Cl solution (30 mL) and DCM (2×50 mL). The organic layer was dried over anhydrous Na$_2$SO$_4$, filtered and concentrated under reduced pressure. The residue was purified by column chromatography to obtain compound M-2-18 (906.7 mg, 76%). EI-MS m/z: 571 (M$^+$+1).

Preparation of PBD Compound Bearing C2-Aryl Substituents

PBD compounds were synthesized via a similar synthetic route as described in WO2005/085251 and Tetrahedron Letters 56(2015) 4512-4515, both of which are fully incorporated by reference herein.

Example 40: Preparation of Compound M-3

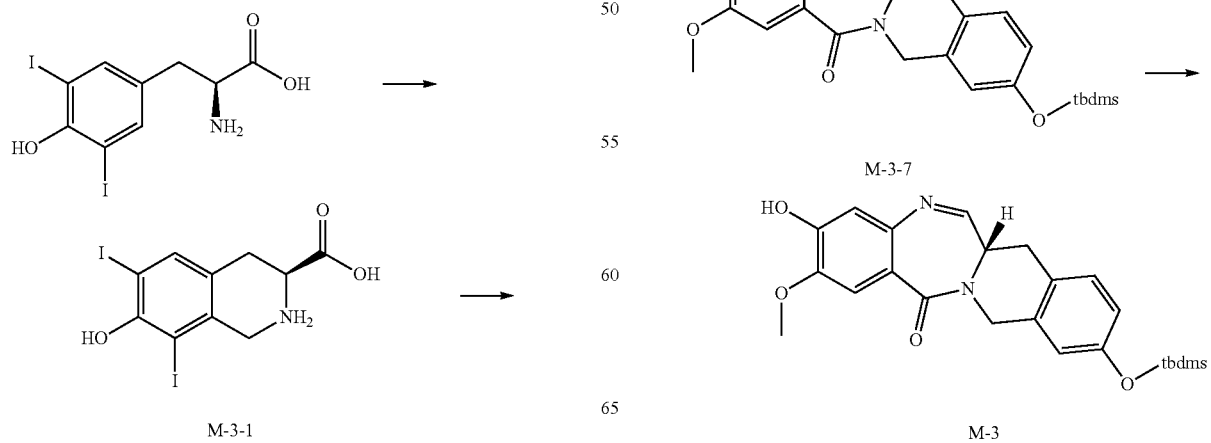

Preparation of Compound M-3-1

To a solution of (S)-2-amino-3-(4-hydroxy-3,5-diiodophenyl)propanoic acid (8.0 g, 18.48 mmol) in concentrated aqueous HCl (90 mL) was added 1,2-dimethoxyethane (7.5 mL) and paraformaldehyde (37% wt. in $H_2O$, 92.38 mmol). The mixture was stirred vigorously and slowly heated to 72° C. The reaction mixture was stirred overnight at 72° C. The suspension was then cooled in an ice bath and the solids collected by filtration, washed thoroughly with 1,2-dimethoxyethane (3×10 mL) and dried under vacuum to obtain compound M-3-1 (2.49 g, yield 28%).

$^1$H NMR (400 MHz, DMSO-d6) δ 10.02 (br s, 1H), 9.69 (s, 1H), 7.73 (s, 1H), 4.31 (dd, J=6.8 Hz, 4.4 Hz, 1H), 4.05 (q, J=18.8 Hz, 16 Hz, 2H), 3.21 (dd, J=12 Hz, 4.8 Hz, 1H), 3.12-3.02 (m, 1H); EI-MS m/z: 446 ($M^+$+1).

Preparation of Compound M-3-2

A mixture of M-3-1 (1.4 g, 3.1 mmol), TEA (1.4 mL, 10.38 mmol) and 5% Pd/C (335 mg, 0.16 mmol) in EtOH/$H_2O$ (40 mL/mL) was stirred at room temperature under $H_2$ atmosphere for 3 hours. The mixture was filtered through Celite and the filtrate concentrated. The resultant residue was diluted with water and the precipitate was filtered. The solid was washed with cold water and dried under high vacuum to obtain compound M-3-2 (337.3 mg, 60%).

$^1$H NMR (400 MHz, DMSO-d6) δ 9.55 (br s, 1H), 9.69 (s, 1H), 6.98 (d, J=9.0 Hz, 1H), 6.64 (d, J=8.4 Hz, 1H), 6.57 (s, 1H), 4.06 (s, 2H), 3.46 (dd, J=6.0 Hz, 4.8 Hz, 1H), 3.46 (dd, J=11.6 Hz, 5.2 Hz, 1H), 2.82-2.75 (m, 1H); EI-MS m/z: 194 ($M^+$+1).

Preparation of Compound M-3-3

To a solution M-3-2 (337.3 mg, 1.74 mmol) in MeOH (5.0 mL) was added dropwise $SOCl_2$ (380 uL, 5.24 mmol) to 0° C. under $N_2$ atmosphere. After reflux for 2 hours, the reaction mixture was concentrated under reduced pressure and used directly in the next step without further purification (406 mg, yield 96%).

$^1$H NMR (400 MHz, DMSO-d6) δ 9.83 (br s, 2H), 9.56 (s, 1H), 7.05 (d, J=8.0 Hz, 1H), 6.70 (d, J=8.0 Hz, 1H), 6.63 (s, 1H), 4.53-4.49 (m, 1H), 4.28-4.22 (m, 2H), 3.81 (s, 1H), 3.18 (dd, J=11.6 Hz, 5.2 Hz, 1H), 3.04-2.97 (m, 1H); EI-MS m/z: 208 ($M^+$+1).

Preparation of Compound M-3-4

To a solution of compound Int-1 (640.9 mg, 1.86 mmol) in anhydrous THF (4.0 mL) was added compound M-3-3 (350 mg, 1.43 mmol) in DMF (5.0 mL) followed by DIPEA (750 uL, 4.3 mmol) at 0° C. After stirring for 2 hours at room temperature, the mixture was diluted with distilled water (10 mL) and EA (2×50 mL). The organic layer was dried over anhydrous $Na_2SO_4$, filtered and concentrated under reduced pressure. The residue was purified by column chromatography to obtain compound M-3-4 (616 mg, 87%); EI-MS m/z: 493 ($M^+$+1).

Preparation of Compound M-3-5 t-Butyldimethylsilyl chloride (188.5 mg, 1.25 mmol) was added to a solution of M-3-4 (616 mg, 1.25 mmol) and imidazole (102.2 mg, 1.50 mmol) in anhydrous DCM (6.0 mL) at 0° C. The reaction mixture was stirred overnight at room temperature. The reaction was quenched with 2N HCl (5 mL) and brine (10 mL) and extracted with DCM (10 mL×2). The organic layer was dried over anhydrous $Na_2SO_4$, filtered and concentrated under reduced pressure. The residue was purified by column chromatography to obtain compound M-3-5 (655.2 mg, 86%). EI-MS m/z: 607 ($M^+$+1).

Preparation of Compound M-3-6

To a solution of compound M-3-5 (309 mg, 0.51 mmol) in anhydrous DCM (1.5 mL) and toluene (3.5 mL) at −78° C. under $N_2$ atmosphere was added dropwise DIBAL (990 uL, 0.99 mmol, 1.0M in toluene). After stirring for 1.5 hours, the reaction was quenched with MeOH (0.4 mL) and 2N HCl (15 mL) at −78° C., then extracted with $H_2O$ (20 mL) and EA (30 mL×2). The organic layer was dried over anhydrous $Na_2SO_4$, filtered and concentrated under reduced pressure. The residue was purified by column chromatography to obtain compound M-3-6 (280.4 mg, 95%); EI-MS m/z: 577 ($M^+$+1).

Preparation of Compound M-3-7

To a solution of compound M-3-6 (280.4 mg, 0.49 mmol) in THF (6.0 mL) and distilled water (86 mL) was added $Na_2S_2O_4$ (677.2 mg, 3.89 mmol) at room temperature. After stirring for 5 h, the mixture was concentrated under reduced pressure four times by using toluene as a co-solvent, thereby removing water. The obtained yellow solid was dissolved in anhydrous MeOH (12 mL). Acetyl chloride (345.6 uL, 4.86 mmol) was added thereto. After stirring 15 minutes, the reaction mixture was filtered and filtrate was stirred for 1 h. The reaction mixture was adjusted to pH 7 by addition of saturated $NaHCO_3$ solution and diluted with distilled water (10 mL) and EA (2×50 mL). The organic layer was dried over anhydrous $Na_2SO_4$, filtered and concentrated under reduced pressure. The residue was purified by column chromatography to obtain compound M-3-7 (107.7 mg, 42%).

$^1$H NMR (400 MHz, $CDCl_3$) δ 7.55 (s, 1H), 7.48-7.31 (m, 6H), 7.16 (d, J=8.4 Hz, 1H), 6.94 (s, 1H), 6.82-6.76 (m, 2H), 5.28-5.15 (m, 2H), 4.93 (d, J=15.6 Hz, 1H), 4.46 (d, J=15.6 Hz, 1H), 3.97 (s, 3H), 3.92-3.86 (m, 1H), 3.18 (dd, J=9.6 Hz, 5.6 Hz, 1H), 3.10-3.02 (m, 1H), 0.99 (s, 9H), 0.21 (s, 6H); EI-MS m/z: 529 ($M^+$+1).

Preparation of Compound M-3

To a solution of compound M-3-7 (53.4 mg, 0.1 mmol) in EtOH (6.0 mL) was added 5% Pd/C (107.5 mg, 0.05 mmol) under $N_2$ atmosphere. And then 1,4-cyclohexadiene (764.4 uL, 8.08 mmol) was added in reaction mixture. After stirring for 3 hours, the mixture was filtered through Celite to remove Pd/C, and concentrated under reduced pressure. The residue was purified by column chromatography to obtain compound M-3 (30.3 mg, 68%).

$^1$H NMR (400 MHz, $CDCl_3$) δ 7.54 (s, 1H), 7.47 (d, J=5.2 Hz, 1H), 7.20 (d, J=8.82 Hz, 1H), 6.87 (s, 1H), 6.84-6.75 (m, 2H), 5.98 (s, 1H), 4.93 (d, J=15.6 Hz, 1H), 4.47 (d, J=15.2 Hz, 1H), 3.98 (s, 3H), 3.94-3.85 (m, 1H), 3.19 (dd, J=11.2 Hz, 5.2 Hz, 1H), 3.12-3.02 (m, 1H), 0.99 (s, 9H), 0.21 (s, 6H); EI-MS m/z: 439 ($M^+$+1).

Example 41: Preparation of Compound M-4

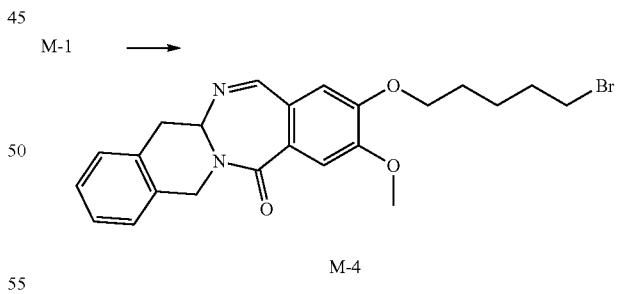

M-1 →

M-4

A yellow solution of compound M-1 (6.0 mg, 0.019 mmol) and 1,5-dibromopentane (5.26 uL, 0.038 mmol, 2.0 eq.) in DMF (1 mL) at room temperature under $N_2$ atmosphere was treated $K_2CO_3$ (2.7 mg, 0.019 mmol, 1.0 eq.) and stirred for 7 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound 115 (7.3 mg, 82%) as white solid.

EI-MS m/z: 458 ($M^+$+1).

Preparation of Homo-Dimers

Example 42: Preparation of Compound Ref-1

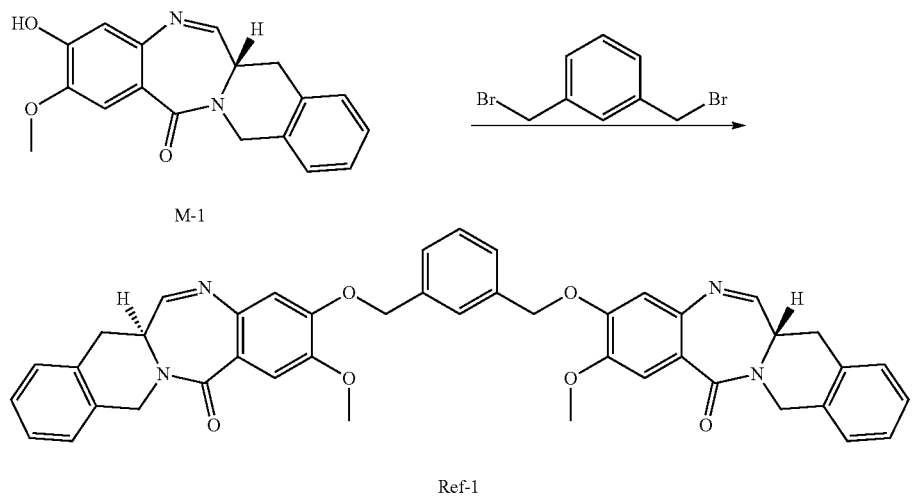

M-1

Ref-1

Ref-1 was synthesized via a similar synthetic route as described in WO2016/115191 A1. To a solution of compound M-1 (10.0 mg, 0.03 mmol) and 1,3-bis(bromomethyl)benzene (4.1 mg, 0.015 mmol) in DMF (1.0 mL) was added $K_2CO_3$ (4.7 mg, 0.034 mmol) under $N_2$ atmosphere. The mixture was stirred overnight at room temperature and concentrated under reduced pressure. The residue was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound Ref-1 (8.0 mg, 71%).

EI-MS m/z: 719 ($M^+$+1).

Example 43: Preparation of (Phenol)-PBD-Dimer (D-1)

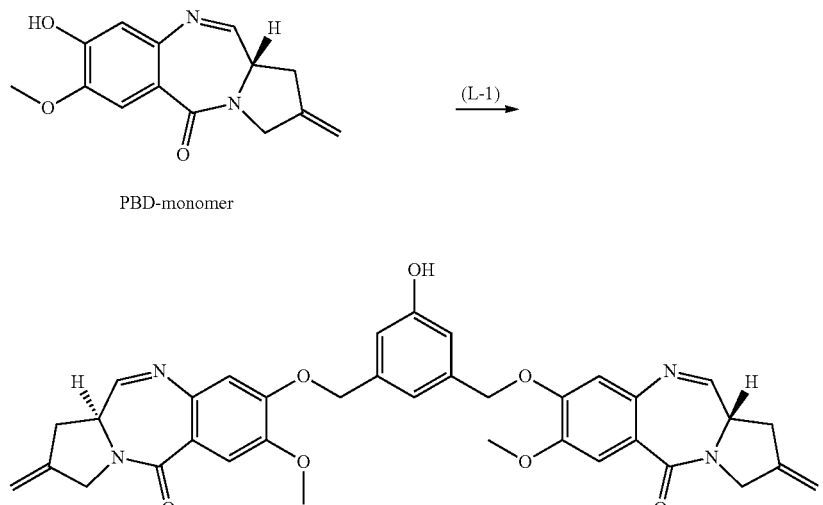

PBD-monomer

D-1

To a solution of compound PBD-monomer (Reference EP20071813614 A1, 29 mg, 0.11 mmol) and compound L-1 (20 mg, 0.05 mmol) in DMF (2 mL) was added $K_2CO_3$ (15.4 mg, 0.11 mmol) at room temperature under $N_2$ atmosphere. After stirring for 17 hours, the mixture was diluted with EA (1 mL) and added with 1M TBAF in THF (51 uL, 0.05 mmol). The mixture was stirred for a further 1 hour and washed with $H_2O$ (50 mL) and 2N HCl aqueous solution (5 mL) and extracted with EA (100 mL). The obtained organic layer was dried over anhydrous $Na_2SO_4$, filtered and concentrated under reduced pressure. The residue was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-1 (17 mg, 53%). EI-MS m/z: 635 ($M^+$+1).

Example 44: Preparation of (Pyridine)-PBD-Dimer (D-2)

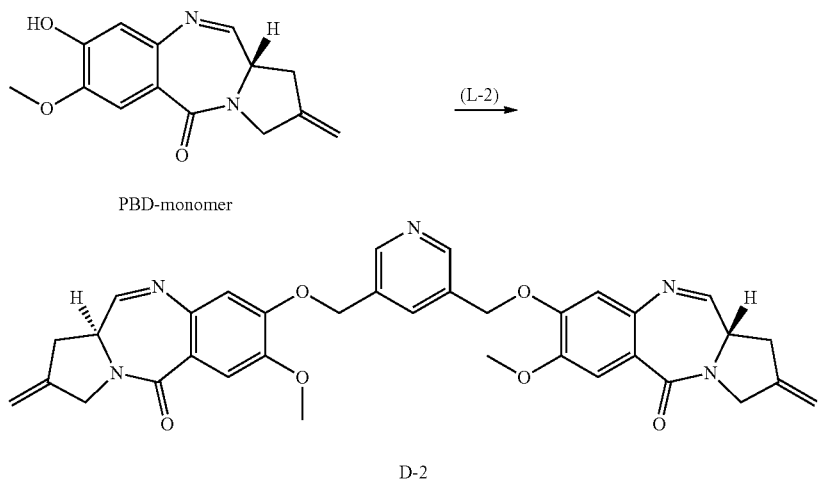

To a solution of compound PBD-monomer (Reference EP20071813614 A1, 39 mg, 0.15 mmol) and compound L-2 (20 mg, 0.08 mmol) in DMF (2 mL) was added $K_2CO_3$ (21 mg, 0.15 mmol) at room temperature under $N_2$ atmosphere. After stirring for 5 hours, the mixture was diluted with EA (100 mL). The organic layer was washed with $H_2O$ (50 mL) and 2N HCl aqueous solution (5 mL) and dried over anhydrous $Na_2SO_4$, filtered and concentrated under reduced pressure. The residue was purified by column chromatography to obtain a compound D-2 (46.4 mg, 52%).
EI-MS m/z: 620 ($M^+$).

Example 45: Preparation of (Phenol)-TBD-Dimer (D-3)

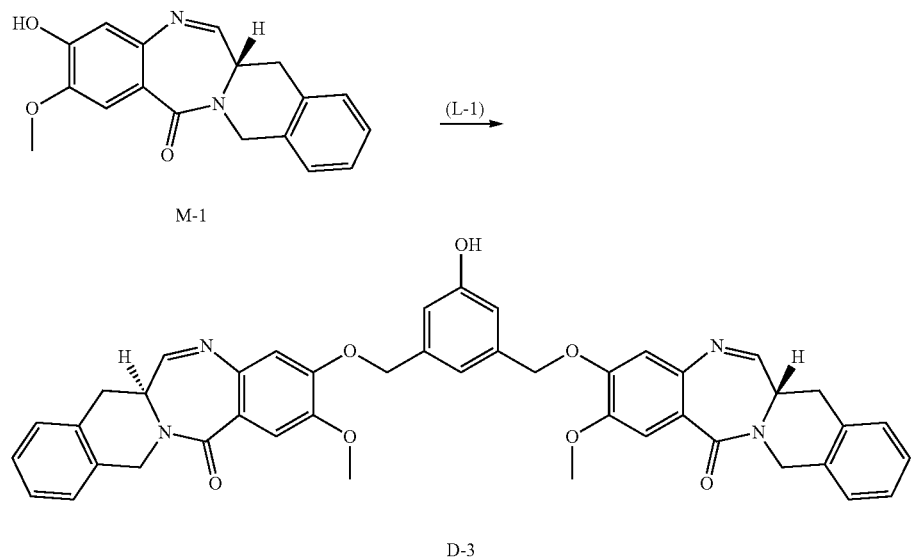

To a solution of Compound M-1 (31 mg, 0.10 mmol) and compound L-1 (20 mg, 0.05 mmol) in DMF (1.0 mL) was added K₂CO₃ (14 mg, 0.10 mmol) under N₂ atmosphere. After stirring for 7 hours at room temperature, the reaction mixture was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-3 (13 mg, 30%).

EI-MS m/z: 734 (M⁺+1).

Example 46: Preparation of (Pyridine)-TBD-Dimer (D-4)

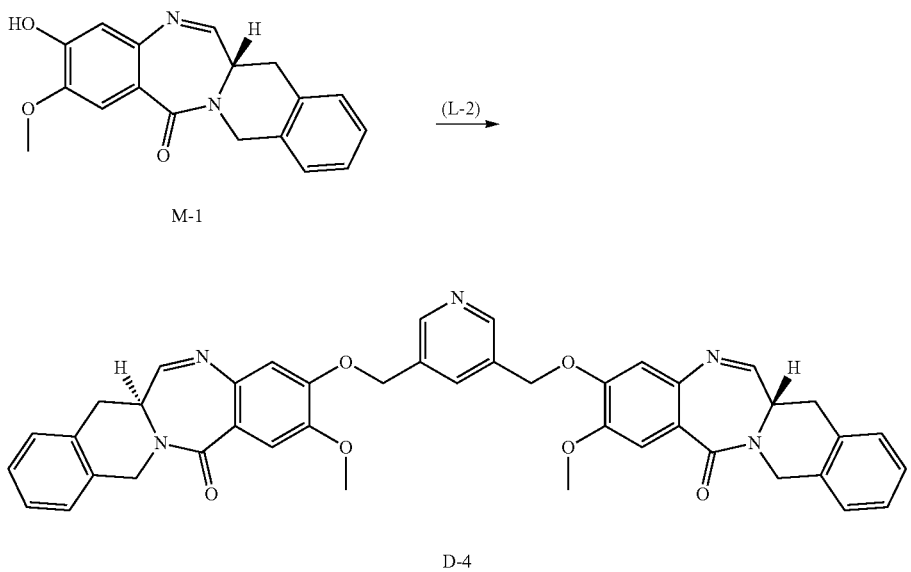

Compound D-4 was synthesized via a similar synthetic route as described in Example 44 (yield 85%).
EI-MS m/z: 720 (M⁺+1).

Example 47: Preparation of (N,N-dimethylbenzyl)-TBD-Dimer (D-5)

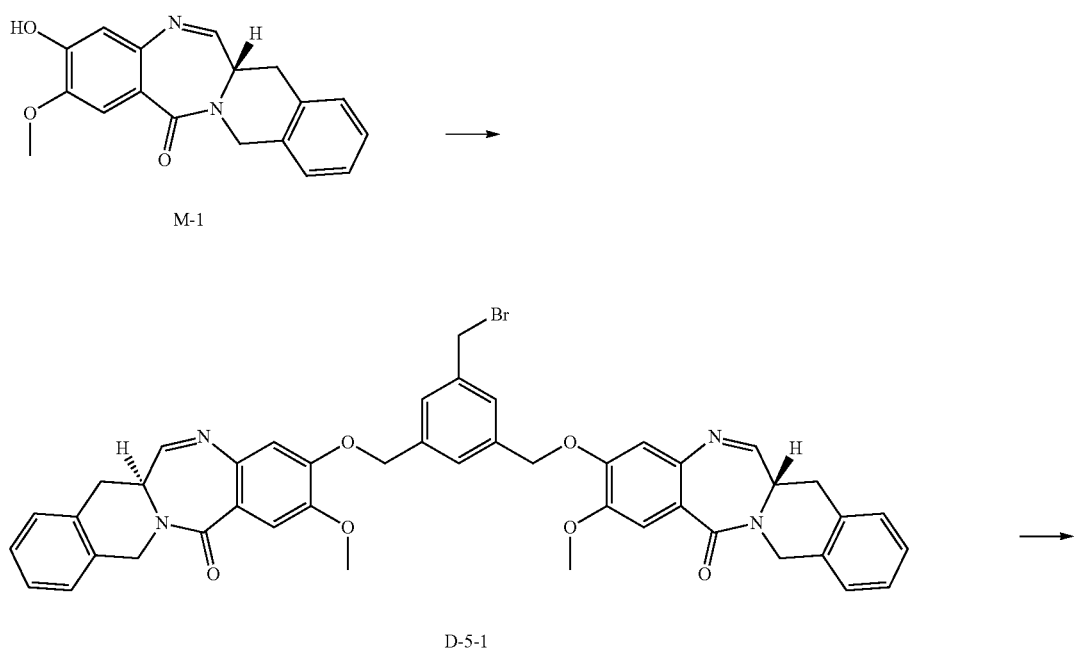

-continued

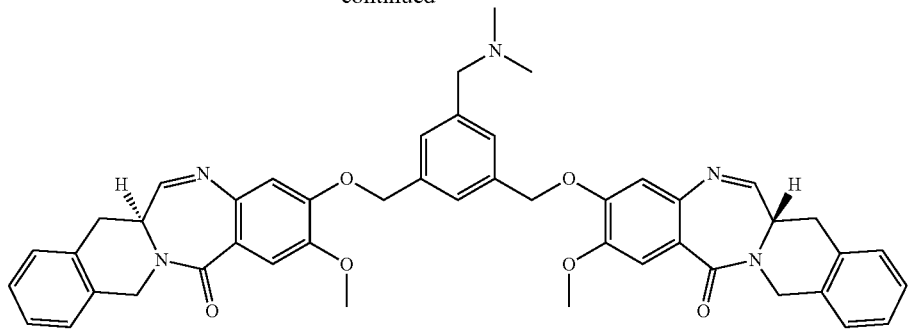

D-5

Preparation of Compound D-5-1

To a solution of compound M-1 (100 mg, 0.32 mmol) and 1,3,5-tris(bromomethyl)benzene (57 mg, 0.16 mmol) in DMF (1 mL) was added K$_2$CO$_3$ (45 mg, 0.32 mmol) at room temperature under N$_2$ atmosphere. After stirring for 4 hours, EA (100 mL), H$_2$O (50 mL) and 2N HCl aqueous solution (5 mL) were added to perform extraction, the obtained organic layer was dried over anhydrous Na$_2$SO$_4$, filtered and concentrated under reduced pressure. The residue was purified by column chromatography to obtain a compound D-5-1 (54 mg, 42%).

EI-MS m/z: 812 (M$^+$).

Preparation of Compound D-5

Compound D-5-1 (50 mg, 0.01 mmol) was dissolved in dimethylamine (1 mL) at room temperature under N$_2$ atmosphere. After stirring for 1 h, the mixture was purified by preparative HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-5 (2.2 mg, 17%).

EI-MS m/z: 776 (M$^+$+1).

Example 48: Preparation of (N-Pyridine)-TBD-Dimer (D-6)

To a solution of compound M-1 (16 mg, 0.05 mmol) and compound L-3 (10 mg, 0.03 mmol) in DMF (1 mL) was added K$_2$CO$_3$ (11 mg, 0.08 mmol) at 50° C. under N$_2$ atmosphere. After stirring for 5 hours, the mixture was purified by preparative HPLC (Column: Innoval ODS-2 10 um, 100 Å, 50×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-6 (10.5 mg, 53%). EI-MS m/z: 763 (M*).

Example 49: Preparation of (Phenol)-IBD-Dimer (D-7)

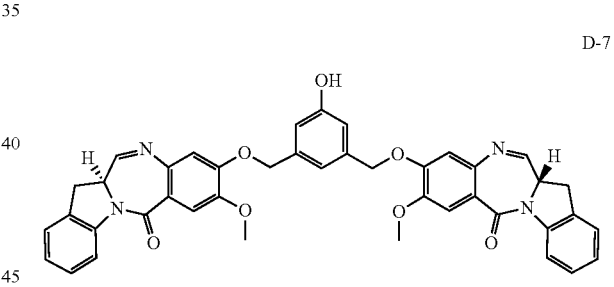

D-7

Compound D-7 was synthesized via a similar synthetic route as described in Example 43. EI-MS m/z: 707 (M$^{+1}$).

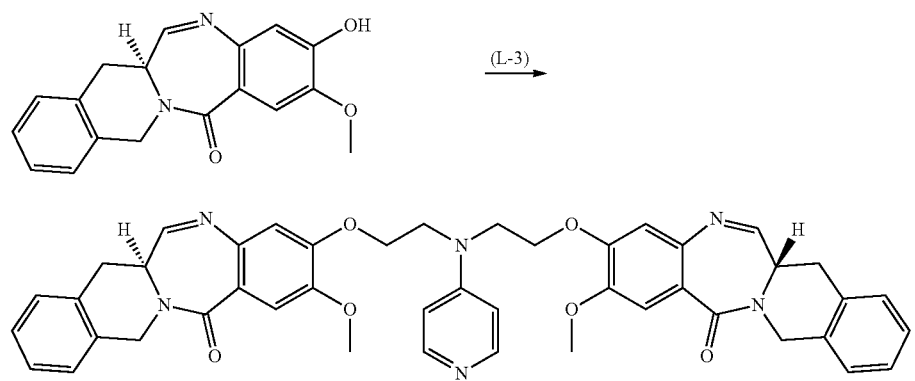

D-6

Example 50: Preparation of (N,N-dimethylbenzyl)-IBD-Dimer (D-8)

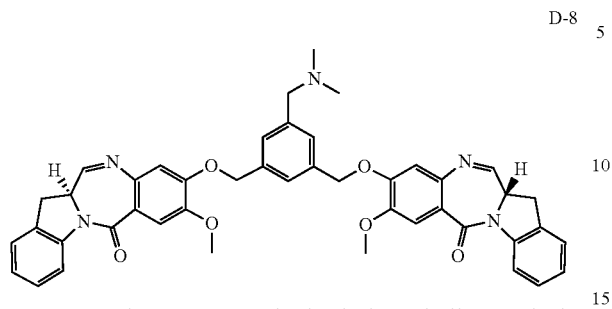

D-8

Compound D-8 was synthesized via a similar synthetic route as described in Example 47 (yield 50%). EI-MS m/z: 748 ($M^{+1}$).

Example 51: Preparation of Compound D-9

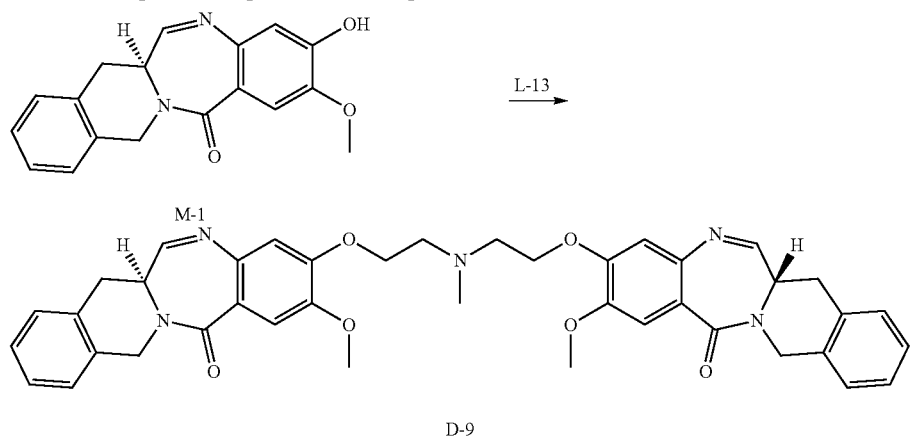

A yellow solution of compound M-1 (50 mg, 0.16 mmol) and compound L-13 (19.8 mg, 0.081 mmol, 0.5 eq.) in DMF (3 mL) at room temperature under $N_2$ atmosphere was treated $K_2CO_3$ (112 mg, 0.81 mmol, 5.0 eq.) and stirred for 3 hours. The reaction mixture was purified by preparative HPLC (Column: Innoval ODS-2 10 um, 100 Å, 21.2×250 mm; flow rate: 40 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-9 (31 mg, 55%) as white solid.

EI-MS m/z: 700 ($M^+$+1).

Example 52: Preparation of Compound D-10

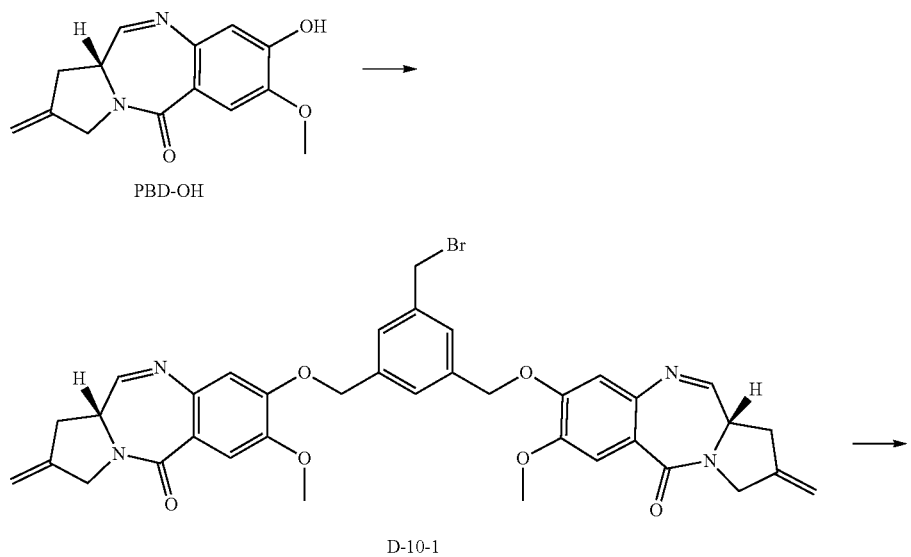

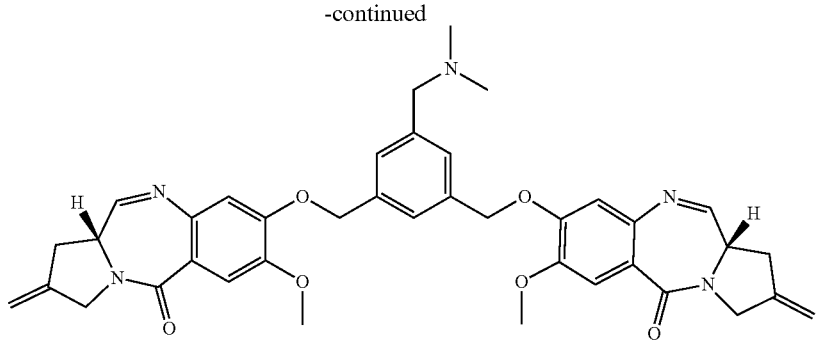

D-10

Preparation of Compound D-10-1

A yellow solution of compound PBD-OH (250 mg, 0.97 mmol) and 1,3,5-trisbromomethyl benzene (172.7 mg, 0.48 mmol, 0.5 eq.) in DMF (2.0 mL) at room temperature under $N_2$ atmosphere was treated $K_2CO_3$ (200.8 mg, 1.45 mmol, 1.5 eq.) and stirred for 3 hours. The compound D-10-1 was used directly in the next step without further purification.

Preparation of Compound D-10

Compound D-10 was synthesized via a similar synthetic route as described in Example 47.

Yield 23% as white solid. EI-MS m/z: 658 (M$^+$+1).

Example 53: Preparation of Compound D-11

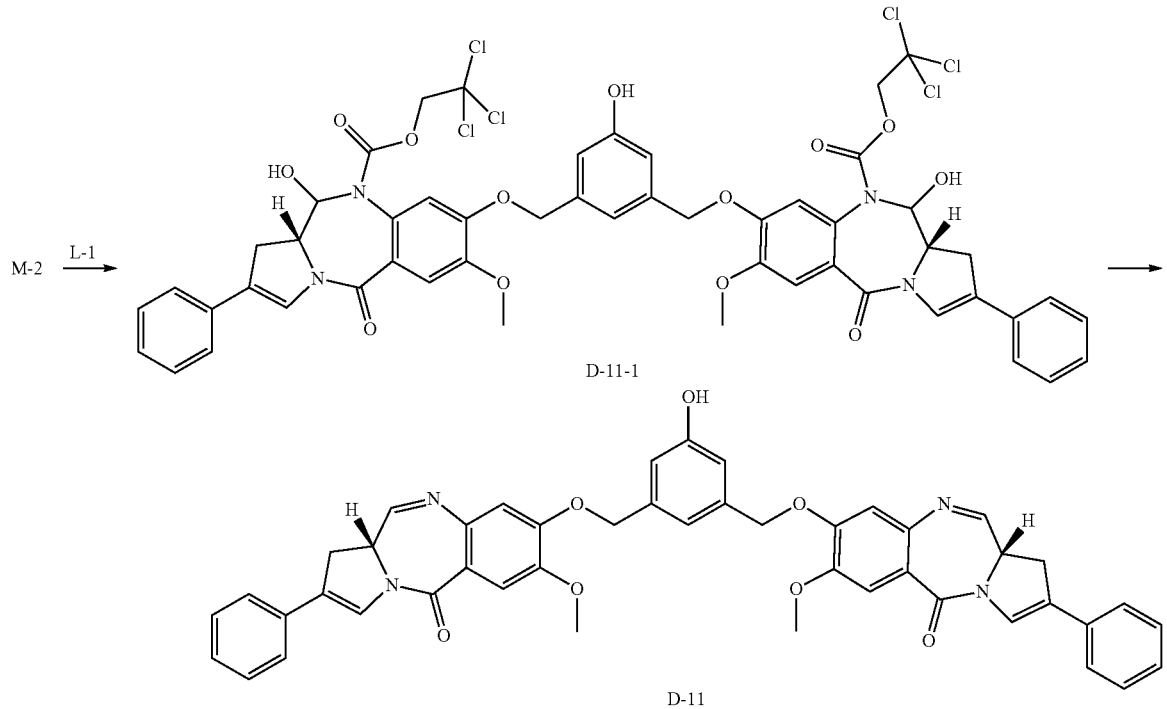

Preparation of Compound D-11-1

A yellow solution of compound M-2 (20 mg, 0.038 mmol) and L-1 (7.6 mg, 0.019 mmol, 0.5 eq.) in DMF (1 mL) at room temperature under $N_2$ atmosphere was treated $K_2CO_3$ (6.6 mg, 0.048 mmol, 4.0 eq) and stirred for 20 hours. The reaction mixture was purified by preparative HPLC (Column: Innoval ODS-2 10 um, 100 Å, 21.2×250 mm; flow rate: 40 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-11-1 (10 mg, 46%) as white solid.

EI-MS m/z: 1146 (M$^+$+1).

Preparation of Compound D-11

A homogeneous solution of compound D-11-1 (10 mg, 0.009 mmol) 10% Cd/Pb (200 mg) in THE (1.0 mL) at room temperature under $N_2$ atmosphere was treated 1N $NH_4OAc$ (500 uL) and stirred for 7 days. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound D-11 (0.6 mg, 10%) as white solid.

EI-MS m/z: 759 (M$^+$+1).

151
Preparation of Hetero-Dimers
152
TABLE B
| Compound No. | Structure |
|---|---|
| D-13 | 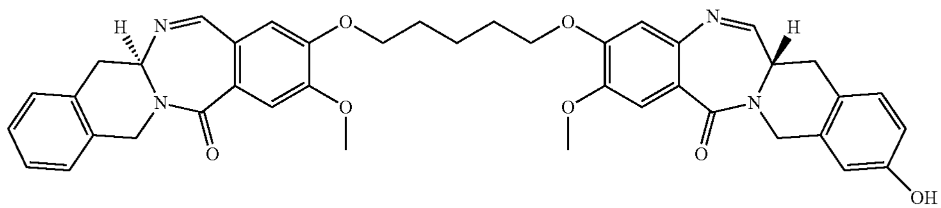 [SMILES: COc1cc2c(cc1OCCCCCOc1cc3c(cc1OC)C(=O)N1Cc4cc(O)ccc4C[C@H]1C=N3)C=N[C@@H]1Cc3ccccc3CN1C2=O] |
| D-12 | 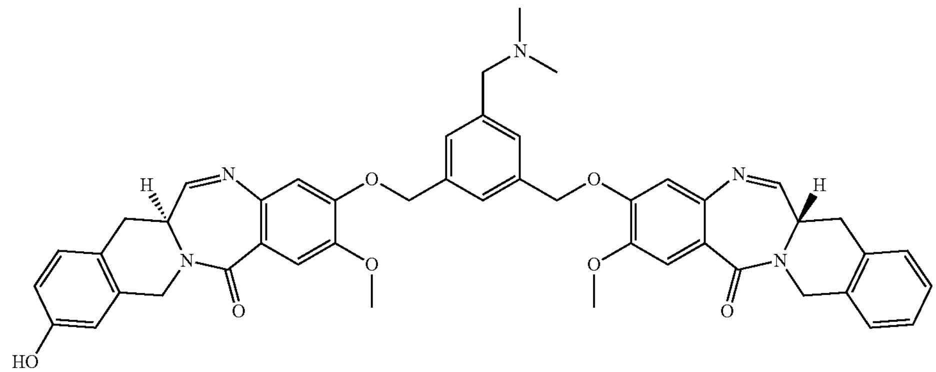 [SMILES: COc1cc2c(cc1OCc1cc(COc3cc4c(cc3OC)C(=O)N3Cc5cc(O)ccc5C[C@H]3C=N4)cc(CN(C)C)c1)N=C[C@@H]1Cc3ccccc3CN1C2=O] |
Example 54: Preparation of Compound D-12
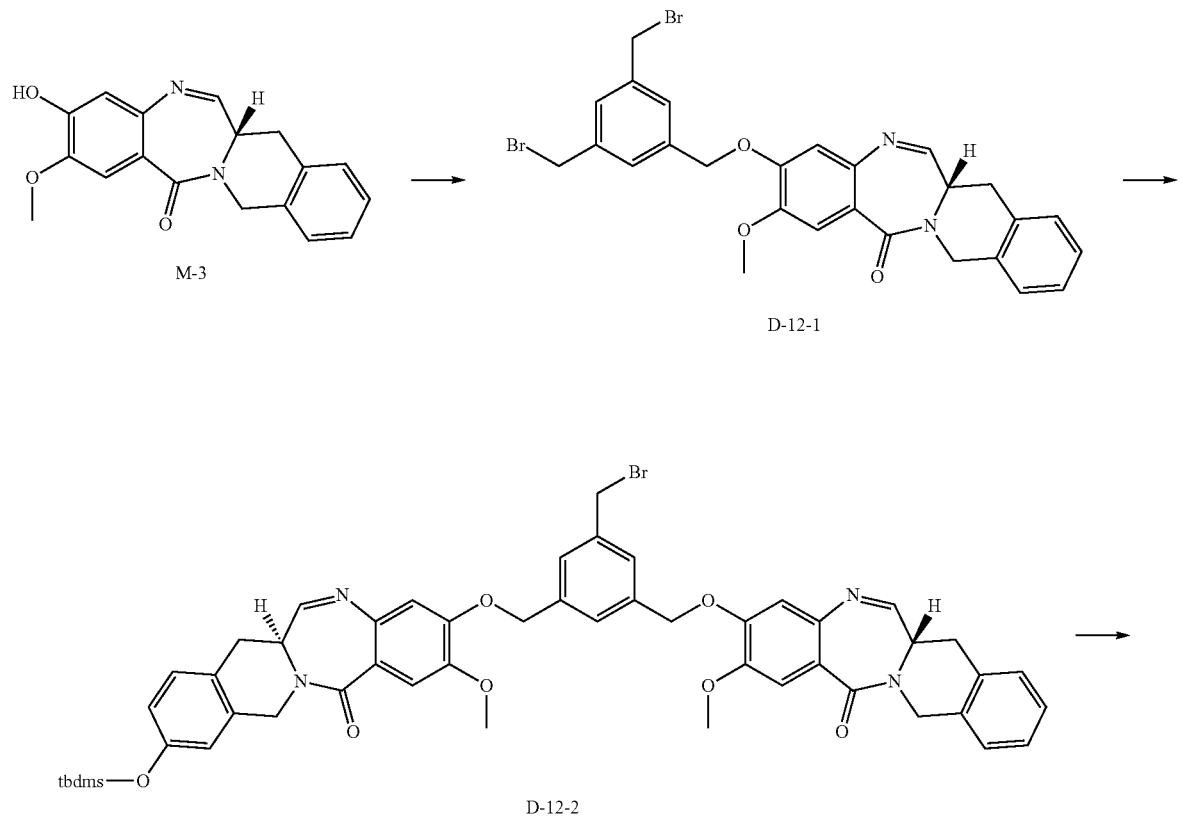

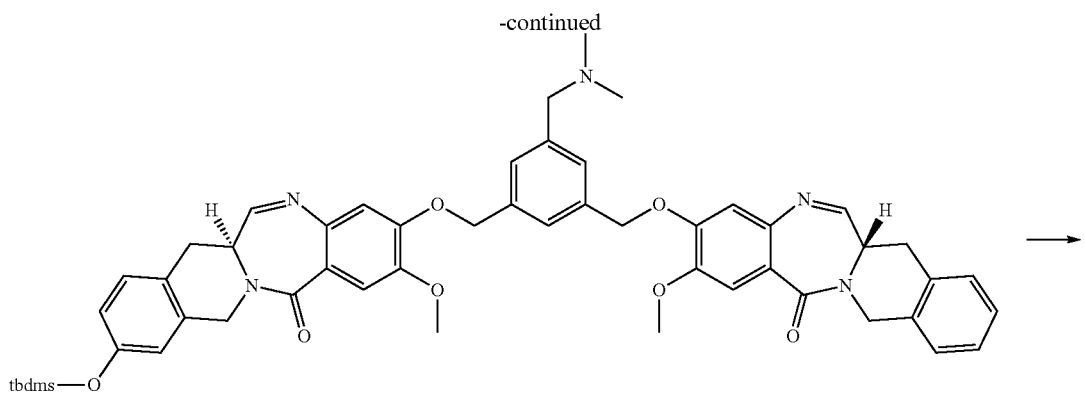

D-12-3

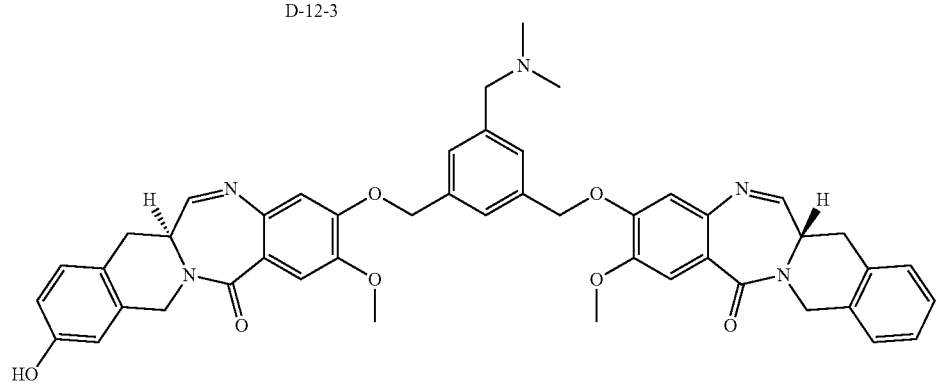

D-12

Preparation of Compound D-12-1

To a solution of compound M-1 (40 mg, 0.13 mmol) and 1,3,5-tris(bromomethyl)benzene (69.4 mg, 0.19 mmol) in DMF (1 mL) was added $K_2CO_3$ (17.9 mg, 0.13 mmol) at room temperature under $N_2$ atmosphere. After stirring for 5 hours, EA (2×10 mL), $H_2O$ (5 mL) and 2N HCl aqueous solution (3 mL) were added to perform extraction, the obtained organic layer was dried over anhydrous $Na_2SO_4$, filtered and concentrated under reduced pressure. The residue was purified by column chromatography to obtain a compound D-12-1 (54 mg, 42%).

EI-MS m/z: 585 ($M^+$+1).

Preparation of Compound D-12-2

To a solution of compound M-3 (10 mg, 0.023 mmol) and D-12-1 (13.3 mg, 0.023 mmol) in DMF (2.0 mL) was added $K_2CO_3$ (7.9 mg, 0.056 mmol) at room temperature under $N_2$ atmosphere. After stirring for 8 hours, EA (2×15 mL), $H_2O$ (5 mL) and 2N HCl aqueous solution (3 mL) were added to perform extraction, the obtained organic layer was dried over anhydrous $Na_2SO_4$, filtered and concentrated under reduced pressure. The residue was purified by column chromatography to obtain a compound D-12-2 (2.5 mg, 12%).

EI-MS m/z: 943 ($M^+$+1).

Preparation of Compound D-12-3

Dimethylamine (5.2 uL, 0.008 mmol) was added to a solution of compound D-12-2 (2.5 mg, 0.003 mmol) in DMF (0.5 mL) at room temperature under $N_2$ atmosphere. The mixture was stirred for 1 hour. After the reaction was completed, the mixture was purified by preparative HPLC (Column: Innoval ODS-2 10 um, 100 Å, 50×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-12-3 (1.5 mg, 63%).

EI-MS m/z: 907 ($M^+$+1).

Preparation of Compound D-12

To a solution of compound D-12-3 (1.5 mg, 0.002 mmol) dissolved in THF (1.0 mL) and $H_2O$ (200 uL) was added conc. HCl (100 uL), then the mixture was stirred for 1 hour at 0° C. under $N_2$ atmosphere. The mixture was purified by preparative HPLC (Column: Innoval ODS-2 10 um, 100 Å, 50×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-12 (0.3 mg, 23%).

EI-MS m/z: 792 ($M^+$+1).

Example 55: Preparation of Compound D-13

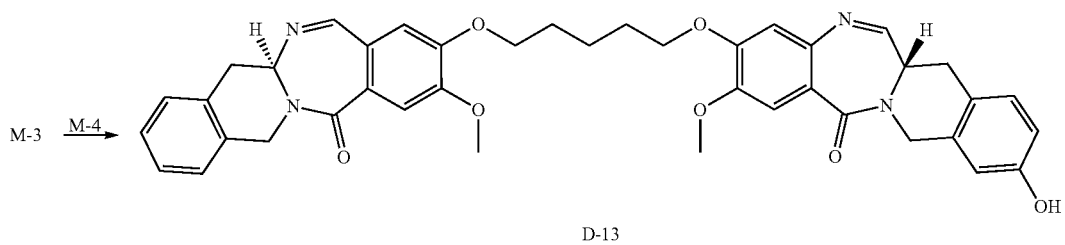

D-13

A yellow solution of compound M-3 (2.3 mg, 0.0056 mmol) and M-4 (3.8 mg, 0.0084 mmol, 1.5 eq) in DMF (500 uL) at room temperature under N₂ atmosphere was treated with K₂CO₃ (3.9 mg, 0.028 mmol, 5.0 eq) and stirred overnight. The mixture was diluted with distilled water (2.0 mL) and extracted with EA (5 mL×2). The organic layer was dried over anhydrous Na₂SO₄, filtered and concentrated under reduced pressure. The residue was diluted with MeOH (1.0 mL) and AcCl (100 uL) was added and the mixture stirred at the same temperature under N₂ atmosphere for 30 minutes. The mixture was directly purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound D-13 (1.1 mg, 28%) as white solid. EI-MS m/z: 701 (M⁺+1).

Example 56: Preparation of Compound T-Int-1

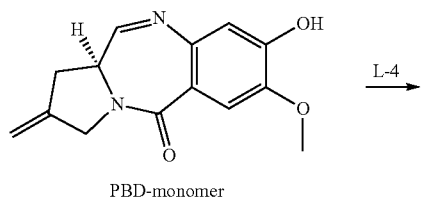

PBD-monomer

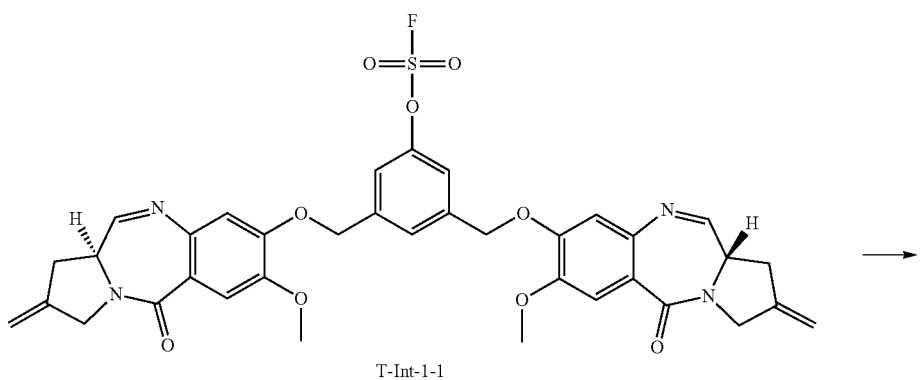

T-Int-1-1

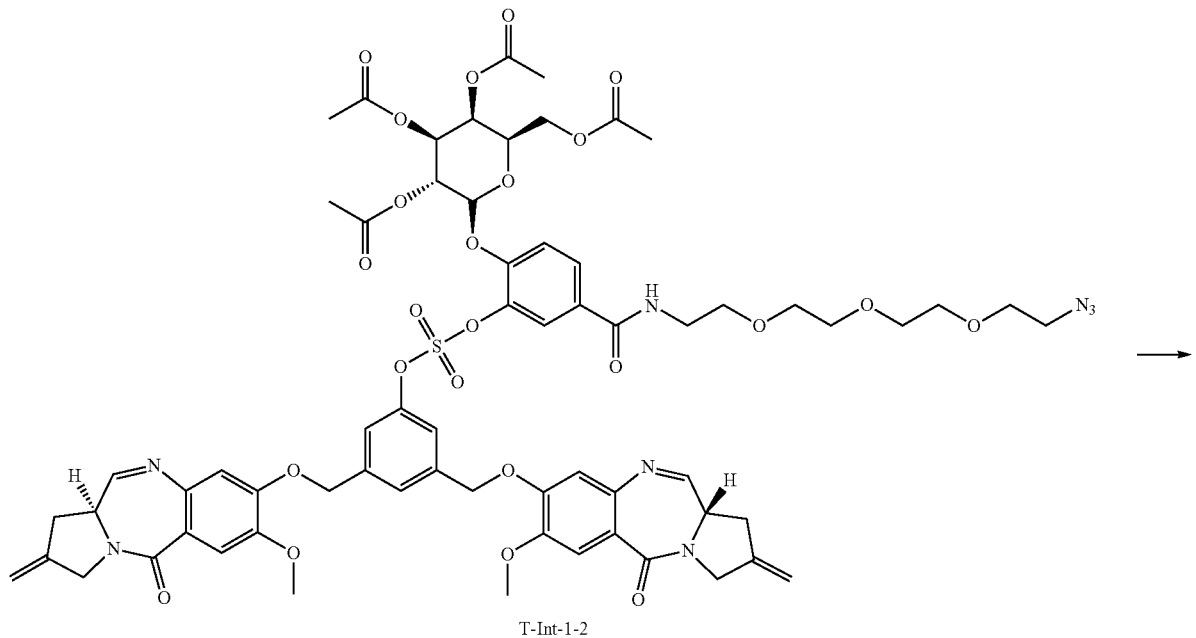

T-Int-1-2

-continued

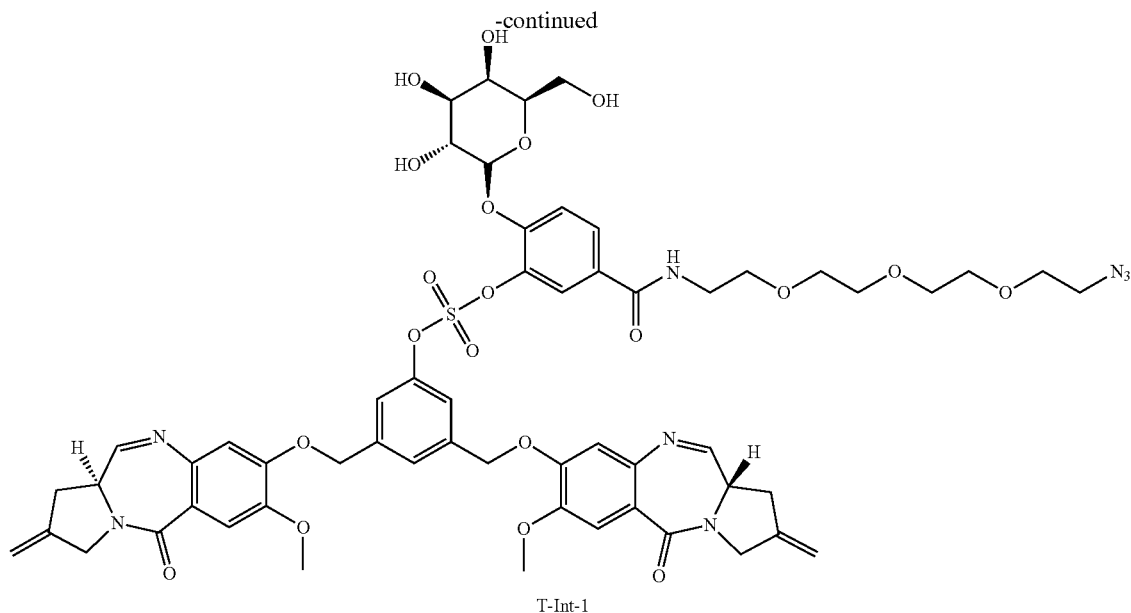

T-Int-1

Preparation of Compound T-Int-1-1

To a solution of compound PBD-monomer (Reference EP20071813614 A1, 22 mg, 0.08 mmol) and compound L-4 (14 mg, 0.04 mmol) in DMF (1 mL) was added $K_2CO_3$ (12 mg, 0.08 mmol) at room temperature under $N_2$ atmosphere. After stirring for 15 hours at room temperature, the reaction mixture was purified by HPLC (Column: Innoval ODS-2 10 um, 100 Å, 50×250 mm; flow rate: 15 mL/min, A buffer 0.10% Formic acid in water/B buffer 0.10% Formic acid in ACN, method gradient, solvent A:solvent B 80:20 to 20:80, 45 minutes, wavelength 214 nm) to obtain compound T-Int-1-1 (13.8 mg, 51%). EI-MS m/z: 717 ($M^+$+1).

Preparation of Compound T-Int-1-2

To a solution of compound T-Int-1-1 (10 mg, 0.01 mmol) and compound Int-TG1 (11 mg, 0.01 mmol) in ACN (1 mL) was added BEMP (0.8 mg, 0.003 mmol) at room temperature under $N_2$ atmosphere. After stirring for 1 hour at room temperature, the reaction mixture was purified by HPLC to obtain compound T-Int-1-2 (12 mg, 63%). EI-MS m/z: 1382 ($M^{+1}$).

Preparation of Compound T-Int-1

To a solution of Compound T-Int-1-2 (10 mg, 0.007 mmol) in MeOH (1.0 mL) was added $K_2CO_3$ (5 mg, 0.036 mmol) under $N_2$ atmosphere. After stirring for 2 hours at room temperature, the mixture was purified by HPLC to obtain compound T-Int-1 (7.4 mg, 85%). EI-MS m/z: 1214 ($M^{+1}$).

Example 57: Preparation of Compound T-Int-2 and T-Int-3

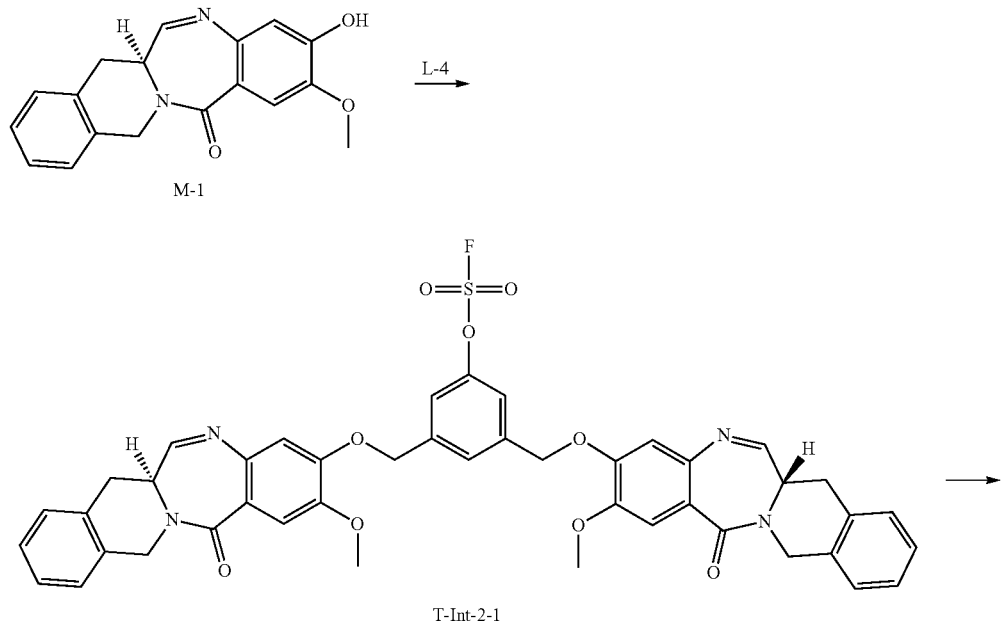

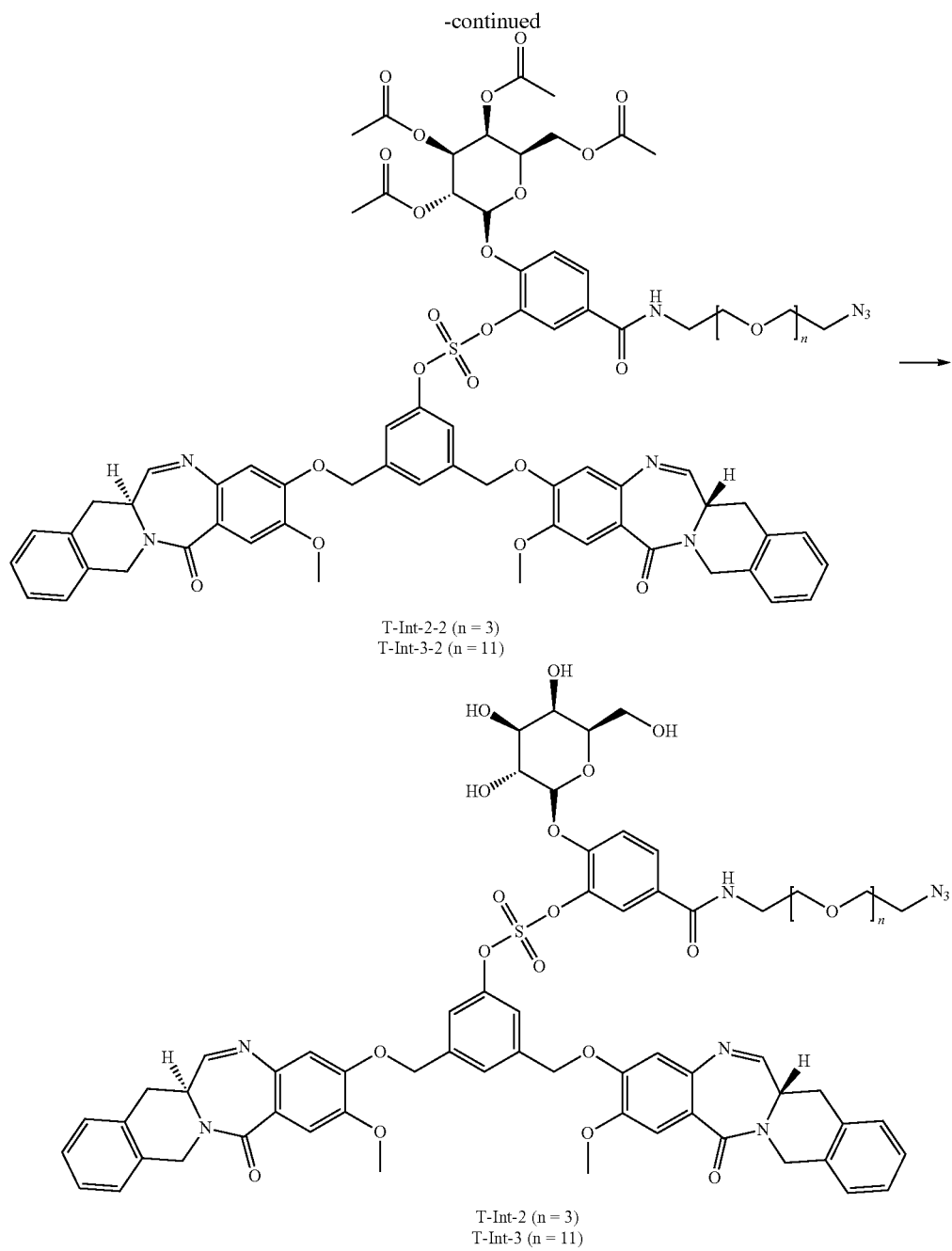

T-Int-2-2 (n = 3)
T-Int-3-2 (n = 11)

T-Int-2 (n = 3)
T-Int-3 (n = 11)

Preparation of Compound T-Int-2-1

To a solution of compound M-1 (179 mg, 0.58 mmol) and compound L-4 (100 mg, 0.28 mmol) in DMF (5 mL) was added $K_2CO_3$ (80 mg, 0.58 mmol) at room temperature under $N_2$ atmosphere. After stirring for 7 hours at room temperature, EA (100 mL) and $H_2O$ (50 mL) were added to perform extraction, the obtained organic layer was dried over anhydrous $Na_2SO_4$, filtered and concentrated under reduced pressure. The residue was purified by column chromatography to obtain a compound T-Int-2-1 (117 mg, 52%). EI-MS m/z: 817 (M*).

Preparation of Compound T-Int-2-2

To a solution of compound T-Int-2-1 (45 mg, 0.06 mmol) and compound Int-TG1 (55 mg, 0.07 mmol) in ACN (1 mL) was added BEMP (20 uL, 0.07 mmol) at room temperature under $N_2$ atmosphere. After stirring for 5 hours at room temperature, the reaction mixture was purified by HPLC (Column: Innoval ODS-2 10 um, 100 Å, 50×250 mm; flow rate: 40 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound T-Int-2-2 (67 mg, 83%). EI-MS m/z: 1482 ($M^{+1}$).

Preparation of Compound T-Int-3-2

Yield 63%

EI-MS m/z: 1834 ($M^{+1}$).

Preparation of compound T-Int-2

To a solution of Compound T-Int-2-2 (67 mg, 0.05 mmol) in MeOH (4 mL) was added $K_2CO_3$ (31 mg, 0.27 mmol) under $N_2$ atmosphere. After stirring for 2 hours at room temperature, the reaction mixture was purified by HPLC to obtain compound T-Int-2 (42 mg, 71%). EI-MS m/z: 1314 ($M^+1$).

Preparation of compound T-Int-3
Yield 83%
EI-MS m/z: 1666 (M$^{+1}$).
Example 58: Preparation of Compound T-Int-4
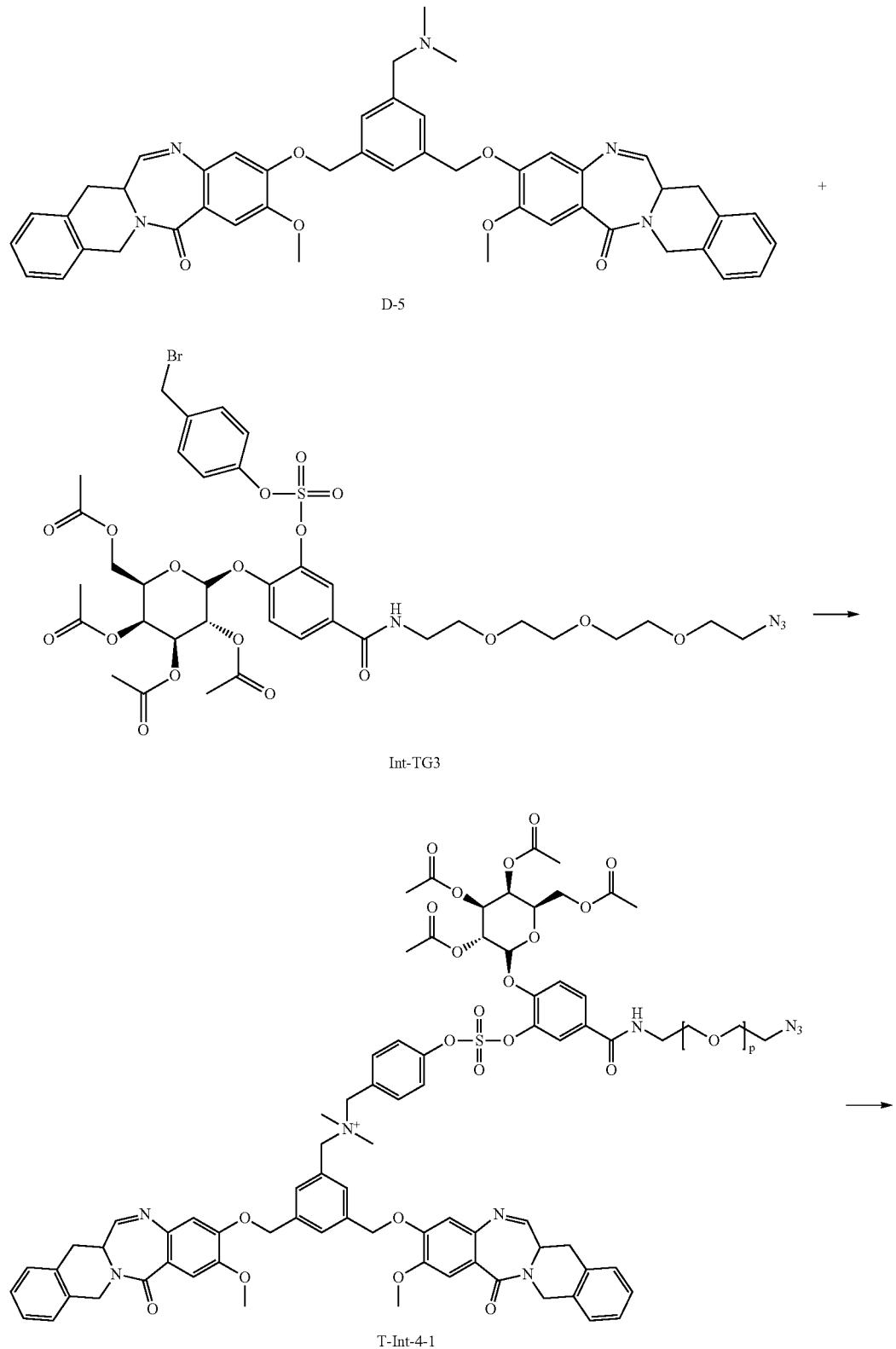

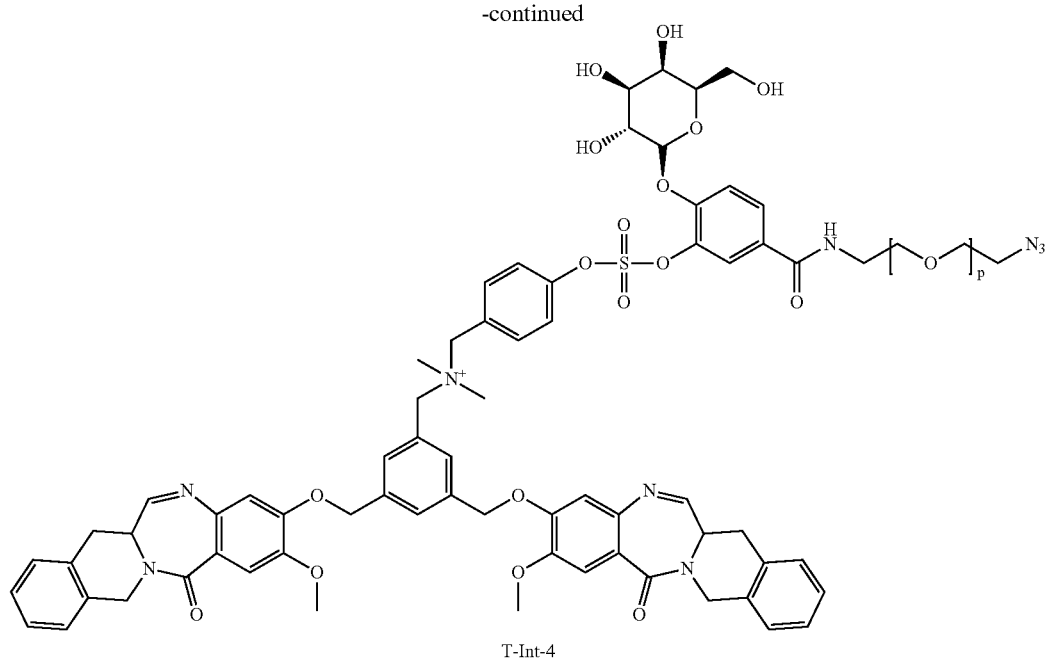

T-Int-4

Preparation of Compound T-Int-4-1

To a solution of compound D-5 (8.0 mg, 0.01 mmol) and compound Int-TG3 (11.5 mg, 0.01 mmol) in DMF (1 mL) was added DIPEA (5.4 µL, 0.03 mmol) at room temperature under $N_2$ atmosphere. After stirring for 6 hours at room temperature, the reaction mixture was purified by HPLC to obtain compound T-Int-4-1 (11.9 mg, 71%). EI-MS m/z: 1630 ($M^{+1}$).

Preparation of Compound T-Int-4

To a solution of Compound T-Int-3-1 (11.9 mg, 0.01 mmol) in MeOH (1 mL) was added $K_2CO_3$ (5 mg, 0.04 mmol) under $N_2$ atmosphere. After stirring for 1 hours at room temperature, the reaction mixture was purified by HPLC (Column: Innoval ODS-2 10 um, 100 Å, 50×250 mm; flow rate: 15 mL/min, A buffer 0.1% Formic acid in water/B buffer 0.1% Formic acid in ACN, method gradient, solvent A:solvent B 80:20 to 20:80, 45 minutes, wavelength 214 nm) to obtain compound T-Int-4 (6.4 mg, 60%). EI-MS m/z: 1462 ($M^{+1}$).

Example 59: Preparation of Compound T-Int-5

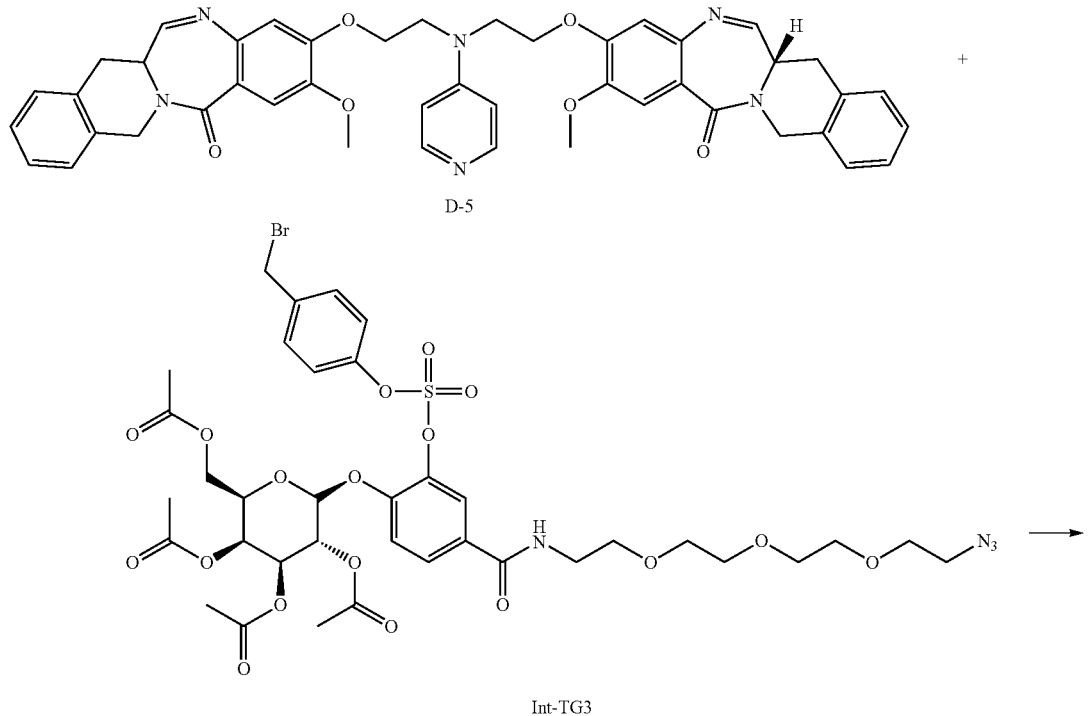

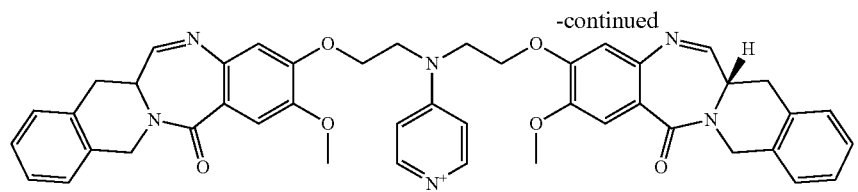

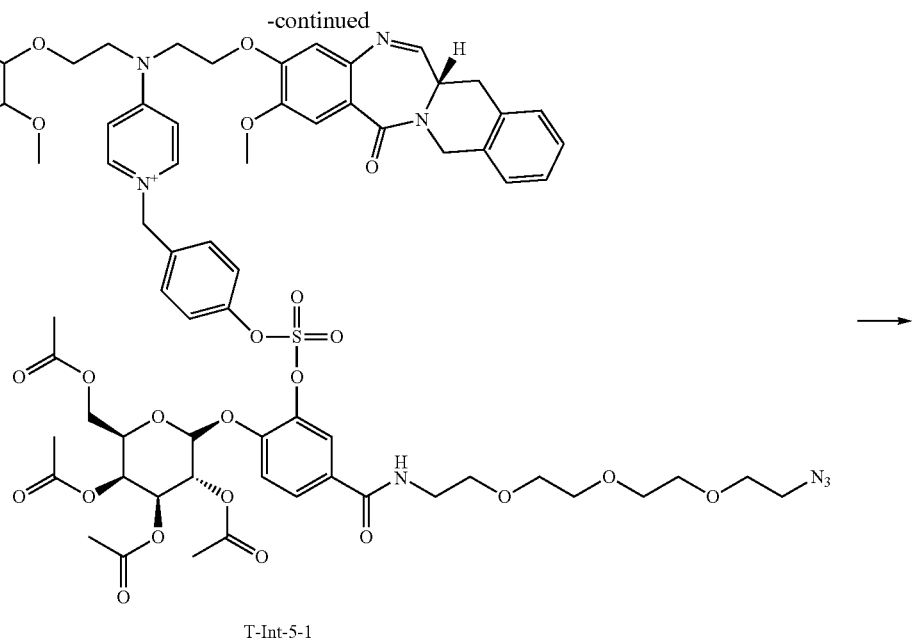

T-Int-5-1

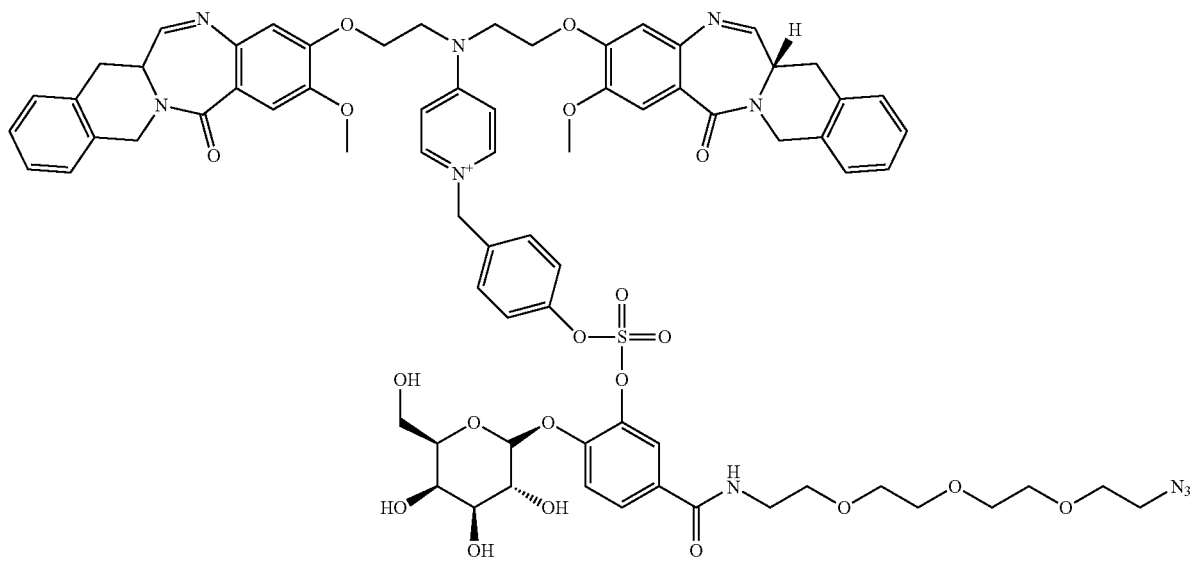

T-Int-5

Preparation of Compound T-Int-5-1

To a solution of compound D-6 (5.0 mg, 0.006 mmol) and Int-TG3 (9.0 mg, 0.009 mmol) in DMF (1 mL) was added DIPEA (5.0 uL, 0.029 mmol) at room temperature under $N_2$ atmosphere. After stirring for 6 hours at room temperature, the reaction mixture was purified by HPLC (reverse phase, C18, gradient $H_2O$/ACN/0.1% Formic acid) to obtain compound T-Int-5-1 (10.0 mg, 94%). EI-MS m/z: 1617 ($M^{+1}$).

Preparation of Compound T-Int-5

To a solution of compound T-Int-5-1 (10.0 mg, 0.006 mmol) in MeOH (1 mL) was added $K_2CO_3$ (4.3 mg, 0.031 mmol) under $N_2$ atmosphere. After stirring for 1 hours at room temperature, the reaction mixture was purified by HPLC (reverse phase, C18, gradient $H_2O$/ACN/0.1% Formic acid) to obtain compound T-Int-5 (6.1 mg, 68%). EI-MS m/z: 1449 ($M^{+1}$).

Example 60: Preparation of Compound T-Int-6
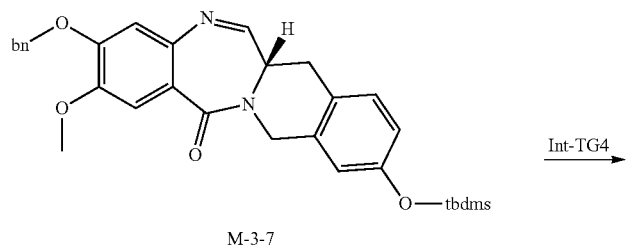
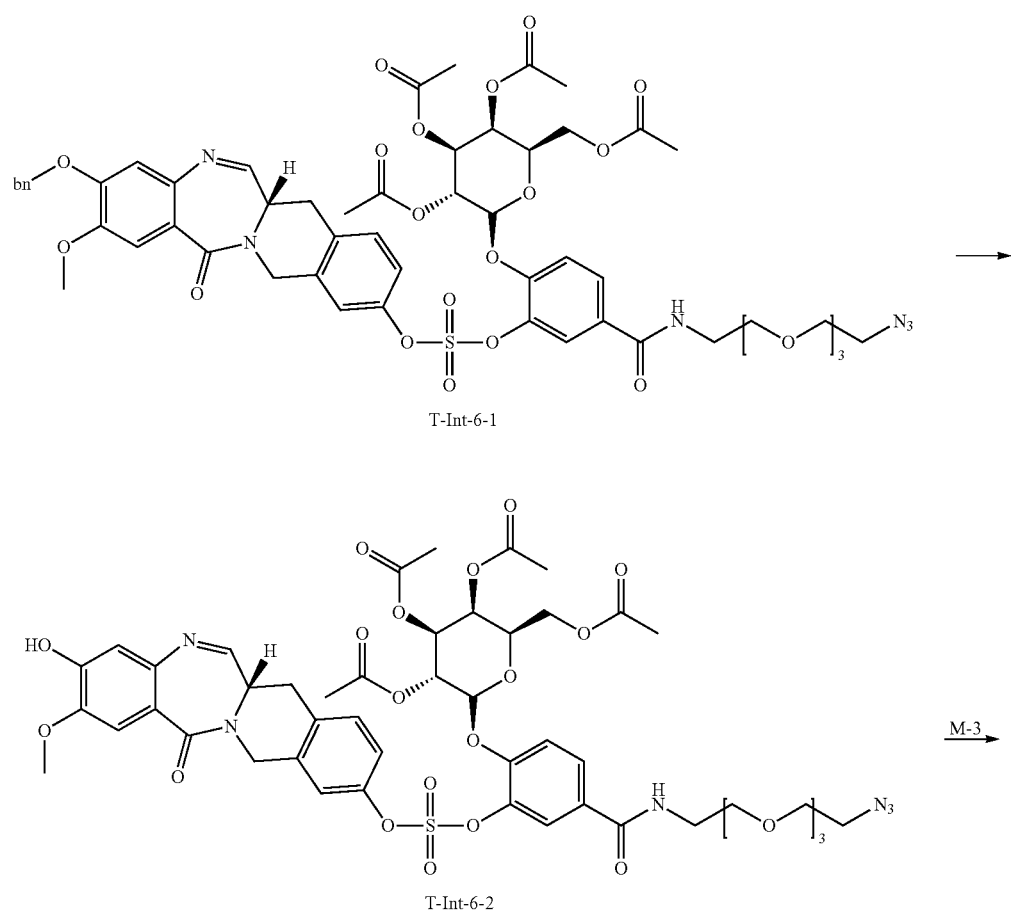
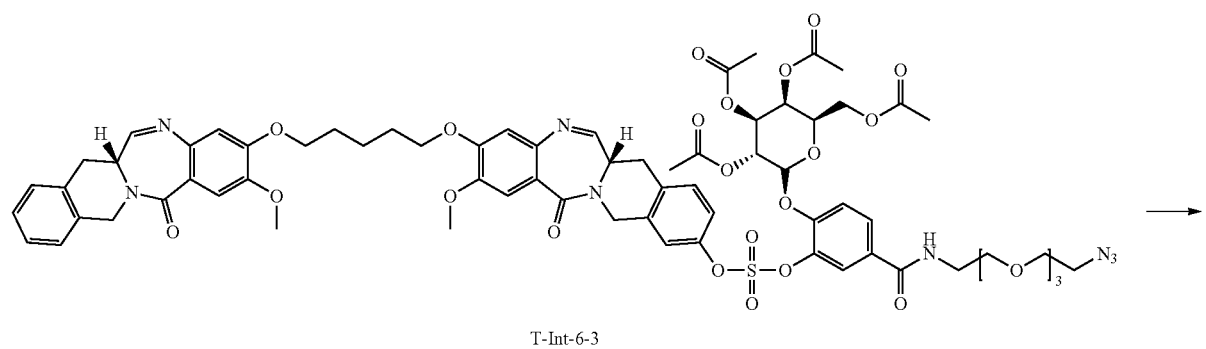

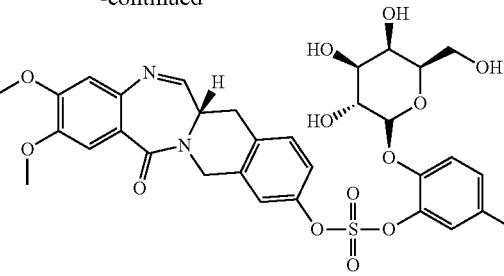

T-Int-6

Preparation of Compound T-Int-6-1

A homogeneous solution of M-3-7 (23 mg, 0.043 mmol) and Int-TG4 (33.4 mg, 0.043 mmol, 1.0 eq.) in ACN (2.0 mL) at room temperature under $N_2$ atmosphere was treated BEMP (5.0 uL, 0.017 mmol, 0.4 eq.) and stirred for 2 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-6-1 (37.8 mg, 75%) as yellow solid.

EI-MS m/z: 1162 (M$^+$+1).

Preparation of Compound T-Int-6-2

A homogeneous solution of T-Int-6-1 (36.8 mg, 0.032 mmol) in dry DCM (3.0 mL) at 0° C. under $N_2$ atmosphere was treated methanesulfonic acid (0.5 mL) in DCM (2 mL) and stirred for 2 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-6-2 (17.7 mg, 52%) as white solid.

EI-MS m/z: 1072 (M$^+$+1).

Preparation of Compound T-Int-6-3

Compound T-Int-6-3 was synthesized via a similar synthetic route as described in Example 55.

Yield 64% as white solid.

EI-MS m/z: 1448 (M$^+$+1).

Preparation of Compound T-Int-6

A homogeneous solution of compound T-Int-6-3 (20.7 mg, 0.014 mmol) in MeOH (1.0 mL) at 0° C. under $N_2$ atmosphere was treated $K_2CO_3$ (11.9 mg, 0.086 mmol, 6.0 eq.) and stirred for 30 minutes. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-6 (18.3 mg, 67%) as white solid.

EI-MS m/z: 1280 (M$^+$+1).

Example 61: Preparation of Compound T-Int-7 and T-Int-8

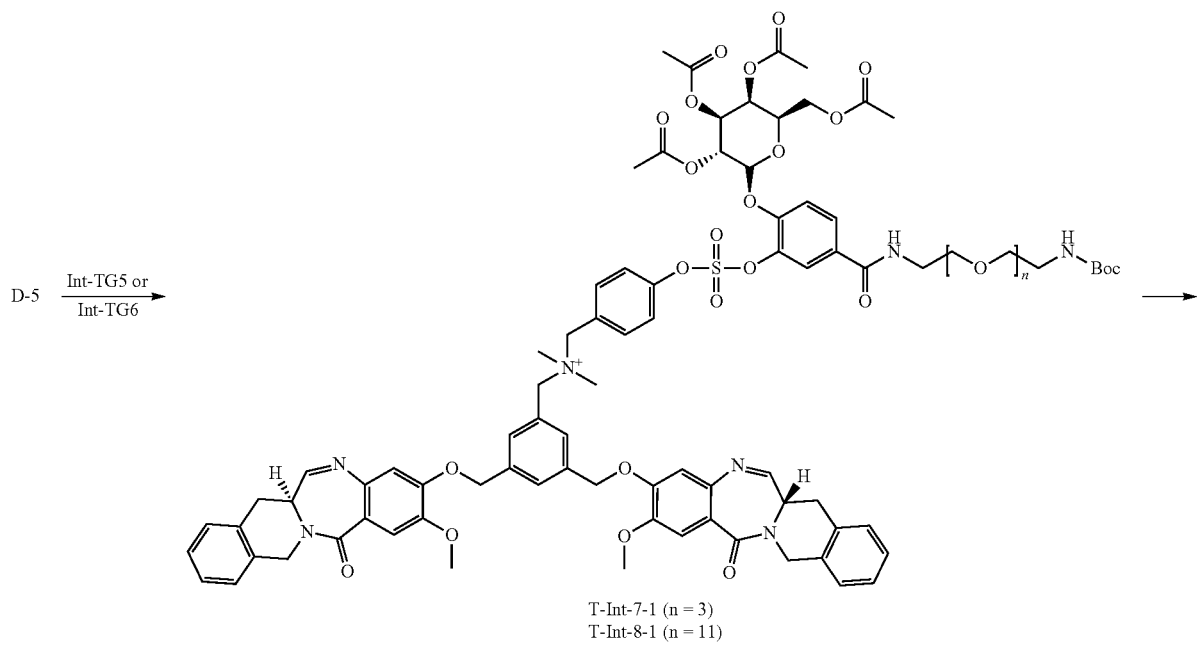

T-Int-7-1 (n = 3)
T-Int-8-1 (n = 11)

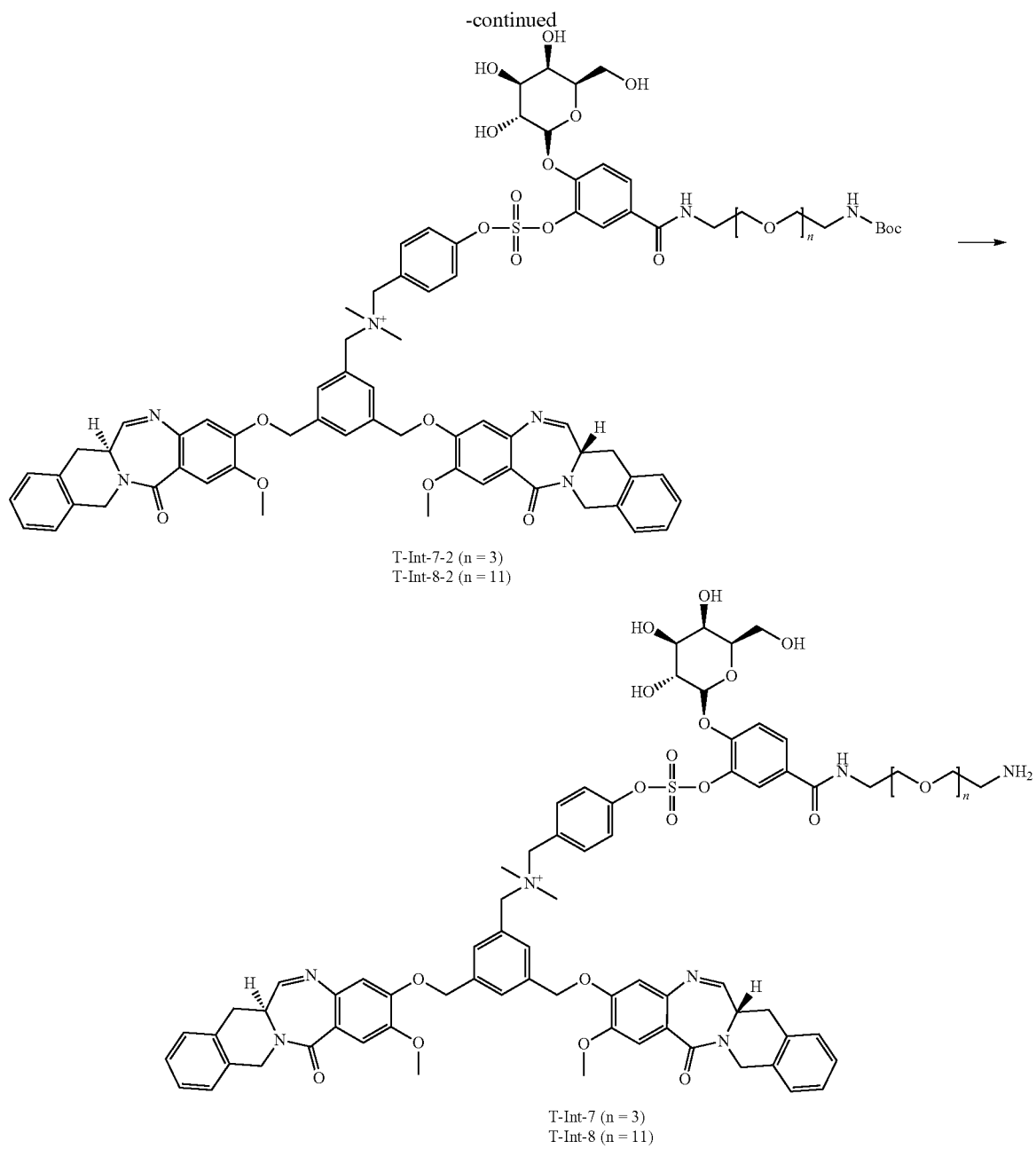

T-Int-7-2 (n = 3)
T-Int-8-2 (n = 11)

T-Int-7 (n = 3)
T-Int-8 (n = 11)

Preparation of Compound T-Int-7-1

A homogeneous solution of D-5 (50 mg, 0.064 mmol) and Int-TG5 (64.9 mg, 0.064 mmol, 1.0 eq.) in DMF (2.0 mL) at room temperature under $N_2$ atmosphere was treated DIPEA (44.9 uL, 0.26 mmol, 4.0 eq.) and stirred for 4 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-7-1 (77 mg, 70%) as white solid.

EI-MS m/z: 1704 ($M^+$+1).

Preparation of Compound T-Int-7-2

Compound T-Int-7-2 was synthesized via a similar manner to the preparation method of the compound T-Int-6 of Example 60.

Yield 81%, white solid

EI-MS m/z: 1536 ($M^+$+1).

Preparation of Compound T-Int-7

A homogeneous solution of compound T-Int-7-2 (56 mg, 0.036 mmol) in anhydrous DCM (1.0 mL) at 0° C. under $N_2$ atmosphere was treated TFA (0.2 mL) in DCM (1 mL) and stirred for 2 hours. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-7 (44.4 mg, 82%) as ivory solid.

EI-MS m/z: 1436 ($M^+$+1).

T-Int-8 was synthesized via a similar manner to the preparation method of the compound T-Int-7.

Preparation of Compound T-Int-8-1
Yield 84%, yellow solid
EI-MS m/z: 2057 (M$^+$+1), 1029 (M/2$^+$+1).
Preparation of Compound T-Int-8-2
Yield 84%, colorlessness oil
EI-MS m/z: 1889 (M$^+$+1), 945 (M/2$^+$+1).
Preparation of compound T-Int-8
Yield 74%, ivory solid
EI-MS m/z: 1789 (M$^+$+1), 895 (M/2$^+$+1).
Example 62: Preparation of Compound T-Int-9 and T-Int-10
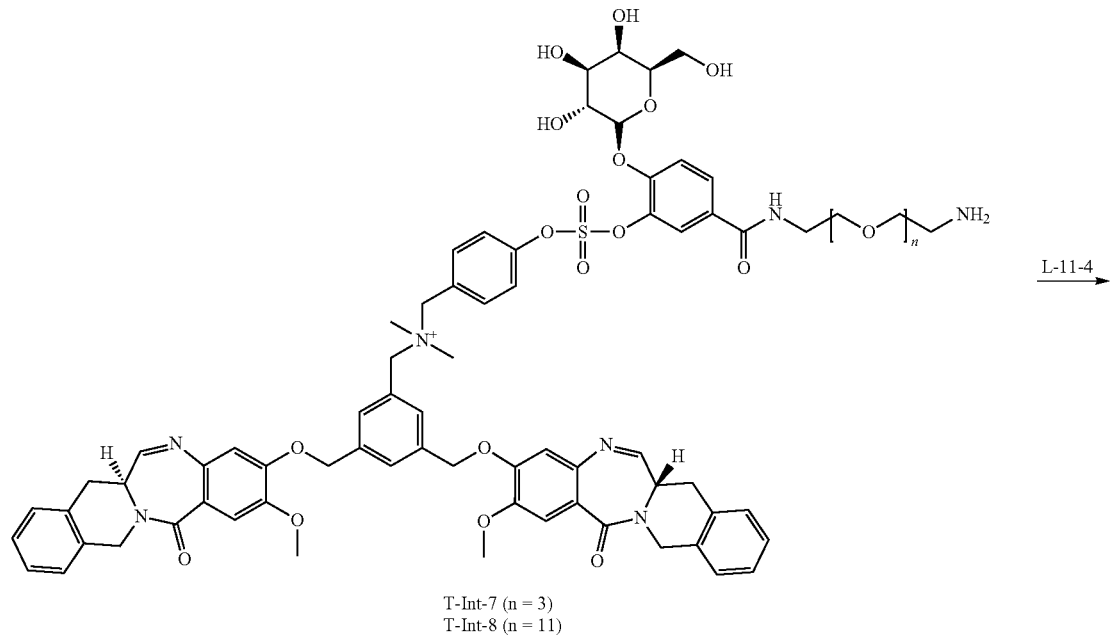
T-Int-7 (n = 3)
T-Int-8 (n = 11)
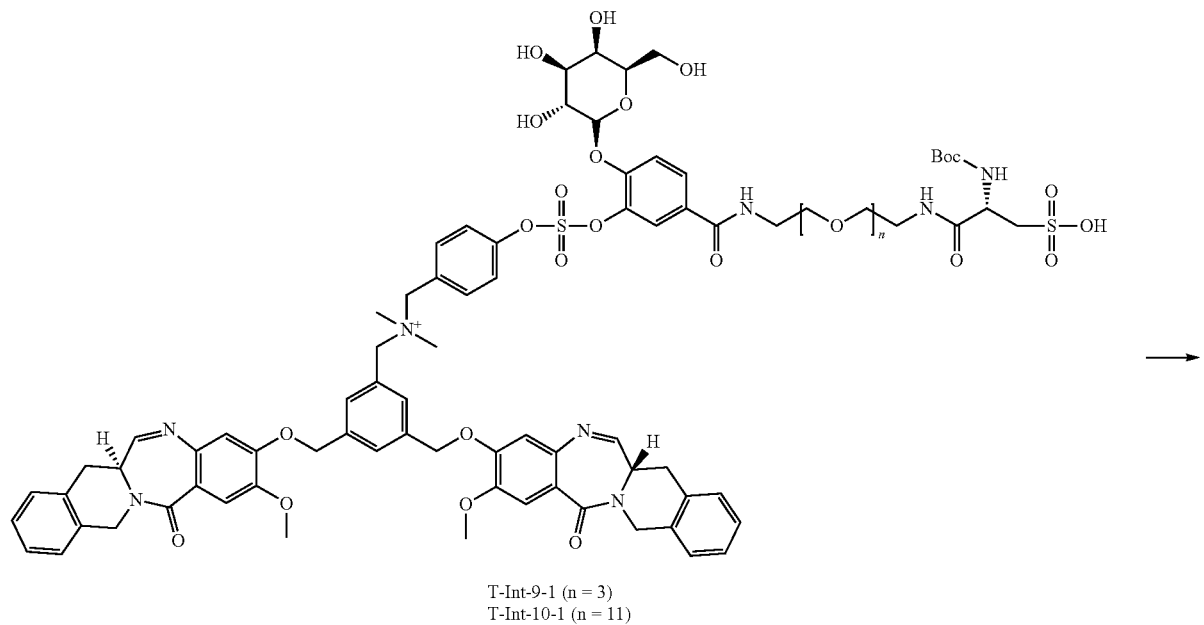
T-Int-9-1 (n = 3)
T-Int-10-1 (n = 11)

-continued

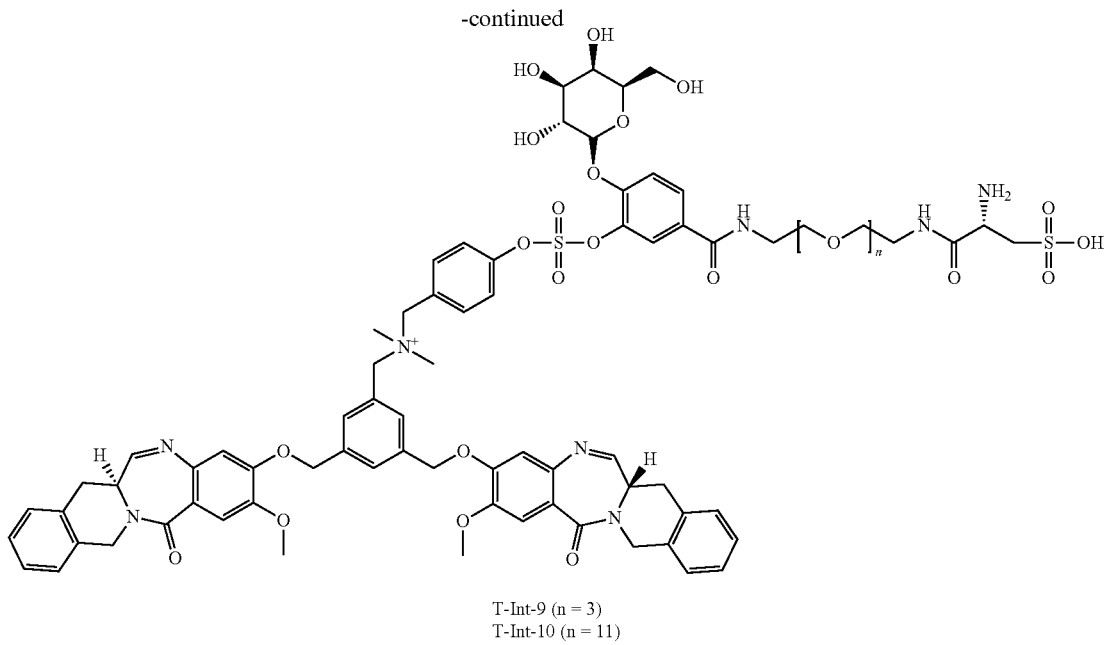

T-Int-9 (n = 3)
T-Int-10 (n = 11)

Preparation of Compound T-Int-9-1

A homogeneous solution of T-Int-7 (20 mg, 0.014 mmol) and L-11-4 (5.1 mg, 0.014 mmol, 1.0 eq.) in DMF (2.0 mL) at room temperature under $N_2$ atmosphere was treated DIPEA (7.3 uL, 0.042 mmol, 3.0 eq.) and stirred for 2 hours. The mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-9-1 (19.9 mg, 85%) as yellow solid.

EI-MS m/z: 1687 ($M^+$+1), 844 ($M/2^+$+1).

Preparation of Compound T-Int-9

T-Int-9 was synthesized via a similar synthetic route as described in Example 62.

Yield 72%, ivory solid

EI-MS m/z: 1789 ($M^+$+1), 895 ($M/2^+$+1).

T-Int-10 was synthesized via a similar manner to the preparation method of the compound T-Int-9.

Preparation of Compound T-Int-10-1

Yield 75%, ivory solid

EI-MS m/z: 2040 ($M^+$+1), 1010 ($M/2^+$+1).

Preparation of Compound T-Int-10

Yield 60%, ivory solid

EI-MS m/z: 1940 ($M^+$+1), 970 ($M/2^+$+1).

Example 63: Preparation of Compound T-Int-11

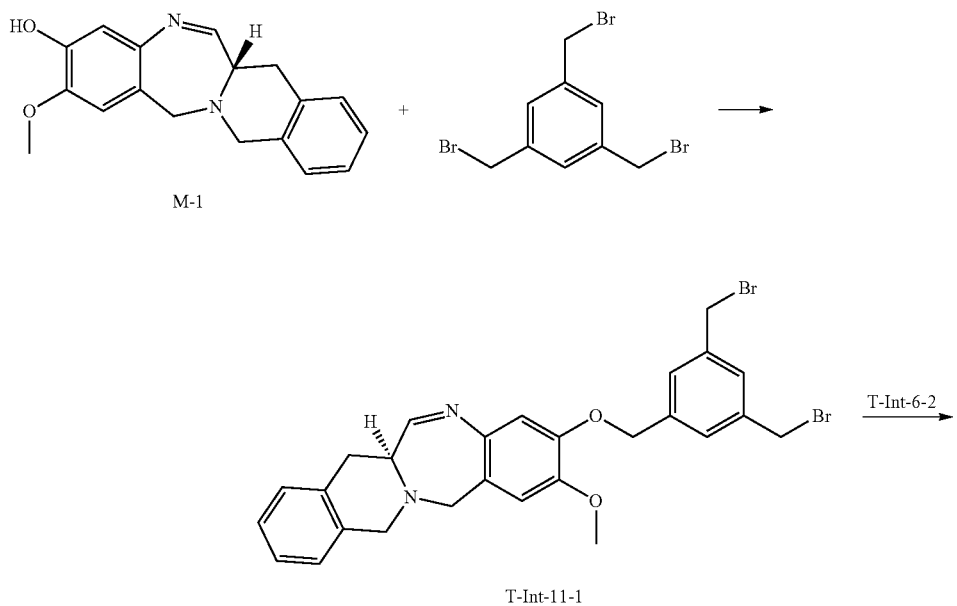

T-Int-11-1

-continued

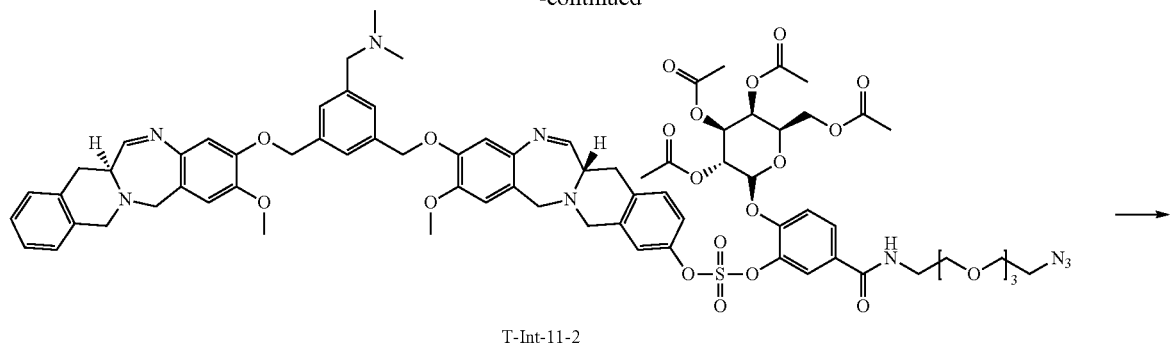

T-Int-11-2

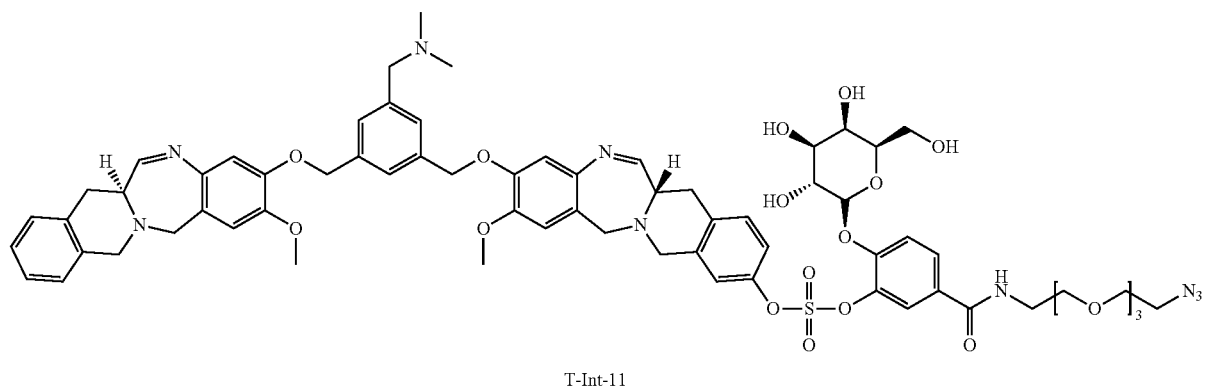

T-Int-11

Preparation of Compound T-Int-11-1

A Yellow solution of compound M-1 (50 mg, 0.13 mmol) and 1,3,5-tris(bromomethyl)benzene (173.6 mg, 0.49 mmol, 3.0 eq.) in DMF (2 mL) at room temperature under $N_2$ atmosphere was treated $K_2CO_3$ (44.8 mg, 0.32 mmol, 2.0 eq.) and stirred for 3 hours. The reaction mixture was purified by preparative HPLC (Column: Innoval ODS-2 10 um, 100 Å, 21.2×250 mm; flow rate: 15 mL/min, A buffer 0.100 Formic acid in water/B buffer 0.1% Formic acid in ACN, method gradient, solvent A:solvent B 95:5 to 5:95, 1 hour, wavelength 214 nm) to obtain compound T-Int-11-1 (35 mg, 37%) as ivory solid EI-MS m/z: 585 ($M^+$+1).

Preparation of Compound T-Int-11-2

Compound T-Int-11-2 was synthesized via a similar manner to the preparation method of the compound D-12-2 of Example 54.

Yield 600%, ivory solid
EI-MS m/z: 1539 ($M^+$+1).

Preparation of Compound T-Int-11

Compound T-Int-11 was synthesized via a similar manner to the preparation method of the compound T-Int-1 of Example 56.

Yield 72%, white solid
EI-MS m/z: 1371 ($M^+$+1).

Example 64: Preparation of Compound T-Int-12

D-9 $\xrightarrow{\text{Int-TG3}}$

-continued
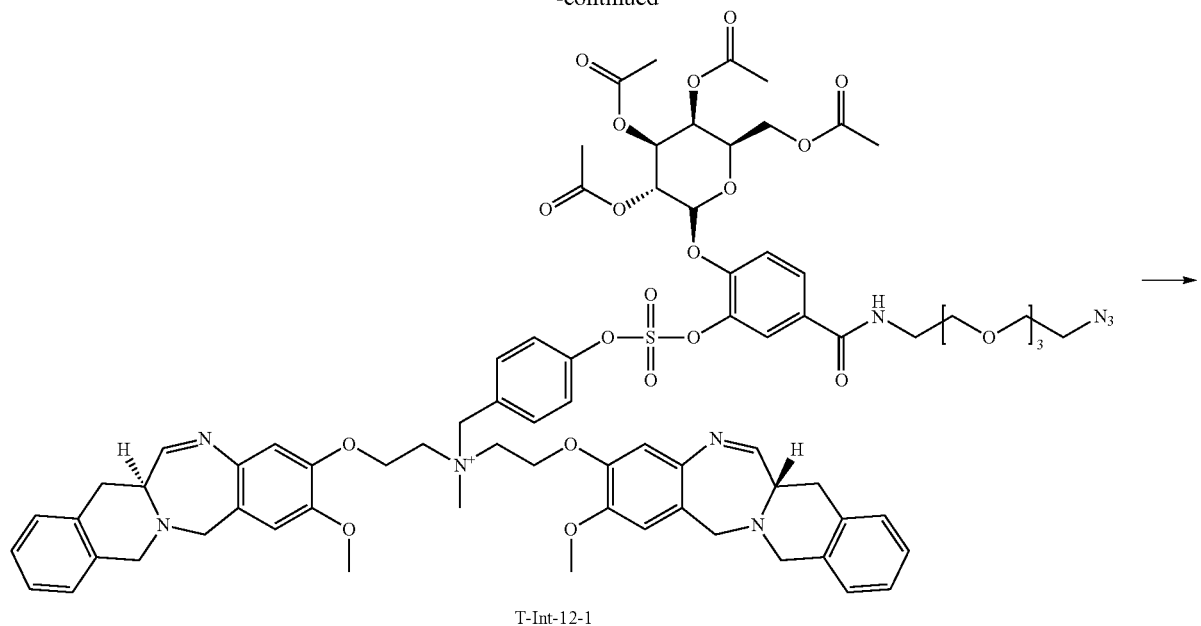
T-Int-12-1
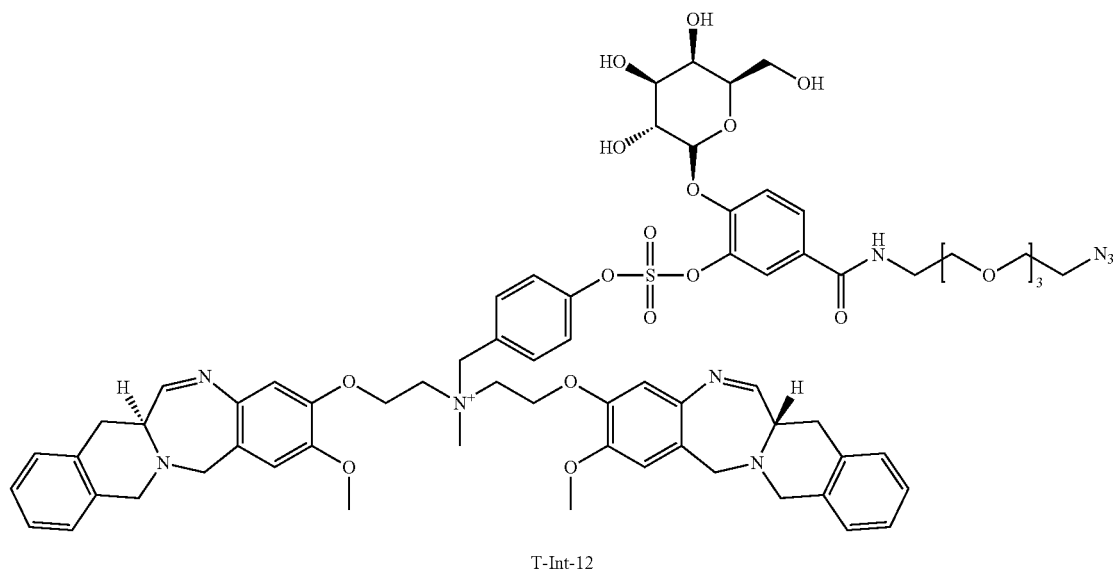
T-Int-12
Compound T-Int-12 was synthesized via a similar synthetic route as described in Example 59.
Preparation of compound T-Int-12-1
Yield 54%, ivory solid
EI-MS m/z: 1544 (M$^+$+1).
Preparation of compound T-Int-12
Yield 74%, yellow solid
EI-MS m/z: 1386 (M$^+$+1).

Example 65: Preparation of Compound T-Int-13
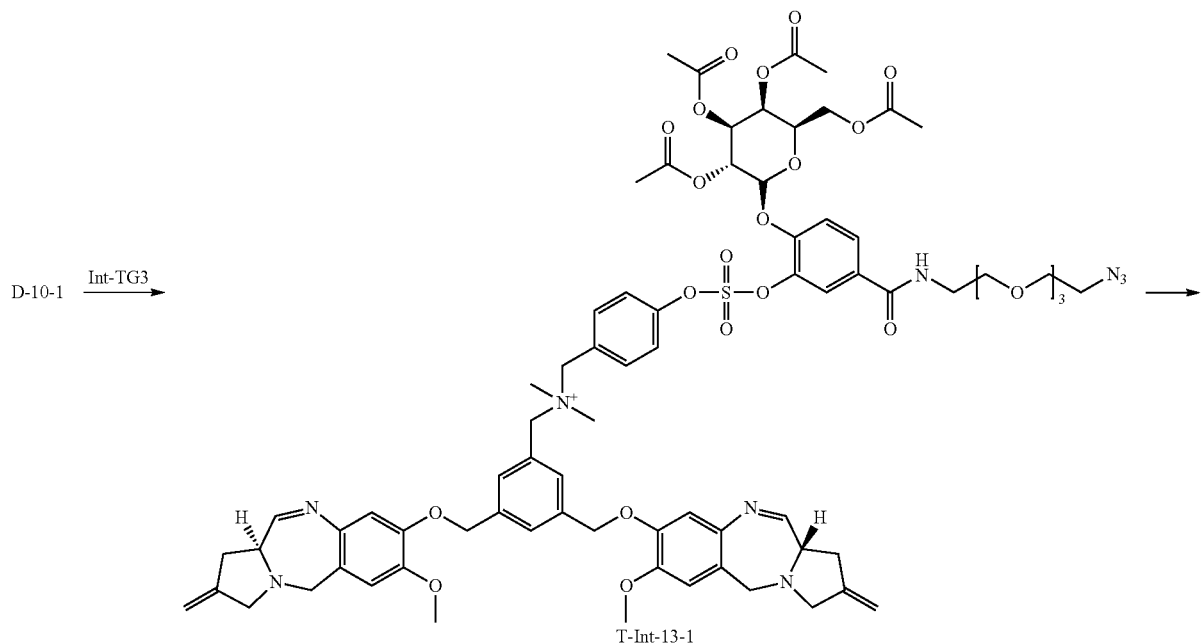
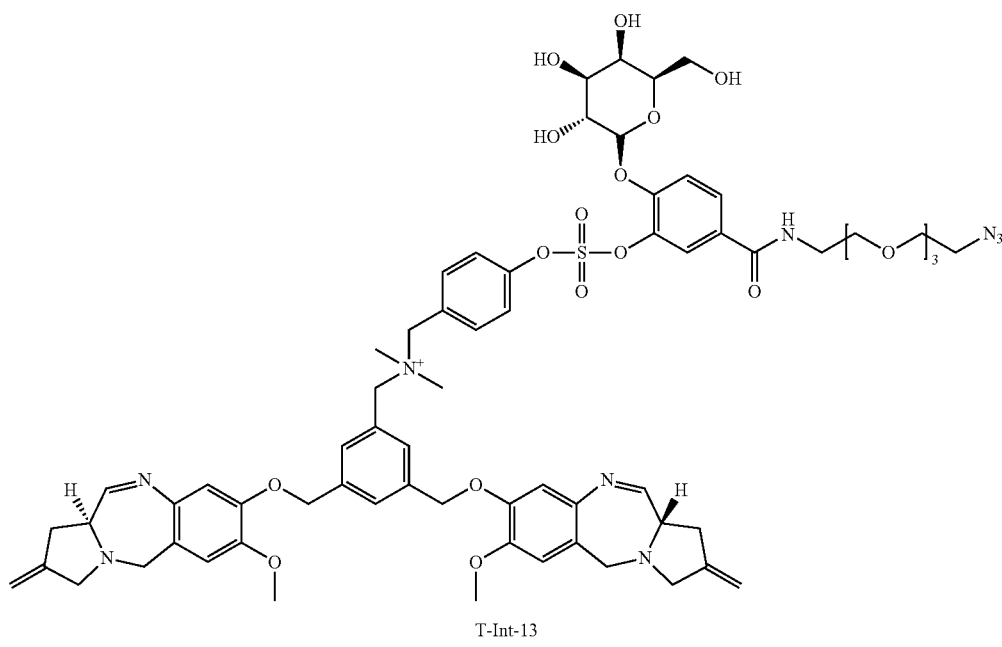
Compound T-Int-13 was synthesized via a similar synthetic route as described in Example 59.
Preparation of compound T-Int-13-1
Yield 53%, white solid
EI-MS m/z: 1530 (M$^+$+1).
Preparation of Compound T-Int-13
Yield 81%, yellow solid
EI-MS m/z: 1362 (M$^+$+1).

Example 66: Preparation of Compound T-Int-14

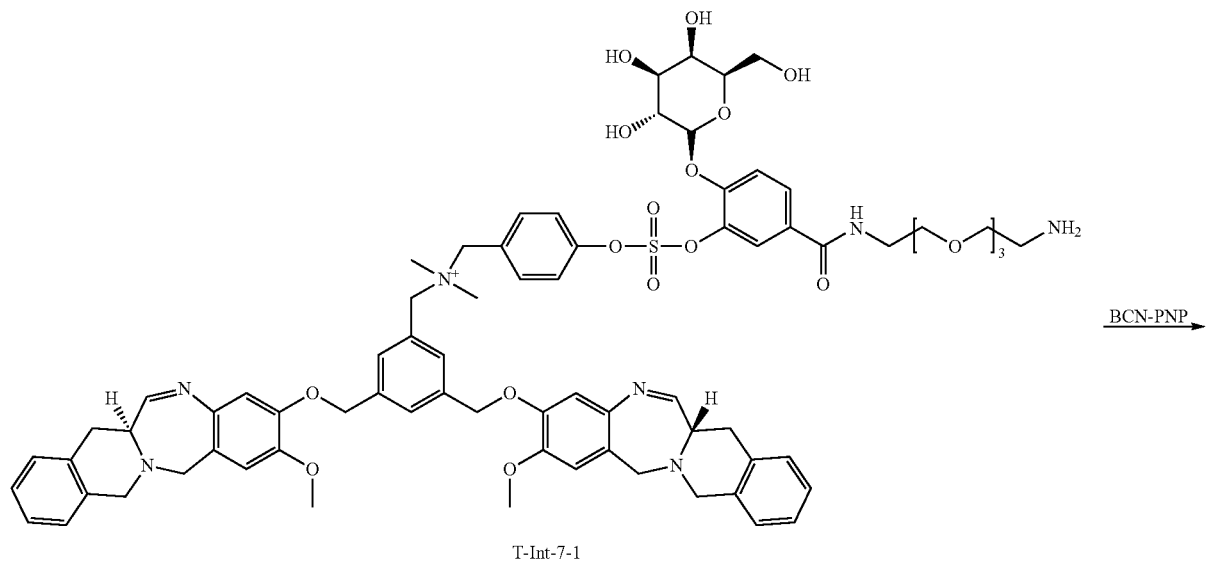

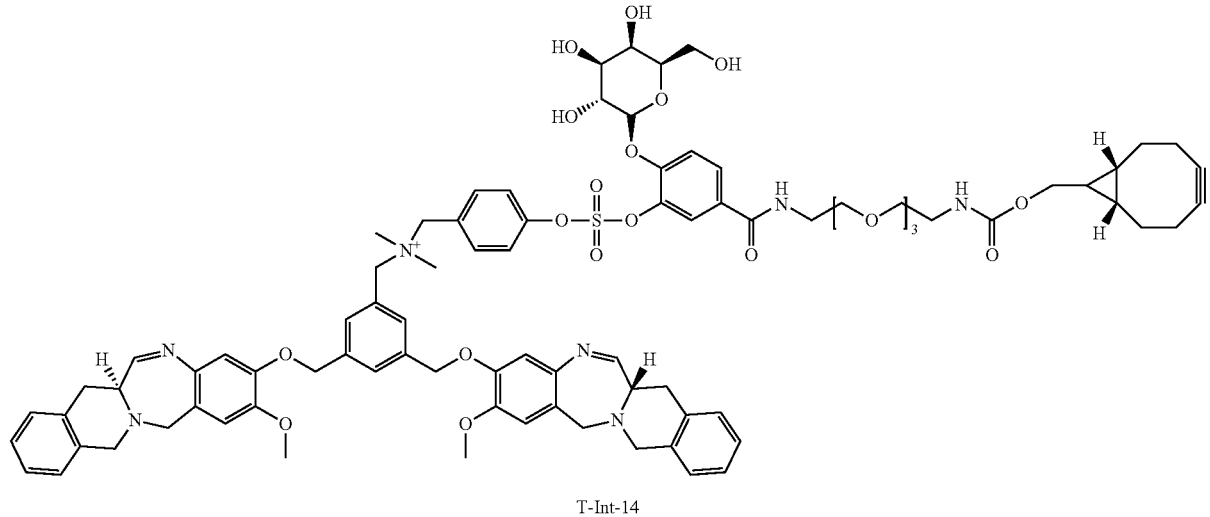

A homogeneous solution of compound T-Int-7 (50 mg, 0.035 mmol) and BCN-PNP (11 mg, 0.035 mmol, 1.0 eq.) in DMF (3.0 mL) at room temperature under $N_2$ atmosphere was treated DIPEA (11 uL, 0.068 mmol, 2.0 eq.) and stirred for 2 hours. The mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-Int-14 (22 mg, 39%) as beige solid.

EI-MS m/z: 1612 ($M^+$+1).

Example 67: Preparation of Compound T-Int-15 and T-Int-16

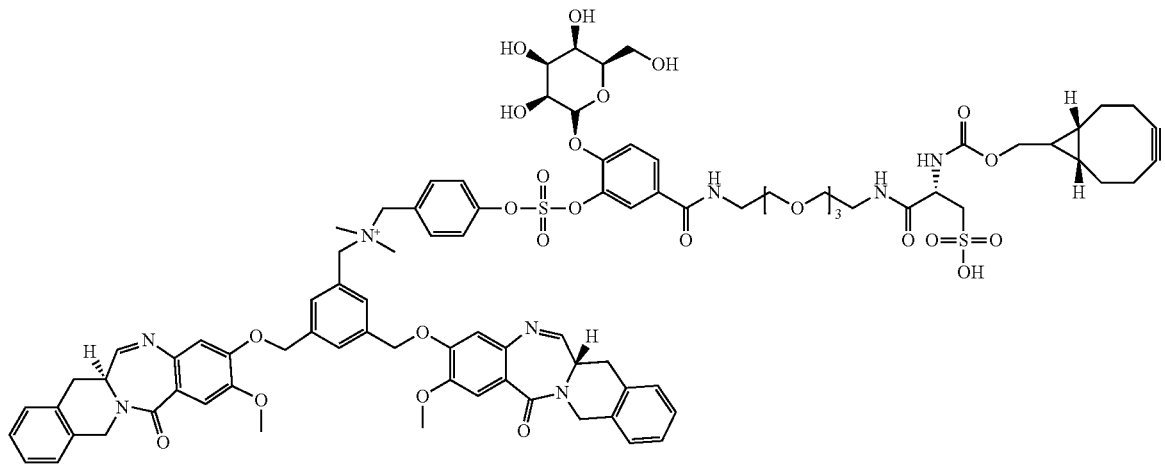

T-Int-15 (n = 3)
T-Int-16 (n = 11)

Compound T-Int-15 and T-Int-16 were synthesized via a similar synthetic route as described in Example 66.

Compound T-Int-15
Yield 35%, white solid; EI-MS m/z: 1763 (M$^+$+1), 882 (M/2$^+$+1).

Compound T-Int-16
Yield 11%, white solid; EI-MS m/z: 2116 (M$^+$+1), 1058 (M/2$^+$+1).

Example 68: Preparation of Compound T-1

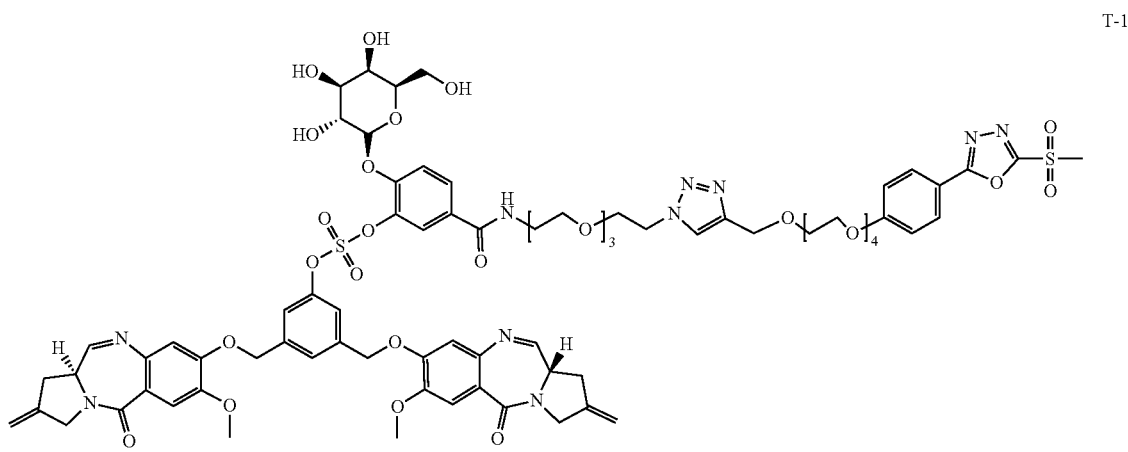

T-1

DMSO (8643 µL) was added at room temperature under a nitrogen atmosphere, and the compound T-Int-1 (15 mg, 0.012 mmol) was dissolved in DMSO (1237 µL) and added thereto. (BimC$_4$A)$_3$ prepared to have a concentration of 10 mmol was added thereto in an amount of 4207 L. Then, CuBr prepared to have a concentration of 100 mmol was added thereto in an amount of 1237 µL. Then, the mixture was stirred for 2 minutes. The POS-D1 (5.3 mg, 0.012 mmol) was dissolved in DMSO (1176 µL) and added thereto, followed by stirring for 10 minutes. After the reaction was completed, the mixed solution was separated and purified by preparative HPLC (reverse phase, C18, gradient H$_2$O/ACN/0.1% Formic acid) to obtain a compound T-1 (2.5 mg, 12%).

EI-MS m/z: 1668 (M$^{+1}$).

Example 69: Preparation of Compound T-2

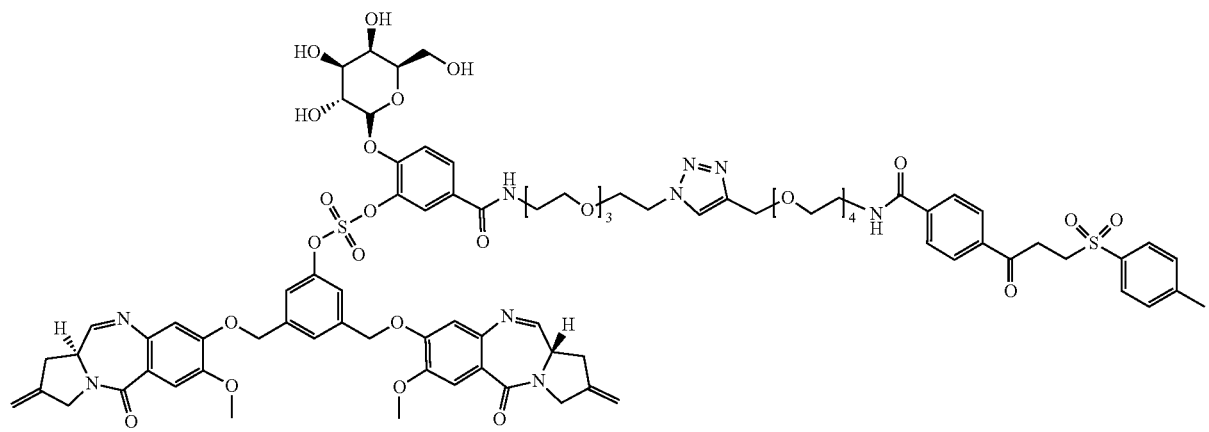

T-2

Compound T-Int-1 and MPS-D2 were reacted in a similar route to the preparation method of the compound T-1 of Example 68, thereby obtaining a compound T-2 (yield 7%).
EI-MS m/z: 1759 (M$^{+1}$).

Example 70: Preparation of Compound T-3 and T-4

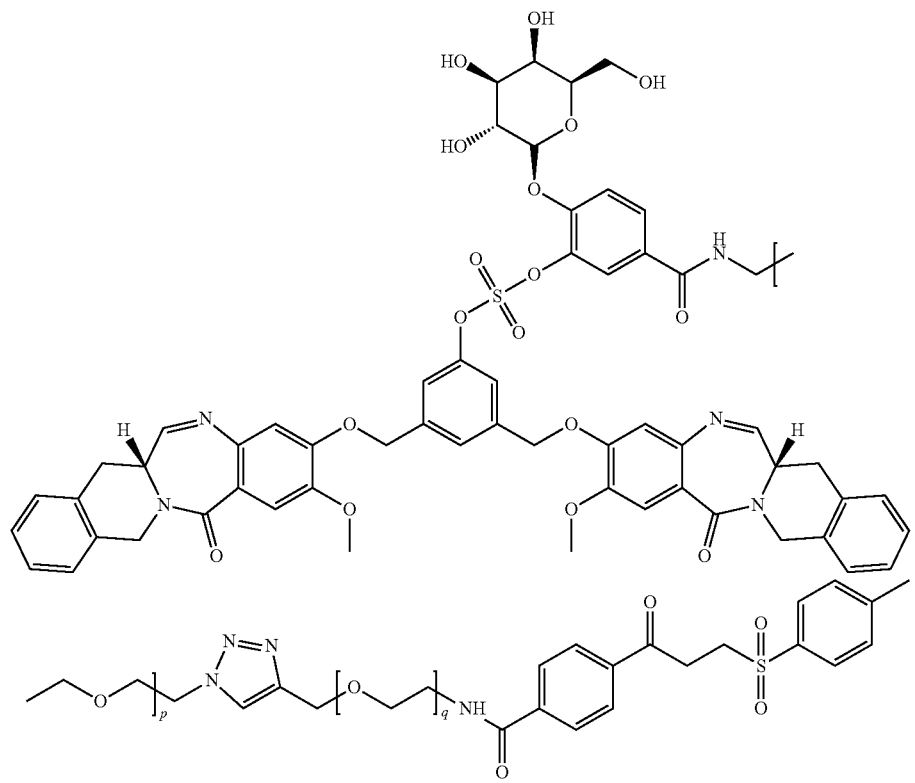

T-3 (p = 3, q = 4)
T-4 (p = 11, q = 12)

Compound T-3 and T-4 were synthesized via a similar synthetic route as described in Example 68.
Compound T-3
Yield 9.0%; EI-MS m/z: 1860 (M$^{+1}$).
Compound T-4
Yield 26%; EI-MS m/z: 1282 (M/2$^{+1}$).

Example 71: Preparation of Compound T-5
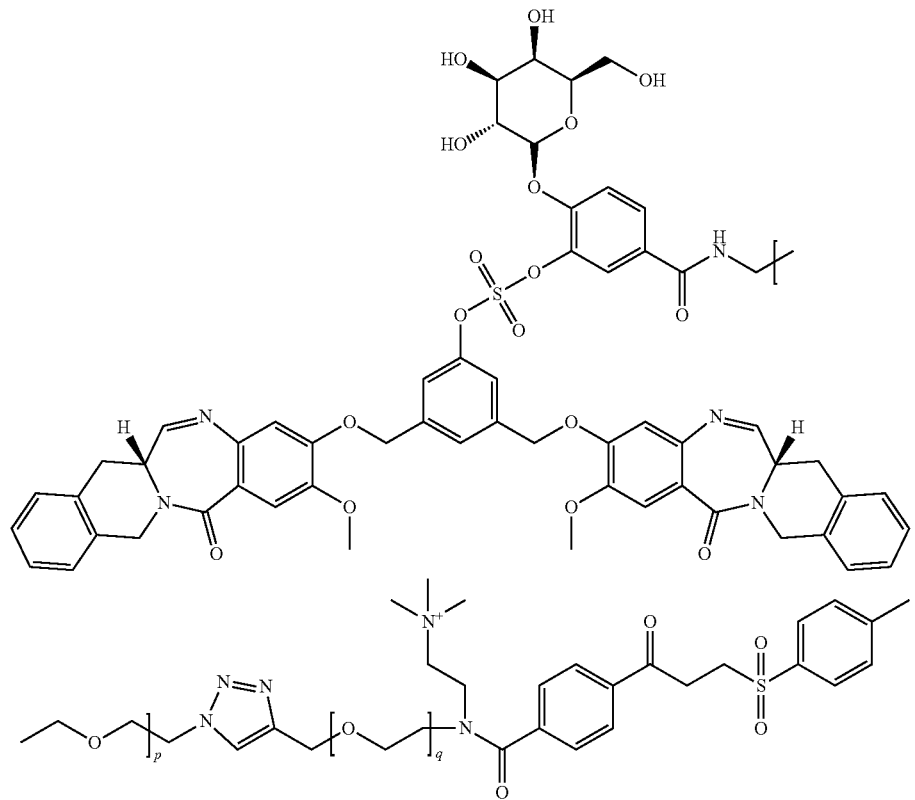
Compound T-5 was synthesized via a similar synthetic route as described in Example 68.
Yield 27%
EI-MS m/z: 1945 (M$^{+1}$).
Example 72: Preparation of Compound T-6 and T-7
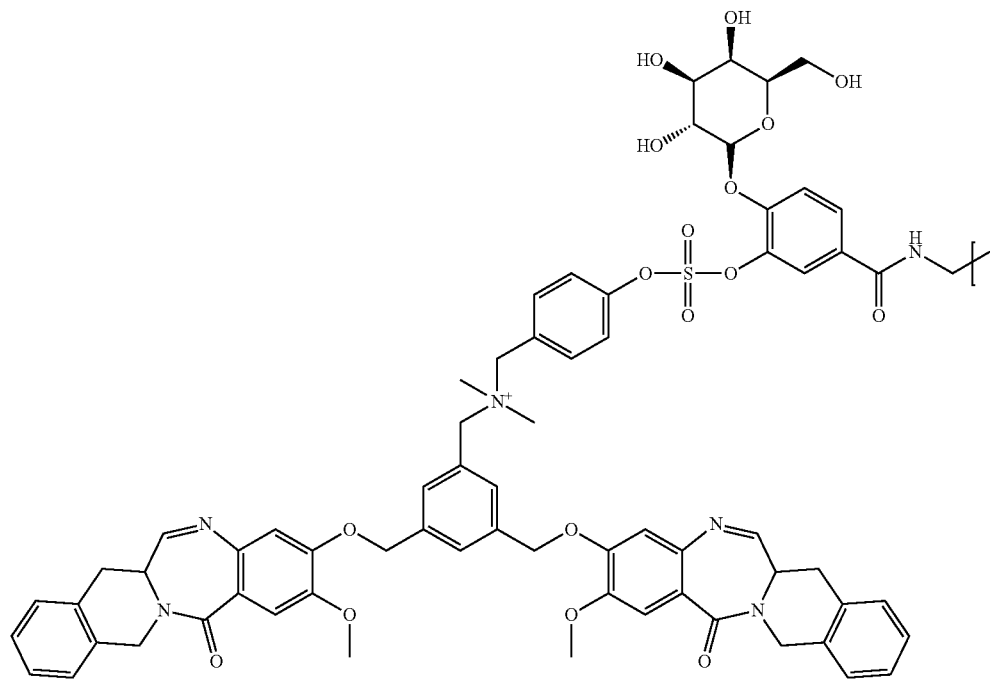

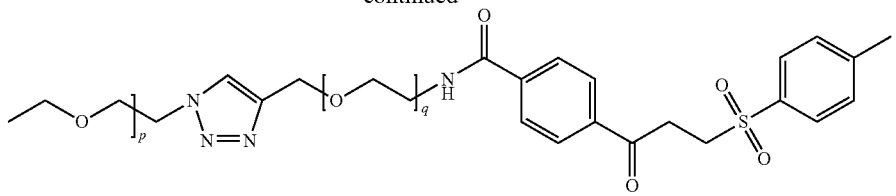
T-6 (p = 3, q = 4)
T-7 (p = 3, q = 12)
Compound T-6 and T-7 were synthesized via a similar synthetic route as described in Example 68.
Compound T-6
Yield 25%
EI-MS m/z: 1004 (M/2$^{+1}$).
Compound T-7
Yield 62%
EI-MS m/z: 1180 (M/2$^{+1}$).
Example 73: Preparation of Compound T-8
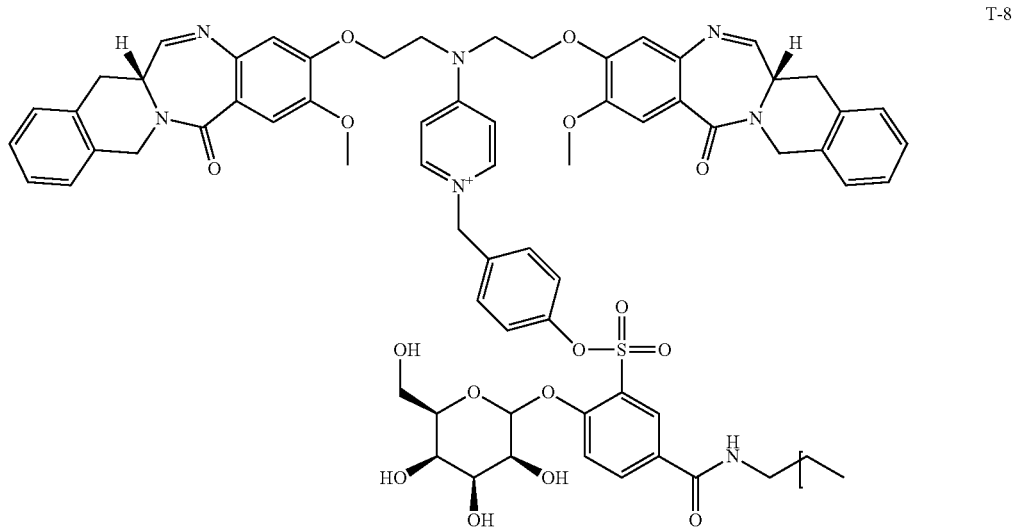
T-8
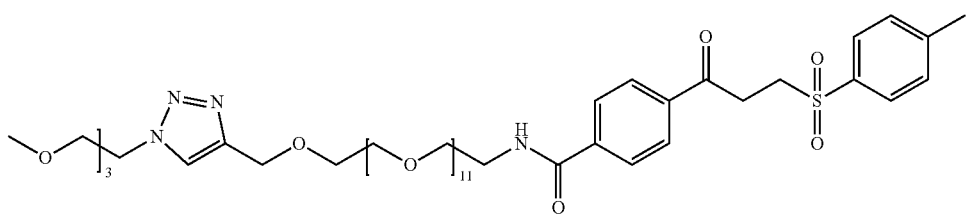
Compound T-8 was synthesized via a similar synthetic route as described in Example 68.
Yield 27%
EI-MS m/z: 1174 (M/2$^{+1}$).

Example 74: Preparation of Compound T-9

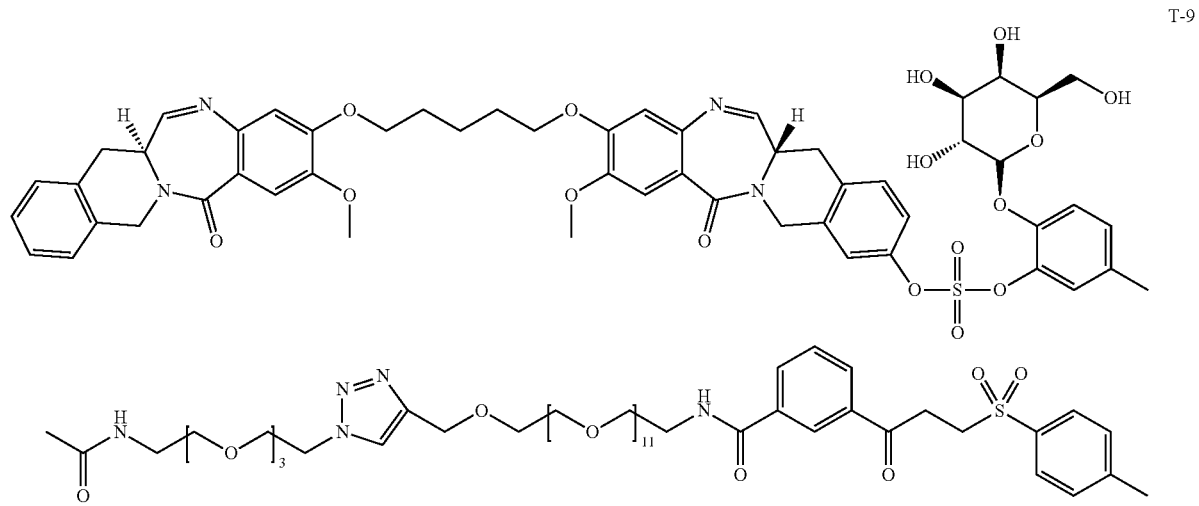

A homogeneous solution of T-Int-6 (2.2 mg, 0.0017 mmol) and MPS-D4 (3.9 mg, 0.004 mmol, 2.5 eq.) in DMSO (2720 uL) at room temperature under $N_2$ atmosphere was treated 5 mM $(BimC_4A)_3$ in DMSO (1120 uL, 0.006 mmol, 3.5 eq.) and stirred for 10 minutes. And 10 mM CuBr in DMSO (160 uL, 0.017 mmol, 10 eq.) was added in the reaction mixture and stirred for 15 minutes. The reaction mixture was purified by preparative HPLC (Column: Innoval ODS-2 10 um, 100 Å, 21.2×250 mm; flow rate: 15 mL/min, A buffer 0.1% Formic acid in water/B buffer 0.1% Formic acid in ACN, method gradient, solvent A:solvent B 95:5 to 5:95, 1 hour, wavelength 214 nm) to obtain compound T-9 (2.4 mg, 64%) as white solid.

EI-MS m/z: 2178 ($M^+$+1), 1089 ($M/2^+$+1).

Example 75: Preparation of Compound T-10

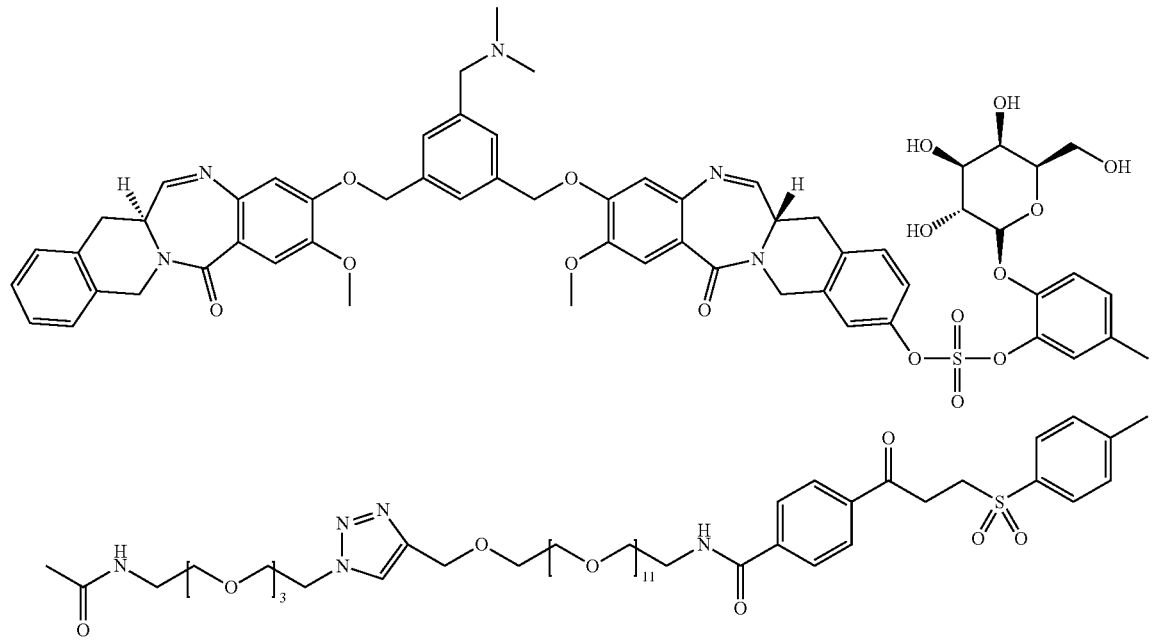

Compound T-10 was synthesized via a similar synthetic route as described in Example 74 (yield 56%) as white solid.

EI-MS m/z: 2269 ($M^+$+1), 1135 ($M/2^+$+1).

Example 76: Preparation of Compound T-11
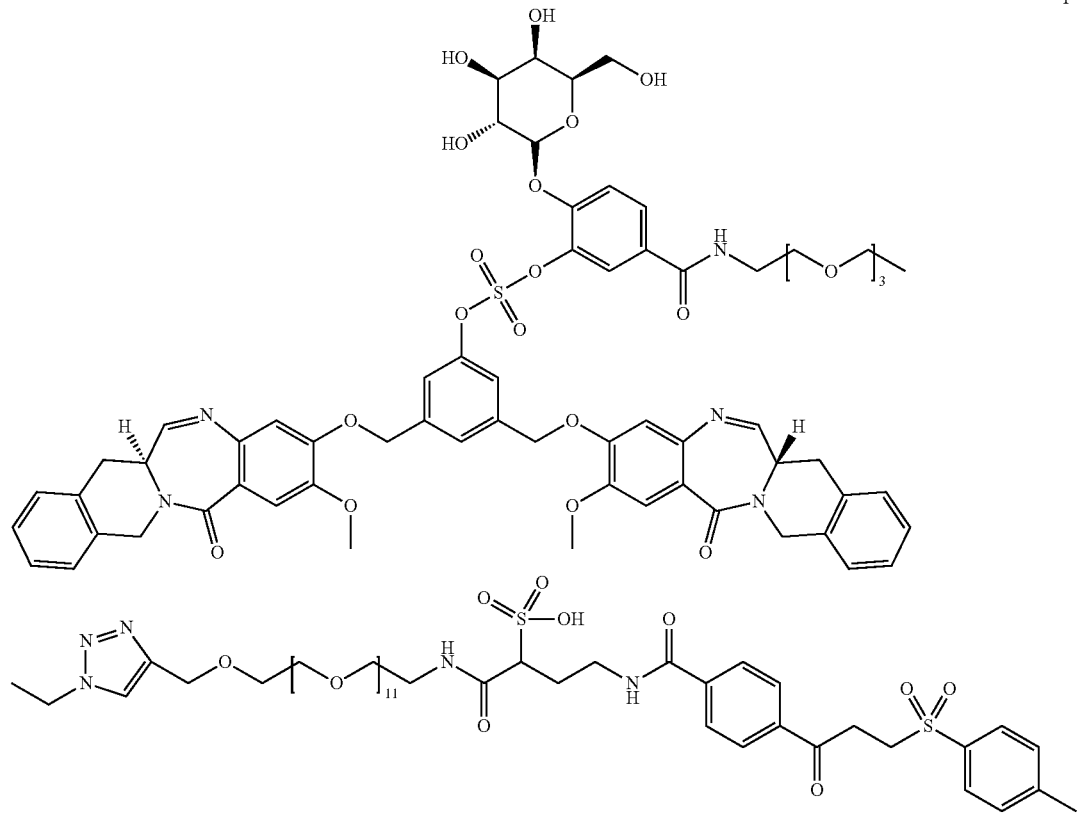
T-11
Compound T-11 was synthesized via a similar synthetic route as described in Example 74 (yield 34%) as white solid. EI-MS m/z: 2377 (M$^+$+1), 1189 (M/2$^+$+1).
Example 77: Preparation of Compound T-12
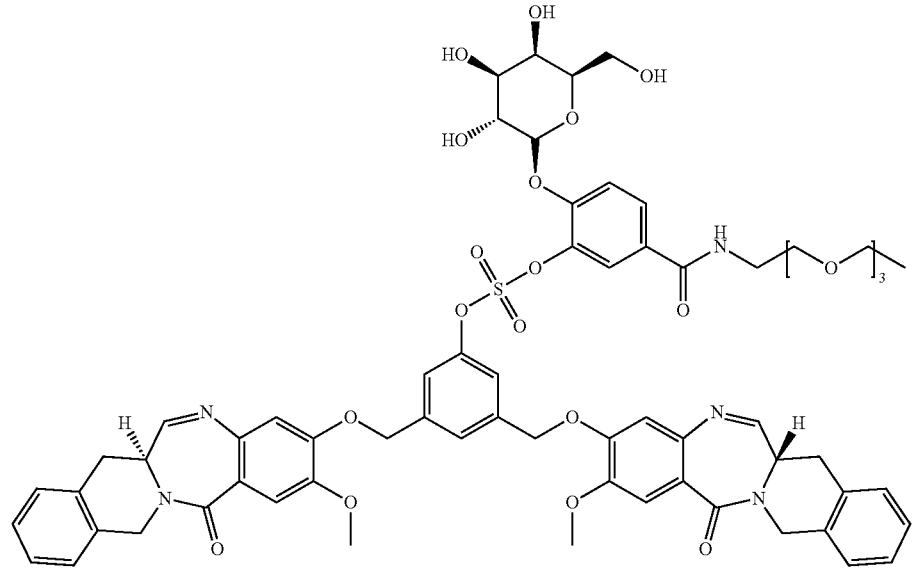
T-12

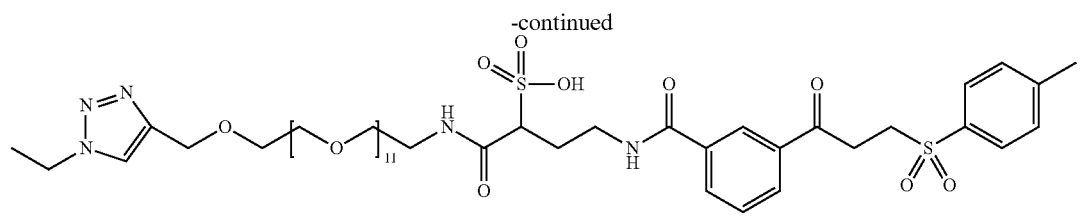
Compound T-12 was synthesized via a similar synthetic route as described in Example 74 (yield 58%) as white solid.
EI-MS m/z: 2377 (M$^+$+1), 1189 (M/2$^+$+1).
Example 78: Preparation of Compound T-13
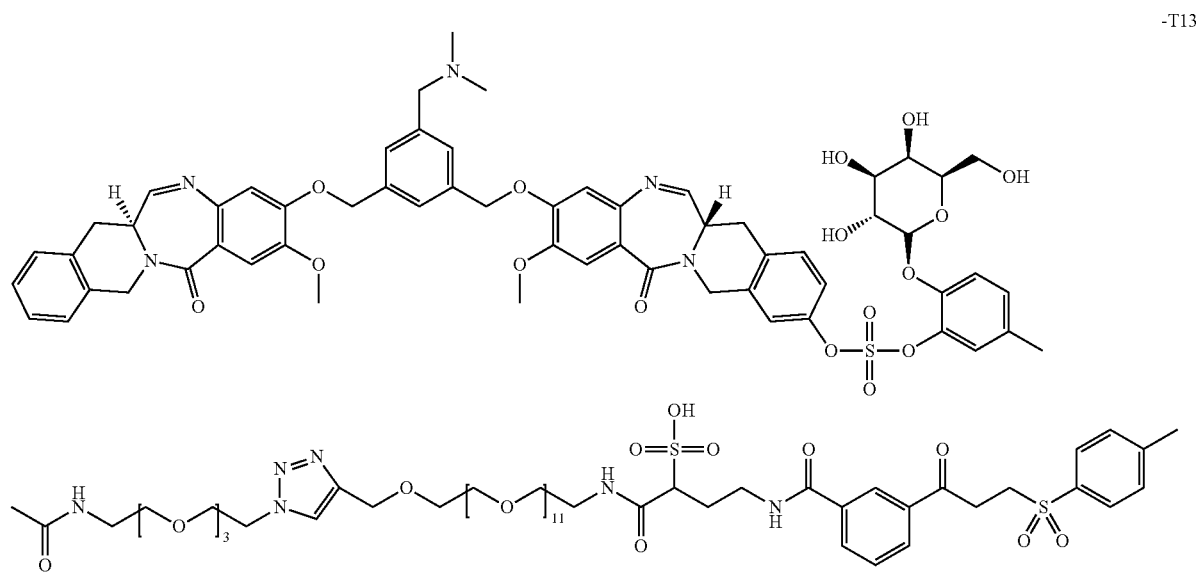
Compound T-13 was synthesized via a similar synthetic route as described in Example 74 (yield 58%) as white solid.
EI-MS m/z: 2434 (M$^+$+1), 1217 (M/2$^+$+1).
Example 79: Preparation of Compound T-14
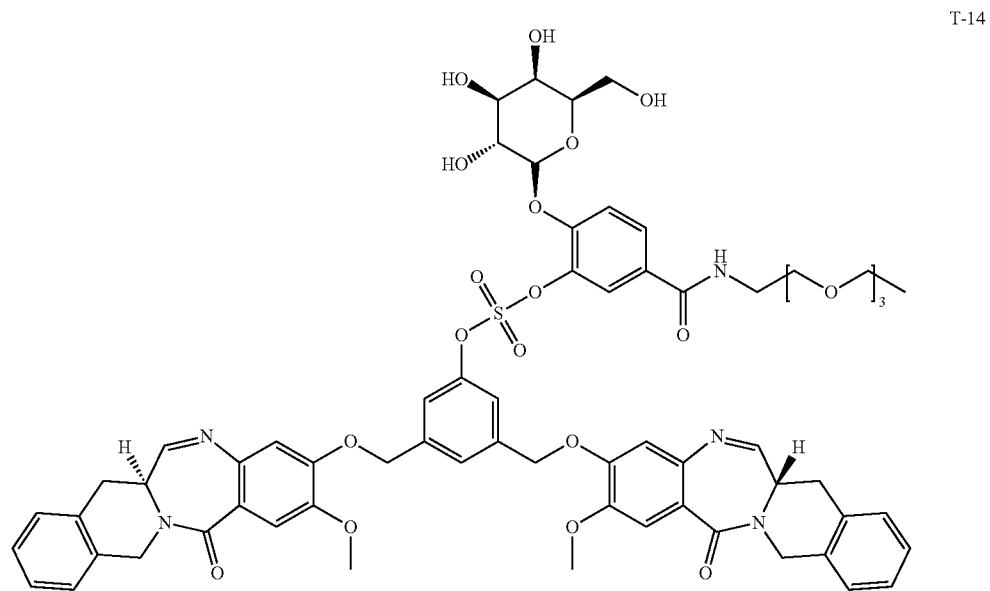

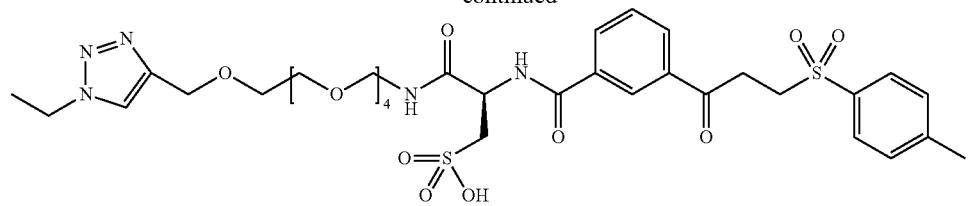
Compound T-14 was synthesized via a similar synthetic route as described in Example 74 (yield 72%) as white solid.
EI-MS m/z: 2011 (M$^+$+1), 1006 (M/2$^+$+1).
Example 80: Preparation of Compound T-15
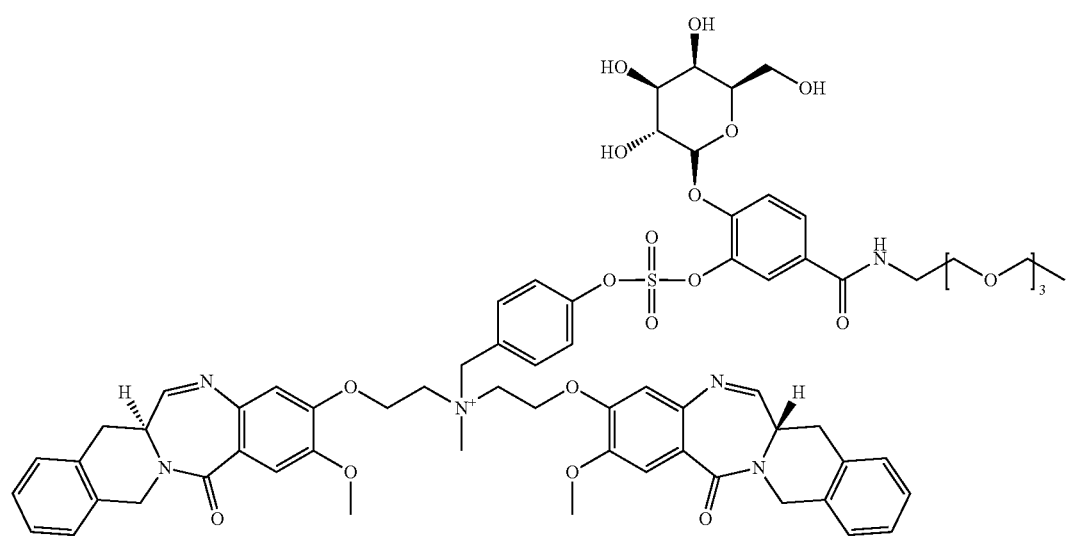
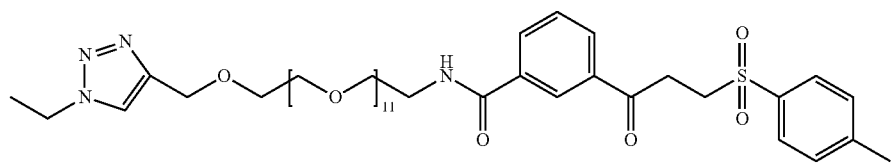
Compound T-15 was synthesized via a similar synthetic route as described in Example 74 (yield 48%) as pale yellow solid.
EI-MS m/z: 2284 (M$^+$+1), 1142 (M/2$^+$+1).

Example 81: Preparation of Compound T-16
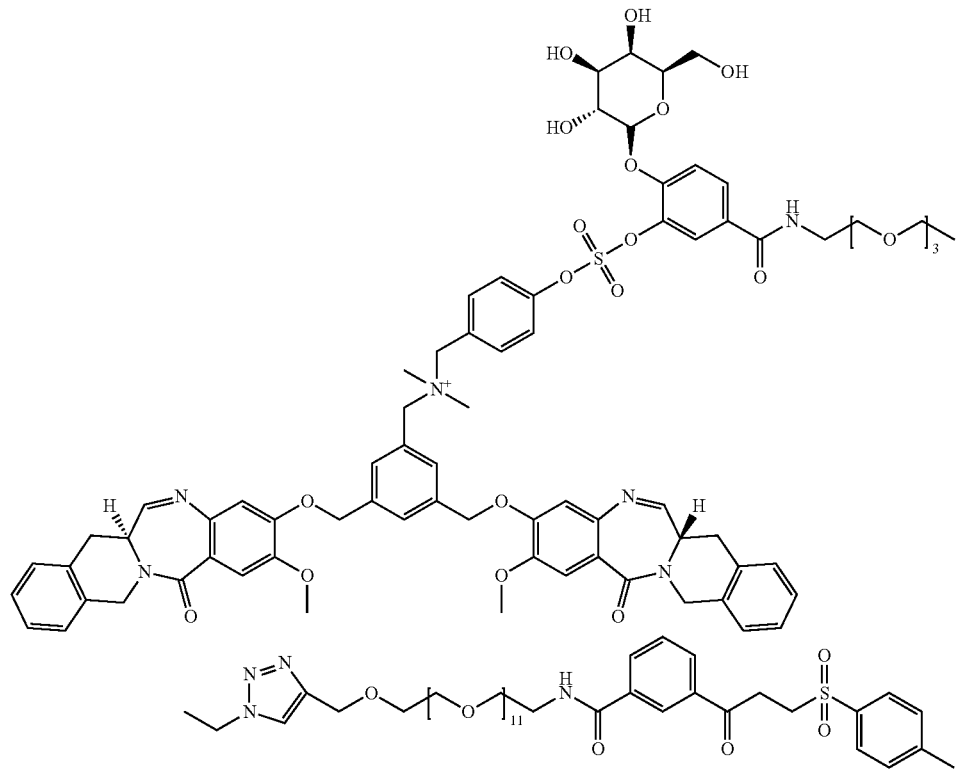
T-16
Compound T-16 was synthesized via a similar synthetic route as described in Example 74 (yield 69%) as pale yellow solid.
EI-MS m/z: 2360 (M$^+$+1), 1180 (M/2$^+$+1).
Example 82: Preparation of Compound T-17
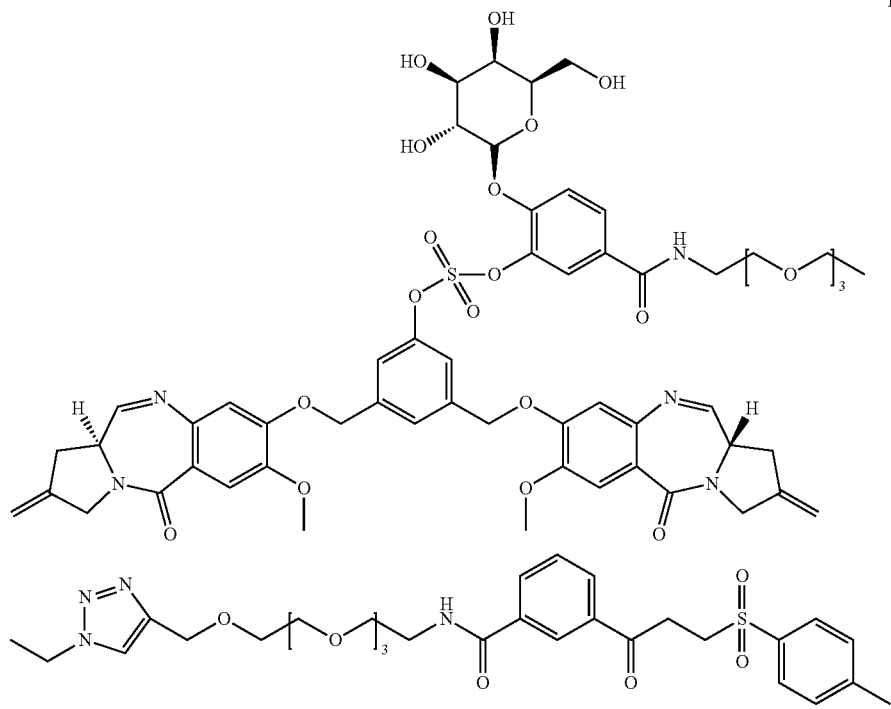
T-17

Compound T-17 was synthesized via a similar synthetic route as described in Example 74 (yield 40%) as white solid.
EI-MS m/z: 1759 (M$^+$+1), 880 (M/2$^+$+1).

Example 83: Preparation of Compound T-18

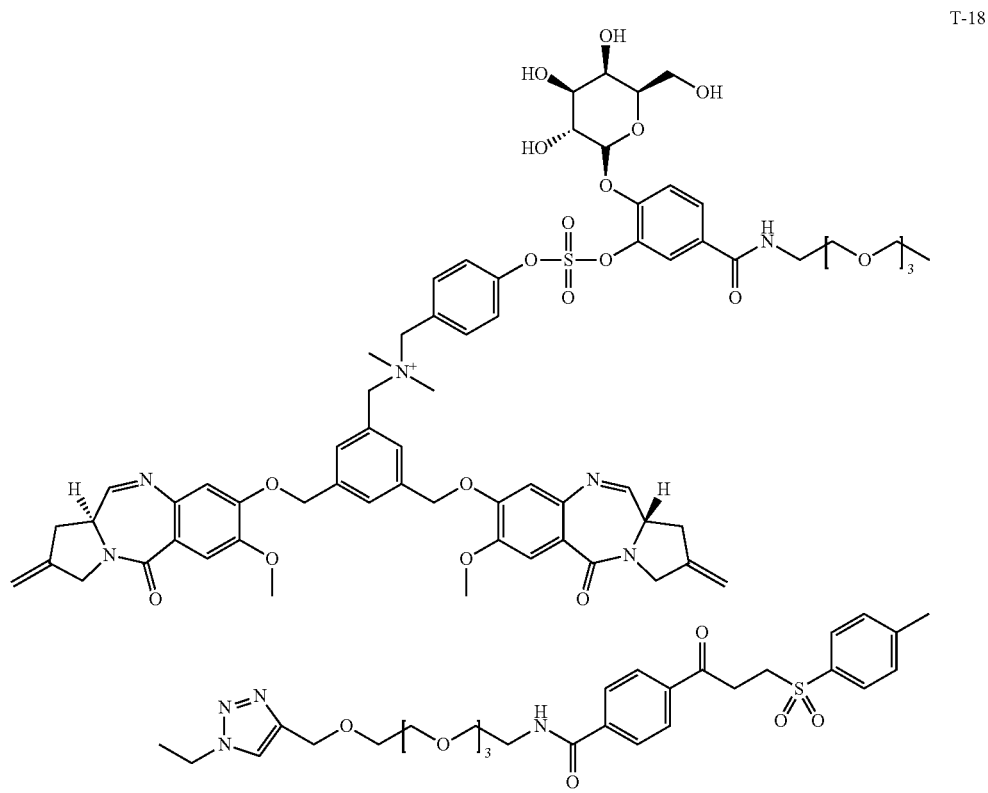

Compound T-18 was synthesized via a similar synthetic route as described in Example 74 (yield 71%) as ivory solid.
EI-MS m/z: 1908 (M$^+$+1), 954 (M/2$^+$+1).

Example 84: Preparation of (N,N-dimethylbenzyl)-PBD-Dimer (D-14)

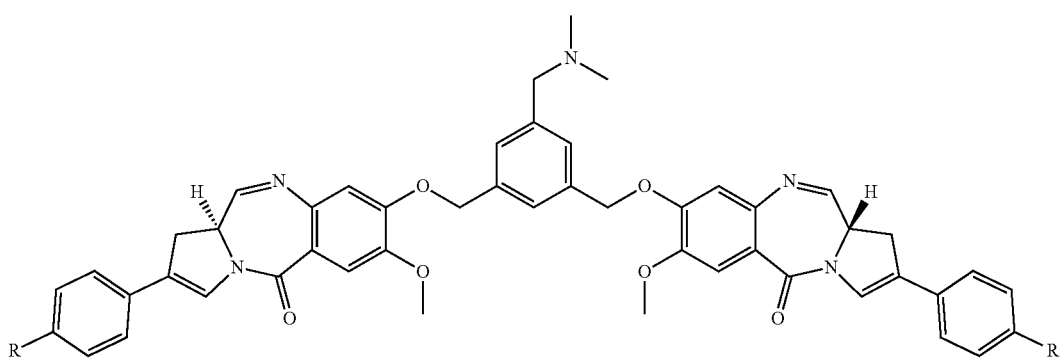

Compound D-9 was synthesized via a similar synthetic route as described in Example 47 (yield 50%).
EI-MS m/z: 800 (M$^+$+1).

Biological Testing

Example 85: In Vitro Analysis of Benzodiazepine Dimer Derivatives A-498, HCT-116, JIMT-1, MIA-PaCa-2 and HEK-293E were seeded into 24-well plates at $10\times10^3$ cells/1 mL medium/well. Calu-6, PC-3 and SK-OV-3 were seeded into 24-well plates at $15\times10^3$ cells/1 mL medium/well. NCI-N87 was seeded into 24-well plates at $25\times10^3$ cells/1 mL medium/well. The plates were incubated for 24 hours at 37° C. in a humidified 5% $CO_2$-in-air atmosphere. Benzodiazepine dimer derivatives were dissolved initially in DMSO at a concentration of 10 mM. Serial dilutions were made in DMSO. The series of compound dilutions in DMSO were added to triplicate wells of 24-well plates at 5 μL per well. Three wells on each individual plate received 5 μL of DMSO without compound as controls. The final concentration of DMSO per well was 0.5%. The plates were incubated for 6 days at 37° C. in a humidified 5% $CO_2$-in-air atmosphere. Cell viability was determined by the MTT assay and $IC_{50}$ was generated using a sigmoidal dose-response non-linear regression curve fit (GraphPad Software Inc.). Results thereof are shown in Tables 1A and 1B (below).

TABLE 1A

In Vitro Biological and Pharmacokinetic Data

| | NCI-N87 ($IC_{50}$ pM) | JIMT-1 ($IC_{50}$ pM) | SK-OV3 ($IC_{50}$, pM) | MIA-PaCa2 ($IC_{50}$, pM) | HCT-116 ($IC_{50}$, pM) |
|---|---|---|---|---|---|
| D-1 | 191.1 | 102 | 175 | 105 | 109 |
| D-2 | 104.4 | 34 | 74 | 44 | 36 |
| D-3 | 32.2 ± 21.3 | 31.0 ± 15 | 59.6 ± 18.2 | 10.6 ± 4.6 | 13.7 ± 8.6 |
| D-4 | 3.8 ± 2.4 | 1.7 ± 0.6 | | | |
| D-5 | 0.5 ± 0.2 | 1.7 ± 0.5 | 10.9 ± 2.7 | 1.9 ± 1.6 | 1.4 ± 0.6 |
| D-6 | 4,111 ± 1,076 | 2,982 ± 499 | | | |
| D-7 | 0.118 ± 0.009 | | | | |
| D-8 | 0.062 ± 0.002 | | | | |
| D-9 | 0.184 ± 0.036 | | | | |
| D-10 | 0.663 ± 0.116 | | | | |
| D-11 | 0.173 ± 0.034 | | | | |
| D-12 | 2,028 ± 1,225 | | | | |
| D-13 | 2.028 ± 1.225 | | | | |
| Ref-1 | 3.5 ± 2.8 | 5.4 ± 1.6 | | | |
| MMAF-OMe | 182.4 | 161 | 244 | 852 | 392 |

TABLE 1B

In Vitro Biological and Pharmacokinetic Data

| | Calu-6 ($IC_{50}$ pM) | A-498 ($IC_{50}$ pM) | PC-3 ($IC_{50}$, pM) | HEK-293E ($IC_{50}$, pM) | Solubility improvement |
|---|---|---|---|---|---|
| D-1 | 89 | 414 | 126 | 216 | + |
| D-2 | 29 | 64 | 49 | 79 | + |
| D-3 | 6.2 | 139 | 32.6 ± 10.3 | 11.4 ± 2.6 | + |
| D-4 | | | | | + |
| D-5 | 1.4 | 2.9 | 4.4 ± 2.1 | 2.2 ± 1.1 | + |
| D-6 | | | | | ++ |
| D-7 | | | | | |
| D-8 | | | | | |
| D-9 | | | | | |
| Ref-1 | | | | | |
| MMAF-OMe | 162 | 233 | 212 | 970 | |

Example 86: Reduction/Oxidation of Antibodies for Conjugation

Cysteine engineered monoclonal antibodies were reduced with about a 20-50 fold excess of TCEP (tris(2-carboxyethyl)phosphine hydrochloride or DTT (dithiothreitol) in 4 mM Tris pH 7.3 with 1 mM EDTA for 1 hours at 37 TC. The reduced thiomab was diluted and loaded onto a PD-10 column in PBS. The column was eluted with 10 mM PBS pH 7.3. The eluted reduced thiomab was re-established by air oxidation. The thiol/Ab value was checked by determining the reduced antibody concentration form the absorbance at 280 nm of the solution and the thiol concentration by reaction with DTNB (Aldrich, CAS No D8130) and determination of the absorbance at 412 nm.

Example 87: Preparation of Conjugate (Albumin & Antibody)

Conjugation Method 1: After the reduction and reoxidation reaction, the antibody was dissolved in PBS. A solution of compound T-2 (329.6 uL, 3.0 mmol, as linker-toxin intermediate) in DMSO was treated with the reduced, reoxidized antibody (1650 uL, 0.083 mmol) and agitated gently for 3 hours at room temperature. Hydroxylamine (329.6 uL, 1,500 mmol) was added to a solution of the reaction mixture and incubated at 37° C. for 8 hours to block a reversible deconjugation reaction. The conjugation mixture was loaded and eluted through PD-10 column to remove excess drug-linker intermediate and other impurities. The mixture was concentrated by centrifugal ultrafiltration and the conjugate was purified with HIC NPR column (TOSOH #0007656 TSKgel Phenyl-5PW, 21.5×150 mm, 13 μm) and eluted with a linear gradient from 40 to 100% B at 0.8 ml/min (A buffer 1.5 M ammonium sulfate in 50 mM sodium phosphate (pH 7.0); B buffer 20% acetonitrile in 50 mM sodium phosphate (pH 7.0)). DAR (drug to antibody ratio) of conjugated antibody was analyzed by HIC and results of the analysis were shown in Table 2.

Compounds T-3, T-7, T-8, T-9, T-11, T-12, T-13, T-14, T-15, T-16, and T-17 obtained in Examples 70, 72, 73, 74, 76, 77, 78, 79, 80, 81 and 82 were used to perform conjugation reaction to a thiol group of engineered cysteine of trastuzumab (or human serum albumin etc.), thereby preparing T-3-AB, T-7-AB, T-8-AB, T-9-AB, T-11-AB, T-12-AB, T-13-AB, T-14-AB, T-15-AB, T-16-AB, and T-17-AB as thiomab drug conjugates (TDC), respectively, with reference to methods presented in document. [see Nature Biotechnology, 2008, 26, 925-932, Bioconjugate Chem., 2013, 24, 1256-1263, Bioconjugate Chem., 2016, 27, 1324-1331, Bioconjugate Chem. 2014, 25, 460-469].

Conjugation Method 2: Each compound MPS-D10 obtained in Example 34, MPS-D9 obtained in Example 27, and mMPS-D6 obtained in Example 32 were used to perform 1st step conjugation reaction with thiol groups of engineered cysteine of antibody (ex. Trastuzumab).

After the reduction and reoxidation procedures of Example 84, the antibody in PBS was treated with each compounds (6.62 uL, 3.0 mmol) in DMSO. After 3 hours, sodium borohydride (6.62 ul, 300 mmol) was added to the conjugated solution to block a reversible de-conjugation reaction at RT for 1 hour. And 1st conjugated antibodies were purified by PD-10 column. For 2nd conjugation, T-Int-1 (13.24 uL, 3.0 mmol) obtained in Example 56 or T-Int-2 (20.0 uL, 3.0 mmol) obtained in Example 57 with a functional group such as $N_3$ to be promoted cycloaddition in the absence of a Cu(I) catalyst was subjected to MIPS-D10 conjugated antibody (7.4 uL, 0.117 mmol) and incubated at 37. After approximately 24 hours, antibody drug conjugates (T-Int-1-AB and T-Int-2-AB) were purified by PD-10 column and concentrated by centrifugal ultrafiltration. As same protocol, compound T-int-14 obtained in Example 66 was added to MPS-D9 or mMPS-D6 conjugated antibody to prepare T-Int-14-AB or mT-Int-14-AB. DAR (drug to antibody ratio) of conjugated antibodies were analyzed by HIC and results of the analysis were shown in Table 2.

TABLE 2

Antibody-Drug Conjugates (ADCs)

| ADCs | DAR | Conjugation metod | Linker-Toxin, Example |
|---|---|---|---|
| T-2-AB | 1.9 | 1 | T-2, Example 69 |
| T-3-AB | 1.37 | 1 | T-3, Example 70 |
| T-7-AB | 2.0 | 1 | T-7, Example 72 |
| T-8-AB | 1.34 | 1 | T-8, Example 73 |
| T-9-AB | 1.16 | 1 | T-9, Example 74 |
| T-11-AB | 1.25 | 1 | T-11, Example 76 |
| T-12-AB | 0.76 | 1 | T-12, Example 77 |
| T-13-AB | 1.01 | 1 | T-13, Example 78 |
| T-14-AB | 1.11 | 1 | T-14, Example 79 |
| T-15-AB | 1.26 | 1 | T-15, Example 80 |
| T-16-AB | 1.02 | 1 | T-16, Example 81 |
| T-17-AB | 1.48 | 1 | T-17, Example 82 |
| T-Int-1 AB | 1.53 | 2 | MPS-D10, Example 34 T-Int-1, Example 56 |
| T-Int-2 AB | 1.00 | 2 | MPS-D10, Example 34 T-Int-2, Example 57 |
| T-Int-14 AB | 1.37 | 2 | MPS-D9, Example 27 T-Int-14, Example 66 |
| mT-Int-14 AB | 1.33 | 2 | mMPS-D6, Example 32 T-Int-14, Example 66 |

Example 88: In Vitro Analysis of Protein-Drug Conjugates

Figure 10:
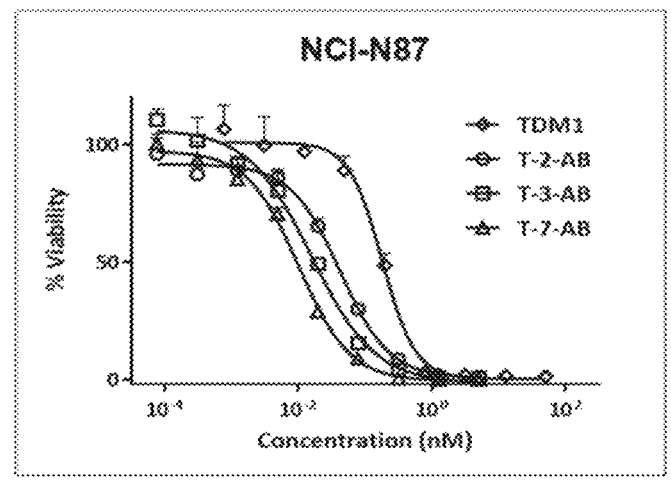
FIG. 10 shows the in vitro analysis of conjugates T-2-AB, T-3-AB, and T-7-AB against NCI-N87.
Figure 11:
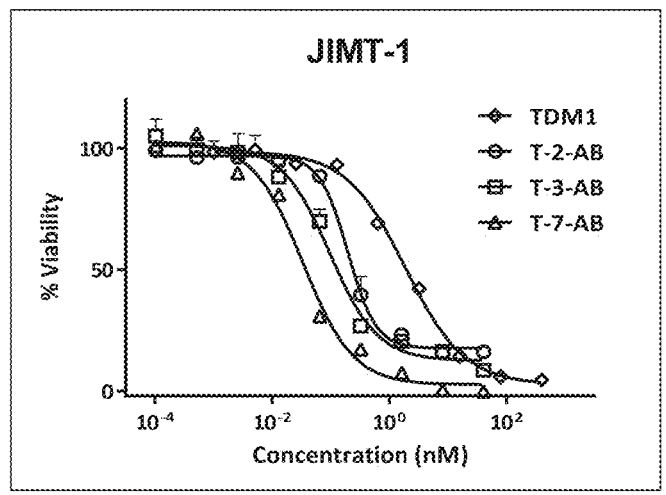
FIG. 11 shows the in vitro analysis of conjugates T-2-AB, T-3-AB, and T-7-AB against JIMT-1.
Figure 12:
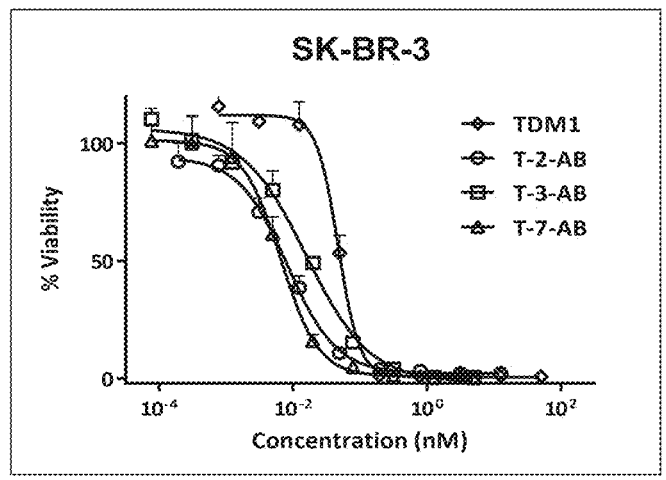
FIG. 12 shows the in vitro analysis of conjugates T-2-AB, T-3-AB, and T-7-AB against SK-BR-3

NCI-N87, JNMT-2, SK-BR3, and SK-V3 cancer cells were seeded in 96-well plates at a density of 2,000 to 8,000 cells per well in 100 μL of medium, and cultured for 24 hours. The four compounds obtained in Example 46 were treated by serial dilutions of 1:4 from 600 nM to 0.009 nM, and the antibody drug conjugate T-DM1 was treated by serial dilutions of 1:4 from 200 nM to 0.003 nM. Experiments were performed in a similar manner to Test Example 1 to quantify living cells 96 hours later, and results are shown in Table 2 below. Further, results of in vitro analysis of compound T-2-AB, T-3-AB, T-7-AB T-8-AB, T-9-AB, T-11-AB, T-12-AB, T-13-AB, T-14-AB, T-15-AB, T-16-AB, T-17-AB, T-Int-1-AB, T-Int-2-AB, T-Int-14-AB and mT-Int-8-AB were shown in FIG. 10, FIG. 11, FIG. 12, and Table 3.

TABLE 3

Cell cytotoxicity of antibody-drug conjugate

| ADCs | DAR | $IC_{50}$(nM) | | | |
|---|---|---|---|---|---|
| | | NCI-N87 | JIMT-1 | SK-BR3 | SK-OV3 |
| T-2-AB | 1.9 | 0.015 | 0.075 | 0.013 | 0.018 |
| T-3-AB | 1.37 | 0.016 | 0.096 | | |
| T-7-AB | 2.0 | 0.015 ± 0.009 | 0.056 ± 0.022 | 0.003 | 0.050 ± 0.012 |
| T-8-AB | 1.34 | >50 | >50 | 0.504 | 3.329 |
| T-9-AB | 1.16 | 0.020 | 0.228 | | |
| T-11-AB | 1.25 | 0.015 | 0.100 | | |
| T-12-AB | 0.76 | 0.042 | | | |
| T-13-AB | 1.01 | 0.063 | | | |
| T-14-AB | 1.11 | 0.025 | | | |
| T-15-AB | 1.26 | 0.322 | | | |
| T-16-AB | 1.02 | 0.009 | 0.045 | | |
| T-17-AB | 1.48 | 0.063 | | | |
| T-Int-1 AB | 1.53 | 0.038 | | | |
| T-Int-2 AB | 1.00 | 0.020 | | | |
| T-Int-14 AB | 1.37 | | | 0.003 | |
| mT-Int-14 AB | 1.33 | | | 0.003 | |
| T-DM1 | 3.5 | 0.234 ± 0.096 | 3.153 ± 1.762 | 0.037 ± 0.012 | 0.109 ± 0.004 |

(*T-DM1: Roche CAS number; 1018448-65-1)

Example 89: In Vivo Efficacy

T-2-AB and T-7-AB were prepared with 15 mg scale reaction. After purification by HIC column, The LC/MS analysis confirmed that the molecular weight of the thiomab (Trastuzumab A121C) was 145,324 Da. LC/MS analysis of the prepared antibody drug conjugate T-2-AB revealed the presence of masses about 148,497 Da. These mass shifts were consistent with the conjugation of two molecules of D-1. And T-7-AB revealed the presence of masses about 149,671 Da which were similar with two molecules of D-4.

Figure 13:
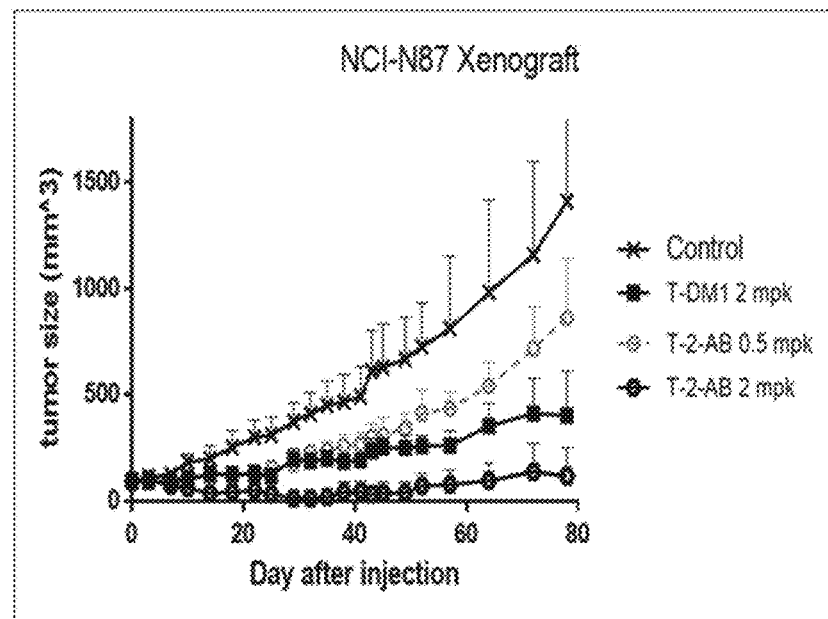
FIGS. 13 and 14 show in vivo testing of conjugate T-2-AB.
Figure 14:
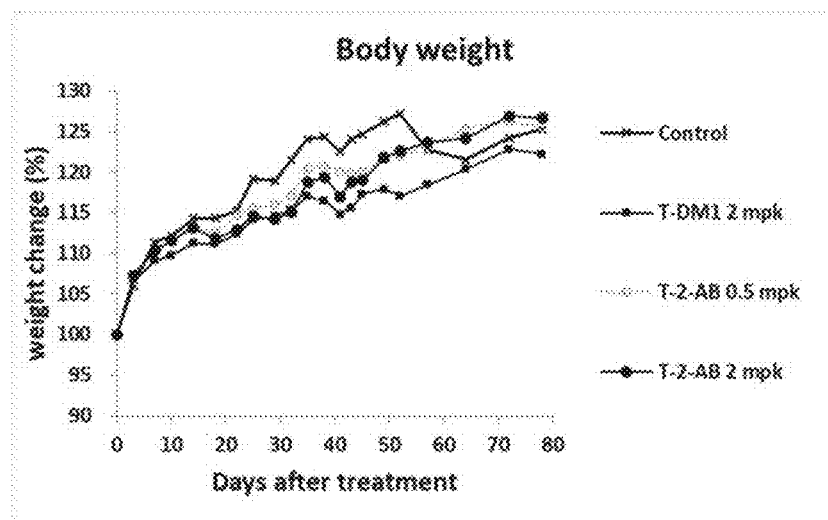

In vivo efficacy of antibody-drug conjugates of the invention was measured by tumor xenograft studies in mice. Male BALB/c nu/nu were injected subcutaneously in the right flank with suspensions of 5×10$^6$ of NCI-N87 cells respectively in PBS. Mice were randomized into study groups when tumors reached approximately 95 mm$^3$. T-DM1 (2 mg/kg) and T-2-AB conjugates (0.5 mg/kg or 2 mg/kg) were given i.v. (single injection on treatment day 0). All treatment groups consisted of 6 to 10 animals per group, and tumor size was monitored twice weekly using caliper measurement. The tumor mass was calculated as volume=(width× width×length)/2. Conjugates T-2-AB led to tumor regression within the period of observation, i.e. 80 days from the initiation of the experiment. The control conjugate, T-DM1 was less active than the conjugates of the invention. These results were shown in FIG. 13 and FIG. 14.

T-7-AB was progressed in the same method except initial tumor size was 150 mm$^3$. The conjugates made the tumor regressed during 120 days from the initiation of the experiment. These results were shown in FIG. 15, and FIG. 16.

These in vivo experiments were performed by CACT (center for advancing cancer therapeutics, Asan Medical Center, project code number: HI15C0972)

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:
1. A compound having the structure of Formula (II), (IIa), or (IIb)

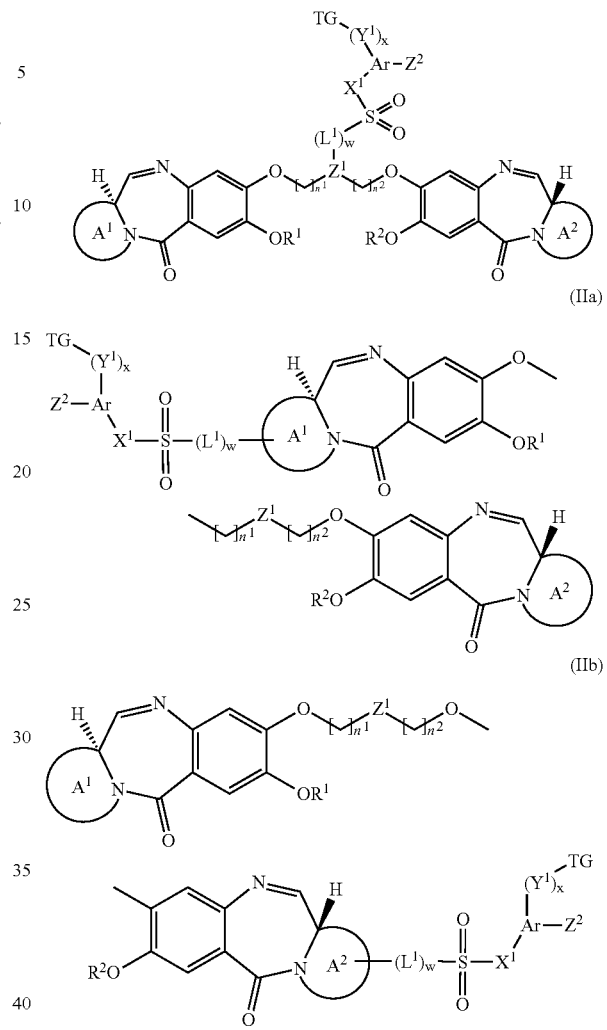

or a pharmaceutically acceptable salt thereof,
wherein:
A$^1$ and A$^2$ each independently represent a heterocyclic ring;
R$^1$ and R$^2$ are each independently an alkyl group;
Z$^1$ is a linking group;
n$^1$ and n$^2$ are each independently an integer having a value of 1 to 5;
Z$^2$ is a linking group;
L$^1$, when present, is a linking group attached to the SO$_2$ via a heteroatom selected from O, S, and N, and is selected such that cleavage of the bond between L$^1$ and SO$_2$ promotes cleavage of the bond between L$^1$ and Z$^1$, A$^1$, or A$^2$ to release the active agent;
X$^1$ is —O—, —CR$^b{}_2$—, or —NR$^a$—;
Ar is selected from aryl or heteroaryl;
Y$^1$ is —(CR$^b{}_2$)$_y$N(R$^a$)—, —(CR$^b{}_2$)$_y$O—, or —(CR$^b{}_2$)$_y$S—, positioned such that the N, O, or S atom is attached to TG if y is 1-10; wherein X$^1$ and Y$^1$ are positioned on adjacent atoms of Ar;
TG is a triggering group that, when activated, generates an N, O, or S atom capable of reacting with the SO$_2$ to displace Z$^1$, A$^1$, or A$^2$ and form a 5-6-membered ring including X$^1$—SO$_2$ and the intervening atoms of Ar;

w and x are each independently an integer having a value of 0 or 1;

each $R^a$ is independently hydrogen or lower alkyl;

each $R^b$ is independently hydrogen or lower alkyl; or two $R^b$, together with the carbon atom to which they are attached, form a 3-5-membered ring; and y is an integer having a value of 0-10.

2. The compound of claim 1, wherein $X^1$ is —O—.

3. The compound of claim 1, wherein Ar is phenyl or naphthyl.

4. The compound of claim 1, wherein $Z^2$ is a linking group comprising one or more groups selected from isocyanide, isothiocyanide, 2-pyridyl disulfide, haloacetamide (—NHC(O)CH$_2$-halo), maleimide, diene, alkene, halide, tosylate (TsO-), aldehyde, sulfonate (R—SO$_3^-$),

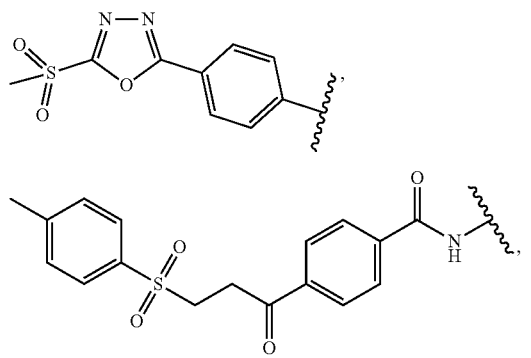

phosphonic acid (—P(=O)(OH)$_2$), ketone, C8-C10 cycloalkynyl, —OH, —NHOH, —NHNH$_2$, —SH, carboxylic acid (—COOH), acetylene (—C≡CH), azide (—N$_3$), amino (—NH$_2$), sulfonic acid (—SO$_3$H), an alkynone derivative (—C(O)C≡CR$^a$ wherein R$^a$ is C$_{1-10}$ alkyl), and dihydrogen phosphate (—OP(=O)(OH)$_2$).

5. The compound of claim 1, wherein x is 0.

6. The compound of claim 5, wherein TG is —NO$_2$, —OC(O)(CH$_2$)$_r$C(O)R$^1$, NHNH$_2$, —BR$^2$R$^3$, or

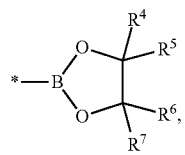

wherein:

$R^1$ is C$_1$-C$_6$ alkyl;

$R^2$ and $R^3$ are each independently hydrogen, C$_1$-C$_6$ alkyl, C$_1$-C$_6$ alkoxy, or hydroxy;

$R^4$, $R^5$, $R^6$, and $R^7$ are each independently hydrogen or C$_1$-C$_6$ alkyl; and r is an integer having a value of 1, 2, 3, 4, or 5.

7. The compound of claim 1, wherein TG is selected from:

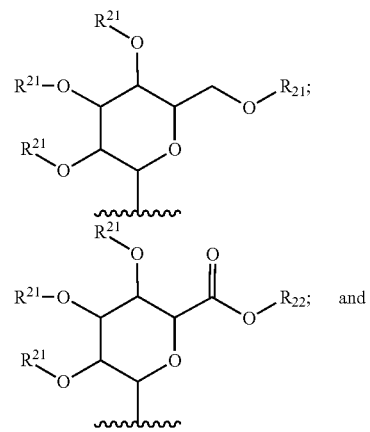

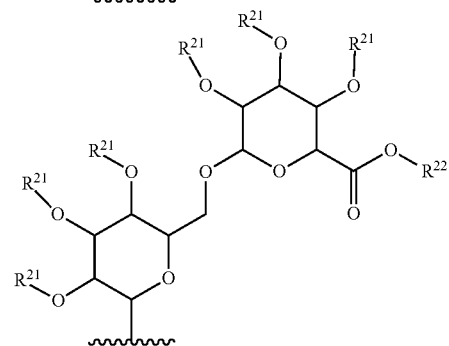

wherein:

each $R^{21}$ is independently hydrogen or acetyl; and $R^{22}$ is hydrogen or lower alkyl.

8. The compound of claim 1, wherein TG is selected from —NO$_2$, —C(O)—(CH$_2$)$_2$C(O)-alkyl, and nitrobenzyl.

9. A conjugate having the structure of Formula (III):

(D-L)$_{dl}$-LG-(CB)$_{cb}$   (III)

or a pharmaceutically acceptable salt thereof, wherein:

LG is a linking group;

CB is a cell-binding agent;

cb and dl are each independently integers having a value of 1 to about 20; and each D-L independently is a group having the structure of a compound of claim 1.

10. The conjugate of claim 9, wherein LG is a C$_{10}$-C$_{100}$ linear or branched, saturated or unsaturated alkylene moiety comprising at least two of the following:

(i) at least one heteroatom selected from —NH—, —C(=O), —O—, —S— and —P—;

(ii) at least one heteroarylene;

(iii) at least one amino acid moiety, sugar bond, peptide bond, or amide bond; and (iv) one or more substitutents selected from the group consisting of C$_1$-C$_{20}$ alkyl, C$_6$-C$_{20}$ aryl C$_1$-C$_8$ alkyl, —(CH$_2$)$_s$COOH, and —(CH$_2$)$_p$NH$_2$, s is an integer having a value of 0 to 10, and p is an integer having a value of 1 to about 10.

11. The conjugate of claim 9, wherein LG is a functional group that can be produced through a click chemical reaction.

12. The conjugate of claim 9, wherein LG is:

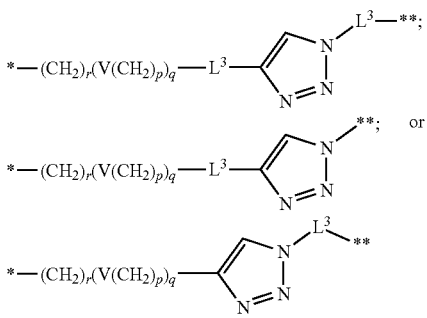

wherein:
* represents the point to attachment to $(D-L)_{dl}$;
** represent the point of attachment to CB;
each V is independently a single bond, —O—, —S—, —NR$^{21}$—, —C(O)NR$^{22}$—, —NR$^{23}$C(O)—, —NR$^{24}$SO$_2$—, or —SO$_2$NR$^{25}$—;
R$^{21}$, R$^{22}$, R$^{23}$, R$^{24}$, and R$^{25}$ are each independently hydrogen, $(C_1-C_6)$alkyl, $(C_1-C_6)$alkyl$(C_6-C_{20})$aryl, or $(C_1-C_6)$alkyl$(C_3-C_{20})$heteroaryl;
r is an integer having a value of 1 to about 10;
p is an integer having a value of 0 to about 10;
q is an integer having a value of 1 to about 10; and
L$^3$ is a single bond.

13. The conjugate of claim 9, wherein LG comprises $(CH_2)_b$, $L^c$, $(P^1)_a$, $W^{a1}$, $W^{a2}$, $W^{a3}$, $Y^3$ and $Y^4$ groups connected to each other in a linear chain by covalent bonds, wherein:
$W^{a1}$, $W^{a2}$, and $W^{a3}$ are each independently —NH—, —C(O)—, or —CH$_2$—;
$P^1$ is an amide bond, an amino acid residue, or a peptide;
$L^c$ is alkylene;
$Y^3$ is —(CH$_2$)$_q$—(CH$_2$CH$_2$X$^4$)$_o$— or —(CH$_2$)$_q$—(X$^4$CH$_2$CH$_2$X$^3$)$_o$—;
$X^3$ and $X^4$ are each independently —O—, —S—, —NH— or —CH$_2$—;
$Y^4$ is a single bond or a group selected from:

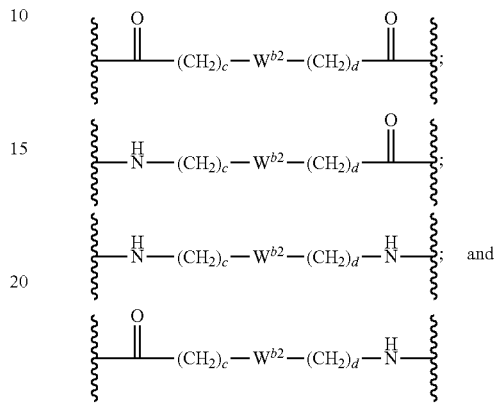

$W^{b2}$ is an amide bond or triazolylene;
a is 0 to 10;
b, c, and d are each independently an integer having a value of 1 to about 10; and
and q are each independently an integer having a value of 1 to about 10.

14. The conjugate of claim 9, wherein LG is a linking group of Formula (IIIb), (IIIc), (IIId), (IIIe), (IIIf), (IIIg), (IIIh), or (IIIj):

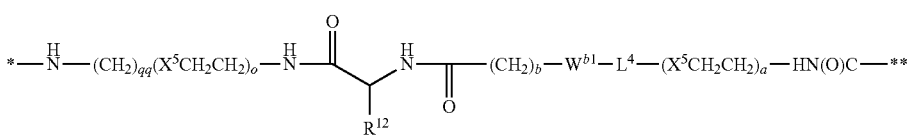

(IIIb)

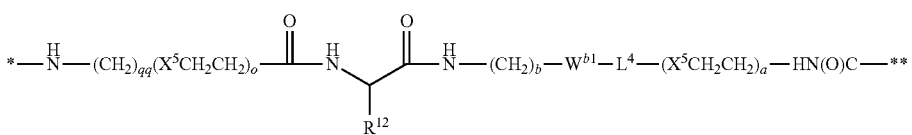

(IIIc)

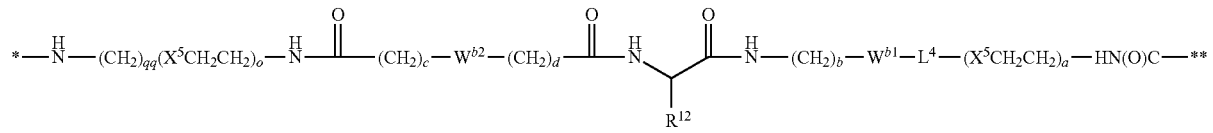

(IIId)

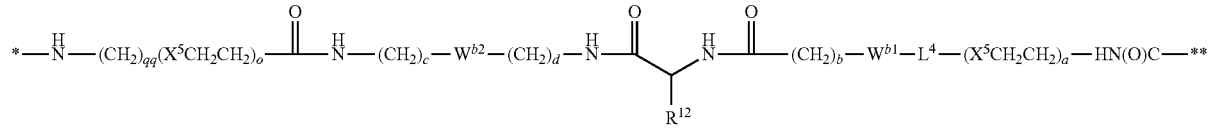

(IIIe)

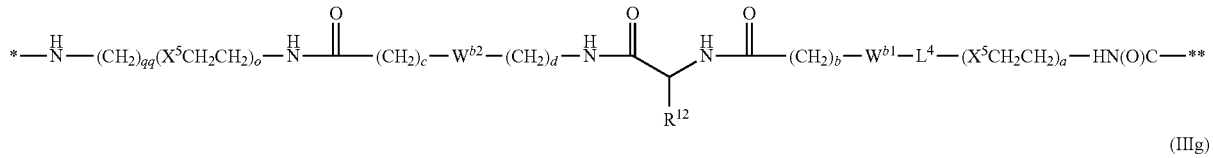
(IIIf)

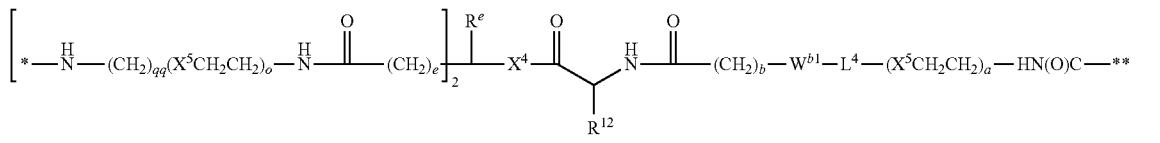
(IIIg)

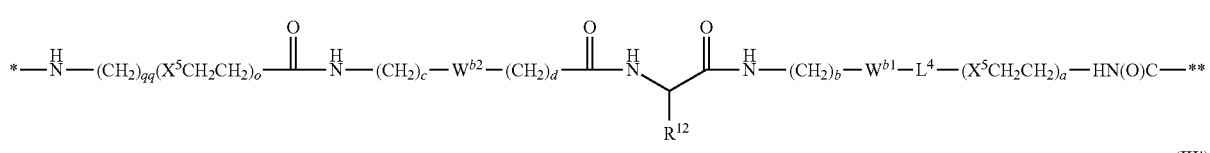
(IIIh)

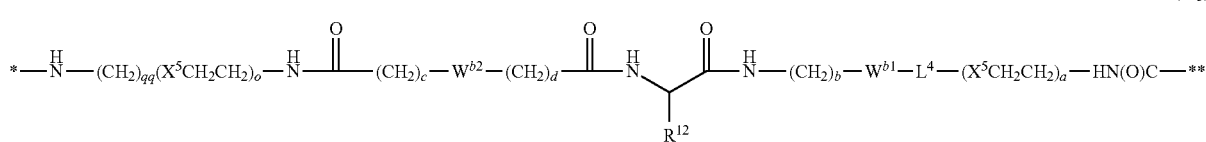
(IIIj)

wherein:
* represents the point to attachment to (D-L)$_{dl}$:
** represent the point of attachment to CB:
$R^e$ is alkyl:
$L^4$ is a spacer moiety, unsubstituted or substituted with one or more $C_1$-$C_6$ alkyl, $C_5$-$C_{14}$ aryl, and $C_3$-$C_8$ heteroaryl, wherein the alkyl, aryl and heteroaryl are unsubstituted or substituted with one or more substituents selected from $C_1$-$C_{10}$ alkyl, —(CH$_2$)$_u$NH$_2$, —(CH$_2$)$_u$NR$^{u1}$R$^{u2}$, —(CH$_2$)$_u$CO$_2$H, —(CH$_2$)$_u$CO$_2$R$^{u1}$, and —(CH$_2$)$_u$SO$_2$R$^{u3}$, wherein R$^{u1}$, R$^{u2}$, and R$^{u3}$ are each independently hydrogen, $C_1$-$C_{15}$ alkyl, $C_6$-$C_{20}$ aryl or $C_3$-$C_{10}$ heteroaryl; and u is an integer having a value of 1 to 10:
$W^{b1}$ and $W^{b2}$ are each independently —C(O)NH—, —NHC(O)—,

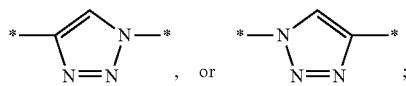 [SMILES: *c1cn(*)nn1 ; *c1cn(*)nn1], or $R^{12}$ is hydrogen, alkyl, an amino acid side chain, —(CH$_2$)$_s$C(O)R$^{13}$ or —(CH$_2$)$_p$NR$^{14}$R$^{15}$;
$R^{13}$ is OH or —NH(CH$_2$)$_{s'}$(X$^4$CH$_2$CH$_2$)$_{s''}$Z"—(CB)$_m$;
$R^{14}$ and $R^{15}$ are each independently hydrogen or —C(O) (CH$_2$)$_{s'}$(X'''CH$_2$CH$_2$)$_{s''}$Z"—(CB)$_m$;
Z" is a linking group connecting CB to the remainder of $R^{14}$ or $R^{15}$: or Z" is a linking group comprising a reactive group:
X''' is —O—, —S—, —NH—, or —CH$_2$—;
s and s" are each independently an integer having a value of 0 to about 10;
m is an integer having a value of 0 or 1;
$X^4$ and $X^5$ are each independently —O—, —S—, —NH—, or —CH$_2$—; and
a, b, c, d, e, o, p, s' and qq are each independently an integer having a value of 1 to about 10.

15. The conjugate of claim 9, wherein the cell-binding agent binds to target cells selected from tumor cells, virus infected cells, microorganism cells, activated cells, myeloid cells, activated T-cells, B cells, or melanocytes; cells expressing the CD4, CD6, CD19, CD20, CD22, CD30, CD33, CD37, CD38, CD40, CD44, CD56, EpCAm, CanAg, CALLA, or Her-2 antigens; Her-3 antigens or cells expressing insulin growth factor receptor, epidermal growth factor receptor, and folate receptor.

16. The conjugate of claim 15, wherein the tumor cells are selected from breast cancer cells, prostate cancer cells, ovarian cancer cells, colorectal cancer cells, gastric cancer cells, squamous cancer cells, small-cell lung cancer cells, and testicular cancer cells.

17. The conjugate of claim 15, wherein the cell-binding agent is an antibody, a single chain antibody, an antibody fragment that specifically binds to the target cell, a monoclonal antibody, a single chain monoclonal antibody, or a monoclonal antibody fragment that specifically binds to the a target cell, a chimeric antibody, a chimeric antibody fragment that specifically binds to the target cell, a domain antibody, a domain antibody fragment that specifically binds to the target cell, a lymphokine, a hormone, a vitamin, a growth factor, a colony stimulating factor, or a nutrient-transport molecule.

18. The conjugate of claim 17, wherein the antibody is a resurfaced antibody, a resurfaced single chain antibody, or a resurfaced antibody fragment; a monoclonal antibody, a single chain monoclonal antibody, or a monoclonal antibody fragment thereof; a chimeric antibody fragment, a domain antibody, or a domain antibody fragment; a humanized antibody, a humanized single chain antibody, or a humanized antibody fragment.

19. A pharmaceutical composition comprising the conjugate of claim 9, or a pharmaceutically acceptable salt thereof, and a pharmaceutically acceptable carrier.

20. A method of treating a cancer in a mammal, comprising administering to said mammal a therapeutically effective amount of the conjugate of claim 9, or a pharmaceutically acceptable salt thereof.

* * * * *

UNITED STATES PATENT AND TRADEMARK OFFICE
CERTIFICATE OF CORRECTION

PATENT NO. : 11,807,628 B2
APPLICATION NO. : 17/363814
DATED : November 7, 2023
INVENTOR(S) : Taekyo Park et al.

Page 1 of 2

It is certified that error appears in the above-identified patent and that said Letters Patent is hereby corrected as shown below:

In the Claims

In Claim 1, at Column 210, Lines 15-27, please replace:

"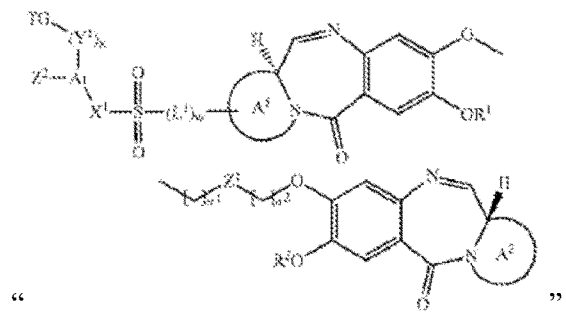"

With:

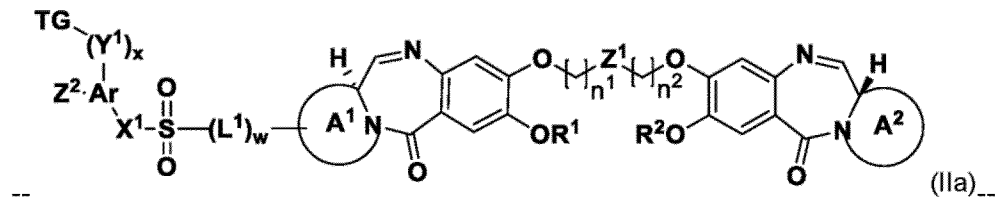 --

Signed and Sealed this
Ninth Day of July, 2024

Katherine Kelly Vidal
*Director of the United States Patent and Trademark Office*

CERTIFICATE OF CORRECTION (continued)
U.S. Pat. No. 11,807,628 B2

In Claim 1, at Column 210, Lines 28-42, please replace:

"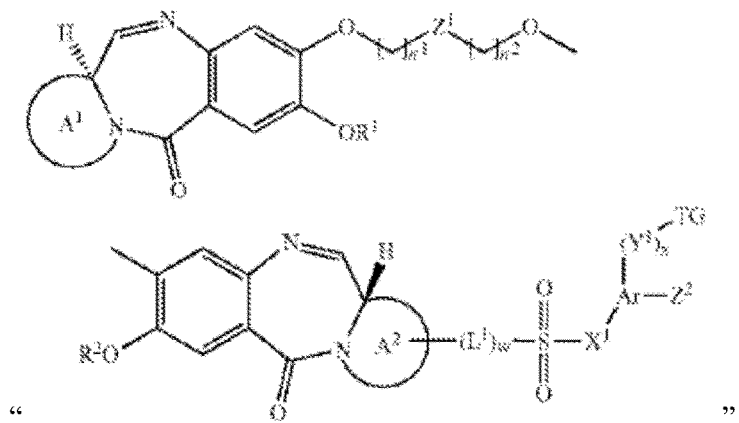"

With:

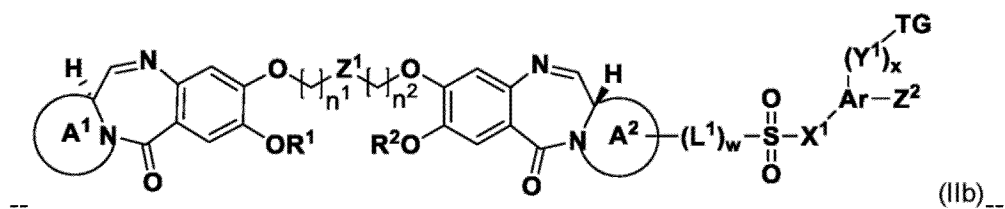
--

In Claim 6, at Column 211, Line 48:
"NHNH$_2$"
Should read:
-- –NHNH$_2$--

In Claim 13, at Column 214, Lines 31-32:
"and q are each independently an integer having a value of 1 to about 10."
Should read:
--o and q are each independently an integer having a value of 1 to about 10.--